(12) United States Patent
Hill et al.

(10) Patent No.: US 9,238,806 B2
(45) Date of Patent: Jan. 19, 2016

(54) CELLULASE ENZYME MIXTURES FOR DEPILLING AND USES THEREOF

(75) Inventors: Christopher Hill, Nepean (CA); John J. Tomashek, Ottawa (CA); Loreta Gudynaite-Savitch, Kanata (CA); Guylaine Therrien, Gatineau (CA); Sophie Calixte, Ottawa (CA)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/981,198

(22) PCT Filed: Feb. 9, 2012

(86) PCT No.: PCT/CA2012/050074
§ 371 (c)(1),
(2), (4) Date: Aug. 28, 2013

(87) PCT Pub. No.: WO2012/106824
PCT Pub. Date: Aug. 16, 2012

(65) Prior Publication Data
US 2013/0337542 A1    Dec. 19, 2013

Related U.S. Application Data

(60) Provisional application No. 61/440,985, filed on Feb. 9, 2011.

(51) Int. Cl.
| | |
|---|---|
| *C12N 9/42* | (2006.01) |
| *C12N 1/00* | (2006.01) |
| *D06M 16/00* | (2006.01) |
| *C07K 1/00* | (2006.01) |
| *C07H 21/04* | (2006.01) |

(52) U.S. Cl.
CPC ........ *C12N 9/2437* (2013.01); *C12Y 302/01004* (2013.01); *C12Y 302/01091* (2013.01); *D06M 16/00* (2013.01); *D06M 16/003* (2013.01)

(58) Field of Classification Search
CPC .. C12N 9/2437; D06M 16/00; D06M 16/003; C12Y 302/01004; C12Y 302/01091
USPC ............. 435/209, 254.6, 263; 536/23.1, 23.2; 530/350
See application file for complete search history.

(56) References Cited

U.S. PATENT DOCUMENTS

| | | | |
|---|---|---|---|
| 5,213,581 A | 5/1993 | Olson et al. | |
| 5,691,178 A | 11/1997 | Shulein et al. | |
| 5,792,641 A * | 8/1998 | Schulein et al. | 435/209 |
| 5,811,381 A | 9/1998 | Emalfarb et al. | |
| 5,866,407 A * | 2/1999 | Foody et al. | 435/263 |
| 5,874,293 A | 2/1999 | Miettinen-Oinonen et al. | |
| 5,916,798 A | 6/1999 | Lund et al. | |
| 5,948,672 A | 9/1999 | Rasmussen et al. | |
| 5,958,083 A | 9/1999 | Onishi et al. | |
| 6,001,639 A | 12/1999 | Schulein et al. | |
| 6,071,735 A | 6/2000 | Schulein et al. | |
| 6,114,296 A | 9/2000 | Schulein et al. | |
| 6,159,720 A | 12/2000 | Murashima et al. | |
| 6,162,782 A | 12/2000 | Clarkson et al. | |
| 6,268,196 B1 | 7/2001 | Fowler et al. | |
| 6,458,955 B1 | 10/2002 | Gattuso | |
| 6,723,549 B2 | 4/2004 | Miettinen-Oinonen et al. | |
| 6,855,531 B2 | 2/2005 | Schulein et al. | |
| 6,921,655 B1 | 7/2005 | Nakamura et al. | |
| 7,041,488 B2 | 5/2006 | Outtrup et al. | |
| 7,049,125 B2 | 5/2006 | Dunn-Coleman et al. | |
| 7,138,261 B2 | 11/2006 | Nakane et al. | |
| 7,226,773 B2 | 6/2007 | Schulein et al. | |
| 7,256,032 B2 | 8/2007 | Valtakari et al. | |
| 7,273,748 B2 | 9/2007 | Miettinen-Oinonen et al. | |
| 7,374,921 B2 | 5/2008 | Okakura et al. | |
| 7,445,922 B2 | 11/2008 | Nakane et al. | |
| 7,449,318 B2 | 11/2008 | Jones et al. | |
| 7,741,093 B2 | 6/2010 | Vehmaanpera et al. | |
| 7,785,854 B2 * | 8/2010 | St-Pierre et al. | 435/200 |
| 8,043,828 B2 * | 10/2011 | Bodie et al. | 435/18 |
| 8,044,264 B2 * | 10/2011 | Lopez de Leon et al. | 800/288 |
| 8,609,387 B2 * | 12/2013 | Valtakari et al. | 435/209 |
| 8,609,388 B2 * | 12/2013 | Masri et al. | 435/209 |

(Continued)

FOREIGN PATENT DOCUMENTS

| | | |
|---|---|---|
| EP | 0 866 165 B2 | 8/2003 |
| WO | 92/17574 A1 | 10/1992 |

(Continued)

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*

(Continued)

*Primary Examiner* — Ganapathirama Raghu
(74) *Attorney, Agent, or Firm* — Elias Lambiris

(57) ABSTRACT

The present invention relates to a depilling composition comprising an enzyme mixture that comprises a Family 45 cellulase and one or more additional cellulases selected from a Family 5 cellulase, a Family 6 cellulase or a combination thereof. The enzyme mixture may be characterized in that the Family 45 and Family 5 cellulases or the Family 45 and Family 6 cellulases are present at a weight ratio that exhibits synergy in an assay that measures specific depilling activity. The enzyme mixture may be secreted by a genetically modified microbe overexpressing the foregoing cellulases. Also provided is a process for depilling that comprises a step of contacting cellulose-containing goods with the depilling composition.

19 Claims, 31 Drawing Sheets

(56) References Cited

U.S. PATENT DOCUMENTS

| | | | |
|---|---|---|---|
| 8,679,791 B2* | 3/2014 | Festersen et al. ............ 435/93 |
| 2003/0054539 A1 | 3/2003 | Schulein et al. |
| 2003/0129723 A1 | 7/2003 | Ishikawa et al. |
| 2007/0111278 A1 | 5/2007 | Koga et al. |

FOREIGN PATENT DOCUMENTS

| | | | |
|---|---|---|---|
| WO | 97/14804 A1 | 4/1997 |
| WO | 2007/057418 A1 | 5/2007 |
| WO | 2007/071820 A1 | 6/2007 |
| WO | 2007/118935 A1 | 10/2007 |
| WO | 2007/147264 A1 | 12/2007 |
| WO | 2008/088724 A2 | 7/2008 |
| WO | 2010/076388 A1 | 7/2010 |

OTHER PUBLICATIONS

Witkowski et al., Conversion of b-ketoacyl synthase to a Malonyl Decarboxylase by replacement of the active cysteine with glutamine. Biochemistry, 1999, vol. 38: 11643-11650.*
Boisset et al., Biotechnology and Bioengineering, vol. 72, No. 3, pp. 339-345 (2001).
Gusakov et al., Biotechnology and Bioengineering, vol. 97, No. 5, pp. 1028-1038 (2007).
Miettinen-Oinonen et al., Applied and Environmental Microbiology, vol. 68, No. 8, pp. 3956-3964 (2002).
Andersen et al, Enzyme and Microbiol Technology, vol. 42, pp. 362-370 (2008).
Andersen J, Enzymatic Hyrdrolysis of Cellulose, pp. 1-162—(2007).
Anu Nutt, Hydrolytic and Oxidative Mechanisms Involved in Cellulose Degradation, 1-52 (2006).
Azevedo et al, Enzyme and Microbiol Technology, vol. 27, pp. 325-329 (2000).
Azevedo et al, Applied Biochemistry and Biotechnology, vol. 101, pp. 61-76 (2002).
Cavaco-Paulo et al, Textile Research Journal, vol. 68, No. 6, pp. 398-401 (1998).
Cavaco-Paulo et al, Textile Research Journal, vol. 68, No. 4, pp. 273-280 (1998).
Cavaco-Paulo et al, Enzyme Technology, pp. 28-32 (1996).
Cavaco-Paulo, Carbohydrate Polymers, vol. 37, pp. 273-277 (1998).
Christopher French, Journal of the Royal Society, pp. 1-13 (2009).
Dashtban et al, International Journal of Biological Sciences, vol. 5, No. 6, pp. 578-595 (2009).
Eberhardt et al, Microbiology, vol. 146, pp. 1999-2008 (2000).
Enebro et al, Cellulose, vol. 16, pp. 271-280 (2009).
Heikinheimo et al, Textile Research Journal, vol. 71, No. 8, pp. 672-677 (2001).
Heikinheimo, VTT Publication 483, 1-82 (2002).
Herpoel-Gimbert et al, Biotechnology for Biofuels, pp. 1-12 (2008).
Hetti Palonen, VTT Publications 520, pp. 1-84 (2004).
Igarashi et al, Applied and Environmental Microbiology, vol. 74, No. 18, pp. 5628-5634 (2008).
Jahangeer et al, Screening and Characterization of Fungal Cellulases, vol. 37, No. 3, pp. 739-748 (2005).
Koga et al, Applied and Environmental Microbiology, vol. 74, No. 13, pp. 4210-4217 (2008).
Matthew et al, Journal of Scientific and Industrial Research, vol. 67, pp. 898-907 (2008).
Mats Sandgren, Structural and Functional Studies of Glycoside Hydrolase Family, vol. 12, pp. 1-70 (2003).
Miettinen-Oionen, VTT Publications 550, pp. 1-153 (2004).
MK Bhat, Biotechnology Advances, vol. 18, pp. 355-383 (2000).
Murashima et al, Biosci. Biotechnol. Biochem, vol. 70, No. 9, pp. 2205-2212 (2006).
Pere et al, J. Biotechnol, vol. 89, No. 2-3, pp. 247-255 (2001).
Ramos et al, Biocatalysis and Biotransformation, vol. 25, No. 1, pp. 35-42 (2007).
Rosgaard et al, Biotechnol. Prog. vol. 23, pp. 1270-1276 (2007).
Sarah Teter and Joel Cherry, Improving Cellulose Hydrolysis, 1-7 (2001).
Shimonaka et al, Biosci Biotechnol Biochem, vol. 70, No. 4, pp. 1013-1016 (2006).
Shimonaka et al, Biosci Biotechnol Biochem, vol. 70, No. 10, pp. 2460-2466 (2006).
Cavaco-Paulo, The Treatment of Cotton Cellulose with Thrichoderma Reesei Engineered Cellulases, pp. 227-234 (1998).
Szijarto et al, Journal of Biotechnology, vol. 136, 140-147 (2008).
Szijarto N., Thesis of Applied Biotechnology, pp. 1-12 (2007).
Pritt Valjamae, The Kinetics of Cellulose Enzymatic Hydrolysis, pp. 1-55 (2002).
Tamaru et al, Environmental Technology, vol. 31, No. 8,9, pp. 889-903 (2010).
Viviana Kopcke, pp. 1-63 (2008).
Vlasenko et al, Bioresource Technology, vol. 101, pp. 2405-2411 (2010).
Zhang et al, Biotechnol Bioeng, vol. 88, No. 7, pp. 797-824 (2004).
Zhang et al, Biotechnology Advances, vol. 24, pp. 452-481 (2006).
Tzanov et al, Journal of Biotechnology, vol. 6, No. 3 pp. 146-154 (2003).
Cavaco-Paulo Almeida, Textile Research Journal, vol. 66, No. 5, pp. 287-294 (1996).
Cavaco-Paulo et al., Textile Chemist and Colorist, pp. 28-32 (Jun. 1996).
Miettinen-Oinonen et al., Journal of Biotechnology, vol. 116, No. 3, pp. 305-317 (2005).
Yamada et al., Biosci. Biotechnol. Biochem., vol. 60, No. 1, pp. 45-50 (2005).
Chhavi et al., The Proteins Behind Fuzz Removal, pp. 1-5 (2007).

* cited by examiner

```
TrCel45A (SEQ ID NO: 4)    1   YKATTTRYYDGQEGACGCGSSSGAFPWQLGIGNGVYTAAG  40
TvEGV (SEQ ID NO:8)            YKATTTRYYDGQEGACGCGSSSGAFPWQLGIGNGVYTAAG
PdCel45A (SEQ ID NO:9)         YKATTTRYYDGQEGACGCGSSSGLFPWQLGIGNGVYTAAG
AnAN6786.2 (SEQ ID NO:10)      ASSSCPGYHN---CACGCGNKIGTYDWSYGIANKVYTAAA
HddEG1 (SEQ ID NO:11)          HCASTTRYNDGHKGACGCG--QNDTPFPWNNNQ--YVAAA
AcEG27I (SEQ ID NO:12)         PCASTTRYVDGHKGACGCGQKGSDTPFPWNIQK--HVTAP
AcEG27II (SEQ ID NO:13)        PCASTTRYVDGHKGACGCGQKGSDTPFPWNLQK--HVTAP
MeEg (SEQ ID NO:14)            SCASTTNYHDSHKGACGCGPASGDAQFGWNAGS--FVAAA
PcCel45A (SEQ ID NO:15)        EKRATGGYVQQATGQASFTMYSGCGSPACGKAASGFTAAI

TrCel45A (SEQ ID NO: 4)   41   SQALFDTAG---ASWCGAGCGKCYQLTSTGQAPCSSCGTG  77
TvEGV (SEQ ID NO:8)            SQALFDTAG---ASWCGAGCGKCYQLTSTGQAPCSSCGTG
PdCel45A (SEQ ID NO:9)         SQALFDTAG---ADWCGAGCGKCYKLTSTGEPPCKDCGTG
AnAN6786.2 (SEQ ID NO:10)      NQALFDSGPNDATHWCGNGCGKCYRLTSTGVSTCETCGAG
HddEG1 (SEQ ID NO:11)          NQKLFSNSG--ST-WCGDSCGKCVKLTTTG-GSIPGAGTG
AcEG27I (SEQ ID NO:12)         SERYFDGGG--SSLWCGRNCGKCVKLTPTG-GFVPGKGNA
AcEG27II (SEQ ID NO:13)        SERYFDDGG--SNLWCGKNCGKCVRLTPTG-GFVPGKGGA
MeEg (SEQ ID NO:14)            SQMYFDSGN--KG-WCGQHCGQCIKLTTTG-GYVPGQGGP
PcCel45A (SEQ ID NO:15)        NQLAFGSAP---GLGAGDACGRCFALTGNHDPYSPN--YT

TrCel45A (SEQ ID NO: 4)   78   GAAGQSIIVMVTNLCP-NNGNAQWC-----PVVGGTNQYG 111
TvEGV (SEQ ID NO:8)            GAAGQSIIVMVTNLCP-NNGNAQWC-----PVVGGTNQYG
PdCel45A (SEQ ID NO:9)         GVAGQSIIVMVTNLCP-YNGNQQWC-----PNPGSTNQYG
AnAN6786.2 (SEQ ID NO:10)      GEQGKSIVVMVTNLCP-FKGNERWC-----PNPGQLNPHG
HddEG1 (SEQ ID NO:11)          AHAGQSHVFMITNDCPDVAPNLEWCAQKGAPGSGHGNTHG
AcEG27I (SEQ ID NO:12)         PPNHNPVVFQVTNACP-INGNEEWCGISGAPGTGHVNSHG
AcEG27II (SEQ ID NO:13)        PPNHNPVVFMVTNACP-INGNEEWCGISGKPGTNHVNSHG
MeEg (SEQ ID NO:14)            VREGLSKTFMITNLCPNIYPNQDWCNQGSQYG-GH-NKYG
PcCel45A (SEQ ID NO:15)        GPFGQTIVVKVTDLCP-VQGNQEFCG---QTTSNPTNQHG

TrCel45A (SEQ ID NO: 4)  112   YSYHFDIMAQNE---IFG----DNVVVDFEPIACPGQA-- 142
TvEGV (SEQ ID NO:8)            YSYHFDIMAQNE---IFG----DNVVVDFEPIACPGQA--
PdCel45A (SEQ ID NO:9)         YSYHFDIMAQNE---IFG----DNVVVDFEPIACPGQA--
AnAN6786.2 (SEQ ID NO:10)      YAYHFDIMGGAG---VFG----DNVVVEFEEVPCPGDA--
HddEG1 (SEQ ID NO:11)          YEVHFDLENNGN---QISKLGWDNPEVTWEWSSCHGSN--
AcEG27I (SEQ ID NO:12)         YEVHFDLQDQVG---QVEALHWDNPEVTWEETSCPGDL--
AcEG27II (SEQ ID NO:13)        YEVHFDLQDQVG---QVEALHWDNPEVTWEEVPCPGDL--
MeEg (SEQ ID NO:14)            YELHLDLENGRS---QVTGMGWNNPETTWEVVNCDSEHNH
PcCel45A (SEQ ID NO:15)        MPFHFDICEDTGGSAKFFPSGHGALTGTFTEVSCSQWSGS

TrCel45A (SEQ ID NO: 4)  143   ------ASDWGTCLCVGQQETDPTPV---LGND 166
TvEGV (SEQ ID NO:8)            ------ASDWGTCLCVGQQETDPTPV---LGND
PdCel45A (SEQ ID NO:9)         ------NSDWQSCVCYGKTETDTTPVGLTAGGG
AnAN6786.2 (SEQ ID NO:10)      ------AFKWAACECHPNLRNKDLTLN--AGAH
HddEG1 (SEQ ID NO:11)          ---TPTDQMWHTCECSH----------------
AcEG27I (SEQ ID NO:12)         ------QSNYQQCECHNSG--------------
AcEG27II (SEQ ID NO:13)        ------QANYQQCECHNSD--------------
MeEg (SEQ ID NO:14)            DHRTPSNSMYGQCQCAHQGKRGLNETSNESL--
PcCel45A (SEQ ID NO:15)        ---DGGQLWNGACLSGETAPNWPSTACGNKGTA
```

FIGURE 1

```
HiCel45A   (SEQ ID NO: 7)    1   ADGRSTRYWDCCKPSCGWAKKAPV---NQPVFSCNANFQR  37
HgEgl3     (SEQ ID NO:16)        ADGKSTRYWDCCKPSCGWAKKAPV---NQPVFSCNANFQR
HnCel45A   (SEQ ID NO:17)        ADGRSTRYWDCCKPSCSWPGKALV---NQPVYARNANFQR
ScSTCE1    (SEQ ID NO:18)        ADGKSTRYWDCCKPSCSWPGKASV---NQPVFACSANFQR
MaCel45A   (SEQ ID NO:19)        ANGQSTRYWDCCKPSCGWRGKGPV---NQPVYSCDANFQR
PaCel45A   (SEQ ID NO:20)        GSGKSTRYWDCCKPSCAWPGKAAV---NRPVFACDANFQR
AtSEQ6     (SEQ ID NO:21)        LDGKSTRYWDCCKPSCGWAGKASV---NQPVFSCSADWQR
TtCel45A   (SEQ ID NO:22)        GSGQSTRYWDCCKPSCAWPGKAAV---SQPVYACDANFQR
TroCel45A  (SEQ ID NO:23)        ADGRSTRYWDCCKPSCSWPDKAPV---GSPVGTCDAGNSP
AtSEQ2     (SEQ ID NO:24)        LDGKSTRYWDCCKPSCGWPGKASV---NQPVFSCSADWQR
FaCel45A   (SEQ ID NO:25)        ADGRSTRYWDCCKPSCSWGGKAAV---SAPALTCDKKDNP
CrCel45A   (SEQ ID NO:26)        ADGRSTRYWDCCKPSCAWSGKASV---SSPVRTCDANNSP
NcCel45A   (SEQ ID NO:27)        GSGQSTRYWDCCKPSCSWSGKAPV---NRPVLACDANNNP
VcSEQ22    (SEQ ID NO:28)        GTGRTTRYWDCCKPSCGWDEKASV---SQPVKTCDRNNNP
GzCel45A   (SEQ ID NO:29)        GSGHSTRYWDCCKPSCSWSGKAKV---SAPALTCDKKDNP
FoCel45A   (SEQ ID NO:30)        GSGHSTRYWDCCKPSCSWSGKAAV---NAPALTCDKNDNP
AsSEQ10    (SEQ ID NO:31)        GKGHTTRYWDCCKTSCAWEGKASV---SEPVLTCNKQDNP
AsSEQ8     (SEQ ID NO:32)        GSGHTTRYWDCCKPSCAWDEKAAV---SRPVTTCDRNNSP
ClCel45A   (SEQ ID NO:33)        GSGQTTRYWDCCKPSCAWPGKG----PSSPVQACDKNDNP
ThSEQ2     (SEQ ID NO:34)        GIGQTTRYWDCCKPSCAWPGKG----PSSPVQACDKNDNP
McMce1     (SEQ ID NO:35)        GSGSTTRYWDCCKASCSWPGKASV---TGPVDTCASNG-I
RshpCel45A (SEQ ID NO:36)        ---KTTRYWDCCKGSCGWEAKADV---SKPIDTCAKDGTT
BxEng1     (SEQ ID NO:37)        DTGKTTRYWDCCKPSCSWPGKAQL--KQGPSKTCDVNDKP
BfCel45A   (SEQ ID NO:38)        GSGTTTRYWDCCKPSCAWSGKATLESGSGPVGTCDINDSP
AtSEQ4     (SEQ ID NO:39)        GTGTTTRYWDCCKPSCAWPLKGN---SPSPVQTCDKNDRP
SbEgI      (SEQ ID NO:40)        GTGTTTRYWDCCKPSCSWPDKAPL--SQGPPMTCDINDNP
SrCBHI     (SEQ ID NO:41)        GDGTTTRYWDCCKASCSWPGKAPV---TNPVGTCAKDG-V
RoRce1     (SEQ ID NO:42)        GNGVTTRYWDCCKASCSWPGKANV---SSPVKSCNKDG-V
CsSEQ16    (SEQ ID NO:43)        TAGVTTRYWDCCKPSCGWSGKASV---SAPVRTCDRNGNT
MpSEQ14    (SEQ ID NO:44)        TAGVTTRYWDCCKPSCGWSGKASV---SAPVRTCDRNGNT
PaCel45B   (SEQ ID NO:45)        GAGKTTRYWDCCKPSCAWPGKST---ASTPVLTCDRNDNP
RoRce3     (SEQ ID NO:46)        GNGVTTRYWDCCKASCSWPGKANV---SSPVKSCNKDG-V
BxEng2     (SEQ ID NO:47)        GTGVTTRYWDCCKSSCAWPGKASL--KSGPIQTCDVHDQP
BxEng3     (SEQ ID NO:48)        GTGVTTRYWDCCKSSCAWPGKATL--KSGPIQTCDVHDQP
HgEgl4     (SEQ ID NO:49)        GSGRTTRYWDCCKPSCAWPGKG-----PAPVRTCDRWDNP
PnPce1     (SEQ ID NO:50)        GNGRTTRYWDCCKPSCAWDGKASV---TKPVLTCAKDG-V
RoRce2     (SEQ ID NO:51)        GNGETTRYWDCCKPSCSWPGKADV---TSPVGSCNKDG-K
MdhsFm4    (SEQ ID NO:52)        GNGQTTRYWDCCKPSCSWSKKAQV---SHVVNSCNANN--
MgCel45A   (SEQ ID NO:53)        GTGATTRYWDCCKPSCGWPGKANL--ASGPLRTCDKADNP
MdhsFm3    (SEQ ID NO:54)        GNGQTTRYWDCCKPSCSWSKKAQV---SHVVNSCNANG--
MdhsFm1    (SEQ ID NO:55)        GNGQTTRYWDCCKPSCSWSKKAQV---SHVVNSCTATG--
MdhsFm2    (SEQ ID NO:56)        GSGKTTRYWDCCKPSCSWSKKAQV---SHVVNSCTASG--
PpCel45A   (SEQ ID NO:57)        -TGRTTRYWDCCKPSCSWPG--KSNSVTGPVRSCGVSGN-
PeCel45A   (SEQ ID NO:58)        QTGKTTRYWDCCLASCSWQENCKNDGAQGVVRSCNVDGIT
AgCelI     (SEQ ID NO:59)        GSGTTTRYWDCCKPSCGWVENL-AKE-GTPVATCSADGST
AgCelII    (SEQ ID NO:60)        GTGKTTRYWDCCKPSCSWKANLSKS-GKPVEACAADGKT
AaK1       (SEQ ID NO:61)        GEAVTTRFWDCCKPSCGWNGKAQF---SRPVESCTADDKP
PcEg       (SEQ ID NO:62)        GYGTTTRYWDCCKPSCAWKENINTPT-MTPVQTCAIDGNT
TeCel45A   (SEQ ID NO:63)        LTGTTTTTWDCCKPACSWTQNAQAGGASGTVATCNINNQV
UmEgl1     (SEQ ID NO:64)        RAGMATRYWDCCLASASWEGKAPV---YAPVDACKADGVT
```

FIGURE 2A

```
HiCel45A   (SEQ ID NO: 7)    38  ITD--F---DAKSGCEPGGVAYSCADQTPW--AVNDDFAL  70
HgEgl3     (SEQ ID NO:16)        LTD--F---DAKSGCEPGGVAYSCADQTPW--AVNDDFAF
HnCel45A   (SEQ ID NO:17)        ITD--P---NAKSGCD-GGSAFSCADQTPW--AVSDDFAY
ScSTCE1    (SEQ ID NO:18)        ISD--P---NVKSGCD-GGSAYACADQTPW--AVNDNFSY
MaCel45A   (SEQ ID NO:19)        IHD--F---DAVSGCE-GGPAFSCADHSPW--AINDNLSY
PaCel45A   (SEQ ID NO:20)        ISD--S---GVASGCN-GGSAYSCADHSAW--AINDNLSY
AtSEQ6     (SEQ ID NO:21)        ISD--F---NAKSGCD-GGSAYSCADQTPW--AVNDNFSY
TtCel45A   (SEQ ID NO:22)        LSD--F---NVQSGCN-GGSAYSCADQTPW--AVNDNLAY
TroCel45A  (SEQ ID NO:23)        LGD--P---LAKSGCE-GGPSYTCANYQPW--AVNDQLAY
AtSEQ2     (SEQ ID NO:24)        ISD--F---NAKSGCD-GGSAYSCADQTPW--AVNDNFSY
FaCel45A   (SEQ ID NO:25)        ISN--L---NAVNGCEGGGSAFACTNYSPW--AVNDNLAY
CrCel45A   (SEQ ID NO:26)        LSD--V---DAKSACD-GGVAYTCSNNAPW--AVNDNLSY
NcCel45A   (SEQ ID NO:27)        LSD--A---SVKSGCD-GGSAYTCANNSPW--AVNDQLSY
VcSEQ22    (SEQ ID NO:28)        LAS------TARSGCDSNGVAYTCNDNQPW--AVNDNLAY
GzCel45A   (SEQ ID NO:29)        ITN--L---NAVNGCESGGSAFACTNYSPW--AVNDDLAY
FoCel45A   (SEQ ID NO:30)        ISN--T---NAVNGCEGGGSAYACTNYSPW--AVNDELAY
AsSEQ10    (SEQ ID NO:31)        IVD--A---NARSGCDGGG-AFACTNNSPW--AVSEDLAY
AsSEQ8     (SEQ ID NO:32)        LSP------GAVSGCDPNGVAFTCNDNQPW--AVNNNVAY
ClCel45A   (SEQ ID NO:33)        LND-GG---STRSGCDAGGSAYMCSSQSPW--AVSDELSY
ThSEQ2     (SEQ ID NO:34)        LND-GG---STRSGCDAGGSAYMCSSQSPW--AVSDELSY
McMce1     (SEQ ID NO:35)        S-LLDA---NAQSGCN-GGNGFMCNNNQPW--AVNDELAY
RshpCel45A (SEQ ID NO:36)        RVASND---TVKSGCD-GGDGYMCYDQTPW--GVNDSYAL
BxEng1     (SEQ ID NO:37)        LSD-G----NIQSGCN-GGSAYACSTDQPW--AVDDNLSY
BfCel45A   (SEQ ID NO:38)        LSDPTA---IAVSGCD-GGNSYMCSDQSPW--AVSDDLAY
AtSEQ4     (SEQ ID NO:39)        LND-GG---NTKSGCDNGGGAFMCSSQSPW--AVNETTSY
SbEgI      (SEQ ID NO:40)        LDD-GG---LTESGCEPGGGAYMCSSHSPW--AVDDELAY
SrCBHI     (SEQ ID NO:41)        K-LVDA---NVQSGCN-GGEGYMCNDNQPW--AIDDNLSY
RoRce1     (SEQ ID NO:42)        TALSDS---NAQSGCN-GGNSYMCNDNQPW--AVNDNLAY
CsSEQ16    (SEQ ID NO:43)        LGP------DVKSGCDSGGTSFTCANNGPF--AIDNNTAY
MpSEQ14    (SEQ ID NO:44)        LGP------DVKSGCDSGGTSFTCANNGPF--AIDNNTAY
PaCel45B   (SEQ ID NO:45)        LND-RG---STRSGCDSGGSAFMCSNQSPW--AVNETVAY
RoRce3     (SEQ ID NO:46)        TALSDS---NVQSGCN-GGNSYMCNDNQPW--AVNDNLAY
BxEng2     (SEQ ID NO:47)        LND-GG---NTQSGCN-GGSAYSCSTEQPY--AVNDTLSF
BxEng3     (SEQ ID NO:48)        LND-GG---NTQSGCN-GGSAYSCSTEQPY--AVNDTLSF
HgEgl4     (SEQ ID NO:49)        LFD-GG---NTRSGCDAGGGAYMCSDQSPW--AVSDDLAY
PnPce1     (SEQ ID NO:50)        S-RLGS---DVQSGCV-GGQAYMCNDNQPW--VVNDDLAY
RoRce2     (SEQ ID NO:51)        T-LADN---NTQNGCV-GGSSYTCNDNQPW--VVSDDLAY
MdhsFm4    (SEQ ID NO:52)        QHDSTV---DLKSGCD-GGPSYACADQAPW--AVNSSYFM
MgCel45A   (SEQ ID NO:53)        LND-GG---NTKSGCDNGGGAFMCSSQEPL--AVDDSLAY
MdhsFm3    (SEQ ID NO:54)        QHDSTV---DLKSGCD-GGPSYACTDQAPW--AVNSSYFM
MdhsFm1    (SEQ ID NO:55)        SHDTTV---DLKSGCD-GGPSYVCVDQAPW--AVNSSYFM
MdhsFm2    (SEQ ID NO:56)        QHDTTV---DLKSGCD-GGPSYVCVDQAPW--AVNSSYFM
PpCel45A   (SEQ ID NO:57)        -VLDAN----AQSGCI-GGEAFTCDEQQPW--SINDDLAY
PeCel45A   (SEQ ID NO:58)        PFTDLSNLWRVKSGCN-GGSVYMCNDQQPW--AINDNVAY
AgCelI     (SEQ ID NO:59)        TVA------ASVKSSCVGGT-SYMCSNQQPK--SVNSTFAL
AgCelII    (SEQ ID NO:60)        VVK------ESTKSACEEGAGAYMCSDQQPK--VVNSTFAL
AaK1       (SEQ ID NO:61)        TDI------AAGTGCN-SGSAFQCSNQQPW--AINDTLSY
PcEg       (SEQ ID NO:62)        VVN------ASVQSGCIGGS-SYMCSNQQAF--VVNSTLAF
TeCel45A   (SEQ ID NO:63)        LSNGAS----APSACQ-GGDAYSCSDFQPI--IISDTLSY
UmEgl1     (SEQ ID NO:64)        LIDSKKD-PSGQSGCN-GGNKFMCSCMQPFDDETDPTLAF
```

FIGURE 2B

```
HiCel45A   (SEQ ID NO: 7)    71  GFAATSIA-----GSNEAGWCCACYELTFTSGPV----AG  101
HgEgl3     (SEQ ID NO:16)        GFAATSIA-----GSNEAGWCCACYELTFTSGPV----AG
HnCel45A   (SEQ ID NO:17)        GFAATALA-----GQSESSWCCACYELTFTSGPV----AG
ScSTCE1    (SEQ ID NO:18)        GFAATSIS-----GGNEASWCCGCYELTFTSGPV----AG
MaCel45A   (SEQ ID NO:19)        GFAATALS-----GQTEESWCCACYALTFTSGPV----AG
PaCel45A   (SEQ ID NO:20)        GFAATALS-----GGSEASWCCACYELTFTDGPV----AG
AtSEQ6     (SEQ ID NO:21)        GFAATAIA-----GGSESSWCCACYALTFNSGPV----AG
TtCel45A   (SEQ ID NO:22)        GFAATSIA-----GGSESSWCCACYALTFTSGPV----AG
TroCel45A  (SEQ ID NO:23)        GFAATAIN-----GGTEDSWCCACYKLTFTDGPA----SG
AtSEQ2     (SEQ ID NO:24)        GFAATAIA-----GGSESSWCCACYALTFNSGPV----AG
FaCel45A   (SEQ ID NO:25)        GFAATKLA-----GGSEGSWCCACYALTFTTGPV----KG
CrCel45A   (SEQ ID NO:26)        GFAATAIN-----GGSESSWCCACYKLTFTSGPA----SG
NcCel45A   (SEQ ID NO:27)        GFAATKLS-----GGTESSWCCACYALTFTSGPV----AG
VcSEQ22    (SEQ ID NO:28)        GFAATAFS-----GGSEASWCCACYALQFTSGPV----AG
GzCel45A   (SEQ ID NO:29)        GFTATKLA-----GGTEASWCCACYALTFTTGPV----KG
FoCel45A   (SEQ ID NO:30)        GFAATKIS-----GGSEASWCCACYALTFTTGPV----KG
AsSEQ10    (SEQ ID NO:31)        GFAATALS-----GGTEGSWCCACYAITFTSGPV----AG
AsSEQ8     (SEQ ID NO:32)        GFAATAFP-----GGNEASWCCACYALQFTSGPV----AG
ClCel45A   (SEQ ID NO:33)        GWAAVKLA-----GSSESQWCCACYELTFTSGPV----AG
ThSEQ2     (SEQ ID NO:34)        GWAAVKLA-----GSSESQWCCACYELTFTSGPV----AG
McMce1     (SEQ ID NO:35)        GFAAASIA-----GSNEAGWCCGCYELTFTSGAA----SG
RshpCel45A (SEQ ID NO:36)        GFAAAAIS-----GG-EKAACCNCYELTFTSGPV----NG
BxEng1     (SEQ ID NO:37)        GFAAVKLA-----GKQESDWCCSCYELTFTDGPV----AG
BfCel45A   (SEQ ID NO:38)        GYAAVNIA-----GGSEASWCCACYELTFTSTAL----AG
AtSEQ4     (SEQ ID NO:39)        GWAAVRIA-----GSTESAWCCACYELTFTSGPV----SG
SbEgI      (SEQ ID NO:40)        GWAAVNIG-----GQTESDWCCACYELEFTTGAV----SG
SrCBHI     (SEQ ID NO:41)        GFAAASIS-----GKSESDFCCSCYELTFSSGEI----EG
RoRce1     (SEQ ID NO:42)        GFAAAAIS-----GGGESRWCCSCFELTFTSTSV----AG
CsSEQ16    (SEQ ID NO:43)        GFAAAHLA-----GSSEAAWCCQCYELTFTSGPV----VG
MpSEQ14    (SEQ ID NO:44)        GFAAAHLA-----GSSEAAWCCQCYELTFTSGPV----VG
PaCel45B   (SEQ ID NO:45)        GWAAVNIA-----GSNEASWCCSCYELTFTSGPV----SG
RoRce3     (SEQ ID NO:46)        GFAAAAIS-----GGGESRWCCSCFELTFTSTSV----AG
BxEng2     (SEQ ID NO:47)        GFAAVKLA-----GGSESSWCCACYELTFTSGSV----NG
BxEng3     (SEQ ID NO:48)        GFAAVKLA-----GGSESTWCCACYELTFTSGSV----AG
HgEgl4     (SEQ ID NO:49)        GWAAVNIA-----GSNERQWCCACYELTFTSGPV----AG
PnPce1     (SEQ ID NO:50)        GFAAASLG-----SAGASAFCCGCYELTFTNTAV----AG
RoRce2     (SEQ ID NO:51)        GFAAASIS-----GGSEATWCCACFELTFTSTAV----KG
MdhsFm4    (SEQ ID NO:52)        GTAAAALS-----GASEADLCCKCFELTFTSGTP----NG
MgCel45A   (SEQ ID NO:53)        GFAAVRIS-----GQRESDWCCACYELTFTN--------
MdhsFm3    (SEQ ID NO:54)        GTAAAALS-----GGSESDLCCKCFELTFTSGTP----NG
MdhsFm1    (SEQ ID NO:55)        GTAAAALS-----GGSESDLCCRCFELTFTSGQP----NG
MdhsFm2    (SEQ ID NO:56)        GTAAAALS-----GGSESDLCCRCFELTFTSGQS----NG
PpCel45A   (SEQ ID NO:57)        GFAAASLA-----GGSEDSSCCTCMKLTFTSSSI----AG
PeCel45A   (SEQ ID NO:58)        GFVAS-----------HEKCCTCQRLKFTSGPI----AG
AgCelI     (SEQ ID NO:59)        GFVAASFT-----GGADTNYCCACIKLTFQD-AL----QG
AgCelII    (SEQ ID NO:60)        GYVAASFT-----GGIDVNMCCACLRLKFQG-DL----SG
AaK1       (SEQ ID NO:61)        GYAGVYITPDLTHGGIEDAWCCACYQLNFTSEPL----IG
PcEg       (SEQ ID NO:62)        GFAAGSFT-----GGVDNNLCCSCMLLTFQG-QL----AG
TeCel45A   (SEQ ID NO:63)        GFAGN----------WETSNCCKCFQFTWTSGAG----AG
UmEgl1     (SEQ ID NO:64)        GFGAFTTG-------QESDTDCACFYAEFEHDAQGKAMKR
```

FIGURE 2C

```
HiCel45A   (SEQ ID NO:7)    102  KKMVVQSTSTGGDLGSN---HFDLNIPGGGVGIFD-GCTP  137
HgEgl3     (SEQ ID NO:16)        KKMVVQSTSTGGDLGSN---HFDLNIPGGGVGIFD-GCTP
HnCel45A   (SEQ ID NO:17)        KKMAVQSTSTGGDLGSN---HFDLNMPGGGVGIFD-GCSP
ScSTCE1    (SEQ ID NO:18)        KTMVVQSTSTGGDLGTN---HFDLAMPGGGVGIFD-GCSP
MaCel45A   (SEQ ID NO:19)        KTMVVQSTSTGGDLGSN---HFDLNIPGGGVGLFD-GCTP
PaCel45A   (SEQ ID NO:20)        KKMVVQSTSTGGDLGSN---HFDLNIPGGGVGLFD-GCKP
AtSEQ6     (SEQ ID NO:21)        KTMVVQSTSTGGDLGSN---QFDLAIPGGGVGIFN-GCAS
TtCel45A   (SEQ ID NO:22)        KTMVVQSTSTGGDLGSN---QFDIAMPGGGVGIFN-GCSS
TroCel45A  (SEQ ID NO:23)        KTMIVQSTNTGGDLSDN---HFDLLIPGGGVGIFD-GCTS
AtSEQ2     (SEQ ID NO:24)        KTMVVQSTSTGGDLGSN---QFDLAIPGGGVGIFN-GCAS
FaCel45A   (SEQ ID NO:25)        KTMVVQSTNTGGDLGDN---HFDLMMPGGGVGIFD-GCTS
CrCel45A   (SEQ ID NO:26)        KVMVVQSTNTGYDLSNN---HFDILMPGGGVGAFD-GCSR
NcCel45A   (SEQ ID NO:27)        KTLVVQSTSTGGDLGSN---HFDINMPGGGVGLFD-GCKR
VcSEQ22    (SEQ ID NO:28)        KTMVVQSTNTGGDLSGN---HFDILMPGGGLGIFD-GCTP
GzCel45A   (SEQ ID NO:29)        KKMIVQSTNTGGDLGDN---HFDLMMPGGGVGIFD-GCTS
FoCel45A   (SEQ ID NO:30)        KKMIVQSTNTGGDLGDN---HFDLMMPGGGVGIFD-GCTS
AsSEQ10    (SEQ ID NO:31)        KKMVVQSTNTGGDLSNN---HFDLMIPGGGLGIFD-GCSA
AsSEQ8     (SEQ ID NO:32)        KTMVVQSTNTGGDLSGT---HFDIQMPGGGLGIFD-GCTP
ClCel45A   (SEQ ID NO:33)        KKMIVQATNTGGDLGDN---HFDLAIPGGGVGIFN-ACTD
ThSEQ2     (SEQ ID NO:34)        KKMIVQATNTGGDLGDN---HFDLAIPGGGVGIFN-ACTD
McMce1     (SEQ ID NO:35)        KKMVVQVTNTGGDLGSN---HFDLQMPGGGVGIFN-GCAA
RshpCel45A (SEQ ID NO:36)        KKMTVQVTNTGGDLGSN---QFDLAIPGGGVGIYN-GCTA
BxEng1     (SEQ ID NO:37)        KKFVVQATNTGGDLGDN---HFDLMIPGGGVGIFN-GCQA
BfCel45A   (SEQ ID NO:38)        KKMIVQATNTGGDLGSN---QFDLAIPGGGVGIFN-GCTK
AtSEQ4     (SEQ ID NO:39)        KKLIVQATNTGGDLGSN---HFDLAIPGGGVGQSN-ACTN
SbEgI      (SEQ ID NO:40)        KKMIVQATNTGGDLGNN---HFDIAMPGGGVGIFN-GCTD
SrCBHI     (SEQ ID NO:41)        KKMVVQVTNTGGDLSNN---HFDLQIPGGGVGIFN-GCQT
RoRce1     (SEQ ID NO:42)        KKMVVQVTNTGGDLGSSTGAHFDLQMPGGGVGIFN-GCSS
CsSEQ16    (SEQ ID NO:43)        KKLTVQVTNTGGDLGNN---HFDLMIPGGGVGLFTQGCPA
MpSEQ14    (SEQ ID NO:44)        KKLTVQVTNTGGDLGNN---HFDLMIPGGGVGLFTQGCPA
PaCel45B   (SEQ ID NO:45)        KKMIVQATNTGGDLGNN---HFDIAMPGGGVGIFN-ACTQ
RoRce3     (SEQ ID NO:46)        KKMVIQVTNTGGDLGSSTGAHFDLQMPGGGVGIFN-GCSK
BxEng2     (SEQ ID NO:47)        KKFVIQATNTGGDLGDN---HFDLAIPGGGVGIFN-GCTA
BxEng3     (SEQ ID NO:48)        KKFVIQATNTGGDLGDN---HFDLAIPGGGVGIFN-GCTA
HgEgl4     (SEQ ID NO:49)        KRMIVQASNTGGDLGNN---HFDIAMPGGGVGIFN-ACTD
PnPce1     (SEQ ID NO:50)        KKFVVQVTNTGDDLSTN---HFDLQMPGGGVGYFN-GCQS
RoRce2     (SEQ ID NO:51)        KKMVVQVTNTGSDLGSNTGAHFDLQMPGGGVGIYN-GCAT
MdhsFm4    (SEQ ID NO:52)        KKMLVQITNTGSDLSGN---QFDLLIPGGGVGIFD-GCTR
MgCel45A   (SEQ ID NO:53)        -----LLRNTGGDLGQN---HFDIAMPGGGVGIFN-ACTE
MdhsFm3    (SEQ ID NO:54)        KKMLVQITNTGSDLSGN---QFDLLIPGGGVGIFD-GCTR
MdhsFm1    (SEQ ID NO:55)        KKMLVQVTNTGSDLSGN---QFDLLIPGGGVGIFD-GCSR
MdhsFm2    (SEQ ID NO:56)        KKMLVQITNTGSDLSGN---QFDLLIPGGGVGIFD-GCSR
PpCel45A   (SEQ ID NO:57)        KTMIVQLTNTGADLGSN---HFDIALPGGGLGIFTEGCSS
PeCel45A   (SEQ ID NO:58)        KQMIVQTTNTGGDLSSN---HFDIQMPGGGFGIF-DGCTS
AgCelI     (SEQ ID NO:59)        KTMVVQVTNTGGDLGSN---QFDIAIPGGGVGIFTDGCSS
AgCelII    (SEQ ID NO:60)        KQMIVQVTNTGSDLGSN---QFDIAIPGGGVGIFTKGCSS
AaK1       (SEQ ID NO:61)        KSMIVQASNTAYDVTNAN--RFSLAVPGGNTTSTN-ACAQ
PcEg       (SEQ ID NO:62)        KQFLVQITNTGGDLGST---SSIWPFPGGGVGIFTQGCHD
TeCel45A   (SEQ ID NO:63)        KSMIVQVVNSGG-VSTG---DFDIYTPGGGVGDY-NACTS
UmEgl1     (SEQ ID NO:64)        NKLIFQVTNVGGDVQSQ---NFDFQIPGGGLGAFPKGCPA
```

FIGURE 2D

```
HiCel45A  (SEQ ID NO: 7)   138 QFG-GLPGQ--RYGGIS-SRNECDRFPDALKPGCYWRFDW 173
HgEgl3    (SEQ ID NO:16)       QFG-GLPGQ--RYGGIS-SRNECDRFPDALKPGCYWRFDW
HnCel45A  (SEQ ID NO:17)       QVG-GLAGQ--RYGGVS-SRSECDSFPAALKPGCYWRYDW
ScSTCE1   (SEQ ID NO:18)       QFG-GLAGD--RYGGVS-SRSQCDSFPAALKPGCYWRFDW
MaCel45A  (SEQ ID NO:19)       QFG-GLPGA--RYGGIS-SRQECDSFPEPLKPGCQWRFDW
PaCel45A  (SEQ ID NO:20)       QFG-GLPGA--TYGGIS-DRSQCASFPDALKPGCNWRFDW
AtSEQ6    (SEQ ID NO:21)       QFG-GLPGA--QYGGIS-DRSQCSSFPAPLQPGCQWRFDW
TtCel45A  (SEQ ID NO:22)       QFG-GLPGA--QYGGIS-SRDQCDSFPAPLKPGCQWRFDW
TroCel45A (SEQ ID NO:23)       QYGQALPGA--QYGGVS-SRAECDQMPEAIKAGCQWRYDW
AtSEQ2    (SEQ ID NO:24)       QFG-GLPGA--QYGGIS-DRSQCSSFPAPLQPGCQWRFDW
FaCel45A  (SEQ ID NO:25)       QFGKALGGA--QYGGIS-SRSECDSFPETLKDGCHWRFDW
CrCel45A  (SEQ ID NO:26)       QYG-SIPGE--RYGGVT-SRDQCDQMPSALKQGCYWRFDW
NcCel45A  (SEQ ID NO:27)       QFG-GLPGA--QYGGIS-SRSQCDSFPAALKPGCWRFDW
VcSEQ22   (SEQ ID NO:28)       QWGVSFPGN--RYGGTT-SRSQCSQIPSALQPGCNWRYDW
GzCel45A  (SEQ ID NO:29)       EFGKPLGGA--QYGGIS-SRSQCDSFPELLKDGCHWRFDW
FoCel45A  (SEQ ID NO:30)       EFGKALGGA--QYGGIS-SRSECDSYPELLKDGCHWRFDW
AsSEQ10   (SEQ ID NO:31)       QFGQLLPGE--RYGGVS-SRSQCDGMPELLKDGCQWRFDW
AsSEQ8    (SEQ ID NO:32)       QFGFTFPGN--RYGGTT-SRSQCAELPSVLRDGCHWRYDW
ClCel45A  (SEQ ID NO:33)       QYGAPPNGWGDRYGGIH-SKEECESFPEALKPGCNWRFDW
ThSEQ2    (SEQ ID NO:34)       QYGAPPNGWGDRYGGIH-SKEECESFPEALKPGCNWRFDW
McMce1    (SEQ ID NO:35)       QWGAPNDGWGARYGGVS-SVSDCASLPSALQAGCKWRFNW
RshpCel45A(SEQ ID NO:36)       QSGAPADGWGSRYGGVS-SRSECSQLPSGLQAGCQWRFDW
BxEng1    (SEQ ID NO:37)       QWKSPAEGWGQRYGGVS-SKADCATLPTALQPGCNWRFDW
BfCel45A  (SEQ ID NO:38)       EFGAPSSGWGAQYGGVA-AVSSCAAFPEALKPGCSFRFDW
AtSEQ4    (SEQ ID NO:39)       QYGAPPNGWGDRYGGVH-SRSDCDSFPAALKAGCYWRFDW
SbEgI     (SEQ ID NO:40)       QWGSPPNGWGDRYGGVH-TRADCDSFPEALKAGCEWRFDW
SrCBHI    (SEQ ID NO:41)       QWDAPSDGWGQRYGGIS-SASECSQLPKQLQDGCKWRFDW
RoRce1    (SEQ ID NO:42)       QWGAPNDGWGSRYGGIS-SASDCSSLPSALQAGCKWRFNW
CsSEQ16   (SEQ ID NO:43)       QFGSWNGGA--QYGGVS-SRDQCSQLPAAVQAGCQFRFDW
MpSEQ14   (SEQ ID NO:44)       QFGSWNGGA--QYGGVS-SRDQCSQLPAAVQAGCQFRFDW
PaCel45B  (SEQ ID NO:45)       QYGAPPNGWGERYGGVG-SKSACESFPDKLKAGCNWRFDW
RoRce3    (SEQ ID NO:46)       QWGAPNDGWGSRYGGIS-SASDCSSLPSALQAGCKWRFNW
BxEng2    (SEQ ID NO:47)       QWGAPSSGWGAQYGGVS-SRSDCSQLPAKLQPGCDWRFDW
BxEng3    (SEQ ID NO:48)       QWGAPSSGWGSQYGGVS-SRSDCSQLPATLQPGCDWRFDW
HgEgl4    (SEQ ID NO:49)       QYGAPPNGWGQRYGGIS-QRHECDAFPEKLKPGCYWRFDW
PnPce1    (SEQ ID NO:50)       QWNTNTDGWGARYGGIS-SISECDKLPTQLQAGCKWRFGW
RoRce2    (SEQ ID NO:51)       QWGAPTDGWGARYGGVS-SASDCSNLPSALQAGCKWRFGW
MdhsFm4   (SEQ ID NO:52)       QYPG-SYDWGQRYGGVT-SRDGCSKLPSTLQTGCQFRFDY
MgCel45A  (SEQ ID NO:53)       QYGAPANGWGERYGGVR-SRSECDAFPEKLKKGCYWRFDW
MdhsFm3   (SEQ ID NO:54)       QYPG-SYDWGQRYGGVT-SRDGCSKLPSALQSGFQFRFDY
MdhsFm1   (SEQ ID NO:55)       QYPGGNYDWGQRYGGVT-SKAGCAKIPAELKAGCEFRFDY
MdhsFm2   (SEQ ID NO:56)       QYPGGNYDWGQRYGGVT-SKAGCAKIPAELKAGCEFRFDY
PpCel45A  (SEQ ID NO:57)       QFGSGYQ-WGNQYGGIS-SLAECDGLPSELQPGCQFRFGW
PeCel45A  (SEQ ID NO:58)       QFGGSYQ-WGERYGGIS-SASQCANLPPQLKAGCEWRFNW
AgCelI    (SEQ ID NO:59)       QWGTPSNGWGDQYWWVWGSEADCAQLPSDLQEGCKFRFEF
AgCelII   (SEQ ID NO:60)       QWGTPSNGWGDQYGGVS-SESQCSQLPSSLREGCKFRFTF
AaK1      (SEQ ID NO:61)       QYGVSQSVFGENMAGVK-SIDDCQNLPENLRAGCEWRFDW
PcEg      (SEQ ID NO:62)       QWTPRGAAGGDQYGGVY-SVEQCSDLPEVLQPGCRFRFEF
TeCel45A  (SEQ ID NO:63)       QYGAPPQGWGAQYGGVS-SDAECDQLPSILQPGCHWRFEW
UmEgl1    (SEQ ID NO:64)       QWGVEASLWGDQYGGVK-SATECSKLPKPLQEGCKWRFSE
```

FIGURE 2E

```
HiCel45A   (SEQ ID NO: 7)   174  FKNADN-PSFSFRQVQCPAELVARTGCRRNDDGNFPAVQ-  211
HgEgl3     (SEQ ID NO:16)        FKNADN-PSFSFRQVQCPAELVARTGCRRNDDGNFPAVQ-
HnCel45A   (SEQ ID NO:17)        FKNADN-PSFSFRQVQCPAELVARTGCRRNDDGNFPAVQ-
ScSTCE1    (SEQ ID NO:18)        FKNADN-PTFTFRQVQCPSELVARTGCRRNDDGNFPVFT-
MaCel45A   (SEQ ID NO:19)        FQNADN-PSFTFERVQCPEELVARTGCRRHDDGGFAVFK-
PaCel45A   (SEQ ID NO:20)        FKNADN-PSFTFRQVQCPSELTARSGCKRDDDSRFPVFS-
AtSEQ6     (SEQ ID NO:21)        FQNADN-PTFTFQRVQCPSELTSRTGCKRDDDASYPVFN-
TtCel45A   (SEQ ID NO:22)        FQNADN-PTFTFQQVQCPAEIVARSGCKRNDDSSFPVFT-
TroCel45A  (SEQ ID NO:23)        FKNADN-PSFSFRQVQCPAELVARTGCRRNDDGNFPAVQ-
AtSEQ2     (SEQ ID NO:24)        FQNADN-PTFTFQRVQCPSELTSRTGCKRDDDASYPVFN-
FaCel45A   (SEQ ID NO:25)        FKNADN-PSFSFRQVQCPAELVARTGCRRNDDGNFPAVQ-
CrCel45A   (SEQ ID NO:26)        FKNADN-PSFSFRQVQCPAELVARTGCRRNDDGNFPAVQ-
NcCel45A   (SEQ ID NO:27)        FQNADN-PNFTFKQVQCPSELTSRTGCKRNDDSQFPVFT-
VcSEQ22    (SEQ ID NO:28)        FNDADN-PDVSWRRVQCPAALTDRTGCRRSDDGNYPVFQ-
GzCel45A   (SEQ ID NO:29)        FKNADN-PDFTFEQVQCPKELLAISGCKRDDDSSFPAFKG
FoCel45A   (SEQ ID NO:30)        FENADN-PDFTFEQVQCPKALLDISGCKRDDDSSFPAFKG
AsSEQ10    (SEQ ID NO:31)        FKNSDN-PDIEFEQVQCPKELIAVSGCVRDDDSSFPVFQG
AsSEQ8     (SEQ ID NO:32)        FNDADN-PNVNWRRVRCPAALTNRSGCVRNDDNSYPVFE-
ClCel45A   (SEQ ID NO:33)        FQNADN-PSVTFQEVACPSELTSKSGCSR-----------
ThSEQ2     (SEQ ID NO:34)        FQNADN-PSVTFQEVACPSELTSKSGCSR-----------
McMce1     (SEQ ID NO:35)        FKNSDN-PTMTFKEVTCPAELTTRSGCERK----------
RshpCel45A (SEQ ID NO:36)        FQNADN-PSMNFNVVSCPSELIAKTNCRRN----------
BxEng1     (SEQ ID NO:37)        FKNADN-PGMTFKRVKCPAEITAKSGCIRSDDA-------
BfCel45A   (SEQ ID NO:38)        FEGADN-PTVNFKQVNCPAELTKSTGCKRADDSSMPAPDA
AtSEQ4     (SEQ ID NO:39)        FQGADN-PSVSFKQVACPAAITAKSGCTRQNDAINETPTG
SbEgI      (SEQ ID NO:40)        FGGTDN-PDVSFREVECPAELVQKSQCQRS----------
SrCBHI     (SEQ ID NO:41)        FKNADN-PNVSFKQVSCPAELVKKTGCERTS---------
RoRce1     (SEQ ID NO:42)        FKNADN-PSMTYKEVTCPKEITAKTGCSRK----------
CsSEQ16    (SEQ ID NO:43)        MGGADN-PNVTFRPVTCPAQLTNISGCVRK----------
MpSEQ14    (SEQ ID NO:44)        MGGADN-PNVTFRPVTCPAQLTNISGCVRK----------
PaCel45B   (SEQ ID NO:45)        FMGADN-PDVRFRQVACPAAITAKSQCVRQRDVIDQTPTG
RoRce3     (SEQ ID NO:46)        FKNADN-PSMTYKEVTCPKEITAKTGCSRK----------
BxEng2     (SEQ ID NO:47)        FGNSDN-PGVTFKQVTCPKTLTDKSKCIRADD--------
BxEng3     (SEQ ID NO:48)        FGNSDN-PGVTFKQVTCPKTITDKSKCIRADD--------
HgEgl4     (SEQ ID NO:49)        CVSLFP-P-LSLSLPPGTGQTMGRS-CVFFPLSAN-----
PnPce1     (SEQ ID NO:50)        FKNADN-PEVTFKAVTCPAEIIAKTGCERK----------
RoRce2     (SEQ ID NO:51)        FKNADN-PTMTYKQVTCPKAITAKSGCSRK----------
MdhsFm4    (SEQ ID NO:52)        IG--DN-PSVSFKSTHCPDSIVGKTNSRRNDDA-------
MgCel45A   (SEQ ID NO:53)        FKGADN-PSVSFKQVTCPSELTSKSGCVRA----------
MdhsFm3    (SEQ ID NO:54)        IA--DN-PSVSFKSTHCPDTIVSKPTCRRNDDS-------
MdhsFm1    (SEQ ID NO:55)        IG--DN-PSVSFKSVHCPDTITSKTNCRRNDDN-------
MdhsFm2    (SEQ ID NO:56)        IG--DN-PSVSFKSVHCPDTITSKTNCRRNDDQ-------
PpCel45A   (SEQ ID NO:57)        FENADN-PSVEFEQVSCPPEITSITGCARTDE--------
PeCel45A   (SEQ ID NO:58)        FKNADN-PAVVFERVQCPKELTEITGCVPGDDASAKKLPW
AgCelI     (SEQ ID NO:59)        MEGASN-PGVTFEQVDCPSELVSITGCNY-----------
AgCelII    (SEQ ID NO:60)        MKSVSN-PAVTFEQVSCPSEIVSASGCNYS----------
AaK1       (SEQ ID NO:61)        FKNASF-PSANFKRVVCPSEITAKTNCIRNDDK-------
PcEg       (SEQ ID NO:62)        LENVSN-PQVSFQQVQCPAEIVAISNCAL-----------
TeCel45A   (SEQ ID NO:63)        AGGGINGWTTEYEEVDCPSQLTSISGCYP-----------
UmEgl1     (SEQ ID NO:64)        WGDNPV-LKGSPKRVKCPKSLIDRSGCQRKDDNTISPYSG
```

FIGURE 2F

```
HiCel45A    (SEQ ID NO: 7)    212 -------IP
HgEgl3      (SEQ ID NO:16)        -------IP
HnCel45A    (SEQ ID NO:17)        -------IP
ScSTCE1     (SEQ ID NO:18)        -------PP
MaCel45A    (SEQ ID NO:19)        -------AP
PaCel45A    (SEQ ID NO:20)        -------PP
AtSEQ6      (SEQ ID NO:21)        -------PP
TtCel45A    (SEQ ID NO:22)        -------PP
TroCel45A   (SEQ ID NO:23)        -------IP
AtSEQ2      (SEQ ID NO:24)        -------PP
FaCel45A    (SEQ ID NO:25)        -------IP
CrCel45A    (SEQ ID NO:26)        -------IP
NcCel45A    (SEQ ID NO:27)        -------PP
VcSEQ22     (SEQ ID NO:28)        --------P
GzCel45A    (SEQ ID NO:29)        NTTPSNAKP
FoCel45A    (SEQ ID NO:30)        DTSASKPQP
AsSEQ10     (SEQ ID NO:31)        SGSGDVNPP
AsSEQ8      (SEQ ID NO:32)        --------P
ClCel45A    (SEQ ID NO:33)        ---------
ThSEQ2      (SEQ ID NO:34)        ---------
McMce1      (SEQ ID NO:35)        ---------
RshpCel45A  (SEQ ID NO:36)        ---------
BxEng1      (SEQ ID NO:37)        ---------
BfCel45A    (SEQ ID NO:38)        SGSASASPV
AtSEQ4      (SEQ ID NO:39)        PSTVPTYTA
SbEgI       (SEQ ID NO:40)        ---------
SrCBHI      (SEQ ID NO:41)        ---------
RoRce1      (SEQ ID NO:42)        ---------
CsSEQ16     (SEQ ID NO:43)        ---------
MpSEQ14     (SEQ ID NO:44)        ---------
PaCel45B    (SEQ ID NO:45)        PSTVPTWTP
RoRce3      (SEQ ID NO:46)        ---------
BxEng2      (SEQ ID NO:47)        ---------
BxEng3      (SEQ ID NO:48)        ---------
HgEgl4      (SEQ ID NO:49)        ---------
PnPce1      (SEQ ID NO:50)        ---------
RoRce2      (SEQ ID NO:51)        ---------
MdhsFm4     (SEQ ID NO:52)        ---------
MgCel45A    (SEQ ID NO:53)        ---------
MdhsFm3     (SEQ ID NO:54)        ---------
MdhsFm1     (SEQ ID NO:55)        ---------
MdhsFm2     (SEQ ID NO:56)        ---------
PpCel45A    (SEQ ID NO:57)        ---------
PeCel45A    (SEQ ID NO:58)        ---------
AgCelI      (SEQ ID NO:59)        ---------
AgCelII     (SEQ ID NO:60)        ---------
AaK1        (SEQ ID NO:61)        ---------
PcEg        (SEQ ID NO:62)        ---------
TeCel45A    (SEQ ID NO:63)        ---------
UmEgl1      (SEQ ID NO:64)        KVDSANTAA
```

FIGURE 2G

```
TrCel5A  (SEQ ID NO:2)  71  ----------------GVRF-AG--VNIAGFD-FGCTTDGTCVTSKVYPPLKNFTGSNNYPDG 113
PjEgl2   (SEQ ID NO:65)     ----------------TGKVRF-AG--VNIAGFD-FGVVTSG--TQDLSQVVDESVD-----G
MpEgl2   (SEQ ID NO:66)     -APTSTLKAAAASKVKF-AG--VNIAGFD-FGCGTDGTCTQTASTATDPLTD-----SDG
CfEgl1   (SEQ ID NO:67)     -APLAGDSALHRRSLPR-LGG-VNLAGCD-FGIDIYGN---------SG-TPACP-------G
AnEglA   (SEQ ID NO:68)     ----------------AFTW-LG--TNEAGAE-FGEGSYPG------ELGTEYIWP-------D
AkCel5A  (SEQ ID NO:69)     --LPSRQMKKRDSGFKW-VG--TSESGAE-FG-SALPG------TLGTDYTWP-------E
MpEgl1   (SEQ ID NO:70)     ----------------ASNFQF-FG--VNESGPE-FGETKLPG------TKNTDYVWP-------T
VvEG1    (SEQ ID NO:71)     ----------------ATKFRF-FG--VNQAGAE-FGENVIPG------ELGTHYTWP-------S
TaEgl    (SEQ ID NO:72)     ----------------AKVFQW-FG--SNESGAE-FGSQNLPG------VEGKDYIWP-------D
AaCel1   (SEQ ID NO:73)     ----------------ASVFEW-IG--SNESDAE-FG-TAIPG------TWGIDYIFP-------D
HiCMC3   (SEQ ID NO:74)     ----------------KGKFKW-FG--INQSCAE-FGKGEYPG------LWGKHFTFP-------S
OjCelB29 (SEQ ID NO:75) MRNIPSKDLVKELNIGWNLGNALDAHCLDKLDYNKDQL------ASETCWANP-----KAT
AcCel5A  (SEQ ID NO:76)     -AGGGYWHTSGREILDA-NNVPVRIAGINWFGFETCNY------VVHGLWSRD-------Y
BsCel5A  (SEQ ID NO:77)     ----------------AGTKTPVAK-NGQ-LSIKGTQ-LVNRDGKA------VQLKGISSH-------G
BcNK1    (SEQ ID NO:78)     ----------------DDYSVVEE-HGQ-LSISNGE-LVNDRGEP------VQLKGMSSH-------G
```

FIGURE 3A

```
TrCel5A (SEQ ID NO:2) 114 IGQMQHFVNDDGMTIFRLPVGWQYLVNNNLG----------GNLDS-TSISKYDQLVQGCL 163
PjEgl2  (SEQ ID NO:65)    VNQMSHFVNADTFNIFRLPTGWQFIVNNNLG----------GSLDS-NNFGKYEQVGSGLS
MpEgl2  (SEQ ID NO:66)    QGQMDHFVKDDKLNAFRLPVGWQYLVANKLG----------GDLDS-ANAGKYDNLVQGCL
CfEgl1  (SEQ ID NO:67)    TEQVGHFIA-DGANLFRLPAGWQYLVGNNQAS---------TSLAP-DFFAQYDALVQAVI
AnEglA  (SEQ ID NO:68)    LGTIGTLRN-EGMNIFRVAFSMERLVPDSLA----------GPVAD-EYFQDLVETVNGIT
AkCel5A (SEQ ID NO:69)    TSKIQVLRN-KGMNIFRIPFLMERLTPDGLT----------GSFAS-TYLSDLKSTVEFVT
MpEgl1  (SEQ ID NO:70)    LSTIDTFVG-KGMNTFRVNILMERLTHNSLT----------ASLDS-QYLADLKTTVNYIT
VvEGI   (SEQ ID NO:71)    PSSIDYFVN-QGFNTFRVAFKIERLSPPGTG-LT-------GPFDQ-AYLNGLKTIVNYIT
TaEgl   (SEQ ID NO:72)    PNTIDTLIS-KGMNIFRVPFMMERLVPNSMT----------GSPDP-NYLADLIATVNAIT
AaCel1  (SEQ ID NO:73)    TSAIATLVS-KGMNIFRVQFMMERLVPNSMT----------GSYDD-AYLNNLTTVVNAIA
HiCMC3  (SEQ ID NO:74)    TSSIQTHIN-DGFNMFRVAFSMERLAPNQLN----------AAFDA-NYLRNLTETVNFIT
OjCelB29 (SEQ ID NO:75)   PGLFSALKN-QGFNVFRIPTTWTGHFGNGPD----------YKISD-VWMRRVHEVVDYAL
AcCel5A (SEQ ID NO:76)    RSMLDQIKS-LGYNTIRLPYSDDILKPGTMPNSINFYQMNQDLQGLTSLQVMDKIVAYAG
BsCel5A (SEQ ID NO:77)    LQWYGEFVNKDSLKWLRDDWGITVFRAAMYTADG-------GYIDNPSVKNKVKEAVEAAK
BcNK1   (SEQ ID NO:78)    LQWYGQFVNYESMKWLRDDWGITVFRAAMYTSSG-------GYIEDPSVKEKVKEAVEAAI
```

FIGURE 3B

```
TrCel5A (SEQ ID NO:2) 164 SLG-AYCIVDIH--NYARW-NGGIIGQGGPTNAQFTSLWSQLASKYASQ-SRVWFGIMNE 218
PjEgl2  (SEQ ID NO:65)    LSG-AYCIVDIH--NYARW-NGGVIGQGGPTDDQFISLWTQLATHYKSN-SRVIFGIMNE
MpEgl2  (SEQ ID NO:66)    KSGAELCIIDIH--NYALL-ERPDHRQGGPTNDQFVSLWKQLATKYKDN-TKVAFGVMNE
CfEgl1  (SEQ ID NO:67)    SKG-AYAIIDVH--NYARW-NGAIIGQGGPSNQDFANLWTLLATKVTSNDPNVIFGLMNE
AnEglA  (SEQ ID NO:68)    ALG-AYAVLDPH--NYGRY-YGNIIT-----STDDFAAFWTILATEFASN-ELVIFDTNNE
AkCel5A (SEQ ID NO:69)    NSG-AYAVLDPH--NYGRF-DGSIIE-----STSDFKTWWKNVATEFADN-DKVIFDTNNE
MpEgl1  (SEQ ID NO:70)    GKG-AYAMIVPH--NYGRF-NSQIIT-----DTAGFKTWTNVAKEFAGN-SKVIFDINNE
VvEG1   (SEQ ID NO:71)    GKN-AYAVLDPH--NYMRY-NGNVIT-----STSNFQTWWNKLATEFRSN-TRVIFDVMNE
TaEg1   (SEQ ID NO:72)    QKG-AYAVVDPH--NYGRY-YNSIIS-----SPSDFQTFWKTVASQFASN-PLVIFDTNNE
AaCel1  (SEQ ID NO:73)    AAG-VHAIVDPH--NYGRY-NNEIIS-----STADFQTFWQNLAGQFKDN-DLVIFDTNNE
HiCMC3  (SEQ ID NO:74)    GKG-KYAMLDPH--NFGRY-YERIIT-----DKAAFASFFTKLATHFASN-PLVVFDTNNE
OjCelB29 (SEQ ID NO:75)   NTG-SYVILNIHHENWNYAFSNNLQK-----AKPILAAIWKQIAAEFANYDEHLIFEGMNE
AcCel5A (SEQ ID NO:76)    QIG-LRIILDRH--RPDCSGQSALWYTSSVSEATWISDLQALAQRYKGNPTVVGFDLHNE
BsCel5A (SEQ ID NO:77)    ELG-IYVIIDWH--ILNDG-NPNQNK------EKAKEFFKEMSSLYGNT-PNVIYEIANE
BcNK1   (SEQ ID NO:78)    DLG-IYVIIDWH--ILSDN-DPNIYK------EEAKDFFDEMSELYGDY-PNVIYEIANE
```

FIGURE 3C

```
TrCel5A (SEQ ID NO:2)219   PHD----VNIN-TWAATVQEVVTAIRNA-GATSQ-FISLPGND----WQSAGAFI--SDGS 266
PjEgl2  (SEQ ID NO:65)     PHD----LNIA-TWAATVQKTVTAIRNT-GATSQ-MILLPGTD----YTSAANFI--ENGS
MpEgl2  (SEQ ID NO:66)     PHD----VPDINKWADTVQQVTAIRNR-GATTQ-YVLLPGND----WTSAAAFI--DNGS
CfEgl1  (SEQ ID NO:67)     PHD----LDVS-TWAGSVQAAVNAIRAA-GATSQ-YILIPGTG----FTNANAWF--QGQD
AnEglA  (SEQ ID NO:68)     YHT----MDQS-LVLNLNQAAIDAIRAS-GATSQ-YIFAEGNS----WTGAWTWV--DVND
AkCel5A (SEQ ID NO:69)     YHD----MEQS-LVLNLNQAAINGIRAA-GATTQ-YIFVEGNA----YTGAWDWT--TYND
MpEgl1  (SEQ ID NO:70)     FHD----MDQT-LVVNLNQAGIDGIRAA-GATSQ-YITAEGNS----WTGAWTWT--TSEN
VvEG1   (SEQ ID NO:71)     PYQ----IDAS-VVFNLNQAAINGIRAS-GATSQ-LILVEGTA----WTGAWSWE--SSGN
TaEgl   (SEQ ID NO:72)     YHD----MDQT-LVLNLNQAAIDGIRSA-GATSQ-YIFVEGNS----WTGAWTWT--NVND
AaCel1  (SEQ ID NO:73)     YNT----MDQT-LVLDLNQAAIDGIRAA-GATSQ-YIFAEGNS----WSGAWTWA--DIND
HiCMC3  (SEQ ID NO:74)     YHD----MDQQ-LVFDLNQAAIDAIRAA-GATSQ-YIMVEGNS----WTGAWTWN--VTNN
OjCelB29(SEQ ID NO:75)     PRK----VDHPNEWNGGDQKGWDFVNEMNAVFLQ-TVRASGGNNAIRHLMIPTYAACVNNG
AcCel5A (SEQ ID NO:76)     PHDPACWGCGDPSIDWRLAAERAGNAVLSVNPNLLIFVEGVQ---SYNGDSYWWGGNLQG
BsCel5A (SEQ ID NO:77)     PNG----DVN-WKRDIKPYAEEVISVIRKNDPD-NIIIVG------TGTWSQD--VNDA
BcNK1   (SEQ ID NO:78)     PNG----SDVT-WDNQIKPYAEEVIPVIRNNDPN-NIIIVG------TGTWSQD--VHHA
```

FIGURE 3D

```
TrCel5A (SEQ ID NO:2) 267AAALSQVTNPDGSTTNLIFDVHKYLD-----SDNSGTHAECTTNNIDG-AFSPLATWLRQ 320
PjEgl2  (SEQ ID NO:65)    GAALLPVTNPDGSTTNLIFDVHKYLD-----SDNSGTHAECVTNNAD--AFNNLATWLRS
MpEgl2  (SEQ ID NO:66)    AAALKKVTNPDGSTDNLIFDVHKYLD-----SDNSGTHTECVTNNIDD-AFKPLADWLRQ
CfEgl1  (SEQ ID NO:67)    N-ALLGVTDPVGGTDKLLLDVHRYND-----VDFSGTHAECTTNSLD--VLSSLDSWLKG
AnEglA  (SEQ ID NO:68)    N--MKALTDPQD---KLIYEMHQYLD-----SDGSGTNTACVSSTIGSERVTAATNWLRE
AkCel5A (SEQ ID NO:69)    D--LSGLTDSED---KIIYEMHQYLD-----SDSSGTSETCVSSTIGKERIEKATEWLKT
MpEgl1  (SEQ ID NO:70)    N--KLIYQMHQYLD-----SDGSGTNEACVSSTIGKERITAATKWLKD
VvEG1   (SEQ ID NO:71)    GKTMAALKDPQN---KLIYQMHQYLD-----SDGSGTNEACVSSTIGKERITAATKWLKD
TaEgl   (SEQ ID NO:72)    GAVFGAIRDPNN---NTAIEMHQYLD-----SDSSGTSATCVSSTVGVERLRVATDWLRR
AaCel1  (SEQ ID NO:73)    N--MKSLTDPSD---KIIYEMHQYLD-----SDGSGTSATCVSSTIGQERITSATQWLRA
HiCMC3  (SEQ ID NO:74)    N--MKALTDPQD---KLVYEMHQYLD-----SDGSGTSGVCVSETIGAERLQAATQWLKD
OjCelB29(SEQ ID NO:75)    N--LAALRDPEN---KLVYQMHQYLD-----SDGSGTSTACVSTQVGLQRVIGATNWLRQ
AcCel5A (SEQ ID NO:76)    ALESYFKKSPTND-NKVIASVHSYVPYNFALNTGAGAEKTFGSTSDIEWAMNNIKRFLVD
BsCel5A (SEQ ID NO:77)    AGQYPVVLNVPN---RLVYSAHDYATS--VYPQTWFSDPTFPNNMPGIWNKNWGYLFNQ
BcNK1   (SEQ ID NO:78)    A--DDQLKDAN----VMYALHFY--------------AGTHGQFLRDKAN---------YALS
                          A--DNQLTDPN----VMYAFHFY--------------AGTHGQNLRDQVD---------YALD
```

FIGURE 3E

```
TrCel5A (SEQ ID NO:2)   321 NNRQAILTETGGNVQ-SCIQDMCQQIQYLNQNSDVYLLGYVGWGAGSFDSTYVLTETPTG 379
PjEgl2  (SEQ ID NO:65)      NKRQALLSETGGGNVQ-SCATYMCQQLDIINANSDVYLGWTSWSAGGFQASWNYVLTEVP
MpEgl2  (SEQ ID NO:66)      NKRMAINTESGGGNTD-SCEKYFCEQIQYLNQNADVFLGYTAWSAGGFDQTYELVQTPIS
CfEgl1  (SEQ ID NO:67)      NGRKAIVSETGGGHTT-SCETDLGEFLNGIKEDYPSVLGFAVWAAGSFDPSYVLSITPTN
AnEglA  (SEQ ID NO:68)      NGKLGVLGEFAGANNQ-VCKDAVADLLEYLEENSDVWLGALWWAAGPWWGDYMFNMEPTS
AkCel5A (SEQ ID NO:69)      NNKQGIIGEFAGGVNS-VCEEAVEGMLAYMSENSDVWVGASWWSAGPWWGTYMYSLEPTD
MpEgl1  (SEQ ID NO:70)      NGKKGLIGEFAGGNNS-QCKTAVEGMLTYMQENKDVWTGALWWAAGPWWASYMFSMEPKT
VvEG1   (SEQ ID NO:71)      NNLKGFLGEMGAGSND-VCIAAVKGALCAMQQ-SGVWIGYLWWAAGPWWGTYFQSIEPPN
TaEg1   (SEQ ID NO:72)      NGKKGIIGEFAGGAND-VCETAITGMLDYMAQNTDVWTGAIWWAAGPWWGDYIFSMEPDN
AaCel1  (SEQ ID NO:73)      NGKVDILGEYAGGAND-VCRTAIAGMLEYMANNTDVWKGAVWTAGPMWADYMFSMEPPS
HiCMC3  (SEQ ID NO:74)      NGKVGLLGEFAGGANS-VCQQAIEGMLTHLQENSDVWTGALWWAGGPWWGDYIYSFEPPS
OjCelB29 (SEQ ID NO:75)     RNIPVIIGEFGAMNRD-NESERARWAEYYIKSATAMGVPCVLWDNGYTQGTGELFGVIDR
AcCel5A (SEQ ID NO:76)      NIAPVWLGEFGTTLQSTTDQTWLKTLVQYLRPTAQYGADSFQWTFWSWNPD-SGDTGGIL
BsCel5A (SEQ ID NO:77)      KGAPVFVTEWGTSDASGNGGVFLDQSREWLNYLDSKTISWVNWNLSDKQESSSALKPGAS
BcNK1   (SEQ ID NO:78)      QGAAIFVSEWGTSEATGDGGVFLDEAQVWIDFMDERNLSWANWSLTHKDESSAALMPGAS
```

FIGURE 3F

```
TrCel5A  (SEQ ID NO:2)    380  SGNSWTDTSLVSS----CLARK-------------  397
PjEgl2   (SEQ ID NO:65)        VNG--VDQYLVQQ----CFVPKWKN----------
MpEgl2   (SEQ ID NO:66)        SPMARTKILHSRRSALLVLGRMLEGRHEFMY----
CfEgl1   (SEQ ID NO:67)        GVDNQLFDIAVKP----NLP---------------
AnEg1A   (SEQ ID NO:68)        GIAYQEYSEILQP----YFVGSQ------------
AkCel5A  (SEQ ID NO:69)        GTAYSTYLPILEK----YF----------------
MpEgl1   (SEQ ID NO:70)        GTAYTAYLDLISK----FK----------------
VvEG1    (SEQ ID NO:71)        GASIARILPEALKP----FV---------------
TaEg1    (SEQ ID NO:72)        GIAYQQILPILTP----YL----------------
AaCel1   (SEQ ID NO:73)        GPAYSGMLDVLEP----YLG---------------
HiCMC3   (SEQ ID NO:74)        GIGYTYNSLLKK----YVP----------------
OjCelB29 (SEQ ID NO:75)        NFYRIIFQQFING----LMKGLGGKKT--------
AcCel5A  (SEQ ID NO:76)        KDDWQTVDTVKDG----YLAPIKSSIFDPV-----
BsCel5A  (SEQ ID NO:77)        KTGGWRLSDLSASG--TFVRENILGTKDSTKDIPE
BcNK1    (SEQ ID NO:78)        PTGGWTEAELSPSG--TFVREKIRE----------
```

FIGURE 3G

```
SEQ ID NO:3    83  SGTATYSGNPFVG--------VTPWANAYYASEVSSLAIP  114
SEQ ID NO:79       ---ATYSGNPFVG--------VTPWANAYYASEVSSLAIP
SEQ ID NO:80       ---ATYSGNPFVG--------VTPWANAYYASEVSSLAIP
SEQ ID NO:81       ---ATYSGNPFVG--------VTPWANAYYASEVSSLAIP
SEQ ID NO:82       ---ATYSGNPFVG--------VTPWANAYYASEVSSLAIP
SEQ ID NO:83       ---ATYSGNPFVG--------VTPWANAYYASEVSSLAIP
SEQ ID NO:84       ---ATASGNPFSG--------YQLYVNPYYSSEVQSIAIP
SEQ ID NO:85       ---ASASGNPFSG--------YQLYVNPYYSSEVASLAIP
SEQ ID NO:86       ---ATAGGNPFEG--------YDLYVNPYYKSEVESLAIP
SEQ ID NO:87       ---ASATGNPFEG--------YQLYANPYYKSQVESSAIP
SEQ ID NO:88       ---AAASGNPFSG--------YQLYANPYYSSEVHTLAIP
SEQ ID NO:89       ---ASASGNPFEG--------YQLYANPYYASEVISLAIP
SEQ ID NO:90       ---PVATNNPFSG--------VDLWANNYYRSEVSTLAIP
SEQ ID NO:91       ---PAASDNPYAG--------VDLWANNYYRSEVMNLAVP
SEQ ID NO:92       ---ASFTGNPFLG--------VQGWANSYYSSEIYNHAIP
SEQ ID NO:93       ---VQATGNPFEG--------YQLYANPYYSSEVMTLAVP
SEQ ID NO:94       ---ASATGNPFEG--------YQLYVNPYYKSQVESSAIP
SEQ ID NO:95       ---ASFTGNPFAG--------VNLFPNKFYSSEVHTLAIP
SEQ ID NO:96       ---ASYNGNPFSG--------VQLWANTYYSSEVHTLAIP
SEQ ID NO:97       ---ASYNGNPFSG--------VQLWANTYYSSEVHTLAIP
SEQ ID NO:98       ---ATYTGNPFLG--------VNQWANNFYRSEIMNIAVP
SEQ ID NO:99       ---ASYNGNPFEG--------VQLWANNYYRSEVHTLAIP
SEQ ID NO:100      ------GNPFEG--------VQLWANNYYRSEVHTLAIP
SEQ ID NO:101      ---AAPSGNPFAG--------KNFYANPYYSSEVHTLAMP
SEQ ID NO:102      ------AGNPYTG--------KTVWLSPFYADEVAQAAAD
SEQ ID NO:103      ---TPAAGNPFVG--------VTPFLSPYYAAEVAAAADA
SEQ ID NO:104      ---TPAAGNPFTG--------YEIYLSPYYANEIAAAVTQ
SEQ ID NO:105      ---TPAAGNPFT---------EQIYLSPYYANEIAAAVTQ
SEQ ID NO:106      ---QANSSNPFAG--------HTIYPNPYYSNEIDEFAIP
SEQ ID NO:107      ---PPSANNPWTG--------FQIFLSPYYANEVAAAAKQ
SEQ ID NO:108      ---VPAAGNPYTG--------YEIYLSPYYAAEAQAAAAQ
SEQ ID NO:109      ---LDASTNVFQQ--------YTLHPNNFYRAEVEAAAEA
SEQ ID NO:110      ---TPDAGNPYIGYDVSHVLWCQIYLSPYYADEVAAAVSA
SEQ ID NO:111      ---TPAAGNPFTG--------FQVYLSPYYSAEIASAAAA
SEQ ID NO:112      ---LDASTNVWKK--------YTLHANKFYRTEVEAAVAA
SEQ ID NO:113      ---LDASTNVFSK--------YTLHPNSFYRAEVEAAAEA
```

Figure 9A

```
SEQ ID NO:3     115 SLTG---AMATAAAAVAKVPSFMWLDTLDKTP-LMEQTLA 150
SEQ ID NO:79        SLTG---AMATAAAAVAKVPSFMWLDTLDKTP-LMEQTLA
SEQ ID NO:80        SLTG---AMATAAAAVAKVPSFMWLDTLDKTP-LMEQTLA
SEQ ID NO:81        SLTG---AMATAAAAVAKVPSFMWLDTFDKTP-LMEQTLA
SEQ ID NO:82        SLTG---AMATAAAAVAKVPSSMWLDTFDKTP-LMEQTLA
SEQ ID NO:83        SLTG---AMATAAAAVAKVPSFMWLDTLDKTP-LMEQTLA
SEQ ID NO:84        SLTGTLSSLAPAATAAAKVPSFVWLDVAAKVP-TMATYLA
SEQ ID NO:85        SLTGSLSSLQAAATAAAKVPSFVWLDTAAKVP-TMGDYLA
SEQ ID NO:86        SMTG---SLAEKASAAANVPSFHWLDTTDKVP-QMGEFLE
SEQ ID NO:87        SLSAS--SLVAQASAAADVPSFYWLDTADKVP-TMGEYLE
SEQ ID NO:88        SLTG---SLAAAATKAAEIPSFVWLDTAAKVP-TMGTYLA
SEQ ID NO:89        SLSS---ELVPKASEVAKVPSFVWLDQAAKVP-SMGDYLK
SEQ ID NO:90        KLS---GAMATAAAKVADVPSFQWMDT-YDHISFMEDSLA
SEQ ID NO:91        KLS---GAKATAAAKVADVPSFQWMDT-YDHISLMEDTLA
SEQ ID NO:92        SMT---GSLAAQASAVAKVPTFQWLDRNVTVDTLMKSTLE
SEQ ID NO:93        SMTG---SLAEQATHAAEIPSFHWLDTTAKVP-TMGEYLA
SEQ ID NO:94        SLSAS--SLVAQASAAADVPSFYWLDTADKVP-TMGEYLD
SEQ ID NO:95        SLTG---SLVAKASAVAQVPSFQWLDIAAKVETLMPGALA
SEQ ID NO:96        SLS---PELAAKAAKVAEVPSFQWLDRNVTVDTLFSGTLA
SEQ ID NO:97        SLS---PELAAKAAKVAEVPSFQWLDRNVTVDTLFSGTLA
SEQ ID NO:98        SLS---GAMATAAAKVADVPTFQWIDK-MDKLPLIDEALA
SEQ ID NO:99        QITD--PALRAAASAVAEVPSFQWLDRNVTVDTLLVETLS
SEQ ID NO:100       QITD--PALRAAASAVAEVPSFQWLDRNVTVDTLLVQTLS
SEQ ID NO:101       SLPA---SLKPAATAVAKVGSFVWMDTMAKVP-LMDTYLA
SEQ ID NO:102       ISNP---SLATKAASVAKIPTFVWFDTVAKVP-DLGGYLA
SEQ ID NO:103       ITDS---TLKAKAASVAKIPTFTWLDSVAKVP-DLGTYLA
SEQ ID NO:104       ISDP---TTAAAAAKVANIPTFIWLDQVAKVP-DLGTYLA
SEQ ID NO:105       ISDP---TTAAAAAKVANIPTFIWLDQVAKVP-DLGTYLA
SEQ ID NO:106       ALQETDPALVEKAALVKEVGTFFWIDVVAKVP-DIGPYLQ
SEQ ID NO:107       ITDP---TLSSKAASVANIPTFTWLDSVAKIP-DLGTYLA
SEQ ID NO:108       ISDA---TQKAKALKVAQIPTFTWFDVIAKTS-TLGDYLA
SEQ ID NO:109       ISDS---ALAEKARKVADVGTFLWLDTIENIG-RLEPALE
SEQ ID NO:110       ISNP---ALAAKAASVANIPTFIWFDVVAKVP-TLGTYLA
SEQ ID NO:111       VTDS---SLKAKAASVANIPTFTWLDSVAKVP-DLGTYLA
SEQ ID NO:112       ISDS---SLAAKAAKVANVGSFLWLDSIENIG-KLEPALE
SEQ ID NO:113       ISDS---TLKAQALKVADVGSFLWIDTISAIS-RIEPGVS
```

Figure 9B

```
SEQ ID NO:3     151 DIRTANKNGGN--YAGQFVVYDLPDRDCAALASNGEYSIA
SEQ ID NO:79        DIRTANKNGGN--YAGQFVVYDLPDRDCAALASNGEYSIA
SEQ ID NO:80        DIRTANKNGGN--YAGQFVVYDLPDRDCAALASNGEYSIA
SEQ ID NO:81        DIRTANKNGGN--YAGQFVVYDLPDRDCAALASNGEYSIA
SEQ ID NO:82        DIRTANKNGGN--YAGQFVVYDLPDRDCAALASNGEYSIA
SEQ ID NO:83        DIRTANKNGGN--YAGQFVVYDLPDRDCAALASNGEYSIA
SEQ ID NO:84        DIRSQNAAGANPPIAGQFVVYDLPDRDCAALASNGEFAIS
SEQ ID NO:85        DIQSQNAAGANPPIAGQFVVYDLPDRDCAALASNGEYSIA
SEQ ID NO:86        DIKTKNAAGANPPTAGIFVVYDLPDRDCAALASNGEFLIS
SEQ ID NO:87        DIQTQNAAGASPPIAGIFVVYDLPDRDCSALASNGEYSIS
SEQ ID NO:88        NIEAANKAGASPPIAGIFVVYDLPDRDCAAAASNGEYTVA
SEQ ID NO:89        DIQSQNAAGADPPIAGIFVVYDLPDRDCAAAASNGEFSIA
SEQ ID NO:90        DIRKANKAGGN--YAGQFVVYDLPDRDCAAAASNGEYSLD
SEQ ID NO:91        DIRKANKAGGK--YAGQFVVYDLPNRDCAAAASNGEYSLD
SEQ ID NO:92        EIRAANKAGANPPYAAHFVVYDLPDRDCAAAASNGEFSIA
SEQ ID NO:93        DIKEQNDAGANPPIAGIFVVYNLPDRDCAALASNGELSIA
SEQ ID NO:94        DIQTQNAAGANPPIAGIFVVYDLPDRDCAALASNGEYAIS
SEQ ID NO:95        DVRAANAAGGN--YAAQLVVYDLPDRDCAAAASNGEFSIA
SEQ ID NO:96        EIRAANQRGANPPYAGIFVVYDLPDRDCAAAASNGEWSIA
SEQ ID NO:97        EIRAANQRGANPPYAGIFVVYDLPDRDCAAAASNGEWSIA
SEQ ID NO:98        DVRAANARGGN--YASILVVYNLPDRDCAAAASNGEFAIA
SEQ ID NO:99        EIRAANQAGANPPYAAQIVVYDLPDRDCAAAASNGEWAIA
SEQ ID NO:100       EIREANQAGANPQYAAQIVVYDLPDRDCAAAASNGEWAIA
SEQ ID NO:101       DIKAKNAAGAN--LMGTFVVYDLPDRDCAALASNGELKID
SEQ ID NO:102       DAR------SKN-QLVQIVVYDLPDRDCAALASNGEFSLA
SEQ ID NO:103       DASALQKSSGQP-QVVQIVVYDLPDRDCAAKASNGEFSIA
SEQ ID NO:104       DASAKQKSEGKN-YLVQIVVYDLPDRDCAALASNGEFTIA
SEQ ID NO:105       DASAKQKSEGKN-YLVQIVVYDLPDRDCAALASNGEFTIA
SEQ ID NO:106       GIQEANAAGQNPPYIGAIVVYDLPNRDCAAAASNGEFSLE
SEQ ID NO:107       SASALGKSTGTK-QLVQIVIYDLPDRDCAAKASNGEFSIA
SEQ ID NO:108       EASALGKSSGKK-YLVQIVVYDLPDRDCAALASNGEFSIA
SEQ ID NO:109       DVPCENIVG-------LVIYDLPGRDCAAKASNGELKVG
SEQ ID NO:110       DALSIQQSTGRN-QLVQIVVYDLPDRDCAALASNGEFSIA
SEQ ID NO:111       DASSIQTKTGQK-QLVPIVVYELPDRDCAAKASNGEFSIA
SEQ ID NO:112       DVPCDHILG-------LVIYDLPGRDCAAKASNGELAVG
SEQ ID NO:113       DQPCDHILG-------LVIYDLPGRDCAAKASNGELKVG
```

Figure 9C

```
SEQ ID NO:3    189 DGGVAKYK-NYIDTIRQIVV-----------------EY 209
SEQ ID NO:79       DGGVAKYK-NYIDTIRQIVV-----------------EY
SEQ ID NO:80       DGGVAKYK-NYIDTIRQIVV-----------------EY
SEQ ID NO:81       DGGVDKYK-NYIDTIRQIVV-----------------EY
SEQ ID NO:82       DGGVDKYK-NYIDTIRQIVV-----------------EY
SEQ ID NO:83       DGGVAKYK-NYIDTIRQIVV-----------------EY
SEQ ID NO:84       DGGVQHYK-DYIDSIREILV-----------------EY
SEQ ID NO:85       DNGVEHYK-SYIDSIREILV-----------------QY
SEQ ID NO:86       DGGVEKYK-AYIDSIREQVE-----------------KY
SEQ ID NO:87       DGGVEKYK-AYIDSIREQVE-----------------TY
SEQ ID NO:88       NNGVANYK-AYIDSIVAQLK-----------------AY
SEQ ID NO:89       NNGVALYK-QYIDSIREQLT-----------------TY
SEQ ID NO:90       KDGKNKYK-AYIAD-QGILQ-----------------DY
SEQ ID NO:91       KDGANKYK-AYIAKIKGILQ-----------------NY
SEQ ID NO:92       NGGVANYK-TYINAIRKLLI-----------------EY
SEQ ID NO:93       DGGVEKYK-EYIDAIRAHAV-----------------EY
SEQ ID NO:94       DGGVEKYK-AYIDSIREQVE-----------------TY
SEQ ID NO:95       DGGVVKYK-AYIDAIRKQLL-----------------AY
SEQ ID NO:96       NNGANNYK-RYIDRIRELLI-----------------QY
SEQ ID NO:97       NNGANNLQ-RYIDRIRELLI-----------------QY
SEQ ID NO:98       DGGVAKYK-NYIDEIRKLVI-----------------KY
SEQ ID NO:99       NNGANNYK-GYINRIREILI-----------------SF
SEQ ID NO:100      NNGVNNYK-AYINRIREILI-----------------SF
SEQ ID NO:101      EGGVEKYKTQYIDKIAAIIK-----------------KY
SEQ ID NO:102      NDGLNKYK-NYVDQIAAQIK-----------------QF
SEQ ID NO:103      DGGQAKYY-DYIDQIVAQIK-----------------KF
SEQ ID NO:104      DNGEANYH-DYIDQIVAQIK-----------------QY
SEQ ID NO:105      DNGEANYH-DYIDQIVAQIK-----------------QY
SEQ ID NO:106      DGGEEKYR-GYIDGIREQIE-----------------KY
SEQ ID NO:107      NNGQANYE-NYIDQIVAQIQ-----------------QF
SEQ ID NO:108      NNGLNNYK-GYIDQLVAQIK-----------------KY
SEQ ID NO:109      --ELDRYKTEYIDKIAEILK-----------------AH
SEQ ID NO:110      NNGLANYK-NYVDQIVAQIARTCCPLVTSAITDLACLSEY
SEQ ID NO:111      DAGAENYK-DYIDQIVPQIK-----------------QF
SEQ ID NO:112      --ELSRYKTEYIDAIVKILK-----------------AH
SEQ ID NO:113      --ELAKYKSQYIDPIAALLK-----------------KY
```

Figure 9D

| | | |
|---|---|---|
| SEQ ID NO:3 | 210 | SDIRTLLVIEPDSLANLVTNLGTPKCANAQSAYLECINYA 249 |
| SEQ ID NO:79 | | SDIRTLLVIEPDSLANLVTNLGTPKCANAQSAYLECINYA |
| SEQ ID NO:80 | | SDIRTLLVIEPDSLANLVTNLGTPKCANAPSAYLECINYA |
| SEQ ID NO:81 | | SDIRTLLVIEPDSLANLVTNLGTPKCANAQSAYLECINYA |
| SEQ ID NO:82 | | SDIRTLLVIEPDSLANLVTNLGTPKCANAQSAYLECINYA |
| SEQ ID NO:83 | | SDIRTILVIEPDSLANLVTNLGTPKCANAQSAYLECINYA |
| SEQ ID NO:84 | | SDVHVILVIEPDSLANLVTNLNVAKCANAQSAYLECTNYA |
| SEQ ID NO:85 | | SDVHTLLVIEPDSLANLVTNLNVAKCANAESAYLECTNYA |
| SEQ ID NO:86 | | SDTQIILVIEPDSLANLVTNLNVQKCANAQDAYLECTNYA |
| SEQ ID NO:87 | | SDVQTILIIEPDSLANLVTNLDVAKCANAESAYLECTNYA |
| SEQ ID NO:88 | | PDVHTILIIEPDSLANMVTNLSTAKCAEAQSAYYECVNYA |
| SEQ ID NO:89 | | SDVHTILVIEPDSLANVVTNLNVPKCANAQDAYLECINYA |
| SEQ ID NO:90 | | SDTRIILVIEPDSLANMVTNMNVPKCANAASAYKELTIHA |
| SEQ ID NO:91 | | SDTKVILVIEPDSLANLVTNLNVDKCAKAESAYKELTVYA |
| SEQ ID NO:92 | | SDIRTILVIEPDSLANLVTNTNVAKCANAASAYRECTNYA |
| SEQ ID NO:93 | | SDTNIILIIEPDSLANLVTNLNVEKCANAQDAYLECTNYA |
| SEQ ID NO:94 | | SDVQTILIIEPDSLANLVTNLDVAKCANAQSAYLECTNYA |
| SEQ ID NO:95 | | SDVRTILVIEPDSLANMVTNMGVPKCAGAKDAYLECTIYA |
| SEQ ID NO:96 | | SDIRTILVIEPDSLANMVTNMNVQKCSNAASTYKELTVYA |
| SEQ ID NO:97 | | SDIRTILVIEPDSLANMVTNMNVQKCSNAASTYKELTVYA |
| SEQ ID NO:98 | | NDLRIILVIEPDSLANMVTNMNVAKCQNAASAYRECTNYA |
| SEQ ID NO:99 | | SDVRTILVIEPDSLANMVTNMNVAKCSGAASTYRELTIYA |
| SEQ ID NO:100 | | SDVRTILVIEPDSLANMVTNMNVPKCSGAASTYRELTIYA |
| SEQ ID NO:101 | | PDVKINLAIEPDSLANMVTNMGVQKCSRAAPYYKELTAYA |
| SEQ ID NO:102 | | PDVSVVAVIEPDSLANLVTNLNVQKCANAQSAYKEGVIYA |
| SEQ ID NO:103 | | PDVRVIAVIEPDSLANLVTNLNVQKCANAQTTYKACVTYA |
| SEQ ID NO:104 | | PDVHVVAVIEPDSLANLVTNLSVAKCANAQTTYLECVTYA |
| SEQ ID NO:105 | | PDVHVVAVIEPDSLANLVTNLSVAKCANAQTTYLECVTYA |
| SEQ ID NO:106 | | PDVRVALVIEPDSLANMVTNLNVPKCAESEQAYRDGVAYA |
| SEQ ID NO:107 | | PDVRVVAVIEPDSLANLVTNLNVQKCANAKTTYLACVNYA |
| SEQ ID NO:108 | | PDVRVVAVIEPDSLANLVTNLNVSKCANAQTAYKAGVTYA |
| SEQ ID NO:109 | | SNTAFALVIEPDSLPNLVTNSDLQTCQQSASGYREGVAYA |
| SEQ ID NO:110 | | PQIRVVAVVEPDSLANMVTNLNVPKCAGAQAAYTEGVTYA |
| SEQ ID NO:111 | | PDVRVVAVIEPDSLANLVTNLNVQKCANGG-TYKASVTYA |
| SEQ ID NO:112 | | PKTAFALVIEPDSLPNLVTNSDLQTCKDSASGYRDGVAYA |
| SEQ ID NO:113 | | NNHAFALLIEPDSLPNLVTNSDLSACQQSAAGYRDGVAYA |

Figure 9E

```
SEQ ID NO:3     250 VTQLNLPNVAMYLDAGHAGWLGWPANQDPAAQLFANVYKN 289
SEQ ID NO:79        VTQLNLPNVAMYLDAGHAGWLGWPANQDPAAQLFANVYKN
SEQ ID NO:80        VTQLNLPNVAMYLDAGHAGWLGWPANQDPAAQLFANVYKN
SEQ ID NO:81        VTQLNLPNVAMYLDAGHAGWLGWPANQDPAAQLFANVYKN
SEQ ID NO:82        VTQLNLPNVAMYLDAGHAGWLGWPANQDPAAQLFANVYKN
SEQ ID NO:83        ITQLNLPNIAMYLDAGHAGWLGWPANQDPAAQLFANVYKN
SEQ ID NO:84        VTQLNLPNVAMYLDAGHAGWLGWPANLQPAANLYAGVYSD
SEQ ID NO:85        LTQLNLPNVAMYLDAGHAGWLGWPANQQPAADLFASVYKN
SEQ ID NO:86        LTQLNLPNVAMYLDAGHAGWLGWPANIGPAAELYASVYKN
SEQ ID NO:87        LEQLNLPNVAMYLDAGHAGWLGWPANIGPAAQLYASVYKN
SEQ ID NO:88        LINLNLANVAMYIDAGHAGWLGWSANLSPAAQLFATVYKN
SEQ ID NO:89        ITQLDLPNVAMYLDAGHAGWLGWQANLAPAAQLFASVYKN
SEQ ID NO:90        LKELNLPNVSMYIDAGHGGWLGWPANLPPAAQLYGQLYKD
SEQ ID NO:91        IKELNLPNVSMYLDAGHGGWLGWPANIGPAAKLYAQIYKD
SEQ ID NO:92        ITQLDLPHVAQYLDAGHGGWLGWPANIQPAATLFADIYKA
SEQ ID NO:93        ITQLDLPNVSMYLDAGHAGWLGWPANIGPAAQLFAGVYQD
SEQ ID NO:94        LEQLNLPNVAMYLDAGHAGWLGWPANIGPAAELYASVYKN
SEQ ID NO:95        VKQLNLPHVAMYLDGGHAGWLGWPANLQPAADLFGKLYAD
SEQ ID NO:96        LKQLNLPHVAMYMDAGHAGWLGWPANIQPAAELFAQIYRD
SEQ ID NO:97        LKQLNLPHVAMYMDAGHAGWLGWPANIQPAAELFAQIYRD
SEQ ID NO:98        LTNLDLPNVAQYMDAGHAGWLGWPANITPAAQLFAEVYKQ
SEQ ID NO:99        LKQLDLPHVAMYMDAGHAGWLGWPANIQPAAELFAKIYED
SEQ ID NO:100       LKQLDLPHVAMYMDAGHAGWLGWPANIQPAAELFAKIYED
SEQ ID NO:101       LKTLNFNNVDMYMDGGHAGWLGWDANIGPTAKLFAEVYKA
SEQ ID NO:102       VQKLNAVGVTMYIDAGHAGWLGWPANLSPAAQLFAQIYRD
SEQ ID NO:103       LNQLASVGVYQYMDAGHAGWLGWPANIQPAAQLFADMFKS
SEQ ID NO:104       MQQLSAVGVTMYLDAGHAGWLGWPANLSPAAQLFTSLYSN
SEQ ID NO:105       MQQLSAVGVTMYLDAGHAGWLGWPANLSPAAQLFTSLYSN
SEQ ID NO:106       LKQLDLPNVWTYIDAGHSGWLGWPANIEPAAEIFVEVWNA
SEQ ID NO:107       LTNLAKVGVYMYMDAGHAGWLGWPANLSPAAQLFTQVWQN
SEQ ID NO:108       LQQLNSVGVYMYLDAGHAGWLGWPANLNPAAQLFSQLYRD
SEQ ID NO:109       LKQLNLPNVVMYIDAGHGGWLGWDANLKPGAQELASVYKS
SEQ ID NO:110       LQKLNTVGVYSYVDAGHAGWLGWPANLGPAAQLFANLYTN
SEQ ID NO:111       LQQLSSVGVTMYMDAGHAGWLGWPANIQPGSEVFAEMFKS
SEQ ID NO:112       LRNLNLPNVVMYIDAGHGGWLGWDANLKPGAQELAKAYKA
SEQ ID NO:113       LKTLNLPNVVMYIDAGHGGWLGWNDNLKPGAEELAKAYKA
```

Figure 9F

| | | |
|---|---|---|
| SEQ ID NO:3 | 290 | ASSPRALRGLATNVANYNGWNIT----SPPSYTQGNAVYN 325 |
| SEQ ID NO:79 | | ASSPRALRGLATNVANYNGWNIT----SPPSYTQGNAVYN |
| SEQ ID NO:80 | | ASSPRALRGLATNVANYNGWNIT----SPPSYTQGNAVYN |
| SEQ ID NO:81 | | ASSPRALRGLATNVANYNGWNIT----SPPSYTQGNAVYN |
| SEQ ID NO:82 | | ASSPRALRGLATNVANYNGWNIT----SPPSYTQGNAVYN |
| SEQ ID NO:83 | | ASSPSALRGLATNVANYNGWNIT----SPPSYTQGNAVYN |
| SEQ ID NO:84 | | AGSPAALRGLATNVANYNAWAID----TCPSYTQGNSVCD |
| SEQ ID NO:85 | | ASSPAAVRGLATNVANYNAWTIS----SCPSYTQGNSVCD |
| SEQ ID NO:86 | | ASSPAAVRGLATNVANYNAFSID----SCPSYTQGSTVCD |
| SEQ ID NO:87 | | ASSPAAVRGLATNVANFNAWSID----SCPSYTSGNDVCD |
| SEQ ID NO:88 | | ASAPASLRGLATNVANYNAWSIS----SPPSYTSGDSNYD |
| SEQ ID NO:89 | | ASSPASVRGLATNVANYNAWSIS----RCPSYTQGDANCD |
| SEQ ID NO:90 | | AGKPSRLRGLVTNVSNYNAWKLS----SKPDYTESNPNYD |
| SEQ ID NO:91 | | AGKPSRVRGLVTNVSNYNGWKLS----TKPDYTESNPNYD |
| SEQ ID NO:92 | | AGKPKSVRGLVTNVSNYNGWSLS----SAPSYTTPNPNYD |
| SEQ ID NO:93 | | AGAPAALRGLATNVANYNAFSID----TCPSYTSQNAVCD |
| SEQ ID NO:94 | | ASSPAAVRGLATBVANFNAWSID----TCPSYTSGNDVCD |
| SEQ ID NO:95 | | AGKPSQLRGMATNVANYNAWDLT----TAPSYTTPNPNFD |
| SEQ ID NO:96 | | AGRPAAVRGLATNVANYNAWSIA----SPPSYTSPNPNYD |
| SEQ ID NO:97 | | AGRPAAVRGLATNVANYNAWSIA----SPPSYTSPNPNYD |
| SEQ ID NO:98 | | AGSPKSVRGLAINVSNYNAWSVS----SPPPYTSPNPNYD |
| SEQ ID NO:99 | | AGKPRAVRGLATNVANYNAWSIS----SPPPYTSPNPNYD |
| SEQ ID NO:100 | | AGKPRAVRGLATNVANYNAWSVS----SPPPYTSPNPNYD |
| SEQ ID NO:101 | | AGSPRGVRGIVTNVSNYNALRVS----SCPSITQGNKNCD |
| SEQ ID NO:102 | | AGSPRNLRGIATNVANFNALRAS----SPDPITQGNSNYD |
| SEQ ID NO:103 | | ANSSKFVRGLATNVANYNALSAA----SPDPITQGDPNYD |
| SEQ ID NO:104 | | AGSPSGVRGLATNVANYNALVAT----TPDPITQGDPNYD |
| SEQ ID NO:105 | | AGSPSGVRGLATNVANYNALVAT----TPDPITQGDPNYD |
| SEQ ID NO:106 | | AGRPKSTRGFATNVSNYNGYSLS----TAPPYTEPNPNFD |
| SEQ ID NO:107 | | AGKSPFIKGLATNVANYNALQAA----SPDPITQGNPNYD |
| SEQ ID NO:108 | | AGSPQYVRGLATNVANYNALSAS----SPDPVTQGNPNYD |
| SEQ ID NO:109 | | AGSPSQVRGISTNVAGWNAWDQEPGEFSDASDAQYNKCQN |
| SEQ ID NO:110 | | AGSPSFFRGLATNVANYNLLNAP----SPDPVTSPNANYD |
| SEQ ID NO:111 | | ADFVAFVRAFATNVREYNALTAA----FPRPITQGNPNYD |
| SEQ ID NO:112 | | AGSPKQVRGIATNVAGWNQWDLTPGEFSKASDAKYNKCQN |
| *SEQ ID NO:113* | | AGSPKQFRGFATNVAGWNAWDLTPGEFSSASDAQWNKCQN |

Figure 9G

```
SEQ ID NO:3    326 EKLYIH----------------AIGPLLANHGWSNAFFI 348
SEQ ID NO:79       EKLYIH----------------AIGRLLANHGWSNAFFI
SEQ ID NO:80       EKLYIH----------------AIGPLLANHGWSNAFFI
SEQ ID NO:81       EQLYIH----------------AIGPLLANHGWSNAFFI
SEQ ID NO:82       EQLYIH----------------AIGPLLANHGWSNAFFI
SEQ ID NO:83       EKLYIH----------------AIGPLLANHGWSNAFFI
SEQ ID NO:84       EKDYIN----------------ALAPLLRAQGFD-AHFI
SEQ ID NO:85       EQQYIN----------------AIAPLLQAQGFD-AHFI
SEQ ID NO:86       EKTYIN----------------NFAPQLKSAGFD-AHFI
SEQ ID NO:87       EKSYIN----------------AIAPELSSAGFD-AHFI
SEQ ID NO:88       EKLYIN----------------ALSPLLTSNGWPNAHFI
SEQ ID NO:89       EEDYVN----------------ALGPLFQEQGFP-AYFI
SEQ ID NO:90       EQKYIH----------------ALSPLLEQEGWPGAKFI
SEQ ID NO:91       EQRYIN----------------AFAPLLAQEGWSNVKFI
SEQ ID NO:92       EKKYIE----------------AFSPLLNAAGFP-AQFI
SEQ ID NO:93       EKGYIN----------------SFAPELSAAGWD-AHFI
SEQ ID NO:94       EKSYIN----------------AFAPELSXAGFD-AHFI
SEQ ID NO:95       EKKYIS----------------AFAPLLAAKGWS-AHFI
SEQ ID NO:96       EKHYIE----------------AFAPLLRNQGFD-AKFI
SEQ ID NO:97       EKHYIE----------------AFAPLLRNQGFD-AKFI
SEQ ID NO:98       ERHFVE----------------AFAPLLRQNGWD-AKFI
SEQ ID NO:99       EKHYIE----------------AFRPLLEARGFP-AQFI
SEQ ID NO:100      EKHYIE----------------AFRPLLEARGFP-AQFI
SEQ ID NO:101      EERYIN----------------ALAPLLKNEGFP-AHFI
SEQ ID NO:102      EIHYI----------------EALAPMLSNAGFP-AHFI
SEQ ID NO:103      ELHYIN----------------ALGPMLAQQGFP-AQFV
SEQ ID NO:104      EMLYIE----------------ALAPLLGS--FP-AHFI
SEQ ID NO:105      EMLYIE----------------ALAPLLGS--FP-AHFI
SEQ ID NO:106      EVRYIN----------------AFRPLLEARGFP-AYFI
SEQ ID NO:107      EIHYIN----------------ALAPLQQAGWD-ATFI
SEQ ID NO:108      ELHYIN----------------ALAPALQSGGFP-AHFI
SEQ ID NO:109      EKIYIN----------------TFGAELKSAGMP-NHAI
SEQ ID NO:110      EIHYINVSDCFVLIWTSLTICIIALAPELSSRGFP-AHFI
SEQ ID NO:111      EFPYIQ----------------RVRPMLKSPGFP-AQFV
SEQ ID NO:112      EKLYLD----------------NFGPALKSAGMP-NHAI
SEQ ID NO:113      EKIYVE----------------TFGPLLKNAGMP-NHAI
```

Figure 9H

```
SEQ ID NO:3    349 TDQGRSGKQPTGQQQWGDWCNVIGTGFGIRPSANTGDSLL 388
SEQ ID NO:79       TDQGRSGKQPTGQQQWGDWCNVIGTGFGIRPSANTGDSLL
SEQ ID NO:80       TDQGRSGKQPTGQQQWGDWCNVIGTGFGIRPSANTGDSLL
SEQ ID NO:81       TDQGRSGKQPTGQQQWGDWCNVIGTGFGIRPSANTGDSLL
SEQ ID NO:82       TDQGRSGKQPTGQQQWGDWCNVIGTGFGIRPSANTGDSLL
SEQ ID NO:83       TDQGRSGKQPTGQQQWGDWCNVIGTGFGIRPSSNTGDSLL
SEQ ID NO:84       TDTGRNGKQPTGQQAWGDWCNVIGTGFGARPSTNTGDSLL
SEQ ID NO:85       VDTGRNGKQPTGQQAWGDWCNVINTGFGERPTTDTGDALV
SEQ ID NO:86       VDTGRNGNQPTGQSQWGDWCNVKNTGFGVRPTTDTGDELV
SEQ ID NO:87       TDTGRNGKQPTGQSAWGDWCNVKDTGFGAQPTTDTGDELA
SEQ ID NO:88       MDTSRNGVQPTKQQAWGDWCNVIGTGFGVQPTTNTGDPLE
SEQ ID NO:89       IDTSRNGVRPTKQSQWGDWCNVIGTGFGVRPTTDTGNPLE
SEQ ID NO:90       VDQGRSGKQPTGQKAWGDWCNAPGTGFGLRPSANTGDALV
SEQ ID NO:91       VDQGRSGKQPTGQKAQGDWCNAKGTGFGLRPSTNTGDALA
SEQ ID NO:92       VDTGRSGKQPTGQIEQGDWCNAIGTGFGVRPTTNTGSSLA
SEQ ID NO:93       VDTGRNGKQPTGQIEWGDWCNVKGTGFGVRPTTDTGDELV
SEQ ID NO:94       TDTGRNGKQPTGQSAWGDWGNVKDTGFGAXPTTDTGNELA
SEQ ID NO:95       IDQGRSGKQPTGQKEWGHWCNQQGVGFGRRPSANTGSELA
SEQ ID NO:96       VDTGRNGKQPTGQLEWGHWCNVKGTGFGVRPTANTGHELV
SEQ ID NO:97       VDTGRNGKQPTGQLEWGHWCNVKGTGFGVRPTANTGHELV
SEQ ID NO:98       VDQGRSGRQPTGQQEWGHWCNAIGTGFGQRPTSNTGHADV
SEQ ID NO:99       VDQGRSGKQPTGQKEWGHWCNAIGTGFGMRPTANTGHQYV
SEQ ID NO:100      VDQGRSGKQPTGQKEWGHWCNAIGTGFGMRPTANTGHQYV
SEQ ID NO:101      VDQGRSGKVPTNQQEWGDWCNSGAGFGTRPTTNTGNALI
SEQ ID NO:102      VDQGRSGVQ-NIRDQWGDWCNVKGAGFGQRPTTNTGSSLI
SEQ ID NO:103      VDQGRSGQQ-NLRQQWGDWCNIKGAGFGTRPTTNTGSSLI
SEQ ID NO:104      VDQGRSGVQ-DIRQQWGDWCNVLGAGFGTQPTTNTGSSLI
SEQ ID NO:105      VDQGRSGVQ-DIRQQWGDWCNVLGAGFGTQPTTNTGSSLI
SEQ ID NO:106      VDQGRSGVQPTAQIEQGHWCNVIDTGFGTRPTTDTGNEYV
SEQ ID NO:107      VDQGRSGVQ-NIRQQWGDWCNIKGAGFGTRPTTNTGSQFI
SEQ ID NO:108      VDQGRSGVQ-NIRQQWGDWCNVKGAGFGQRPTLSTGSSLI
SEQ ID NO:109      IDTGRNGVT-GLRDEWGDWCNVNGAGFGVRPTANTGDELA
SEQ ID NO:110      VDQGRSAVQ-GIRGAWGDWCNVDNAGFGTRPTTSTGSSLI
SEQ ID NO:111      VDQGRAGQQ-NFRQQWGDWCNIKGAGFGTRPTTSTGNPLI
SEQ ID NO:112      VDTGRNGVS-GLRQEWGNWCNVNGAGFGVRPTSSTGHDLA
SEQ ID NO:113      VDVGRNAVQ-GLREEWGHWCNVNGAGFGVRPTTSTGSSLT
```

Figure 9I

```
SEQ ID NO:3    389 DSFVWVKPGGECDGTS-DSSAPRFDSHCALP-DALQPAPQ 426
SEQ ID NO:79       DSFVWVKPGGECDGTS-DSSAPRFDSHCALP-DALQPAPQ
SEQ ID NO:80       DSFVWVKPGGECDGTS-DSSAPRFDSHCALP-DALQPAPQ
SEQ ID NO:81       DSFVWIKPGGECDGTS-DSSAPRFDSHCALP-DALQPAPQ
SEQ ID NO:82       DSFVWIKPGGECDGTS-DSSAPRFDSHCALP-DALQPAPQ
SEQ ID NO:83       DSFVWVKPGGECDGTS-DSSAPRFDSHCALP-DALQPAPQ
SEQ ID NO:84       DAFVWVKPGGESDGTS-DTSAARYDAHCGYS-DALQPAPE
SEQ ID NO:85       DAFVWVKPGGESDGTS-DSSATRYDAHCGYS-DALQPAPE
SEQ ID NO:86       DAFVWVKPGGESDGTS-DTSAERYDAHCGYA-DALTPAPE
SEQ ID NO:87       DAFVWVKPGGESDGTS-DTSSSRYDAHCGYS-DALQPAPE
SEQ ID NO:88       DAFVWVKPGGESDGTS-NSSATRYDFHCGYS-DALQPAPE
SEQ ID NO:89       DAFVWVKPGGESDGTS-NTTSPRYDYHCGLS-DALQPAPE
SEQ ID NO:90       DAFVWVKPGGESDGTS-DTSAARYDYHCGID-GAVKPAPE
SEQ ID NO:91       DAFVWVKPGGESDGTS-DTSAARYDYHCGLD-DALKPAPE
SEQ ID NO:92       DAFVWVKPGGESDGTS-DTSATRYDYHCGLS-DALKPAPE
SEQ ID NO:93       DAFVWVKPGGESDGTS-DQSAERYDAHCGAA-AALQPAPE
SEQ ID NO:94       DAFVWXNPGGKSDGTS-DTSSSRYDAHCGYS-DALQPAPE
SEQ ID NO:95       DAFVWIKPGGECDGVS-DPTAPRFDHFCGTDYGAMSDAPQ
SEQ ID NO:96       DAFVWVKPGGESDGTSADTSAARYDYHCGLS-DALTPAPE
SEQ ID NO:97       DAFVWVKPGGESDGTS-DTSAARYDYHCGLS-DALTPAPE
SEQ ID NO:98       DAFVWIKPGGECDGTS-DTSAARYDHFCGNP-DALKPAPE
SEQ ID NO:99       DAFVWVKPGGECDGTS-DTTAARYDYHCGLE-DALKPAPE
SEQ ID NO:100      DAFVWVKPGGECDGTS-DTTAARYDYHCGLE-DALKPAPE
SEQ ID NO:101      DAIVWVKPGGESDGTS-DTSAARYDAHCGRN-SAFKPAPE
SEQ ID NO:102      DAIVWVKPGGECDGTS-DNSSPRFDSHCSLS-DAHQPAPE
SEQ ID NO:103      DAIVWVKPGGESDGTS-NSSSPRFDSTCSLS-DATQPAPE
SEQ ID NO:104      DSIVWVKPGGECDGTS-NTSSPRYDAHCGLP-DATPNAPE
SEQ ID NO:105      DSIVWVKPGGECDGTS-NTSSPRYDAHCGLP-DATPNAPE
SEQ ID NO:106      DSIVWVKPGGESDGTS-DTSAERYDYHCGLE-DALKPAPE
SEQ ID NO:107      DSIVWVKPGGECDGTS-NSSSPRYDSTCSLP-DAAQPAPE
SEQ ID NO:108      DAIVWIKPGGECDGTT-NTSSPRYDSHCGLS-DATPNAPE
SEQ ID NO:109      DAFVWVKPGGESDGTS-DSSAARYDSFCGKP-DAFKPSPE
SEQ ID NO:110      DAIVWVKPGGESDGTS-DTSAVRYDGHCGLA-SAKKPAPE
SEQ ID NO:111      DAIIWVKPGGESDGTS-NSSSPRYDSTLLSV-RRDDPAPE
SEQ ID NO:112      DAFVWVKPGGESDGTS-DSSATRYDSFCGKS-DAYQPSPE
SEQ ID NO:113      DALLWVKPGGESDGTS-DTSATRYDSFCGMS-DAYKPSPE
```

Figure 9J

```
SEQ ID NO:3    427 AG------AWFQAYFVQLLTNANPSFL- 447
SEQ ID NO:79       AG------AWFQAYFVQLLTNANPSFL-
SEQ ID NO:80       AG------AWFQAYFVQLLTNANPSFL-
SEQ ID NO:81       AG------AWFQAYFVQLLTNANPSFL-
SEQ ID NO:82       AG------AWFQAYFVQLLTNANPSFL-
SEQ ID NO:83       AG------AWFQAYFVQLLTNANPSFL-
SEQ ID NO:84       AG------TWFQAYFVQLLQNANPSF--
SEQ ID NO:85       AG------TWFQAYFVQLLTNANPAF--
SEQ ID NO:86       AG------TWFQAYFEQLVENANPSL--
SEQ ID NO:87       AG------TWFQAYFEQLLTNANPSL--
SEQ ID NO:88       AG------TWFQAYFVQLLTNANPALV-
SEQ ID NO:89       AG------TWFQAYFEQLLTNANPLF--
SEQ ID NO:90       AG------TWFQAYFEQLLKNANPSFL-
SEQ ID NO:91       AG------TWFQAYFEQLLDNANPSFL-
SEQ ID NO:92       AG------QWFQAYFEQLLKNANPAF--
SEQ ID NO:93       AG------TWFQAYFEQLVANANPPLSS
SEQ ID NO:94       AG------TWFQAYFEQLLTNANPSL--
SEQ ID NO:95       AG------QWFQKYFEMLLTNANPPL--
SEQ ID NO:96       AG------QWFQAYFEQLLINANPPL--
SEQ ID NO:97       AG------QWFQAYFEQLLINANPPF--
SEQ ID NO:98       AG------EWFQAYFEQLLRNANPAF--
SEQ ID NO:99       AG------QWFQAYFEQLLRNANPPF--
SEQ ID NO:100      AG------QWFNEYFIQLLRNANPPF--
SEQ ID NO:101      AG------TWFQAYFEMLLKNANPALA-
SEQ ID NO:102      AG------TWFQAYFETLVANANPAL--
SEQ ID NO:103      AG------TWFQTYFETLVSKANPPL--
SEQ ID NO:104      AG------TWFQAYFETLVEKANPPL--
SEQ ID NO:105      AG------TWFQAYFETLVEKANPPL--
SEQ ID NO:106      AG------QWFQAYFEQLLRNANPPF--
SEQ ID NO:107      AG------TWFQAYFQTLVSAANPPL--
SEQ ID NO:108      AG------QWFQAYFETLVRNASPPL--
SEQ ID NO:109      AG------TWNQAYFEMLLKNANPSF--
SEQ ID NO:110      AMASVYSHSSFQAYFEMLVANAVPAL--
SEQ ID NO:111      AG------TWFQAYFETLVSKPTRPL--
SEQ ID NO:112      AG------SWNQDYFEMLVKNAKPSF--
SEQ ID NO:113      AG------QWNQDYFEMLLRNAKPQF--
```

Figure 9K

SEQUENCE LISTING

<160> NUMBER OF SEQ ID NOS: 115

<210> SEQ ID NO 1
<211> LENGTH: 397
<212> TYPE: PRT
<213> ORGANISM: Trichoderma reesei

<400> SEQUENCE: 1

```
Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile Pro Gly Ala Thr Thr Ile Thr Thr Ser Thr Arg Pro
        35                  40                  45

Pro Ser Gly Pro Thr Thr Thr Thr Arg Ala Thr Ser Thr Ser Ser Ser
    50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

Val Tyr Pro Pro Leu Lys Asn Phe Thr Gly Ser Asn Asn Tyr Pro Asp
            100                 105                 110
```

-continued

Gly Ile Gly Gln Met Gln His Phe Val Asn Asp Asp Gly Met Thr Ile
            115                 120                 125
Phe Arg Leu Pro Val Gly Trp Gln Tyr Leu Val Asn Asn Asn Leu Gly
130                 135                 140
Gly Asn Leu Asp Ser Thr Ser Ile Ser Lys Tyr Asp Gln Leu Val Gln
145                 150                 155                 160
Gly Cys Leu Ser Leu Gly Ala Tyr Cys Ile Val Asp Ile His Asn Tyr
                165                 170                 175
Ala Arg Trp Asn Gly Gly Ile Ile Gly Gln Gly Gly Pro Thr Asn Ala
            180                 185                 190
Gln Phe Thr Ser Leu Trp Ser Gln Leu Ala Ser Lys Tyr Ala Ser Gln
        195                 200                 205
Ser Arg Val Trp Phe Gly Ile Met Asn Glu Pro His Asp Val Asn Ile
    210                 215                 220
Asn Thr Trp Ala Ala Thr Val Gln Glu Val Val Thr Ala Ile Arg Asn
225                 230                 235                 240
Ala Gly Ala Thr Ser Gln Phe Ile Ser Leu Pro Gly Asn Asp Trp Gln
                245                 250                 255
Ser Ala Gly Ala Phe Ile Ser Asp Gly Ser Ala Ala Ala Leu Ser Gln
            260                 265                 270
Val Thr Asn Pro Asp Gly Ser Thr Thr Asn Leu Ile Phe Asp Val His
        275                 280                 285
Lys Tyr Leu Asp Ser Asp Asn Ser Gly Thr His Ala Glu Cys Thr Thr
    290                 295                 300
Asn Asn Ile Asp Gly Ala Phe Ser Pro Leu Ala Thr Trp Leu Arg Gln
305                 310                 315                 320
Asn Asn Arg Gln Ala Ile Leu Thr Glu Thr Gly Gly Gly Asn Val Gln
                325                 330                 335
Ser Cys Ile Gln Asp Met Cys Gln Gln Ile Gln Tyr Leu Asn Gln Asn
            340                 345                 350
Ser Asp Val Tyr Leu Gly Tyr Val Gly Trp Ala Ala Gly Ser Phe Asp
        355                 360                 365
Ser Thr Tyr Val Leu Thr Glu Thr Pro Thr Gly Ser Gly Asn Ser Trp
    370                 375                 380
Thr Asp Thr Ser Leu Val Ser Ser Cys Leu Ala Arg Lys
385                 390                 395

<210> SEQ ID NO 2
<211> LENGTH: 397
<212> TYPE: PRT
<213> ORGANISM: Trichoderma reesei

<400> SEQUENCE: 2

Gln Gln Thr Val Trp Gly Gln Cys Gly Gly Ile Gly Trp Ser Gly Pro
1               5                   10                  15
Thr Asn Cys Ala Pro Gly Ser Ala Cys Ser Thr Leu Asn Pro Tyr Tyr
            20                  25                  30
Ala Gln Cys Ile Pro Gly Ala Thr Thr Ile Thr Thr Ser Thr Arg Pro
        35                  40                  45
Pro Ser Gly Pro Thr Thr Thr Arg Ala Thr Ser Thr Ser Ser Ser
    50                  55                  60
Thr Pro Pro Thr Ser Ser Gly Val Arg Phe Ala Gly Val Asn Ile Ala
65                  70                  75                  80
Gly Phe Asp Phe Gly Cys Thr Thr Asp Gly Thr Cys Val Thr Ser Lys
                85                  90                  95

-continued

```
Val Tyr Pro Pro Leu Lys Asn Phe Thr Gly Ser Asn Asn Tyr Pro Asp
            100                 105                 110

Gly Ile Gly Gln Met Gln His Phe Val Asn Asp Asp Gly Met Thr Ile
        115                 120                 125

Phe Arg Leu Pro Val Gly Trp Gln Tyr Leu Val Asn Asn Asn Leu Gly
130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Gly Ile Ile Gly Gln Gly Gly Pro Thr Asn Ala
            180                 185                 190

Gln Phe Thr Ser Leu Trp Ser Gln Leu Ala Ser Lys Tyr Ala Ser Gln
        195                 200                 205

Ser Arg Val Trp Phe Gly Ile Met Asn Glu Pro His Asp Val Asn Ile
    210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
    290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Gly Ala Gly Ser Phe Asp
        355                 360                 365

Ser Thr Tyr Val Leu Thr Glu Thr Pro Thr Gly Ser Gly Asn Ser Trp
    370                 375                 380

Thr Asp Thr Ser Leu Val Ser Ser Cys Leu Ala Arg Lys
385                 390                 395

<210> SEQ ID NO 3
<211> LENGTH: 447
<212> TYPE: PRT
<213> ORGANISM: Trichoderma reesei

<400> SEQUENCE: 3

Gln Ala Cys Ser Ser Val Trp Gly Gln Cys Gly Gly Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
```

```
                65                  70                  75                  80
Val Gly Ser Gly Thr Ala Thr Tyr Ser Gly Asn Pro Phe Val Gly Val
                        85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
                115                 120                 125

Lys Val Pro Ser Phe Met Trp Leu Asp Thr Leu Asp Lys Thr Pro Leu
                130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                        165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                        245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                        325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                        405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 4
<211> LENGTH: 225
<212> TYPE: PRT
<213> ORGANISM: Trichoderma reesei

<400> SEQUENCE: 4
```

```
Tyr Lys Ala Thr Thr Thr Arg Tyr Tyr Asp Gly Gln Glu Gly Ala Cys
 1               5                  10                  15

Gly Cys Gly Ser Ser Ser Gly Ala Phe Pro Trp Gln Leu Gly Ile Gly
            20                  25                  30

Asn Gly Val Tyr Thr Ala Ala Gly Ser Gln Ala Leu Phe Asp Thr Ala
         35                  40                  45

Gly Ala Ser Trp Cys Gly Ala Gly Cys Gly Lys Cys Tyr Gln Leu Thr
 50                  55                  60

Ser Thr Gly Gln Ala Pro Cys Ser Ser Cys Thr Gly Gly Ala Ala
 65                  70                  75                  80

Gly Gln Ser Ile Ile Val Met Val Thr Asn Leu Cys Pro Asn Asn Gly
                 85                  90                  95

Asn Ala Gln Trp Cys Pro Val Val Gly Gly Thr Asn Gln Tyr Gly Tyr
            100                 105                 110

Ser Tyr His Phe Asp Ile Met Ala Gln Asn Glu Ile Phe Gly Asp Asn
        115                 120                 125

Val Val Val Asp Phe Glu Pro Ile Ala Cys Pro Gly Gln Ala Ala Ser
130                 135                 140

Asp Trp Gly Thr Cys Leu Cys Val Gly Gln Gln Glu Thr Asp Pro Thr
145                 150                 155                 160

Pro Val Leu Gly Asn Asp Thr Gly Ser Thr Pro Gly Ser Pro
                165                 170                 175

Pro Ala Thr Ser Ser Pro Ser Gly Gly Gln Gln Thr Leu
            180                 185                 190

Tyr Gly Gln Cys Gly Gly Ala Gly Trp Thr Gly Pro Thr Thr Cys Gln
        195                 200                 205

Ala Pro Gly Thr Cys Lys Val Gln Asn Gln Trp Tyr Ser Gln Cys Leu
        210                 215                 220

Pro
225

<210> SEQ ID NO 5
<211> LENGTH: 497
<212> TYPE: PRT
<213> ORGANISM: Trichoderma reesei

<400> SEQUENCE: 5

Gln Ser Ala Cys Thr Leu Gln Ser Glu Thr His Pro Pro Leu Thr Trp
 1               5                  10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
         35                  40                  45

Asn Cys Tyr Asp Gly Asn Thr Trp Ser Ser Thr Leu Cys Pro Asp Asn
 50                  55                  60

Glu Thr Cys Ala Lys Asn Cys Cys Leu Asp Gly Ala Ala Tyr Ala Ser
 65                  70                  75                  80

Thr Tyr Gly Val Thr Thr Ser Gly Asn Ser Leu Ser Ile Gly Phe Val
                 85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
130                 135                 140
```

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
            165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
            195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
            245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Lys Lys Leu
            275                 280                 285

Thr Val Val Thr Gln Phe Glu Thr Ser Gly Ala Ile Asn Arg Tyr Tyr
290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
            325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
            355                 360                 365

Asp Tyr Tyr Ala Asn Met Leu Trp Leu Asp Ser Thr Tyr Pro Thr Asn
370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
            435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu

<210> SEQ ID NO 6
<211> LENGTH: 437
<212> TYPE: PRT
<213> ORGANISM: Trichoderma reesei

<400> SEQUENCE: 6

Gln Gln Pro Gly Thr Ser Thr Pro Glu Val His Pro Lys Leu Thr Thr
1               5                   10                  15

-continued

```
Tyr Lys Cys Thr Lys Ser Gly Gly Cys Val Ala Gln Asp Thr Ser Val
             20                  25                  30

Val Leu Asp Trp Asn Tyr Arg Trp Met His Asp Ala Asn Tyr Asn Ser
         35                  40                  45

Cys Thr Val Asn Gly Val Asn Thr Thr Leu Cys Pro Asp Glu Ala
         50                  55                  60

Thr Cys Gly Lys Asn Cys Phe Ile Glu Gly Val Asp Tyr Ala Ala Ser
65                   70                  75                  80

Gly Val Thr Thr Ser Gly Ser Ser Leu Thr Met Asn Gln Tyr Met Pro
                 85                  90                  95

Ser Ser Ser Gly Gly Tyr Ser Ser Val Ser Pro Arg Leu Tyr Leu Leu
             100                 105                 110

Asp Ser Asp Gly Glu Tyr Val Met Leu Lys Leu Asn Gly Gln Glu Leu
             115                 120                 125

Ser Phe Asp Val Asp Leu Ser Ala Leu Pro Cys Gly Glu Asn Gly Ser
             130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                 165                 170                 175

Val Gln Thr Trp Arg Asn Gly Thr Leu Asn Thr Ser His Gln Gly Phe
             180                 185                 190

Cys Cys Asn Glu Met Asp Ile Leu Glu Gly Asn Ser Arg Ala Asn Ala
             195                 200                 205

Leu Thr Pro His Ser Cys Thr Ala Thr Ala Cys Asp Ser Ala Gly Cys
             210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                 245                 250                 255

Thr Asp Asn Gly Ser Pro Ser Gly Asn Leu Val Ser Ile Thr Arg Lys
             260                 265                 270

Tyr Gln Gln Asn Gly Val Asp Ile Pro Ser Ala Gln Pro Gly Gly Asp
             275                 280                 285

Thr Ile Ser Ser Cys Pro Ser Ala Ser Ala Tyr Gly Gly Leu Ala Thr
             290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                 325                 330                 335

Pro Cys Ser Ser Thr Glu Gly Asn Pro Ser Asn Ile Leu Ala Asn Asn
             340                 345                 350

Pro Asn Thr His Val Val Phe Ser Asn Ile Arg Trp Gly Asp Ile Gly
             355                 360                 365

Ser Thr Thr Asn Ser Thr Ala Pro Pro Pro Pro Ala Ser Ser Thr
             370                 375                 380

Thr Phe Ser Thr Thr Arg Arg Ser Ser Thr Thr Ser Ser Ser Pro Ser
385                 390                 395                 400

Cys Thr Gln Thr His Trp Gly Gln Cys Gly Gly Ile Gly Tyr Ser Gly
                 405                 410                 415

Cys Lys Thr Cys Thr Ser Gly Thr Thr Cys Gln Tyr Ser Asn Asp Tyr
             420                 425                 430
```

```
Tyr Ser Gln Cys Leu
        435

<210> SEQ ID NO 7
<211> LENGTH: 284
<212> TYPE: PRT
<213> ORGANISM: Humicola insolens

<400> SEQUENCE: 7

Ala Asp Gly Arg Ser Thr Arg Tyr Trp Asp Cys Cys Lys Pro Ser Cys
1               5                   10                  15

Gly Trp Ala Lys Lys Ala Pro Val Asn Gln Pro Val Phe Ser Cys Asn
            20                  25                  30

Ala Asn Phe Gln Arg Ile Thr Asp Phe Asp Ala Lys Ser Gly Cys Glu
        35                  40                  45

Pro Gly Gly Val Ala Tyr Ser Cys Ala Asp Gln Thr Pro Trp Ala Val
    50                  55                  60

Asn Asp Asp Phe Ala Leu Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
            100                 105                 110

Gly Asp Leu Gly Ser Asn His Phe Asp Leu Asn Ile Pro Gly Gly Gly
        115                 120                 125

Val Gly Ile Phe Asp Gly Cys Thr Pro Gln Phe Gly Gly Leu Pro Gly
    130                 135                 140

Gln Arg Tyr Gly Gly Ile Ser Ser Arg Asn Glu Cys Asp Arg Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
            180                 185                 190

Leu Val Ala Arg Thr Gly Cys Arg Arg Asn Asp Asp Gly Asn Phe Pro
        195                 200                 205

Ala Val Gln Ile Pro Ser Ser Ser Thr Ser Ser Pro Val Asn Gln Pro
    210                 215                 220

Thr Ser Thr Ser Thr Thr Ser Thr Ser Thr Thr Ser Ser Pro Pro Val
225                 230                 235                 240

Gln Pro Thr Thr Pro Ser Gly Cys Thr Ala Glu Arg Trp Ala Gln Cys
                245                 250                 255

Gly Gly Asn Gly Trp Ser Gly Cys Thr Thr Cys Val Ala Gly Ser Thr
            260                 265                 270

Cys Thr Lys Ile Asn Asp Trp Tyr His Gln Cys Leu
        275                 280

<210> SEQ ID NO 8
<211> LENGTH: 247
<212> TYPE: PRT
<213> ORGANISM: Trichoderma viride

<400> SEQUENCE: 8

Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30
```

```
Cys Gly Cys Gly Ser Ser Ser Gly Ala Phe Pro Trp Gln Leu Gly Ile
         35                  40                  45

Gly Asn Gly Val Tyr Thr Ala Ala Gly Ser Gln Ala Leu Phe Asp Thr
 50                  55                  60

Ala Gly Ala Ser Trp Cys Gly Ala Gly Cys Gly Lys Cys Tyr Gln Leu
 65                  70                  75                  80

Thr Ser Thr Gly Gln Ala Pro Cys Ser Ser Cys Gly Thr Gly Gly Ala
                 85                  90                  95

Ala Gly Gln Ser Ile Ile Val Met Val Thr Asn Leu Cys Pro Asn Asn
             100                 105                 110

Gly Asn Ala Gln Trp Cys Pro Val Val Gly Thr Asn Gln Tyr Gly
             115                 120                 125

Tyr Ser Tyr His Phe Asp Ile Met Ala Gln Asn Glu Ile Phe Gly Asp
 130                 135                 140

Asn Val Val Val Asp Phe Glu Pro Ile Ala Cys Pro Gly Gln Ala Ala
 145                 150                 155                 160

Ser Asp Trp Gly Thr Cys Leu Cys Val Gly Gln Gln Glu Thr Asp Pro
                 165                 170                 175

Thr Pro Val Leu Gly Asn Asp Thr Gly Ser Thr Pro Pro Gly Ser Ser
             180                 185                 190

Pro Pro Ala Thr Ser Ser Ser Pro Ser Gly Gly Gln Gln Thr
             195                 200                 205

Leu Tyr Gly Gln Cys Gly Gly Ala Gly Trp Thr Gly Pro Thr Thr Cys
             210                 215                 220

Gln Ala Pro Gly Thr Cys Lys Val Gln Asn Gln Trp Tyr Ser Gln Cys
225                 230                 235                 240

Leu Pro Trp Glu Gly Pro Arg
                 245

<210> SEQ ID NO 9
<211> LENGTH: 266
<212> TYPE: PRT
<213> ORGANISM: Penicillium decumbens

<400> SEQUENCE: 9

Met Lys Gly Lys Val Ala Phe Leu Leu Leu Asp Leu Leu Ala Ser Ala
 1               5                  10                  15

Ala Ala Tyr Lys Ala Thr Thr Thr Arg Tyr Tyr Asp Gly Gln Glu Gly
             20                  25                  30

Ala Cys Gly Cys Gly Ser Ser Ser Gly Leu Phe Pro Trp Gln Leu Gly
         35                  40                  45

Ile Gly Asn Gly Val Tyr Thr Ala Ala Gly Ser Gln Ala Leu Phe Asp
 50                  55                  60

Thr Ala Gly Ala Asp Trp Cys Gly Ala Gly Cys Gly Lys Cys Tyr Lys
 65                  70                  75                  80

Leu Thr Ser Thr Gly Glu Pro Pro Cys Lys Asp Cys Gly Thr Gly Gly
                 85                  90                  95

Val Ala Gly Gln Ser Ile Ile Val Met Val Thr Asn Leu Cys Pro Tyr
             100                 105                 110

Asn Gly Asn Gln Gln Trp Cys Pro Asn Pro Gly Ser Thr Asn Gln Tyr
             115                 120                 125

Gly Tyr Ser Tyr His Phe Asp Ile Met Ala Gln Asn Glu Ile Phe Gly
 130                 135                 140

Asp Asn Val Val Val Asp Phe Glu Pro Ile Ala Cys Pro Gly Gln Ala
145                 150                 155                 160
```

```
Asn Ser Asp Trp Gln Ser Cys Val Cys Tyr Gly Lys Thr Glu Thr Asp
                165                 170                 175

Thr Thr Pro Val Gly Leu Thr Ala Gly Gly Gly Gly Gly Ser Ser
        180                 185                 190

Gln Ser Ser Thr Thr Ser Gln Gly Ser Thr Thr Arg Thr Thr Leu
            195                 200                 205

Thr Ala Thr Thr Thr Ala Gly Ser Gly Ser Gly Ser Gly Ser
    210                 215                 220

Gly Ser Ser Ser Gly Thr Gln Ser Val Tyr Gly Gln Cys Gly Gly Ser
225                 230                 235                 240

Gly Trp Thr Gly Pro Thr Asn Cys Ala Ser Gly Ser Lys Cys Thr Ala
                245                 250                 255

Gln Asn Gln Trp Tyr Ser Gln Cys Leu Pro
            260                 265

<210> SEQ ID NO 10
<211> LENGTH: 247
<212> TYPE: PRT
<213> ORGANISM: Aspergillus nidulans

<400> SEQUENCE: 10

Met Gln Arg Ile Pro Asp Arg Leu Ser Asp Ser Thr Arg Ile Thr Arg
1               5                   10                  15

Pro His Arg Ser Leu Cys Cys Asn Thr Gly Gly Ala Ser Ser Ser Cys
            20                  25                  30

Pro Gly Tyr His Asn Cys Ala Cys Gly Cys Gly Asn Lys Ile Gly Thr
        35                  40                  45

Tyr Asp Trp Ser Tyr Gly Ile Ala Asn Lys Val Tyr Thr Ala Ala Ala
    50                  55                  60

Asn Gln Ala Leu Phe Asp Ser Gly Pro Asn Asp Ala Thr His Trp Cys
65                  70                  75                  80

Gly Asn Gly Cys Gly Lys Cys Tyr Arg Leu Thr Ser Thr Gly Val Ser
                85                  90                  95

Thr Cys Glu Thr Cys Gly Ala Gly Gly Glu Gln Gly Lys Ser Ile Val
            100                 105                 110

Val Met Val Thr Asn Leu Cys Pro Phe Lys Gly Asn Glu Arg Trp Cys
        115                 120                 125

Pro Asn Pro Gly Gln Leu Asn Pro His Gly Tyr Ala Tyr His Phe Asp
130                 135                 140

Ile Met Gly Gly Ala Gly Val Phe Gly Asp Asn Val Val Val Glu Phe
145                 150                 155                 160

Glu Glu Val Pro Cys Pro Gly Asp Ala Ala Phe Lys Trp Ala Ala Cys
                165                 170                 175

Glu Cys His Pro Asn Leu Arg Asn Lys Asp Leu Thr Leu Asn Ala Gly
            180                 185                 190

Ala His Ala Ala Gly Ser Lys Ile Val Gly Pro Ala Gln Ala Ala Ile
        195                 200                 205

Ile Ser Val Asn Gly Leu Pro Ala Pro Ala Ala Met Ala Val Gln Pro
    210                 215                 220

Pro Pro Pro Pro Pro Pro Ala Pro Ala Arg Pro Ala Ile Glu Ile
225                 230                 235                 240

Pro Pro Pro Pro Ala Pro Val
                245
```

```
<210> SEQ ID NO 11
<211> LENGTH: 194
<212> TYPE: PRT
<213> ORGANISM: Haliotis discus discus

<400> SEQUENCE: 11

Met Lys Thr Ala Val Ser Ile Leu Leu Phe Ala Ala Ser Ala Trp
1               5                   10                  15

Ala Asn Gln Lys Cys Gln Met His Asn Gly Ile Arg Met Tyr Asn Gly
                20                  25                  30

Lys His Cys Ala Ser Thr Thr Arg Tyr Asn Asp Gly His Lys Gly Ala
            35                  40                  45

Cys Gly Cys Gly Gln Asn Asp Thr Pro Phe Pro Trp Asn Asn Asn Gln
        50                  55                  60

Tyr Val Ala Ala Asn Gln Lys Leu Phe Ser Asn Ser Gly Ser Thr
65                  70                  75                  80

Trp Cys Gly Asp Ser Cys Gly Lys Cys Val Lys Leu Thr Thr Thr Gly
                85                  90                  95

Gly Ser Ile Pro Gly Ala Gly Thr Gly Ala His Ala Gly Gln Ser His
            100                 105                 110

Val Phe Met Ile Thr Asn Asp Cys Pro Asp Val Ala Pro Asn Leu Glu
        115                 120                 125

Trp Cys Ala Gln Lys Gly Ala Pro Gly Ser Gly His Gly Asn Thr His
130                 135                 140

Gly Tyr Glu Val His Phe Asp Leu Glu Asn Asn Gly Asn Gln Ile Ser
145                 150                 155                 160

Lys Leu Gly Trp Asp Asn Pro Glu Val Thr Trp Glu Trp Ser Ser Cys
                165                 170                 175

His Gly Ser Asn Thr Pro Thr Asp Gln Met Trp His Thr Cys Glu Cys
            180                 185                 190

Ser His

<210> SEQ ID NO 12
<211> LENGTH: 195
<212> TYPE: PRT
<213> ORGANISM: Ampullaria crossean

<400> SEQUENCE: 12

Met Lys Leu Phe Tyr Leu Leu Cys Leu Ala Val Pro Leu Leu Glu Ala
1               5                   10                  15

Ala Gln Leu Cys Gln Pro Asp Ser Arg Gly Val Arg Arg Phe Asn Gly
                20                  25                  30

Lys Pro Cys Ala Ser Thr Thr Arg Tyr Val Asp Gly His Lys Gly Ala
            35                  40                  45

Cys Gly Cys Gly Gln Lys Gly Ser Asp Thr Pro Phe Pro Trp Asn Ile
        50                  55                  60

Gln Lys His Val Thr Ala Pro Ser Glu Arg Tyr Phe Asp Gly Gly
65                  70                  75                  80

Ser Ser Leu Trp Cys Gly Arg Asn Cys Gly Lys Cys Val Lys Leu Thr
                85                  90                  95

Pro Thr Gly Gly Phe Val Pro Gly Lys Gly Asn Ala Pro Asn His
            100                 105                 110

Asn Pro Val Val Phe Gln Val Thr Asn Ala Cys Pro Ile Asn Gly Asn
        115                 120                 125

Glu Glu Trp Cys Gly Ile Ser Gly Ala Pro Gly Thr Gly His Val Asn
130                 135                 140
```

```
Ser His Gly Tyr Glu Val His Phe Asp Leu Gln Asp Gln Val Gly Gln
145                 150                 155                 160

Val Glu Ala Leu His Trp Asp Asn Pro Glu Val Thr Trp Glu Glu Thr
                165                 170                 175

Ser Cys Pro Gly Asp Leu Gln Ser Asn Tyr Gln Gln Cys Glu Cys His
            180                 185                 190

Asn Ser Gly
        195

<210> SEQ ID NO 13
<211> LENGTH: 195
<212> TYPE: PRT
<213> ORGANISM: Ampullaria crossean

<400> SEQUENCE: 13

Met Lys Leu Phe Tyr Leu Leu Cys Leu Ala Val Pro Val Leu Glu Ala
1               5                   10                  15

Ala Gln Leu Cys Gln Pro Asp Ala His Gly Val Arg Arg Phe Asn Gly
            20                  25                  30

Arg Pro Cys Ala Ser Thr Thr Arg Tyr Val Asp Gly His Lys Gly Ala
        35                  40                  45

Cys Gly Cys Gly Gln Lys Gly Ser Asp Thr Pro Phe Pro Trp Asn Leu
    50                  55                  60

Gln Lys His Val Thr Ala Pro Ser Glu Arg Tyr Phe Asp Asp Gly Gly
65                  70                  75                  80

Ser Asn Leu Trp Cys Gly Lys Asn Cys Gly Lys Cys Val Arg Leu Thr
                85                  90                  95

Pro Thr Gly Gly Phe Val Pro Gly Lys Gly Ala Pro Pro Asn His
            100                 105                 110

Asn Pro Val Val Phe Met Val Thr Asn Ala Cys Pro Ile Asn Gly Asn
        115                 120                 125

Glu Glu Trp Cys Gly Ile Ser Gly Lys Pro Gly Thr Asn His Val Asn
    130                 135                 140

Ser His Gly Tyr Glu Val His Phe Asp Leu Gln Asp Gln Val Gly Gln
145                 150                 155                 160

Val Glu Ala Leu His Trp Asp Asn Pro Glu Val Thr Trp Glu Glu Val
                165                 170                 175

Pro Cys Pro Gly Asp Leu Gln Ala Asn Tyr Gln Gln Cys Glu Cys His
            180                 185                 190

Asn Ser Asp
        195

<210> SEQ ID NO 14
<211> LENGTH: 211
<212> TYPE: PRT
<213> ORGANISM: Mytilus edulis

<400> SEQUENCE: 14

Met Lys Tyr Leu Val Leu Ser Leu Leu Val Leu Val Tyr Ser Val Ser
1               5                   10                  15

Ala Asn Gln Lys Cys Ser Gly Asn Pro Arg Arg Tyr Asn Gly Lys Ser
            20                  25                  30

Cys Ala Ser Thr Thr Asn Tyr His Asp Ser Lys Gly Ala Cys Gly
        35                  40                  45

Cys Gly Pro Ala Ser Gly Asp Ala Gln Phe Gly Trp Asn Ala Gly Ser
    50                  55                  60
```

Phe Val Ala Ala Ala Ser Gln Met Tyr Phe Asp Ser Gly Asn Lys Gly
65                  70                  75                  80

Trp Cys Gly Gln His Cys Gly Gln Cys Ile Lys Leu Thr Thr Thr Gly
                85                  90                  95

Gly Tyr Val Pro Gly Gln Gly Pro Val Arg Glu Gly Leu Ser Lys
            100                 105                 110

Thr Phe Met Ile Thr Asn Leu Cys Pro Asn Ile Tyr Pro Asn Gln Asp
            115                 120                 125

Trp Cys Asn Gln Gly Ser Gln Tyr Gly Gly His Asn Lys Tyr Gly Tyr
130                 135                 140

Glu Leu His Leu Asp Leu Glu Asn Gly Arg Ser Gln Val Thr Gly Met
145                 150                 155                 160

Gly Trp Asn Asn Pro Glu Thr Thr Trp Glu Val Val Asn Cys Asp Ser
                165                 170                 175

Glu His Asn His Asp His Arg Thr Pro Ser Asn Ser Met Tyr Gly Gln
            180                 185                 190

Cys Gln Cys Ala His Gln Gly Lys Arg Gly Leu Asn Glu Thr Ser Asn
            195                 200                 205

Glu Ser Leu
    210

<210> SEQ ID NO 15
<211> LENGTH: 206
<212> TYPE: PRT
<213> ORGANISM: Phanerochaete chrysosporium

<400> SEQUENCE: 15

Met Ala Lys Leu Ser Met Phe Leu Gly Phe Val Ala Val Ala Thr Leu
1               5                   10                  15

Ala Ser Ala Leu Thr Val Ser Glu Lys Arg Ala Thr Gly Gly Tyr Val
            20                  25                  30

Gln Gln Ala Thr Gly Gln Ala Ser Phe Thr Met Tyr Ser Gly Cys Gly
        35                  40                  45

Ser Pro Ala Cys Gly Lys Ala Ala Ser Gly Phe Thr Ala Ala Ile Asn
50                  55                  60

Gln Leu Ala Phe Gly Ser Ala Pro Gly Leu Gly Ala Gly Asp Ala Cys
65                  70                  75                  80

Gly Arg Cys Phe Ala Leu Thr Gly Asn His Asp Pro Tyr Ser Pro Asn
                85                  90                  95

Tyr Thr Gly Pro Phe Gly Gln Thr Ile Val Val Lys Val Thr Asp Leu
            100                 105                 110

Cys Pro Val Gln Gly Asn Gln Glu Phe Cys Gly Gln Thr Thr Ser Asn
            115                 120                 125

Pro Thr Asn Gln His Gly Met Pro Phe His Phe Asp Ile Cys Glu Asp
130                 135                 140

Thr Gly Gly Ser Ala Lys Phe Phe Pro Ser Gly His Gly Ala Leu Thr
145                 150                 155                 160

Gly Thr Phe Thr Glu Val Ser Cys Ser Gln Trp Ser Gly Ser Asp Gly
                165                 170                 175

Gly Gln Leu Trp Asn Gly Ala Cys Leu Ser Gly Glu Thr Ala Pro Asn
            180                 185                 190

Trp Pro Ser Thr Ala Cys Gly Asn Lys Gly Thr Ala Pro Ser
            195                 200                 205

```
<210> SEQ ID NO 16
<211> LENGTH: 305
<212> TYPE: PRT
<213> ORGANISM: Humicola grisea var. thermoidea

<400> SEQUENCE: 16

Met Arg Ser Ser Pro Leu Leu Pro Ser Asp Val Ala Ala Leu Pro
1               5                   10                  15

Val Leu Ala Leu Ala Ala Asp Gly Lys Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Leu Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Phe Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225                 230                 235                 240

Pro Val Gly Gln Pro Thr Ser Thr Ser Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305

<210> SEQ ID NO 17
<211> LENGTH: 306
<212> TYPE: PRT
<213> ORGANISM: Humicola nigrescens

<400> SEQUENCE: 17

Pro Phe Met Met Val Ala Trp Trp Ser Leu Phe Leu Tyr Gly Leu Gln
1               5                   10                  15

Val Ala Ala Pro Ala Phe Ala Ala Asp Gly Arg Ser Thr Arg Tyr Trp
```

```
            20                  25                  30
Asp Cys Cys Lys Pro Ser Cys Ser Trp Pro Gly Lys Ala Leu Val Asn
            35                  40                  45
Gln Pro Val Tyr Ala Arg Asn Ala Asn Phe Gln Arg Ile Thr Asp Pro
        50                  55                  60
Asn Ala Lys Ser Gly Cys Asp Gly Gly Ser Ala Phe Ser Cys Ala Asp
65                  70                  75                  80
Gln Thr Pro Trp Ala Val Ser Asp Asp Phe Ala Tyr Gly Phe Ala Ala
                85                  90                  95
Thr Ala Leu Ala Gly Gln Ser Glu Ser Ser Trp Cys Cys Ala Cys Tyr
                100                 105                 110
Glu Leu Thr Phe Thr Ser Gly Pro Val Ala Gly Lys Lys Met Ala Val
                115                 120                 125
Gln Ser Thr Ser Thr Gly Gly Asp Leu Gly Ser Asn His Phe Asp Leu
            130                 135                 140
Asn Met Pro Gly Gly Gly Val Gly Ile Phe Asp Gly Cys Ser Pro Gln
145                 150                 155                 160
Val Gly Gly Leu Ala Gly Gln Arg Tyr Gly Gly Val Ser Ser Arg Ser
                165                 170                 175
Glu Cys Asp Ser Phe Pro Ala Ala Leu Lys Pro Gly Cys Tyr Trp Arg
                180                 185                 190
Tyr Asp Trp Phe Lys Asn Ala Asp Asn Pro Ser Phe Ser Phe Arg Gln
                195                 200                 205
Val Gln Cys Pro Ala Glu Leu Val Ala Arg Thr Gly Cys Arg Arg Asn
            210                 215                 220
Asp Asp Gly Asn Phe Pro Ala Val Gln Ile Pro Ser Ser Ser Thr Ser
225                 230                 235                 240
Ser Pro Val Asn Gln Pro Thr Ser Thr Ser Thr Ser Thr Ser Thr Ser
                245                 250                 255
Thr Ser Ser Pro Pro Val Gln Pro Thr Thr Pro Ser Gly Cys Thr Ala
            260                 265                 270
Glu Arg Trp Ala Gln Cys Gly Gly Asn Gly Trp Ser Gly Cys Thr Thr
            275                 280                 285
Cys Val Ala Gly Ser Thr Cys Thr Lys Ile Asn Asp Trp Tyr His Gln
            290                 295                 300
Cys Leu
305

<210> SEQ ID NO 18
<211> LENGTH: 316
<212> TYPE: PRT
<213> ORGANISM: Staphylotrichum coccosporum

<400> SEQUENCE: 18

Met Arg Ser Ser Pro Val Leu Arg Thr Ala Leu Ala Ala Ala Leu Pro
1               5                   10                  15
Leu Ala Ala Leu Ala Ala Asp Gly Lys Ser Thr Arg Tyr Trp Asp Cys
            20                  25                  30
Cys Lys Pro Ser Cys Ser Trp Pro Gly Lys Ala Ser Val Asn Gln Pro
            35                  40                  45
Val Phe Ala Cys Ser Ala Asn Phe Gln Arg Ile Ser Asp Pro Asn Val
        50                  55                  60
Lys Ser Gly Cys Asp Gly Gly Ser Ala Tyr Ala Cys Ala Asp Gln Thr
65                  70                  75                  80
```

```
Pro Trp Ala Val Asn Asp Asn Phe Ser Tyr Gly Phe Ala Ala Thr Ser
                85                  90                  95

Ile Ser Gly Gly Asn Glu Ala Ser Trp Cys Cys Gly Cys Tyr Glu Leu
            100                 105                 110

Thr Phe Thr Ser Gly Pro Val Ala Gly Lys Thr Met Val Val Gln Ser
            115                 120                 125

Thr Ser Thr Gly Gly Asp Leu Gly Thr Asn His Phe Asp Leu Ala Met
            130                 135                 140

Pro Gly Gly Gly Val Gly Ile Phe Asp Gly Cys Ser Pro Gln Phe Gly
145                 150                 155                 160

Gly Leu Ala Gly Asp Arg Tyr Gly Gly Val Ser Ser Arg Ser Gln Cys
                165                 170                 175

Asp Ser Phe Pro Ala Ala Leu Lys Pro Gly Cys Tyr Trp Arg Phe Asp
            180                 185                 190

Trp Phe Lys Asn Ala Asp Asn Pro Thr Phe Thr Phe Arg Gln Val Gln
            195                 200                 205

Cys Pro Ser Glu Leu Val Ala Arg Thr Gly Cys Arg Arg Asn Asp Asp
210                 215                 220

Gly Asn Phe Pro Val Phe Thr Pro Pro Ser Gly Gly Gln Ser Ser Ser
225                 230                 235                 240

Ser Ser Ser Ser Ser Ala Lys Pro Thr Ser Thr Ser Thr Ser Thr Thr
                245                 250                 255

Thr Ser Thr Lys Ala Thr Ser Thr Thr Ser Thr Ala Ser Ser Gln Thr
            260                 265                 270

Ser Ser Ser Thr Gly Gly Gly Cys Ala Ala Gln Arg Trp Ala Gln Cys
            275                 280                 285

Gly Gly Ile Gly Phe Ser Gly Cys Thr Thr Cys Val Ser Gly Thr Thr
            290                 295                 300

Cys Asn Lys Gln Asn Asp Trp Tyr Ser Gln Cys Leu
305                 310                 315

<210> SEQ ID NO 19
<211> LENGTH: 235
<212> TYPE: PRT
<213> ORGANISM: Melanocarpus albomyces

<400> SEQUENCE: 19

Met Arg Ser Thr Pro Val Leu Arg Ala Leu Leu Ala Ala Ala Leu Pro
1               5                   10                  15

Leu Gly Ala Leu Ala Ala Asn Gly Gln Ser Thr Arg Tyr Trp Asp Cys
            20                  25                  30

Cys Lys Pro Ser Cys Gly Trp Arg Gly Lys Gly Pro Val Asn Gln Pro
            35                  40                  45

Val Tyr Ser Cys Asp Ala Asn Phe Gln Arg Ile His Asp Phe Asp Ala
        50                  55                  60

Val Ser Gly Cys Glu Gly Gly Pro Ala Phe Ser Cys Ala Asp His Ser
65                  70                  75                  80

Pro Trp Ala Ile Asn Asp Asn Leu Ser Tyr Gly Phe Ala Ala Thr Ala
                85                  90                  95

Leu Ser Gly Gln Thr Glu Glu Ser Trp Cys Cys Ala Cys Tyr Ala Leu
            100                 105                 110

Thr Phe Thr Ser Gly Pro Val Ala Gly Lys Thr Met Val Val Gln Ser
            115                 120                 125

Thr Ser Thr Gly Gly Asp Leu Gly Ser Asn His Phe Asp Leu Asn Ile
            130                 135                 140
```

```
Pro Gly Gly Gly Val Gly Leu Phe Asp Gly Cys Thr Pro Gln Phe Gly
145                 150                 155                 160

Gly Leu Pro Gly Ala Arg Tyr Gly Gly Ile Ser Ser Arg Gln Glu Cys
                165                 170                 175

Asp Ser Phe Pro Glu Pro Leu Lys Pro Gly Cys Gln Trp Arg Phe Asp
            180                 185                 190

Trp Phe Gln Asn Ala Asp Asn Pro Ser Phe Thr Phe Glu Arg Val Gln
        195                 200                 205

Cys Pro Glu Glu Leu Val Ala Arg Thr Gly Cys Arg Arg His Asp Asp
    210                 215                 220

Gly Gly Phe Ala Val Phe Lys Ala Pro Ser Ala
225                 230                 235

<210> SEQ ID NO 20
<211> LENGTH: 302
<212> TYPE: PRT
<213> ORGANISM: Podospora anserina

<400> SEQUENCE: 20

Met Arg Ser Ser Thr Val Leu Gln Thr Ser Leu Leu Ala Val Leu Pro
1               5                   10                  15

Leu Ala Val Gln Ala Gln Gly Ala Ser Gly Ser Gly Lys Ser Thr Arg
            20                  25                  30

Tyr Trp Asp Cys Cys Lys Pro Ser Cys Ala Trp Pro Gly Lys Ala Ala
        35                  40                  45

Val Asn Arg Pro Val Phe Ala Cys Asp Ala Asn Phe Gln Arg Ile Ser
    50                  55                  60

Asp Ser Gly Val Ala Ser Gly Cys Asn Gly Gly Ser Ala Tyr Ser Cys
65                  70                  75                  80

Ala Asp His Ser Ala Trp Ala Ile Asn Asp Asn Leu Ser Tyr Gly Phe
                85                  90                  95

Ala Ala Thr Ala Leu Ser Gly Gly Ser Glu Ala Ser Trp Cys Cys Ala
            100                 105                 110

Cys Tyr Glu Leu Thr Phe Thr Asp Gly Pro Val Ala Gly Lys Lys Met
        115                 120                 125

Val Val Gln Ser Thr Ser Thr Gly Gly Asp Leu Gly Ser Asn His Phe
    130                 135                 140

Asp Leu Asn Ile Pro Gly Gly Gly Val Gly Leu Phe Asp Gly Cys Lys
145                 150                 155                 160

Pro Gln Phe Gly Gly Leu Pro Gly Ala Thr Tyr Gly Gly Ile Ser Asp
                165                 170                 175

Arg Ser Gln Cys Ala Ser Phe Pro Asp Ala Leu Lys Pro Gly Cys Asn
            180                 185                 190

Trp Arg Phe Asp Trp Phe Lys Asn Ala Asp Asn Pro Ser Phe Thr Phe
        195                 200                 205

Arg Gln Val Gln Cys Pro Ser Glu Leu Thr Ala Arg Ser Gly Cys Lys
    210                 215                 220

Arg Asp Asp Asp Ser Arg Phe Pro Val Phe Ser Pro Gly Gly Gly
225                 230                 235                 240

Ser Gln Pro Gln Pro Gln Pro Thr Ser Ser Ala Ala Gln Asn Pro Asn
                245                 250                 255

Pro Thr Pro Ser Ala Ala Pro Gly Gly Cys Arg Ala Ala Lys Tyr Ala
            260                 265                 270

Gln Cys Gly Gly Gln Gly Phe Thr Gly Cys Thr Thr Cys Glu Ala Gly
```

```
                275                 280                 285
Ser Thr Cys Thr Ala Ser Asn Gln Trp Tyr Ser Gln Cys Leu
    290                 295                 300

<210> SEQ ID NO 21
<211> LENGTH: 315
<212> TYPE: PRT
<213> ORGANISM: Acremonium thermophilum

<400> SEQUENCE: 21

Met Arg Ser Ser Pro Phe Leu Arg Ala Ala Leu Ala Ala Ala Leu Pro
1               5                   10                  15

Leu Ser Ala His Ala Leu Asp Gly Lys Ser Thr Arg Tyr Trp Asp Cys
            20                  25                  30

Cys Lys Pro Ser Cys Gly Trp Ala Gly Lys Ala Ser Val Asn Gln Pro
        35                  40                  45

Val Phe Ser Cys Ser Ala Asp Trp Gln Arg Ile Ser Asp Phe Asn Ala
    50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
    210                 215                 220

Ala Ser Tyr Pro Val Phe Asn Pro Pro Ser Val Pro Gly Leu Asp Gly
225                 230                 235                 240

Ser Asn Pro Gly Asn Pro Thr Thr Thr Val Pro Pro Ala Ser Thr
                245                 250                 255

Ser Thr Ser Arg Pro Thr Ser Ser Thr Ser Pro Val Ser Thr Pro
            260                 265                 270

Thr Gly Gln Pro Gly Gly Cys Thr Thr Gln Lys Trp Gly Gln Cys Gly
        275                 280                 285

Gly Ile Gly Tyr Thr Gly Cys Thr Asn Cys Val Ala Gly Thr Thr Cys
    290                 295                 300

Thr Gln Leu Asn Pro Trp Tyr Ser Gln Cys Leu
305                 310                 315

<210> SEQ ID NO 22
<211> LENGTH: 299
<212> TYPE: PRT
<213> ORGANISM: Thielavia terrestris
```

<400> SEQUENCE: 22

```
Met Arg Ser Thr Pro Val Leu Arg Thr Thr Leu Ala Ala Ala Leu Pro
1               5                   10                  15

Leu Val Ala Ser Ala Ala Ser Gly Ser Gly Gln Ser Thr Arg Tyr Trp
            20                  25                  30

Asp Cys Cys Lys Pro Ser Cys Ala Trp Pro Gly Lys Ala Ala Val Ser
                35                  40                  45

Gln Pro Val Tyr Ala Cys Asp Ala Asn Phe Gln Arg Leu Ser Asp Phe
    50                  55                  60

Asn Val Gln Ser Gly Cys Asn Gly Gly Ser Ala Tyr Ser Cys Ala Asp
65                  70                  75                  80

Gln Thr Pro Trp Ala Val Asn Asp Asn Leu Ala Tyr Gly Phe Ala Ala
                85                  90                  95

Thr Ser Ile Ala Gly Gly Ser Glu Ser Ser Trp Cys Cys Ala Cys Tyr
            100                 105                 110

Ala Leu Thr Phe Thr Ser Gly Pro Val Ala Gly Lys Thr Met Val Val
                115                 120                 125

Gln Ser Thr Ser Thr Gly Gly Asp Leu Gly Ser Asn Gln Phe Asp Ile
    130                 135                 140

Ala Met Pro Gly Gly Gly Val Gly Ile Phe Asn Gly Cys Ser Ser Gln
145                 150                 155                 160

Phe Gly Gly Leu Pro Gly Ala Gln Tyr Gly Gly Ile Ser Ser Arg Asp
                165                 170                 175

Gln Cys Asp Ser Phe Pro Ala Pro Leu Lys Pro Gly Cys Gln Trp Arg
            180                 185                 190

Phe Asp Trp Phe Gln Asn Ala Asp Asn Pro Thr Phe Thr Phe Gln Gln
                195                 200                 205

Val Gln Cys Pro Ala Glu Ile Val Ala Arg Ser Gly Cys Lys Arg Asn
    210                 215                 220

Asp Asp Ser Ser Phe Pro Val Phe Thr Pro Pro Ser Gly Gly Asn Gly
225                 230                 235                 240

Gly Thr Gly Thr Pro Thr Ser Thr Ala Pro Gly Ser Gly Gln Thr Ser
                245                 250                 255

Pro Gly Gly Gly Ser Gly Cys Thr Ser Gln Lys Trp Ala Gln Cys Gly
            260                 265                 270

Gly Ile Gly Phe Ser Gly Cys Thr Thr Cys Val Ser Gly Thr Thr Cys
                275                 280                 285

Gln Lys Leu Asn Asp Tyr Tyr Ser Gln Cys Leu
    290                 295
```

<210> SEQ ID NO 23
<211> LENGTH: 307
<212> TYPE: PRT
<213> ORGANISM: Trichothecium roseum

<400> SEQUENCE: 23

```
Pro Phe Met Met Val Ala Trp Trp Ser Leu Phe Leu Tyr Gly Leu Gln
1               5                   10                  15

Val Ala Ala Pro Ala Phe Ala Asp Gly Arg Ser Thr Arg Tyr Trp
            20                  25                  30

Asp Cys Cys Lys Pro Ser Cys Ser Trp Pro Asp Lys Ala Pro Val Gly
                35                  40                  45

Ser Pro Val Gly Thr Cys Asp Ala Gly Asn Ser Pro Leu Gly Asp Pro
    50                  55                  60
```

```
Leu Ala Lys Ser Gly Cys Glu Gly Gly Pro Ser Tyr Thr Cys Ala Asn
 65                  70                  75                  80

Tyr Gln Pro Trp Ala Val Asn Asp Gln Leu Ala Tyr Gly Phe Ala Ala
                 85                  90                  95

Thr Ala Ile Asn Gly Gly Thr Glu Asp Ser Trp Cys Cys Ala Cys Tyr
            100                 105                 110

Lys Leu Thr Phe Thr Asp Gly Pro Ala Ser Gly Lys Thr Met Ile Val
        115                 120                 125

Gln Ser Thr Asn Thr Gly Gly Asp Leu Ser Asp Asn His Phe Asp Leu
130                 135                 140

Leu Ile Pro Gly Gly Gly Val Gly Ile Phe Asp Gly Cys Thr Ser Gln
145                 150                 155                 160

Tyr Gly Gln Ala Leu Pro Gly Ala Gln Tyr Gly Gly Val Ser Ser Arg
                165                 170                 175

Ala Glu Cys Asp Gln Met Pro Glu Ala Ile Lys Ala Gly Cys Gln Trp
            180                 185                 190

Arg Tyr Asp Trp Phe Lys Asn Ala Asp Asn Pro Ser Phe Ser Phe Arg
        195                 200                 205

Gln Val Gln Cys Pro Ala Glu Leu Val Ala Arg Thr Gly Cys Arg Arg
210                 215                 220

Asn Asp Asp Gly Asn Phe Pro Ala Val Gln Ile Pro Ser Ser Ser Thr
225                 230                 235                 240

Ser Ser Pro Val Asn Gln Pro Thr Ser Thr Ser Thr Ser Thr Thr Ser
                245                 250                 255

Thr Thr Ser Ser Pro Pro Val Gln Pro Thr Thr Pro Ser Gly Cys Thr
            260                 265                 270

Ala Glu Arg Trp Ala Gln Cys Gly Gly Asn Gly Trp Ser Gly Cys Thr
        275                 280                 285

Thr Cys Val Ala Gly Ser Thr Cys Thr Lys Ile Asn Asp Trp Tyr His
290                 295                 300

Gln Cys Leu
305

<210> SEQ ID NO 24
<211> LENGTH: 297
<212> TYPE: PRT
<213> ORGANISM: Acremonium thermophilum

<400> SEQUENCE: 24

Met Arg Ser Ser Pro Phe Leu Arg Ala Ala Leu Ala Ala Ala Leu Pro
  1               5                  10                  15

Leu Ser Ala His Ala Leu Asp Gly Lys Ser Thr Arg Tyr Trp Asp Cys
                 20                  25                  30

Cys Lys Pro Ser Cys Gly Trp Pro Gly Lys Ala Ser Val Asn Gln Pro
             35                  40                  45

Val Phe Ser Cys Ser Ala Asp Trp Gln Arg Ile Ser Asp Phe Asn Ala
         50                  55                  60

Lys Ser Gly Cys Asp Gly Gly Ser Ala Tyr Ser Cys Ala Asp Gln Thr
 65                  70                  75                  80

Pro Trp Ala Val Asn Asp Asn Phe Ser Tyr Gly Phe Ala Ala Thr Ala
                 85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125
```

```
Thr Ser Thr Gly Gly Asp Leu Gly Ser Asn Gln Phe Asp Leu Ala Ile
            130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
210                 215                 220

Ala Ser Tyr Pro Val Phe Asn Pro Pro Ser Gly Gly Ser Pro Ser Thr
225                 230                 235                 240

Thr Ser Thr Thr Thr Ser Ser Pro Ser Gly Pro Thr Gly Asn Pro Pro
                245                 250                 255

Gly Gly Gly Gly Cys Thr Ala Gln Lys Trp Ala Gln Cys Gly Gly Thr
                260                 265                 270

Gly Phe Thr Gly Cys Thr Thr Cys Val Ser Gly Thr Thr Cys Gln Val
            275                 280                 285

Gln Asn Gln Trp Tyr Ser Gln Cys Leu
    290                 295

<210> SEQ ID NO 25
<211> LENGTH: 308
<212> TYPE: PRT
<213> ORGANISM: Fusarium anguioides

<400> SEQUENCE: 25

Pro Phe Met Met Val Ala Trp Trp Ser Leu Phe Leu Tyr Gly Leu Gln
1               5                   10                  15

Val Ala Ala Pro Ala Phe Ala Ala Asp Gly Arg Ser Thr Arg Tyr Trp
            20                  25                  30

Asp Cys Cys Lys Pro Ser Cys Ser Trp Gly Gly Lys Ala Ala Val Ser
            35                  40                  45

Ala Pro Ala Leu Thr Cys Asp Lys Lys Asp Asn Pro Ile Ser Asn Leu
50                  55                  60

Asn Ala Val Asn Gly Cys Glu Gly Gly Gly Ser Ala Phe Ala Cys Thr
65                  70                  75                  80

Asn Tyr Ser Pro Trp Ala Val Asn Asp Asn Leu Ala Tyr Gly Phe Ala
                85                  90                  95

Ala Thr Lys Leu Ala Gly Gly Ser Glu Gly Ser Trp Cys Cys Ala Cys
            100                 105                 110

Tyr Ala Leu Thr Phe Thr Thr Gly Pro Val Lys Gly Lys Thr Met Val
        115                 120                 125

Val Gln Ser Thr Asn Thr Gly Gly Asp Leu Gly Asp Asn His Phe Asp
130                 135                 140

Leu Met Met Pro Gly Gly Gly Val Gly Ile Phe Asp Gly Cys Thr Ser
145                 150                 155                 160

Gln Phe Gly Lys Ala Leu Gly Gly Ala Gln Tyr Gly Gly Ile Ser Ser
                165                 170                 175

Arg Ser Glu Cys Asp Ser Phe Pro Glu Thr Leu Lys Asp Gly Cys His
            180                 185                 190

Trp Arg Phe Asp Trp Phe Lys Asn Ala Asp Asn Pro Ser Phe Ser Phe
```

```
                    195                 200                 205
Arg Gln Val Gln Cys Pro Ala Glu Leu Val Ala Arg Thr Gly Cys Arg
210                 215                 220

Arg Asn Asp Asp Gly Asn Phe Pro Ala Val Gln Ile Pro Ser Ser Ser
225                 230                 235                 240

Thr Ser Ser Pro Val Asn Gln Pro Thr Ser Thr Ser Thr Thr Ser Thr
                    245                 250                 255

Ser Thr Thr Ser Ser Pro Pro Val Gln Pro Thr Thr Pro Ser Gly Cys
                260                 265                 270

Thr Ala Glu Arg Trp Ala Gln Cys Gly Gly Asn Gly Trp Ser Gly Cys
            275                 280                 285

Thr Thr Cys Val Ala Gly Ser Thr Cys Thr Lys Ile Asn Asp Trp Tyr
        290                 295                 300

His Gln Cys Leu
305

<210> SEQ ID NO 26
<211> LENGTH: 304
<212> TYPE: PRT
<213> ORGANISM: Clonostachys rosea f. catenulata

<400> SEQUENCE: 26

Met Met Val Ala Trp Trp Ser Leu Phe Leu Tyr Gly Leu Gln Val Ala
1               5                   10                  15

Ala Pro Ala Phe Ala Ala Asp Gly Arg Ser Thr Arg Tyr Trp Asp Cys
                20                  25                  30

Cys Lys Pro Ser Cys Ala Trp Ser Gly Lys Ala Ser Val Ser Ser Pro
            35                  40                  45

Val Arg Thr Cys Asp Ala Asn Asn Ser Pro Leu Ser Asp Val Asp Ala
        50                  55                  60

Lys Ser Ala Cys Asp Gly Gly Val Ala Tyr Thr Cys Ser Asn Asn Ala
65                  70                  75                  80

Pro Trp Ala Val Asn Asp Asn Leu Ser Tyr Gly Phe Ala Ala Thr Ala
                85                  90                  95

Ile Asn Gly Gly Ser Glu Ser Ser Trp Cys Cys Ala Cys Tyr Lys Leu
            100                 105                 110

Thr Phe Thr Ser Gly Pro Ala Ser Gly Lys Val Met Val Val Gln Ser
        115                 120                 125

Thr Asn Thr Gly Tyr Asp Leu Ser Asn Asn His Phe Asp Ile Leu Met
130                 135                 140

Pro Gly Gly Gly Val Gly Ala Phe Asp Gly Cys Ser Arg Gln Tyr Gly
145                 150                 155                 160

Ser Ile Pro Gly Glu Arg Tyr Gly Gly Val Thr Ser Arg Asp Gln Cys
                165                 170                 175

Asp Gln Met Pro Ser Ala Leu Lys Gln Gly Cys Tyr Trp Arg Phe Asp
            180                 185                 190

Trp Phe Lys Asn Ala Asp Asn Pro Ser Phe Ser Phe Arg Gln Val Gln
        195                 200                 205

Cys Pro Ala Glu Leu Val Ala Arg Thr Gly Cys Arg Arg Asn Asp Asp
210                 215                 220

Gly Asn Phe Pro Ala Val Gln Ile Pro Ser Ser Ser Thr Ser Ser Pro
225                 230                 235                 240

Val Asn Gln Pro Thr Ser Thr Ser Thr Thr Ser Thr Thr Ser
                245                 250                 255
```

```
Ser Pro Pro Val Gln Pro Thr Thr Pro Ser Gly Cys Thr Ala Glu Arg
            260                 265                 270

Trp Ala Gln Cys Gly Gly Asn Gly Trp Ser Gly Cys Thr Thr Cys Val
            275                 280                 285

Ala Gly Ser Thr Cys Thr Lys Ile Asn Asp Trp Tyr His Gln Cys Leu
            290                 295                 300

<210> SEQ ID NO 27
<211> LENGTH: 293
<212> TYPE: PRT
<213> ORGANISM: Neurospora crassa

<400> SEQUENCE: 27

Met Arg Ser Ser Thr Ile Leu Gln Thr Gly Leu Val Ala Ala Leu Pro
1               5                   10                  15

Phe Ala Val Gln Ala Ala Ser Gly Ser Gly Gln Ser Thr Arg Tyr Trp
            20                  25                  30

Asp Cys Cys Lys Pro Ser Cys Ser Trp Ser Gly Lys Ala Pro Val Asn
            35                  40                  45

Arg Pro Val Leu Ala Cys Asp Ala Asn Asn Asn Pro Leu Ser Asp Ala
    50                  55                  60

Ser Val Lys Ser Gly Cys Asp Gly Gly Ser Ala Tyr Thr Cys Ala Asn
65                  70                  75                  80

Asn Ser Pro Trp Ala Val Asn Asp Gln Leu Ser Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ala Gly Lys Thr Leu Val Val
            115                 120                 125

Gln Ser Thr Ser Thr Gly Gly Asp Leu Gly Ser Asn His Phe Asp Ile
        130                 135                 140

Asn Met Pro Gly Gly Gly Val Gly Leu Phe Asp Gly Cys Lys Arg Gln
145                 150                 155                 160

Phe Gly Gly Leu Pro Gly Ala Gln Tyr Gly Gly Ile Ser Ser Arg Ser
                165                 170                 175

Gln Cys Asp Ser Phe Pro Ala Ala Leu Lys Pro Gly Cys Gln Trp Arg
            180                 185                 190

Phe Asp Trp Phe Gln Asn Ala Asp Asn Pro Asn Phe Thr Phe Lys Gln
            195                 200                 205

Val Gln Cys Pro Ser Glu Leu Thr Ser Arg Thr Gly Cys Lys Arg Asn
        210                 215                 220

Asp Asp Ser Gln Phe Pro Val Phe Thr Pro Pro Ser Gly Gly Gly Ser
225                 230                 235                 240

Asn Pro Ser Thr Pro Thr Pro Pro Ser Ser Gly Gly Gly Ser Gly
                245                 250                 255

Cys Thr Ala Asp Lys Tyr Ala Gln Cys Gly Gly Ser Gly Trp Ser Gly
            260                 265                 270

Cys Thr Asn Cys Pro Ser Gly Ser Thr Cys Lys Thr Ile Asn Asp Tyr
            275                 280                 285

Tyr His Gln Cys Ala
        290

<210> SEQ ID NO 28
<211> LENGTH: 310
<212> TYPE: PRT
<213> ORGANISM: Volutella colletotrichoides
```

-continued

```
<400> SEQUENCE: 28

Met Arg Ser Ser Ala Val Leu Ile Gly Leu Val Ala Gly Val Ala Ala
1               5                   10                  15

Gln Ser Ser Gly Thr Gly Arg Thr Thr Arg Tyr Trp Asp Cys Cys Lys
            20                  25                  30

Pro Ser Cys Gly Trp Asp Glu Lys Ala Ser Val Ser Gln Pro Val Lys
        35                  40                  45

Thr Cys Asp Arg Asn Asn Asn Pro Leu Ala Ser Thr Ala Arg Ser Gly
    50                  55                  60

Cys Asp Ser Asn Gly Val Ala Tyr Thr Cys Asn Asp Asn Gln Pro Trp
65                  70                  75                  80

Ala Val Asn Asp Asn Leu Ala Tyr Gly Phe Ala Ala Thr Ala Phe Ser
                85                  90                  95

Gly Gly Ser Glu Ala Ser Trp Cys Cys Ala Cys Tyr Ala Leu Gln Phe
            100                 105                 110

Thr Ser Gly Pro Val Ala Gly Lys Thr Met Val Val Gln Ser Thr Asn
        115                 120                 125

Thr Gly Gly Asp Leu Ser Gly Asn His Phe Asp Ile Leu Met Pro Gly
    130                 135                 140

Gly Gly Leu Gly Ile Phe Asp Gly Cys Thr Pro Gln Trp Gly Val Ser
145                 150                 155                 160

Phe Pro Gly Asn Arg Tyr Gly Gly Thr Thr Ser Arg Ser Gln Cys Ser
                165                 170                 175

Gln Ile Pro Ser Ala Leu Gln Pro Gly Cys Asn Trp Arg Tyr Asp Trp
            180                 185                 190

Phe Asn Asp Ala Asp Asn Pro Asp Val Ser Trp Arg Arg Val Gln Cys
        195                 200                 205

Pro Ala Ala Leu Thr Asp Arg Thr Gly Cys Arg Arg Ser Asp Asp Gly
    210                 215                 220

Asn Tyr Pro Val Phe Gln Pro Gly Pro Pro Ala Thr Thr Ile Arg
225                 230                 235                 240

Thr Ser Thr Thr Ile Thr Ala Ser Ser Ser Ser Ser Ser Ser Ser Ser
                245                 250                 255

Ser Thr Thr Ala Gly Ser Pro Val Pro Thr Gly Gly Ser Gly
            260                 265                 270

Pro Thr Ser Pro Val Trp Gly Gln Cys Gly Gly Gln Gly Trp Ser Gly
        275                 280                 285

Pro Thr Arg Cys Val Ala Gly Ser Thr Cys Ser Val Val Asn Pro Trp
    290                 295                 300

Tyr Ser Gln Cys Phe Pro
305                 310

<210> SEQ ID NO 29
<211> LENGTH: 355
<212> TYPE: PRT
<213> ORGANISM: Gibberella zeae

<400> SEQUENCE: 29

Met Arg Ser Phe Ala Leu Leu Ala Leu Phe Gly Pro Leu Ala Val Ser
1               5                   10                  15

Ala Ala Ser Gly Ser Gly His Ser Thr Arg Tyr Trp Asp Cys Cys Lys
            20                  25                  30

Pro Ser Cys Ser Trp Ser Gly Lys Ala Lys Val Ser Ala Pro Ala Leu
        35                  40                  45
```

```
Thr Cys Asp Lys Lys Asp Asn Pro Ile Thr Asn Leu Asn Ala Val Asn
     50                  55                  60

Gly Cys Glu Ser Gly Gly Ser Ala Phe Ala Cys Thr Asn Tyr Ser Pro
 65                  70                  75                  80

Trp Ala Val Asn Asp Asp Leu Ala Tyr Gly Phe Thr Ala Thr Lys Leu
                 85                  90                  95

Ala Gly Gly Thr Glu Ala Ser Trp Cys Cys Ala Cys Tyr Ala Leu Thr
                100                 105                 110

Phe Thr Thr Gly Pro Val Lys Gly Lys Lys Met Ile Val Gln Ser Thr
            115                 120                 125

Asn Thr Gly Gly Asp Leu Gly Asp Asn His Phe Asp Leu Met Met Pro
    130                 135                 140

Gly Gly Gly Val Gly Ile Phe Asp Gly Cys Thr Ser Glu Phe Gly Lys
145                 150                 155                 160

Pro Leu Gly Gly Ala Gln Tyr Gly Gly Ile Ser Ser Arg Ser Gln Cys
                165                 170                 175

Asp Ser Phe Pro Glu Leu Leu Lys Asp Gly Cys His Trp Arg Phe Asp
            180                 185                 190

Trp Phe Lys Asn Ala Asp Asn Pro Asp Phe Thr Phe Glu Gln Val Gln
        195                 200                 205

Cys Pro Lys Glu Leu Leu Ala Ile Ser Gly Cys Lys Arg Asp Asp Asp
210                 215                 220

Ser Ser Phe Pro Ala Phe Lys Gly Asn Thr Thr Pro Ser Asn Ala Lys
225                 230                 235                 240

Pro Ser Gly Glu Lys Ser Ala Ala Ala Gln Pro Gln Lys Pro Ser
                245                 250                 255

Thr Lys Ala Ala Thr Glu Pro Ile Ala Thr Lys Pro Ala Thr Val Lys
            260                 265                 270

Pro Ala Pro Val Lys Pro Thr Lys Val Val Asn Lys Pro Lys Thr Ala
        275                 280                 285

Ser Lys Val Gly Gly Thr Lys Thr Arg Gly Lys Cys Pro Ala Thr Lys
    290                 295                 300

Pro Thr Lys Pro Ala Ala Pro Gln Lys Ser Ala Val Ala Ile Tyr His
305                 310                 315                 320

Gln Cys Gly Gly Ser Lys Ser Ala Tyr Pro Asp Gly Ser Leu Ser Cys
                325                 330                 335

Ala Ser Gly Ser Lys Cys Val Lys Met Asn Asp Tyr Tyr Ser Gln Cys
            340                 345                 350

Val Pro Asn
    355

<210> SEQ ID NO 30
<211> LENGTH: 376
<212> TYPE: PRT
<213> ORGANISM: Fusarium oxysporum

<400> SEQUENCE: 30

Met Arg Ser Tyr Thr Leu Leu Ala Leu Ala Gly Pro Leu Ala Val Ser
1               5                   10                  15

Ala Ala Ser Gly Ser Gly His Ser Thr Arg Tyr Trp Asp Cys Cys Lys
                20                  25                  30

Pro Ser Cys Ser Trp Ser Gly Lys Ala Ala Val Asn Ala Pro Ala Leu
            35                  40                  45

Thr Cys Asp Lys Asn Asp Asn Pro Ile Ser Asn Thr Asn Ala Val Asn
```

```
               50                  55                  60
Gly Cys Glu Gly Gly Ser Ala Tyr Ala Cys Thr Asn Tyr Ser Pro
 65                  70                  75                  80

Trp Ala Val Asn Asp Glu Leu Ala Tyr Gly Phe Ala Ala Thr Lys Ile
                 85                  90                  95

Ser Gly Gly Ser Glu Ala Ser Trp Cys Cys Ala Cys Tyr Ala Leu Thr
                100                 105                 110

Phe Thr Thr Gly Pro Val Lys Gly Lys Met Ile Val Gln Ser Thr
                115                 120                 125

Asn Thr Gly Gly Asp Leu Gly Asp Asn His Phe Asp Leu Met Met Pro
                130                 135                 140

Gly Gly Gly Val Gly Ile Phe Asp Gly Cys Thr Ser Glu Phe Gly Lys
145                 150                 155                 160

Ala Leu Gly Gly Ala Gln Tyr Gly Gly Ile Ser Ser Arg Ser Glu Cys
                165                 170                 175

Asp Ser Tyr Pro Glu Leu Leu Lys Asp Gly Cys His Trp Arg Phe Asp
                180                 185                 190

Trp Phe Glu Asn Ala Asp Asn Pro Asp Phe Thr Phe Glu Gln Val Gln
                195                 200                 205

Cys Pro Lys Ala Leu Leu Asp Ile Ser Gly Cys Lys Arg Asp Asp
 210                 215                 220

Ser Ser Phe Pro Ala Phe Lys Gly Asp Thr Ser Ala Ser Lys Pro Gln
225                 230                 235                 240

Pro Ser Ser Ser Ala Lys Lys Thr Thr Ser Ala Ala Ala Ala Gln
                245                 250                 255

Pro Gln Lys Thr Lys Asp Ser Ala Pro Val Val Gln Lys Ser Ser Thr
                260                 265                 270

Lys Pro Ala Ala Gln Pro Glu Pro Thr Lys Pro Ala Asp Lys Pro Gln
                275                 280                 285

Thr Asp Lys Pro Val Ala Thr Lys Pro Ala Ala Thr Lys Pro Ala Gln
                290                 295                 300

Pro Val Asn Lys Pro Lys Thr Thr Gln Lys Val Arg Gly Thr Lys Thr
305                 310                 315                 320

Arg Gly Ser Cys Pro Ala Lys Thr Asp Ala Thr Ala Lys Ala Ser Val
                325                 330                 335

Val Pro Ala Tyr Tyr Gln Cys Gly Gly Ser Lys Ser Ala Tyr Pro Asn
                340                 345                 350

Gly Asn Leu Ala Cys Ala Thr Gly Ser Lys Cys Val Lys Gln Asn Glu
                355                 360                 365

Tyr Tyr Ser Gln Cys Val Pro Asn
                370                 375

<210> SEQ ID NO 31
<211> LENGTH: 349
<212> TYPE: PRT
<213> ORGANISM: Acremonium sp.

<400> SEQUENCE: 31

Met Ile Ser Ala Trp Ile Leu Leu Gly Leu Val Gly Ala Val Pro Ser
  1               5                  10                  15

Ser Val Met Ala Ala Ser Gly Lys Gly His Thr Thr Arg Tyr Trp Asp
                 20                  25                  30

Cys Cys Lys Thr Ser Cys Ala Trp Glu Gly Lys Ala Ser Val Ser Glu
                 35                  40                  45
```

```
Pro Val Leu Thr Cys Asn Lys Gln Asp Asn Pro Ile Val Asp Ala Asn
    50                  55                  60

Ala Arg Ser Gly Cys Asp Gly Gly Ala Phe Ala Cys Thr Asn Asn
65                  70                  75                  80

Ser Pro Trp Ala Val Ser Glu Asp Leu Ala Tyr Gly Phe Ala Ala Thr
                85                  90                  95

Ala Leu Ser Gly Gly Thr Glu Gly Ser Trp Cys Cys Ala Cys Tyr Ala
                100                 105                 110

Ile Thr Phe Thr Ser Gly Pro Val Ala Gly Lys Lys Met Val Val Gln
                115                 120                 125

Ser Thr Asn Thr Gly Gly Asp Leu Ser Asn Asn His Phe Asp Leu Met
    130                 135                 140

Ile Pro Gly Gly Gly Leu Gly Ile Phe Asp Gly Cys Ser Ala Gln Phe
145                 150                 155                 160

Gly Gln Leu Leu Pro Gly Glu Arg Tyr Gly Gly Val Ser Ser Arg Ser
                165                 170                 175

Gln Cys Asp Gly Met Pro Glu Leu Leu Lys Asp Gly Cys Gln Trp Arg
                180                 185                 190

Phe Asp Trp Phe Lys Asn Ser Asp Asn Pro Asp Ile Glu Phe Glu Gln
                195                 200                 205

Val Gln Cys Pro Lys Glu Leu Ile Ala Val Ser Gly Cys Val Arg Asp
    210                 215                 220

Asp Asp Ser Ser Phe Pro Val Phe Gln Gly Ser Gly Ser Gly Asp Val
225                 230                 235                 240

Asn Pro Pro Pro Lys Pro Thr Thr Thr Thr Ser Ser Lys Pro Lys
                245                 250                 255

Thr Thr Ser Ala Pro Ser Thr Leu Ser Asn Pro Ser Ala Pro Gln Gln
                260                 265                 270

Pro Gly Asn Thr Asp Arg Pro Ala Glu Thr Thr Thr Lys Leu Pro
                275                 280                 285

Ala Leu Pro Ala Thr Thr Ser Ser Pro Ala Val Ser Val Pro Ser Ser
                290                 295                 300

Ser Ala Arg Val Pro Leu Trp Gly Gln Cys Asp Ser Glu Ala Ser Trp
305                 310                 315                 320

Asp Ala Pro Lys Lys Cys Ala Lys Gly Thr Lys Cys Val Tyr Val Asn
                325                 330                 335

Asp Trp Tyr Ser Gln Cys Gln Pro Lys Asn Ser Cys Ala
                340                 345

<210> SEQ ID NO 32
<211> LENGTH: 295
<212> TYPE: PRT
<213> ORGANISM: Acremonium sp.

<400> SEQUENCE: 32

Met Arg Ser Thr Ser Ile Leu Ile Gly Leu Val Ala Gly Val Ala Ala
1               5                   10                  15

Gln Ser Ser Gly Ser Gly His Thr Thr Arg Tyr Trp Asp Cys Cys Lys
                20                  25                  30

Pro Ser Cys Ala Trp Asp Glu Lys Ala Ala Val Ser Arg Pro Val Thr
                35                  40                  45

Thr Cys Asp Arg Asn Asn Ser Pro Leu Ser Pro Gly Ala Val Ser Gly
    50                  55                  60

Cys Asp Pro Asn Gly Val Ala Phe Thr Cys Asn Asp Asn Gln Pro Trp
65                  70                  75                  80
```

Ala Val Asn Asn Asn Val Ala Tyr Gly Phe Ala Ala Thr Ala Phe Pro
                85                  90                  95

Gly Gly Asn Glu Ala Ser Trp Cys Cys Ala Cys Tyr Ala Leu Gln Phe
            100                 105                 110

Thr Ser Gly Pro Val Ala Gly Lys Thr Met Val Val Gln Ser Thr Asn
        115                 120                 125

Thr Gly Gly Asp Leu Ser Gly Thr His Phe Asp Ile Gln Met Pro Gly
    130                 135                 140

Gly Gly Leu Gly Ile Phe Asp Gly Cys Thr Pro Gln Phe Gly Phe Thr
145                 150                 155                 160

Phe Pro Gly Asn Arg Tyr Gly Gly Thr Thr Ser Arg Ser Gln Cys Ala
                165                 170                 175

Glu Leu Pro Ser Val Leu Arg Asp Gly Cys His Trp Arg Tyr Asp Trp
            180                 185                 190

Phe Asn Asp Ala Asp Asn Pro Asn Val Asn Trp Arg Arg Val Arg Cys
        195                 200                 205

Pro Ala Ala Leu Thr Asn Arg Ser Gly Cys Val Arg Asn Asp Asp Asn
    210                 215                 220

Ser Tyr Pro Val Phe Glu Pro Gly Thr Gly Thr Pro Thr Pro Thr
225                 230                 235                 240

Thr Thr Thr Thr Ser Ser Pro Pro Gln Pro Thr Asn Gly Gly Gly Gly
                245                 250                 255

Gly Thr Ser Pro His Trp Gly Gln Cys Gly Gly Gln Gly Trp Ser Gly
            260                 265                 270

Pro Thr Ala Cys Ala Gly Gly Ser Thr Cys Asn Leu Ile Asn Pro Trp
        275                 280                 285

Tyr Ser Gln Cys Ile Pro Asn
    290                 295

<210> SEQ ID NO 33
<211> LENGTH: 225
<212> TYPE: PRT
<213> ORGANISM: Chrysosporium lucknowense

<400> SEQUENCE: 33

Met His Leu Ser Ala Thr Thr Gly Phe Leu Ala Leu Pro Ala Leu Ala
1               5                   10                  15

Leu Ala Gln Leu Ser Gly Ser Gly Gln Thr Thr Arg Tyr Trp Asp Cys
                20                  25                  30

Cys Lys Pro Ser Cys Ala Trp Pro Gly Lys Gly Pro Ser Ser Pro Val
            35                  40                  45

Gln Ala Cys Asp Lys Asn Asp Asn Pro Leu Asn Asp Gly Gly Ser Thr
        50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr

```
                145                 150                 155                 160
Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
                180                 185                 190

Trp Arg Phe Asp Trp Phe Gln Asn Ala Asp Asn Pro Ser Val Thr Phe
                195                 200                 205

Gln Glu Val Ala Cys Pro Ser Glu Leu Thr Ser Lys Ser Gly Cys Ser
            210                 215                 220

Arg
225

<210> SEQ ID NO 34
<211> LENGTH: 225
<212> TYPE: PRT
<213> ORGANISM: Thielavia heterothallica

<400> SEQUENCE: 34

Met His Leu Ser Ala Thr Thr Gly Phe Leu Ala Leu Pro Val Leu Ala
1               5                   10                  15

Leu Asp Gln Leu Ser Gly Ile Gly Gln Thr Thr Arg Tyr Trp Asp Cys
            20                  25                  30

Cys Lys Pro Ser Cys Ala Trp Pro Gly Lys Gly Pro Ser Ser Pro Val
        35                  40                  45

Gln Ala Cys Asp Lys Asn Asp Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225

<210> SEQ ID NO 35
<211> LENGTH: 338
<212> TYPE: PRT
<213> ORGANISM: Mucor circinelloides

<400> SEQUENCE: 35

Met Lys Phe Thr Val Ala Ile Thr Ser Ile Ala Val Ala Leu Ala Leu
```

```
  1               5                  10                 15
Ser Ser Ser Ala Glu Ala Ala Ser Cys Ser Ser Val Tyr Gly Gln Cys
                20                  25                 30

Gly Gly Ile Gly Trp Ser Gly Pro Thr Cys Cys Glu Ser Gly Ser Thr
                35                  40                 45

Cys Val Ala Gln Glu Gly Asn Lys Tyr Tyr Ser Gln Cys Leu Pro Gly
 50                 55                  60

Ser His Ser Asn Asn Ala Gly Asn Ala Ser Ser Thr Lys Lys Thr Ser
 65                 70                  75                 80

Thr Lys Thr Ser Thr Thr Thr Ala Lys Ala Thr Ala Val Thr Thr
                85                  90                 95

Lys Thr Val Thr Lys Thr Thr Lys Thr Thr Thr Lys Thr Ser Thr
                100                 105                110

Thr Ala Ala Ala Ser Thr Ser Thr Ser Ser Ser Ala Gly Tyr Lys Val
                115                 120                125

Ile Ser Gly Gly Lys Ser Gly Ser Gly Ser Thr Thr Arg Tyr Trp Asp
130                 135                 140

Cys Cys Lys Ala Ser Cys Ser Trp Pro Gly Lys Ala Ser Val Thr Gly
145                 150                 155                160

Pro Val Asp Thr Cys Ala Ser Asn Gly Ile Ser Leu Leu Asp Ala Asn
                165                 170                175

Ala Gln Ser Gly Cys Asn Gly Gly Asn Gly Phe Met Cys Asn Asn Asn
                180                 185                 190

Gln Pro Trp Ala Val Asn Asp Glu Leu Ala Tyr Gly Phe Ala Ala Ala
                195                 200                205

Ser Ile Ala Gly Ser Asn Glu Ala Gly Trp Cys Cys Gly Cys Tyr Glu
210                 215                 220

Leu Thr Phe Thr Ser Gly Ala Ala Ser Gly Lys Lys Met Val Val Gln
225                 230                 235                240

Val Thr Asn Thr Gly Gly Asp Leu Gly Ser Asn His Phe Asp Leu Gln
                245                 250                255

Met Pro Gly Gly Gly Val Gly Ile Phe Asn Gly Cys Ala Ala Gln Trp
                260                 265                 270

Gly Ala Pro Asn Asp Gly Trp Gly Ala Arg Tyr Gly Gly Val Ser Ser
                275                 280                285

Val Ser Asp Cys Ala Ser Leu Pro Ser Ala Leu Gln Ala Gly Cys Lys
                290                 295                 300

Trp Arg Phe Asn Trp Phe Lys Asn Ser Asp Asn Pro Thr Met Thr Phe
305                 310                 315                320

Lys Glu Val Thr Cys Pro Ala Glu Leu Thr Thr Arg Ser Gly Cys Glu
                325                 330                 335

Arg Lys

<210> SEQ ID NO 36
<211> LENGTH: 220
<212> TYPE: PRT
<213> ORGANISM: Reticulitermes speratus hindgut protist

<400> SEQUENCE: 36

Met Leu Val Phe Val Phe Ser Leu Leu Ala Ser Val Leu Phe Gly Asp
  1               5                  10                 15

Ser Gly Lys Thr Thr Arg Tyr Trp Asp Cys Cys Lys Gly Ser Cys Gly
                20                  25                 30

Trp Glu Ala Lys Ala Asp Val Ser Lys Pro Ile Asp Thr Cys Ala Lys
```

```
            35                  40                  45
Asp Gly Thr Thr Arg Val Ala Ser Asn Asp Thr Val Lys Ser Gly Cys
         50                  55                  60
Asp Gly Gly Asp Gly Tyr Met Cys Tyr Asp Gln Thr Pro Trp Gly Val
 65                  70                  75                  80
Asn Asp Ser Tyr Ala Leu Gly Phe Ala Ala Ala Ile Ser Gly Gly
                 85                  90                  95
Glu Lys Ala Ala Cys Cys Asn Cys Tyr Glu Leu Thr Phe Thr Ser Gly
                100                 105                 110
Pro Val Asn Gly Lys Lys Met Thr Val Gln Val Thr Asn Thr Gly Gly
                115                 120                 125
Asp Leu Gly Ser Asn Gln Phe Asp Leu Ala Ile Pro Gly Gly Gly Val
        130                 135                 140
Gly Ile Tyr Asn Gly Cys Thr Ala Gln Ser Gly Ala Pro Ala Asp Gly
145                 150                 155                 160
Trp Gly Ser Arg Tyr Gly Gly Val Ser Ser Arg Ser Glu Cys Ser Gln
                165                 170                 175
Leu Pro Ser Gly Leu Gln Ala Gly Cys Gln Trp Arg Phe Asp Trp Phe
                180                 185                 190
Gln Asn Ala Asp Asn Pro Ser Met Asn Phe Asn Val Ser Cys Pro
                195                 200                 205
Ser Glu Leu Ile Ala Lys Thr Asn Cys Arg Arg Asn
        210                 215                 220

<210> SEQ ID NO 37
<211> LENGTH: 224
<212> TYPE: PRT
<213> ORGANISM: Bursaphelenchus xylophilus

<400> SEQUENCE: 37

Met Lys Ser Leu Val Phe Leu Ala Val Leu Gly Leu Ala Val Ala Gln
 1               5                  10                  15
Asp Thr Gly Lys Thr Thr Arg Tyr Trp Asp Cys Cys Lys Pro Ser Cys
                 20                  25                  30
Ser Trp Pro Gly Lys Ala Gln Leu Lys Gln Gly Pro Ser Lys Thr Cys
                 35                  40                  45
Asp Val Asn Asp Lys Pro Leu Ser Asp Gly Asn Ile Gln Ser Gly Cys
         50                  55                  60
Asn Gly Gly Ser Ala Tyr Ala Cys Ser Thr Asp Gln Pro Trp Ala Val
 65                  70                  75                  80
Asp Asp Asn Leu Ser Tyr Gly Phe Ala Ala Val Lys Leu Ala Gly Lys
                 85                  90                  95
Gln Glu Ser Asp Trp Cys Cys Ser Cys Tyr Glu Leu Thr Phe Thr Asp
                100                 105                 110
Gly Pro Val Ala Gly Lys Lys Phe Val Val Gln Ala Thr Asn Thr Gly
                115                 120                 125
Gly Asp Leu Gly Ser Asn His Phe Asp Leu Met Ile Pro Gly Gly Gly
        130                 135                 140
Val Gly Ile Phe Asn Gly Cys Gln Ala Gln Trp Lys Ser Pro Ala Glu
145                 150                 155                 160
Gly Trp Gly Gln Arg Tyr Gly Gly Val Ser Ser Lys Ala Asp Cys Ala
                165                 170                 175
Thr Leu Pro Thr Ala Leu Gln Pro Gly Cys Asn Trp Arg Phe Asp Trp
                180                 185                 190
```

```
Phe Lys Asn Ala Asp Asn Pro Gly Met Thr Phe Lys Arg Val Lys Cys
            195                 200                 205

Pro Ala Glu Ile Thr Ala Lys Ser Gly Cys Ile Arg Ser Asp Asp Ala
    210                 215                 220
```

<210> SEQ ID NO 38
<211> LENGTH: 355
<212> TYPE: PRT
<213> ORGANISM: Botryotinia fuckeliana

<400> SEQUENCE: 38

```
Met Gln Val Pro Met Lys Ser Leu Val Ala Leu Leu Pro Phe Phe Leu
1               5                   10                  15

Gln Val Ser Ala Gln Ala Ser Gly Ser Gly Thr Thr Thr Arg Tyr Trp
            20                  25                  30

Asp Cys Cys Lys Pro Ser Cys Ala Trp Ser Gly Lys Ala Thr Leu Glu
        35                  40                  45

Ser Gly Ser Gly Pro Val Gly Thr Cys Asp Ile Asn Asp Ser Pro Leu
    50                  55                  60

Ser Asp Pro Thr Ala Ile Ala Val Ser Gly Cys Asp Gly Gly Asn Ser
65                  70                  75                  80

Tyr Met Cys Ser Asp Gln Ser Pro Trp Ala Val Ser Asp Asp Leu Ala
                85                  90                  95

Tyr Gly Tyr Ala Ala Val Asn Ile Ala Gly Ser Glu Ala Ser Trp
            100                 105                 110

Cys Cys Ala Cys Tyr Glu Leu Thr Phe Thr Ser Thr Ala Leu Ala Gly
        115                 120                 125

Lys Lys Met Ile Val Gln Ala Thr Asn Thr Gly Gly Asp Leu Gly Ser
130                 135                 140

Asn Gln Phe Asp Leu Ala Ile Pro Gly Gly Gly Val Gly Ile Phe Asn
145                 150                 155                 160

Gly Cys Thr Lys Glu Phe Gly Ala Pro Ser Ser Gly Trp Gly Ala Gln
                165                 170                 175

Tyr Gly Gly Val Ala Ala Val Ser Ser Cys Ala Ala Phe Pro Glu Ala
            180                 185                 190

Leu Lys Pro Gly Cys Ser Phe Arg Phe Asp Trp Phe Glu Gly Ala Asp
        195                 200                 205

Asn Pro Thr Val Asn Phe Lys Gln Val Asn Cys Pro Ala Glu Leu Thr
    210                 215                 220

Lys Ser Thr Gly Cys Lys Arg Ala Asp Asp Ser Ser Met Pro Ala Pro
225                 230                 235                 240

Asp Ala Ser Gly Ser Ala Ser Ala Ser Pro Val Ala Ser Thr Ser Ala
                245                 250                 255

Lys Thr Ser Ser Val Ala Pro Thr Ser Val Ser Ser Ser Val Val
            260                 265                 270

Val Ala Pro Ser Ser Ala Thr Ser Ser Pro Val Val Val Pro Thr
        275                 280                 285

Ser Ala Ala Ser Ser Lys Ala Ser Ser Ala Ala Val Val Ser His Pro
    290                 295                 300

Val Val Pro Ser Ser Glu Ala Ser Ser Ala Pro Ala Val Thr Ser His
305                 310                 315                 320

Ser Ser Ala Thr Lys Ser Ala Lys Thr Ser Val Ala Ala Pro His Ser
                325                 330                 335

Thr Ser Ala Ser Thr Gly Tyr Gly Ser Gly Asp Asp Asp Thr Cys
            340                 345                 350
```

-continued

Asp Ala Glu
        355

<210> SEQ ID NO 39
<211> LENGTH: 251
<212> TYPE: PRT
<213> ORGANISM: Acremonium thermophilum

<400> SEQUENCE: 39

Met Arg Leu Pro Leu Pro Thr Leu Leu Ala Leu Leu Pro Tyr Tyr Leu
1               5                   10                  15

Glu Val Ser Ala Gln Gly Ala Ser Gly Thr Gly Thr Thr Thr Arg Tyr
            20                  25                  30

Trp Asp Cys Cys Lys Pro Ser Cys Ala Trp Pro Leu Lys Gly Asn Ser
        35                  40                  45

Pro Ser Pro Val Gln Thr Cys Asp Lys Asn Asp Arg Pro Leu Asn Asp
    50                  55                  60

Gly Gly Asn Thr Lys Ser Gly Cys Asp Asn Gly Gly Ala Phe Met
65                  70                  75                  80

Cys Ser Ser Gln Ser Pro Trp Ala Val Asn Glu Thr Thr Ser Tyr Gly
                85                  90                  95

Trp Ala Ala Val Arg Ile Ala Gly Ser Thr Glu Ser Ala Trp Cys Cys
            100                 105                 110

Ala Cys Tyr Glu Leu Thr Phe Thr Ser Gly Pro Val Ser Gly Lys Lys
        115                 120                 125

Leu Ile Val Gln Ala Thr Asn Thr Gly Gly Asp Leu Gly Ser Asn His
    130                 135                 140

Phe Asp Leu Ala Ile Pro Gly Gly Gly Val Gly Gln Ser Asn Ala Cys
145                 150                 155                 160

Thr Asn Gln Tyr Gly Ala Pro Pro Asn Gly Trp Gly Asp Arg Tyr Gly
                165                 170                 175

Gly Val His Ser Arg Ser Asp Cys Asp Ser Phe Pro Ala Ala Leu Lys
            180                 185                 190

Ala Gly Cys Tyr Trp Arg Phe Asp Trp Phe Gln Gly Ala Asp Asn Pro
        195                 200                 205

Ser Val Ser Phe Lys Gln Val Ala Cys Pro Ala Ala Ile Thr Ala Lys
    210                 215                 220

Ser Gly Cys Thr Arg Gln Asn Asp Ala Ile Asn Glu Thr Pro Thr Gly
225                 230                 235                 240

Pro Ser Thr Val Pro Thr Tyr Thr Ala Ser Gly
                245                 250

<210> SEQ ID NO 40
<211> LENGTH: 229
<212> TYPE: PRT
<213> ORGANISM: Scopulariopsis brevicaulis

<400> SEQUENCE: 40

Met His Val Leu Pro Thr Leu Leu Ala Leu Thr Pro Leu Val Leu Pro
1               5                   10                  15

Ala Ala Ser Gln Ala Ser Gly Thr Gly Thr Thr Thr Arg Tyr Trp Asp
            20                  25                  30

Cys Cys Lys Pro Ser Cys Ser Trp Pro Asp Lys Ala Pro Leu Ser Gln
        35                  40                  45

Gly Pro Pro Met Thr Cys Asp Ile Asn Asp Asn Pro Leu Asp Asp Gly
    50                  55                  60

```
Gly Leu Thr Glu Ser Gly Cys Glu Pro Gly Gly Ala Tyr Met Cys
 65                  70                  75                  80

Ser Ser His Ser Pro Trp Ala Val Asp Asp Glu Leu Ala Tyr Gly Trp
                 85                  90                  95

Ala Ala Val Asn Ile Gly Gly Gln Thr Glu Ser Asp Trp Cys Cys Ala
            100                 105                 110

Cys Tyr Glu Leu Glu Phe Thr Thr Gly Ala Val Ser Gly Lys Lys Met
            115                 120                 125

Ile Val Gln Ala Thr Asn Thr Gly Gly Asp Leu Gly Asn Asn His Phe
130                 135                 140

Asp Ile Ala Met Pro Gly Gly Gly Val Gly Ile Phe Asn Gly Cys Thr
145                 150                 155                 160

Asp Gln Trp Gly Ser Pro Pro Asn Gly Trp Gly Asp Arg Tyr Gly Gly
                165                 170                 175

Val His Thr Arg Ala Asp Cys Asp Ser Phe Pro Glu Ala Leu Lys Ala
            180                 185                 190

Gly Cys Glu Trp Arg Phe Asp Trp Phe Gly Gly Thr Asp Asn Pro Asp
            195                 200                 205

Val Ser Phe Arg Glu Val Glu Cys Pro Ala Glu Leu Val Gln Lys Ser
    210                 215                 220

Gln Cys Gln Arg Ser
225

<210> SEQ ID NO 41
<211> LENGTH: 340
<212> TYPE: PRT
<213> ORGANISM: Syncephalastrum racemosum

<400> SEQUENCE: 41

Met Ile Leu His Arg Thr Glu Lys Asn Asn Asp Met Arg Leu Ser Phe
1               5                   10                  15

Ala Ala Ser Leu Leu Leu Ala Thr Val Gly Met Gln Leu Val Ser Ala
                20                  25                  30

Ala Asp Cys Ser Asn Lys Ala Tyr Ser Gln Cys Gly Gly Gln Asn Trp
            35                  40                  45

Ser Gly Glu Ser Cys Cys Val Ser Gly Tyr Glu Cys Lys Gln Leu Asn
    50                  55                  60

Asp Tyr Tyr His Gln Cys Val Pro Gln Asn Ser Gly Ser Phe Ser Gly
 65                 70                  75                  80

Ser Ser Ser Ala Ala Ala Pro Ser His Met Ala Thr Ser Ser Ala Pro
                85                  90                  95

Ser Ser Ser Lys Ala Pro Ser Ser Pro Ala Ser Ser Lys Thr Pro
            100                 105                 110

Ser Ser Pro Ala Ala Ser Ser Ser Ser Ser Gly Ser Gly Tyr Lys
            115                 120                 125

Pro Ile Ser Gly Gly Ala Ser Gly Asp Gly Thr Thr Thr Arg Tyr Trp
    130                 135                 140

Asp Cys Cys Lys Ala Ser Cys Ser Trp Pro Gly Lys Ala Pro Val Thr
145                 150                 155                 160

Asn Pro Val Gly Thr Cys Ala Lys Asp Gly Val Lys Leu Val Asp Ala
                165                 170                 175

Asn Val Gln Ser Gly Cys Asn Gly Gly Glu Gly Tyr Met Cys Asn Asp
            180                 185                 190

Asn Gln Pro Trp Ala Ile Asp Asp Asn Leu Ser Tyr Gly Phe Ala Ala
```

```
                195                 200                 205
Ala Ser Ile Ser Gly Lys Ser Glu Ser Asp Phe Cys Cys Ser Cys Tyr
    210                 215                 220

Glu Leu Thr Phe Ser Ser Gly Glu Ile Glu Gly Lys Lys Met Val Val
225                 230                 235                 240

Gln Val Thr Asn Thr Gly Gly Asp Leu Ser Asn Asn His Phe Asp Leu
                245                 250                 255

Gln Ile Pro Gly Gly Gly Val Gly Ile Phe Asn Gly Cys Gln Thr Gln
            260                 265                 270

Trp Asp Ala Pro Ser Asp Gly Trp Gly Gln Arg Tyr Gly Gly Ile Ser
        275                 280                 285

Ser Ala Ser Glu Cys Ser Gln Leu Pro Lys Gln Leu Gln Asp Gly Cys
    290                 295                 300

Lys Trp Arg Phe Asp Trp Phe Lys Asn Ala Asp Asn Pro Asn Val Ser
305                 310                 315                 320

Phe Lys Gln Val Ser Cys Pro Ala Glu Leu Val Lys Lys Thr Gly Cys
                325                 330                 335

Glu Arg Thr Ser
            340

<210> SEQ ID NO 42
<211> LENGTH: 338
<212> TYPE: PRT
<213> ORGANISM: Rhizopus oryzae

<400> SEQUENCE: 42

Met Lys Phe Ile Thr Ile Ala Ser Ser Ala Leu Leu Ala Leu Ala Leu
1               5                   10                  15

Gly Thr Glu Met Ala Ser Ala Ala Glu Cys Ser Lys Leu Tyr Gly Gln
            20                  25                  30

Cys Gly Gly Lys Asn Trp Asn Gly Pro Thr Cys Cys Glu Ser Gly Ser
        35                  40                  45

Thr Cys Lys Val Ser Asn Asp Tyr Tyr Ser Gln Cys Leu Pro Ser Gly
    50                  55                  60

Ser Ser Gly Asn Lys Ser Ser Glu Ser Ala His Lys Lys Thr Thr Thr
65                  70                  75                  80

Ala Ala His Lys Lys Thr Thr Thr Ala Ala His Lys Lys Thr Thr Thr
                85                  90                  95

Ala Pro Ala Lys Lys Thr Thr Thr Val Ala Lys Ala Ser Thr Pro Ser
            100                 105                 110

Asn Ser Ser Ser Ser Ser Gly Lys Tyr Ser Ala Val Ser Gly Gly
        115                 120                 125

Ala Ser Gly Asn Gly Val Thr Thr Arg Tyr Trp Asp Cys Cys Lys Ala
    130                 135                 140

Ser Cys Ser Trp Pro Gly Lys Ala Asn Val Ser Ser Pro Val Lys Ser
145                 150                 155                 160

Cys Asn Lys Asp Gly Val Thr Ala Leu Ser Asp Ser Asn Ala Gln Ser
                165                 170                 175

Gly Cys Asn Gly Gly Asn Ser Tyr Met Cys Asn Asp Asn Gln Pro Trp
            180                 185                 190

Ala Val Asn Asp Asn Leu Ala Tyr Gly Phe Ala Ala Ala Ala Ile Ser
        195                 200                 205

Gly Gly Gly Glu Ser Arg Trp Cys Cys Ser Cys Phe Glu Leu Thr Phe
    210                 215                 220
```

```
Thr Ser Thr Ser Val Ala Gly Lys Lys Met Val Gln Val Thr Asn
225                 230                 235                 240

Thr Gly Gly Asp Leu Gly Ser Ser Thr Gly Ala His Phe Asp Leu Gln
                245                 250                 255

Met Pro Gly Gly Gly Val Gly Ile Phe Asn Gly Cys Ser Ser Gln Trp
            260                 265                 270

Gly Ala Pro Asn Asp Gly Trp Gly Ser Arg Tyr Gly Gly Ile Ser Ser
        275                 280                 285

Ala Ser Asp Cys Ser Ser Leu Pro Ser Ala Leu Gln Ala Gly Cys Lys
    290                 295                 300

Trp Arg Phe Asn Trp Phe Lys Asn Ala Asp Asn Pro Ser Met Thr Tyr
305                 310                 315                 320

Lys Glu Val Thr Cys Pro Lys Glu Ile Thr Ala Lys Thr Gly Cys Ser
                325                 330                 335

Arg Lys

<210> SEQ ID NO 43
<211> LENGTH: 226
<212> TYPE: PRT
<213> ORGANISM: Crinipellis scabella

<400> SEQUENCE: 43

Met Val His Pro Asn Met Leu Lys Thr Leu Ala Pro Leu Ile Ile Leu
1               5                   10                  15

Ala Ala Ser Val Thr Ala Gln Thr Ala Gly Val Thr Thr Arg Tyr Trp
            20                  25                  30

Asp Cys Cys Lys Pro Ser Cys Gly Trp Ser Gly Lys Ala Ser Val Ser
        35                  40                  45

Ala Pro Val Arg Thr Cys Asp Arg Asn Gly Asn Thr Leu Gly Pro Asp
    50                  55                  60

Val Lys Ser Gly Cys Asp Ser Gly Gly Thr Ser Phe Thr Cys Ala Asn
65                  70                  75                  80

Asn Gly Pro Phe Ala Ile Asp Asn Asn Thr Ala Tyr Gly Phe Ala Ala
                85                  90                  95

Ala His Leu Ala Gly Ser Ser Glu Ala Ala Trp Cys Cys Gln Cys Tyr
            100                 105                 110

Glu Leu Thr Phe Thr Ser Gly Pro Val Val Gly Lys Lys Leu Thr Val
        115                 120                 125

Gln Val Thr Asn Thr Gly Gly Asp Leu Gly Asn Asn His Phe Asp Leu
    130                 135                 140

Met Ile Pro Gly Gly Gly Val Gly Leu Phe Thr Gln Gly Cys Pro Ala
145                 150                 155                 160

Gln Phe Gly Ser Trp Asn Gly Ala Gln Tyr Gly Gly Val Ser Ser
                165                 170                 175

Arg Asp Gln Cys Ser Gln Leu Pro Ala Ala Val Gln Ala Gly Cys Gln
        180                 185                 190

Phe Arg Phe Asp Trp Met Gly Gly Ala Asp Asn Pro Asn Val Thr Phe
    195                 200                 205

Arg Pro Val Thr Cys Pro Ala Gln Leu Thr Asn Ile Ser Gly Cys Val
210                 215                 220

Arg Lys
225

<210> SEQ ID NO 44
<211> LENGTH: 222
```

```
<212> TYPE: PRT
<213> ORGANISM: Macrophomina phaseolina

<400> SEQUENCE: 44

Met Phe Ser Pro Leu Trp Ala Leu Ser Ala Leu Leu Leu Phe Pro Ala
1               5                   10                  15

Thr Glu Ala Thr Ser Gly Val Thr Thr Arg Tyr Trp Asp Cys Cys Lys
            20                  25                  30

Pro Ser Cys Ala Trp Thr Gly Lys Ala Ser Val Ser Lys Pro Val Gly
        35                  40                  45

Thr Cys Asp Ile Asn Asp Asn Ala Gln Thr Pro Ser Asp Leu Leu Lys
    50                  55                  60

Ser Ser Cys Asp Gly Gly Ser Ala Tyr Tyr Cys Ser Asn Gln Gly Pro
65                  70                  75                  80

Trp Ala Val Asn Asp Ser Leu Ser Tyr Gly Phe Ala Ala Lys Leu
                85                  90                  95

Ser Gly Lys Gln Glu Thr Asp Trp Cys Cys Gly Cys Tyr Lys Leu Thr
            100                 105                 110

Phe Thr Ser Thr Ala Val Ser Gly Lys Gln Met Ile Val Gln Ile Thr
        115                 120                 125

Asn Thr Gly Gly Asp Leu Gly Asn Asn His Phe Asp Ile Ala Met Pro
    130                 135                 140

Gly Gly Gly Val Gly Ile Phe Asn Gly Cys Ser Lys Gln Trp Asn Gly
145                 150                 155                 160

Ile Asn Leu Gly Asn Gln Tyr Gly Gly Phe Thr Asp Arg Ser Gln Cys
                165                 170                 175

Ala Thr Leu Pro Ser Lys Trp Gln Ala Ser Cys Asn Trp Arg Phe Asp
            180                 185                 190

Trp Phe Glu Asn Ala Asp Asn Pro Thr Val Asp Trp Glu Pro Val Thr
        195                 200                 205

Cys Pro Gln Glu Leu Val Ala Arg Thr Gly Cys Ser Arg Thr
    210                 215                 220

<210> SEQ ID NO 45
<211> LENGTH: 245
<212> TYPE: PRT
<213> ORGANISM: Podospora anserina

<400> SEQUENCE: 45

Met Gln Leu Ala Leu Thr Ile Leu Ala Phe Gly Gly Phe Ala Ser Ala
1               5                   10                  15

Gln Gly Ala Gln Gly Ala Gly Lys Thr Thr Arg Tyr Trp Asp Cys Cys
            20                  25                  30

Lys Pro Ser Cys Ala Trp Pro Gly Lys Ser Thr Ala Ser Thr Pro Val
        35                  40                  45

Leu Thr Cys Asp Arg Asn Asp Asn Pro Leu Asn Asp Arg Gly Ser Thr
    50                  55                  60

Arg Ser Gly Cys Asp Ser Gly Gly Ser Ala Phe Met Cys Ser Asn Gln
65                  70                  75                  80

Ser Pro Trp Ala Val Asn Glu Thr Val Ala Tyr Gly Trp Ala Ala Val
                85                  90                  95

Asn Ile Ala Gly Ser Asn Glu Ala Ser Trp Cys Cys Ser Cys Tyr Glu
            100                 105                 110

Leu Thr Phe Thr Ser Gly Pro Val Ser Gly Lys Lys Met Ile Val Gln
        115                 120                 125
```

```
Ala Thr Asn Thr Gly Gly Asp Leu Gly Asn Asn His Phe Asp Ile Ala
    130                 135                 140

Met Pro Gly Gly Val Gly Ile Phe Asn Ala Cys Thr Gln Gln Tyr
145                 150                 155                 160

Gly Ala Pro Pro Asn Gly Trp Gly Glu Arg Tyr Gly Gly Val Gly Ser
                165                 170                 175

Lys Ser Ala Cys Glu Ser Phe Pro Asp Lys Leu Lys Ala Gly Cys Asn
                180                 185                 190

Trp Arg Phe Asp Trp Phe Met Gly Ala Asp Asn Pro Asp Val Arg Phe
                195                 200                 205

Arg Gln Val Ala Cys Pro Ala Ala Ile Thr Ala Lys Ser Gln Cys Val
210                 215                 220

Arg Gln Arg Asp Val Ile Asp Gln Thr Pro Thr Gly Pro Ser Thr Val
225                 230                 235                 240

Pro Thr Trp Thr Pro
                245

<210> SEQ ID NO 46
<211> LENGTH: 366
<212> TYPE: PRT
<213> ORGANISM: Rhizopus oryzae

<400> SEQUENCE: 46

Met Lys Phe Ile Thr Ile Thr Ser Ser Ala Leu Leu Ala Leu Ala Leu
1               5                   10                  15

Gly Thr Glu Met Ala Ser Ala Ala Lys Cys Ser Lys Leu Tyr Gly Gln
                20                  25                  30

Cys Gly Gly Lys Asp Trp Asn Gly Pro Thr Cys Cys Glu Ser Gly Ser
                35                  40                  45

Thr Cys Lys Val Ser Asn Asp Tyr Tyr Ser Gln Cys Leu Ala Pro Glu
            50                  55                  60

Ser Asn Gly Asn Lys Ser Ser Glu Cys Ser Lys Leu Tyr Gly Gln Cys
65                  70                  75                  80

Gly Gly Lys Asp Trp Asn Gly Pro Thr Cys Cys Glu Ser Gly Ser Thr
                85                  90                  95

Cys Lys Val Ser Asn Asp Tyr Tyr Ser Gln Cys Leu Ala Pro Glu Ser
            100                 105                 110

Asn Gly Asn Lys Thr Ser Glu Ser Ala His Lys Thr Thr Thr Thr Thr
                115                 120                 125

Ala Pro Ala Lys Glu Ile Thr Thr Thr Ala Lys Ala Ser Asn Ser Ser
            130                 135                 140

Asn Ser Ser Gly Lys Tyr Ser Ile Val Ser Gly Ala Ser Gly Asn
145                 150                 155                 160

Gly Val Thr Thr Arg Tyr Trp Asp Cys Cys Lys Ala Ser Cys Ser Trp
                165                 170                 175

Pro Gly Lys Ala Asn Val Ser Ser Pro Val Lys Ser Cys Asn Lys Asp
            180                 185                 190

Gly Val Thr Ala Leu Ser Asp Ser Asn Val Gln Ser Gly Cys Asn Gly
            195                 200                 205

Gly Asn Ser Tyr Met Cys Asn Asp Asn Gln Pro Trp Ala Val Asn Asp
210                 215                 220

Asn Leu Ala Tyr Gly Phe Ala Ala Ala Ile Ser Gly Gly Gly Glu
225                 230                 235                 240

Ser Arg Trp Cys Cys Ser Cys Phe Glu Leu Thr Phe Thr Ser Thr Ser
                245                 250                 255
```

```
Val Ala Gly Lys Lys Met Val Ile Gln Val Thr Asn Thr Gly Gly Asp
            260                 265                 270

Leu Gly Ser Ser Thr Gly Ala His Phe Asp Leu Gln Met Pro Gly Gly
        275                 280                 285

Gly Val Gly Ile Phe Asn Gly Cys Ser Lys Gln Trp Gly Ala Pro Asn
    290                 295                 300

Asp Gly Trp Gly Ser Arg Tyr Gly Gly Ile Ser Ser Ala Ser Asp Cys
305                 310                 315                 320

Ser Ser Leu Pro Ser Ala Leu Gln Ala Gly Cys Lys Trp Arg Phe Asn
                325                 330                 335

Trp Phe Lys Asn Ala Asp Asn Pro Ser Met Thr Tyr Lys Glu Val Thr
            340                 345                 350

Cys Pro Lys Glu Ile Thr Ala Lys Thr Gly Cys Ser Arg Lys
        355                 360                 365

<210> SEQ ID NO 47
<211> LENGTH: 286
<212> TYPE: PRT
<213> ORGANISM: Bursaphelenchus xylophilus

<400> SEQUENCE: 47

Met Ala Lys Leu Phe Val Ser Val Leu Val Val Ala Leu Leu Leu Glu
1               5                   10                  15

Val Val Val Glu Cys Lys Ser Ser Lys Thr Lys Lys Thr Lys Ala Thr
            20                  25                  30

Thr Val Lys Ser Thr Lys Ala Thr Ala Ala Pro Thr Lys Ala Thr Ala
        35                  40                  45

Ala Pro Thr Lys Ala Thr Thr Ala Ala Ser Ser Ser Ala Gly Gly Asn
    50                  55                  60

Ser Ala Asp Tyr Ser Tyr Ser Tyr Val Ser Gly Gly Thr Ser Gly Thr
65                  70                  75                  80

Gly Val Thr Thr Arg Tyr Trp Asp Cys Cys Lys Ser Ser Cys Ala Trp
                85                  90                  95

Pro Gly Lys Ala Ser Leu Lys Ser Gly Pro Ile Gln Thr Cys Asp Val
            100                 105                 110

His Asp Gln Pro Leu Asn Asp Gly Gly Asn Thr Gln Ser Gly Cys Asn
        115                 120                 125

Gly Gly Ser Ala Tyr Ser Cys Ser Thr Glu Gln Pro Tyr Ala Val Asn
    130                 135                 140

Asp Thr Leu Ser Phe Gly Phe Ala Ala Val Lys Leu Ala Gly Gly Ser
145                 150                 155                 160

Glu Ser Ser Trp Cys Cys Ala Cys Tyr Glu Leu Thr Phe Thr Ser Gly
                165                 170                 175

Ser Val Asn Gly Lys Lys Phe Val Ile Gln Ala Thr Asn Thr Gly Gly
            180                 185                 190

Asp Leu Gly Asp Asn His Phe Asp Leu Ala Ile Pro Gly Gly Gly Val
        195                 200                 205

Gly Ile Phe Asn Gly Cys Thr Ala Gln Trp Gly Ala Pro Ser Ser Gly
    210                 215                 220

Trp Gly Ala Gln Tyr Gly Gly Val Ser Ser Arg Ser Asp Cys Ser Gln
225                 230                 235                 240

Leu Pro Ala Lys Leu Gln Pro Gly Cys Asp Trp Arg Phe Asp Trp Phe
                245                 250                 255

Gly Asn Ser Asp Asn Pro Gly Val Thr Phe Lys Gln Val Thr Cys Pro

```
              260                 265                 270
Lys Thr Leu Thr Asp Lys Ser Lys Cys Ile Arg Ala Asp Asp
            275                 280                 285

<210> SEQ ID NO 48
<211> LENGTH: 359
<212> TYPE: PRT
<213> ORGANISM: Bursaphelenchus xylophilus

<400> SEQUENCE: 48

Met Asn Lys Leu Leu Val Ser Val Leu Val Leu Ala Leu Leu Phe Glu
1               5                  10                  15

Asn Val Val Glu Gly Lys Thr Cys Gly Pro Leu Thr Thr Ala Ala Gly
                20                  25                  30

Ala Thr Gln Thr Ala Pro Pro Ala Ser Ala Ala Ser Thr Thr Lys Gly
            35                  40                  45

Gln Thr Ala Ala Ser Gly Ser Pro Ala Thr Thr Ala Ser Ala Ala Pro
        50                  55                  60

Thr Lys Ala Ser Ala Ala Pro Ser Thr Ala Ser Ala Ala Pro Ser Lys
65                  70                  75                  80

Ala Ser Ala Ala Pro Ser Thr Ala Ser Ala Ala Pro Ser Thr Ala Ser
                85                  90                  95

Ala Ala Pro Ser Lys Ala Ser Ala Ala Pro Ser Thr Ala Ser Ser Thr
            100                 105                 110

Ala Ser Ser Thr Thr Pro Thr Thr Thr Lys Ala Ser Ser Thr Ala
        115                 120                 125

Ala Ala Thr Thr Gln Ala Ser Gly Asn Ser Ala Asp Tyr Ser Tyr Ser
130                 135                 140

Tyr Ile Ser Gly Gly Thr Ser Gly Thr Gly Val Thr Thr Arg Tyr Trp
145                 150                 155                 160

Asp Cys Cys Lys Ser Ser Cys Ala Trp Pro Gly Lys Ala Thr Leu Lys
                165                 170                 175

Ser Gly Pro Ile Gln Thr Cys Asp Val His Asp Gln Pro Leu Asn Asp
            180                 185                 190

Gly Gly Asn Thr Gln Ser Gly Cys Asn Gly Gly Ser Ala Tyr Ser Cys
        195                 200                 205

Ser Thr Glu Gln Pro Tyr Ala Val Asn Asp Thr Leu Ser Phe Gly Phe
    210                 215                 220

Ala Ala Val Lys Leu Ala Gly Gly Ser Glu Ser Thr Trp Cys Cys Ala
225                 230                 235                 240

Cys Tyr Glu Leu Thr Phe Thr Ser Gly Ser Val Ala Gly Lys Lys Phe
                245                 250                 255

Val Ile Gln Ala Thr Asn Thr Gly Gly Asp Leu Gly Asp Asn His Phe
            260                 265                 270

Asp Leu Ala Ile Pro Gly Gly Val Gly Ile Phe Asn Gly Cys Thr
        275                 280                 285

Ala Gln Trp Gly Ala Pro Ser Ser Gly Trp Gly Ser Gln Tyr Gly Gly
    290                 295                 300

Val Ser Ser Arg Ser Asp Cys Ser Gln Leu Pro Ala Thr Leu Gln Pro
305                 310                 315                 320

Gly Cys Asp Trp Arg Phe Asp Trp Phe Gly Asn Ser Asp Asn Pro Gly
                325                 330                 335

Val Thr Phe Lys Gln Val Thr Cys Pro Lys Thr Ile Thr Asp Lys Ser
            340                 345                 350
```

Lys Cys Ile Arg Ala Asp Asp
        355

<210> SEQ ID NO 49
<211> LENGTH: 227
<212> TYPE: PRT
<213> ORGANISM: Humicola grisea var. thermoidea

<400> SEQUENCE: 49

Met Gln Leu Pro Leu Thr Thr Leu Leu Thr Leu Leu Pro Ala Leu Ala
1               5                   10                  15

Ala Ala Gln Ser Gly Ser Gly Arg Thr Thr Arg Tyr Trp Asp Cys Cys
                20                  25                  30

Lys Pro Ser Cys Ala Trp Pro Gly Lys Gly Pro Ala Pro Val Arg Thr
            35                  40                  45

Cys Asp Arg Trp Asp Asn Pro Leu Phe Asp Gly Gly Asn Thr Arg Ser
        50                  55                  60

Gly Cys Asp Ala Gly Gly Ala Tyr Met Cys Ser Asp Gln Ser Pro
65                  70                  75                  80

Trp Ala Val Ser Asp Asp Leu Ala Tyr Gly Trp Ala Ala Val Asn Ile
                85                  90                  95

Ala Gly Ser Asn Glu Arg Gln Trp Cys Cys Ala Cys Tyr Glu Leu Thr
                100                 105                 110

Phe Thr Ser Gly Pro Val Ala Gly Lys Arg Met Ile Val Gln Ala Ser
            115                 120                 125

Asn Thr Gly Gly Asp Leu Gly Asn Asn His Phe Asp Ile Ala Met Pro
        130                 135                 140

Gly Gly Gly Val Gly Ile Phe Asn Ala Cys Thr Asp Gln Tyr Gly Ala
145                 150                 155                 160

Pro Pro Asn Gly Trp Gly Gln Arg Tyr Gly Gly Ile Ser Gln Arg His
                165                 170                 175

Glu Cys Asp Ala Phe Pro Glu Lys Leu Lys Pro Gly Cys Tyr Trp Arg
            180                 185                 190

Phe Asp Trp Cys Val Ser Leu Phe Pro Pro Leu Ser Leu Ser Leu Pro
        195                 200                 205

Pro Gly Thr Gly Gln Thr Met Gly Arg Ser Cys Val Phe Phe Pro Leu
210                 215                 220

Ser Ala Asn
225

<210> SEQ ID NO 50
<211> LENGTH: 346
<212> TYPE: PRT
<213> ORGANISM: Phycomyces nitens

<400> SEQUENCE: 50

Met Lys Phe Ser Ile Ile Ala Ser Ala Leu Leu Leu Ala Ala Ser Ser
1               5                   10                  15

Thr Tyr Ala Ala Glu Cys Ser Gln Gly Tyr Gly Gln Cys Gly Gly Lys
                20                  25                  30

Met Trp Thr Gly Pro Thr Cys Cys Thr Ser Gly Phe Thr Cys Val Gly
            35                  40                  45

Ala Glu Asn Asn Glu Trp Tyr Ser Gln Cys Ile Pro Asn Asp Gln Val
        50                  55                  60

Gln Gly Asn Pro Lys Thr Thr Thr Thr Thr Thr Lys Ala Ala Thr
65                  70                  75                  80

```
Thr Thr Lys Ala Pro Val Thr Thr Lys Ala Thr Thr Thr Thr
            85                  90                  95

Thr Lys Ala Pro Val Thr Thr Lys Ala Thr Thr Thr Thr Thr
        100                 105                 110

Lys Thr Thr Thr Lys Thr Thr Thr Lys Ala Ala Thr Thr Ser
        115                 120                 125

Ser Ser Asn Thr Gly Tyr Ser Pro Ile Ser Gly Phe Ser Gly Asn
130                 135                 140

Gly Arg Thr Thr Arg Tyr Trp Asp Cys Cys Lys Pro Ser Cys Ala Trp
145                 150                 155                 160

Asp Gly Lys Ala Ser Val Thr Lys Pro Val Leu Thr Cys Ala Lys Asp
                165                 170                 175

Gly Val Ser Arg Leu Gly Ser Asp Val Gln Ser Gly Cys Val Gly Gly
                180                 185                 190

Gln Ala Tyr Met Cys Asn Asp Asn Gln Pro Trp Val Asn Asp Asp
                195                 200                 205

Leu Ala Tyr Gly Phe Ala Ala Ala Ser Leu Gly Ser Ala Gly Ala Ser
210                 215                 220

Ala Phe Cys Cys Gly Cys Tyr Glu Leu Thr Phe Thr Asn Thr Ala Val
225                 230                 235                 240

Ala Gly Lys Lys Phe Val Val Gln Val Thr Asn Thr Gly Asp Asp Leu
                245                 250                 255

Ser Thr Asn His Phe Asp Leu Gln Met Pro Gly Gly Gly Val Gly Tyr
                260                 265                 270

Phe Asn Gly Cys Gln Ser Gln Trp Asn Thr Asn Thr Asp Gly Trp Gly
        275                 280                 285

Ala Arg Tyr Gly Gly Ile Ser Ser Ile Ser Glu Cys Asp Lys Leu Pro
        290                 295                 300

Thr Gln Leu Gln Ala Gly Cys Lys Trp Arg Phe Gly Trp Phe Lys Asn
305                 310                 315                 320

Ala Asp Asn Pro Glu Val Thr Phe Lys Ala Val Thr Cys Pro Ala Glu
                325                 330                 335

Ile Ile Ala Lys Thr Gly Cys Glu Arg Lys
                340                 345

<210> SEQ ID NO 51
<211> LENGTH: 360
<212> TYPE: PRT
<213> ORGANISM: Rhizopus oryzae

<400> SEQUENCE: 51

Met Lys Phe Leu Thr Ile Ala Ser Ser Ala Ile Leu Ala Leu Ala Val
1               5                   10                  15

Gly Thr Glu Met Ala His Ala Ala Glu Cys Ser Lys Ala Tyr Tyr Gln
            20                  25                  30

Cys Gly Gly Lys Asn Trp Asp Gly Pro Thr Cys Cys Glu Ser Gly Ser
        35                  40                  45

Thr Cys Val Asp Tyr Pro Asp Asn Pro Phe Tyr Ser Gln Cys Val Pro
    50                  55                  60

Asn Glu Asn Leu Thr Ser Thr Asn Lys Ser Ser His Lys Thr Thr Thr
65                  70                  75                  80

Thr Glu Ser Ala Lys Lys Thr Thr Thr Lys Gly Ser Lys Lys Thr
                85                  90                  95

Thr Thr Thr Glu Ala Ser Lys Lys Thr Thr Thr Glu Ala Ser Lys
                100                 105                 110
```

```
Lys Thr Thr Thr Thr Glu Ala Ser Lys Lys Thr Thr Thr Thr Thr Lys
            115                 120                 125

Lys Ala Ser Thr Ser Thr Ser Ser Ser Ser Ser Ala Ser Thr Asn
        130                 135                 140

Tyr Ser Ala Val Ser Gly Gly Ala Ser Gly Asn Gly Glu Thr Thr Arg
145                 150                 155                 160

Tyr Trp Asp Cys Cys Lys Pro Ser Cys Ser Trp Pro Gly Lys Ala Asp
                165                 170                 175

Val Thr Ser Pro Val Gly Ser Cys Asn Lys Asp Gly Lys Thr Leu Ala
                180                 185                 190

Asp Asn Asn Thr Gln Asn Gly Cys Val Gly Gly Ser Ser Tyr Thr Cys
            195                 200                 205

Asn Asp Asn Gln Pro Trp Val Val Ser Asp Asp Leu Ala Tyr Gly Phe
            210                 215                 220

Ala Ala Ala Ser Ile Ser Gly Gly Ser Glu Ala Thr Trp Cys Cys Ala
225                 230                 235                 240

Cys Phe Glu Leu Thr Phe Thr Ser Thr Ala Val Lys Gly Lys Lys Met
                245                 250                 255

Val Val Gln Val Thr Asn Thr Gly Ser Asp Leu Gly Ser Asn Thr Gly
            260                 265                 270

Ala His Phe Asp Leu Gln Met Pro Gly Gly Gly Val Gly Ile Tyr Asn
        275                 280                 285

Gly Cys Ala Thr Gln Trp Gly Ala Pro Thr Asp Gly Trp Gly Ala Arg
        290                 295                 300

Tyr Gly Gly Val Ser Ser Ala Ser Asp Cys Ser Asn Leu Pro Ser Ala
305                 310                 315                 320

Leu Gln Ala Gly Cys Lys Trp Arg Phe Gly Trp Phe Lys Asn Ala Asp
                325                 330                 335

Asn Pro Thr Met Thr Tyr Lys Gln Val Thr Cys Pro Lys Ala Ile Thr
            340                 345                 350

Ala Lys Ser Gly Cys Ser Arg Lys
            355                 360

<210> SEQ ID NO 52
<211> LENGTH: 219
<212> TYPE: PRT
<213> ORGANISM: Mastotermes darwiniensis hindgut symbiont sp.

<400> SEQUENCE: 52

Met Phe Val Ala Phe Val Ile Gly Ala Leu Cys Lys Asp Phe Ser Gly
1               5                   10                  15

Asn Gly Gln Thr Thr Arg Tyr Trp Asp Cys Cys Lys Pro Ser Cys Ser
            20                  25                  30

Trp Ser Lys Lys Ala Gln Val Ser His Val Val Asn Ser Cys Asn Ala
        35                  40                  45

Asn Asn Gln His Asp Ser Thr Val Asp Leu Lys Ser Gly Cys Asp Gly
    50                  55                  60

Gly Pro Ser Tyr Ala Cys Ala Asp Gln Ala Pro Trp Ala Val Asn Ser
65                  70                  75                  80

Ser Tyr Phe Met Gly Thr Ala Ala Ala Leu Ser Gly Ala Ser Glu
                85                  90                  95

Ala Asp Leu Cys Cys Lys Cys Phe Glu Leu Thr Phe Thr Ser Gly Thr
            100                 105                 110

Pro Asn Gly Lys Lys Met Leu Val Gln Ile Thr Asn Thr Gly Ser Asp
```

```
            115                 120                 125
Leu Ser Gly Asn Gln Phe Asp Leu Leu Ile Pro Gly Gly Gly Val Gly
    130                 135                 140

Ile Phe Asp Gly Cys Thr Arg Gln Tyr Pro Gly Ser Tyr Asp Trp Gly
145                 150                 155                 160

Gln Arg Tyr Gly Gly Val Thr Ser Arg Asp Gly Cys Ser Lys Leu Pro
                165                 170                 175

Ser Thr Leu Gln Thr Gly Cys Gln Phe Arg Phe Asp Tyr Ile Gly Asp
            180                 185                 190

Asn Pro Ser Val Ser Phe Lys Ser Thr His Cys Pro Asp Ser Ile Val
        195                 200                 205

Gly Lys Thr Asn Ser Arg Arg Asn Asp Asp Ala
    210                 215
```

<210> SEQ ID NO 53
<211> LENGTH: 218
<212> TYPE: PRT
<213> ORGANISM: Magnaporthe grisea

<400> SEQUENCE: 53

```
Met Lys Ile Thr Thr Ser Ala Val Leu Ala Cys Leu Thr Ala Ala Val
1               5                   10                  15

Ser Ala Gln Val Gln Gly Thr Gly Ala Thr Thr Arg Tyr Trp Asp Cys
            20                  25                  30

Cys Lys Pro Ser Cys Gly Trp Pro Gly Lys Ala Asn Leu Ala Ser Gly
        35                  40                  45

Pro Leu Arg Thr Cys Asp Lys Ala Asp Asn Pro Leu Asn Asp Gly Gly
    50                  55                  60

Asn Thr Lys Ser Gly Cys Asp Asn Gly Gly Ala Phe Met Cys Ser
65                  70                  75                  80

Ser Gln Glu Pro Leu Ala Val Asp Asp Ser Leu Ala Tyr Gly Phe Ala
            85                  90                  95

Ala Val Arg Ile Ser Gly Gln Arg Glu Ser Asp Trp Cys Cys Ala Cys
        100                 105                 110

Tyr Glu Leu Thr Phe Thr Asn Leu Leu Arg Asn Thr Gly Gly Asp Leu
    115                 120                 125

Gly Gln Asn His Phe Asp Ile Ala Met Pro Gly Gly Gly Val Gly Ile
130                 135                 140

Phe Asn Ala Cys Thr Glu Gln Tyr Gly Ala Pro Ala Asn Gly Trp Gly
145                 150                 155                 160

Glu Arg Tyr Gly Gly Val Arg Ser Arg Ser Glu Cys Asp Ala Phe Pro
                165                 170                 175

Glu Lys Leu Lys Lys Gly Cys Tyr Trp Arg Phe Asp Trp Phe Lys Gly
            180                 185                 190

Ala Asp Asn Pro Ser Val Ser Phe Lys Gln Val Thr Cys Pro Ser Glu
        195                 200                 205

Leu Thr Ser Lys Ser Gly Cys Val Arg Ala
    210                 215
```

<210> SEQ ID NO 54
<211> LENGTH: 219
<212> TYPE: PRT
<213> ORGANISM: Mastotermes darwiniensis hindgut symbiont sp.

<400> SEQUENCE: 54

Met Phe Val Ala Phe Val Ile Gly Ala Leu Cys Lys Asp Tyr Ser Gly

```
              1               5                  10                 15
            Asn Gly Gln Thr Thr Arg Tyr Trp Asp Cys Cys Lys Pro Ser Cys Ser
                            20                 25                 30

Trp Ser Lys Lys Ala Gln Val Ser His Val Val Asn Ser Cys Asn Ala
                            35                 40                 45

Asn Gly Gln His Asp Ser Thr Val Asp Leu Lys Ser Gly Cys Asp Gly
                            50                 55                 60

Gly Pro Ser Tyr Ala Cys Thr Asp Gln Ala Pro Trp Ala Val Asn Ser
            65                         70                 75                 80

Ser Tyr Phe Met Gly Thr Ala Ala Ala Leu Ser Gly Gly Ser Glu
                            85                 90                 95

Ser Asp Leu Cys Cys Lys Cys Phe Glu Leu Thr Phe Thr Ser Gly Thr
                            100                105                110

Pro Asn Gly Lys Lys Met Leu Val Gln Ile Thr Asn Thr Gly Ser Asp
                            115                120                125

Leu Ser Gly Asn Gln Phe Asp Leu Leu Ile Pro Gly Gly Gly Val Gly
                            130                135                140

Ile Phe Asp Gly Cys Thr Arg Gln Tyr Pro Gly Ser Tyr Asp Trp Gly
            145                        150                155                160

Gln Arg Tyr Gly Gly Val Thr Ser Arg Asp Gly Cys Ser Lys Leu Pro
                            165                170                175

Ser Ala Leu Gln Ser Gly Phe Gln Phe Arg Phe Asp Tyr Ile Ala Asp
                            180                185                190

Asn Pro Ser Val Ser Phe Lys Ser Thr His Cys Pro Asp Thr Ile Val
                            195                200                205

Ser Lys Pro Thr Cys Arg Arg Asn Asp Asp Ser
                            210                215

<210> SEQ ID NO 55
<211> LENGTH: 220
<212> TYPE: PRT
<213> ORGANISM: Mastotermes darwiniensis hindgut symbiont sp.

<400> SEQUENCE: 55

Met Ile Val Val Phe Val Ile Gly Ala Leu Cys Lys Asp Tyr Ser Gly
            1               5                  10                 15

Asn Gly Gln Thr Thr Arg Tyr Trp Asp Cys Cys Lys Pro Ser Cys Ser
                            20                 25                 30

Trp Ser Lys Lys Ala Gln Val Ser His Val Val Asn Ser Cys Thr Ala
                            35                 40                 45

Thr Gly Ser His Asp Thr Thr Val Asp Leu Lys Ser Gly Cys Asp Gly
                            50                 55                 60

Gly Pro Ser Tyr Val Cys Val Asp Gln Ala Pro Trp Ala Val Asn Ser
            65                         70                 75                 80

Ser Tyr Phe Met Gly Thr Ala Ala Ala Leu Ser Gly Gly Ser Glu
                            85                 90                 95

Ser Asp Leu Cys Cys Arg Cys Phe Glu Leu Thr Phe Thr Ser Gly Gln
                            100                105                110

Pro Asn Gly Lys Lys Met Leu Val Gln Val Thr Asn Thr Gly Ser Asp
                            115                120                125

Leu Ser Gly Asn Gln Phe Asp Leu Leu Ile Pro Gly Gly Gly Val Gly
                            130                135                140

Ile Phe Asp Gly Cys Ser Arg Gln Tyr Pro Gly Gly Asn Tyr Asp Trp
            145                        150                155                160
```

```
Gly Gln Arg Tyr Gly Gly Val Thr Ser Lys Ala Gly Cys Ala Lys Ile
                165                 170                 175

Pro Ala Glu Leu Lys Ala Gly Cys Glu Phe Arg Phe Asp Tyr Ile Gly
            180                 185                 190

Asp Asn Pro Ser Val Ser Phe Lys Ser Val His Cys Pro Asp Thr Ile
        195                 200                 205

Thr Ser Lys Thr Asn Cys Arg Arg Asn Asp Asp Asn
    210                 215                 220

<210> SEQ ID NO 56
<211> LENGTH: 220
<212> TYPE: PRT
<213> ORGANISM: Mastotermes darwiniensis hindgut symbiont sp.

<400> SEQUENCE: 56

Met Ile Val Val Phe Val Ile Gly Ala Leu Cys Lys Asp Tyr Ser Gly
1               5                   10                  15

Ser Gly Lys Thr Thr Arg Tyr Trp Asp Cys Cys Lys Pro Ser Cys Ser
            20                  25                  30

Trp Ser Lys Lys Ala Gln Val Ser His Val Val Asn Ser Cys Thr Ala
        35                  40                  45

Ser Gly Gln His Asp Thr Thr Val Asp Leu Lys Ser Gly Cys Asp Gly
    50                  55                  60

Gly Pro Ser Tyr Val Cys Val Asp Gln Ala Pro Trp Ala Val Asn Ser
65                  70                  75                  80

Ser Tyr Phe Met Gly Thr Ala Ala Ala Leu Ser Gly Gly Ser Glu
            85                  90                  95

Ser Asp Leu Cys Cys Arg Cys Phe Glu Leu Thr Phe Thr Ser Gly Gln
            100                 105                 110

Ser Asn Gly Lys Lys Met Leu Val Gln Ile Thr Asn Thr Gly Ser Asp
            115                 120                 125

Leu Ser Gly Asn Gln Phe Asp Leu Leu Ile Pro Gly Gly Gly Val Gly
    130                 135                 140

Ile Phe Asp Gly Cys Ser Arg Gln Tyr Pro Gly Gly Asn Tyr Asp Trp
145                 150                 155                 160

Gly Gln Arg Tyr Gly Gly Val Thr Ser Lys Ala Gly Cys Ala Lys Ile
                165                 170                 175

Pro Ala Glu Leu Lys Ala Gly Cys Glu Phe Arg Phe Asp Tyr Ile Gly
            180                 185                 190

Asp Asn Pro Ser Val Ser Phe Lys Ser Val His Cys Pro Asp Thr Ile
        195                 200                 205

Thr Ser Lys Thr Asn Cys Arg Arg Asn Asp Asp Gln
    210                 215                 220

<210> SEQ ID NO 57
<211> LENGTH: 614
<212> TYPE: PRT
<213> ORGANISM: Pichia pastoris

<400> SEQUENCE: 57

Met Ser Thr Leu Thr Leu Leu Ala Val Leu Leu Ser Leu Gln Asn Ser
1               5                   10                  15

Ala Leu Ala Ala Gln Ala Glu Thr Ala Ser Leu Tyr His Gln Cys Gly
            20                  25                  30

Gly Ala Asn Trp Glu Gly Ala Thr Gln Cys Ile Ser Gly Ala Tyr Cys
        35                  40                  45
```

Gln Ser Gln Asn Pro Tyr Tyr Tyr Gln Cys Val Ala Thr Ser Trp Gly
 50                  55                  60

Tyr Tyr Thr Asn Thr Ser Ile Ser Ser Thr Ala Thr Leu Pro Ser Ser
 65                  70                  75                  80

Ser Thr Thr Val Ser Pro Thr Ser Ser Val Val Pro Thr Gly Leu Val
                 85                  90                  95

Ser Pro Leu Tyr Gly Gln Cys Gly Gly Gln Asn Trp Asn Gly Ala Thr
            100                 105                 110

Ser Cys Ala Gln Gly Ser Tyr Cys Lys Tyr Met Asn Asn Tyr Tyr Phe
            115                 120                 125

Gln Cys Val Pro Glu Ala Asp Gly Asn Pro Ala Glu Ile Ser Thr Phe
            130                 135                 140

Ser Glu Asn Gly Glu Ile Ile Val Thr Ala Ile Glu Ala Pro Thr Trp
145                 150                 155                 160

Ala Gln Cys Gly Gly His Gly Tyr Tyr Gly Pro Thr Lys Cys Gln Val
                165                 170                 175

Gly Thr Ser Cys Arg Glu Leu Asn Ala Trp Tyr Tyr Gln Cys Ile Pro
            180                 185                 190

Asp Asp His Thr Asp Ala Ser Thr Thr Thr Leu Asp Pro Thr Ser Ser
            195                 200                 205

Phe Val Ser Thr Thr Ser Leu Ser Thr Leu Pro Ala Ser Ser Glu Thr
210                 215                 220

Thr Ile Val Thr Pro Thr Ser Ile Ala Ala Glu Gln Val Pro Leu Trp
225                 230                 235                 240

Gly Gln Cys Gly Gly Ile Gly Tyr Thr Gly Ser Thr Ile Cys Glu Gln
                245                 250                 255

Gly Ser Cys Val Tyr Leu Asn Asp Trp Tyr Tyr Gln Cys Leu Ile Ser
            260                 265                 270

Asp Gln Gly Thr Ala Ser Thr Thr Ser Ala Thr Thr Ser Ile Thr Ser
            275                 280                 285

Phe Asn Val Ser Ser Ser Ser Glu Thr Thr Val Ile Ala Pro Thr Ser
290                 295                 300

Ile Ser Thr Glu Asp Val Pro Leu Trp Gly Gln Cys Gly Gly Ile Gly
305                 310                 315                 320

Tyr Thr Gly Ser Thr Thr Cys Ser Gln Gly Ser Cys Val Tyr Leu Asn
                325                 330                 335

Asp Trp Tyr Phe Gln Cys Leu Pro Glu Glu Thr Thr Ser Ser Thr Thr
            340                 345                 350

Ser Ser Ser Ser Ser Ser Ser Ser Thr Ser Ser Ala Ser Ser
            355                 360                 365

Thr Ser Ser Thr Ser Ser Thr Ser Ser Thr Ser Thr Ser Ser Ser Ser
370                 375                 380

Thr Ser Ser Ser Ile Pro Thr Ser Thr Ser Ser Ser Gly Asp Phe
385                 390                 395                 400

Glu Thr Ile Pro Asn Gly Phe Ser Gly Thr Gly Arg Thr Thr Arg Tyr
                405                 410                 415

Trp Asp Cys Cys Lys Pro Ser Cys Ser Trp Pro Gly Lys Ser Asn Ser
            420                 425                 430

Val Thr Gly Pro Val Arg Ser Cys Gly Val Ser Gly Asn Val Leu Asp
            435                 440                 445

Ala Asn Ala Gln Ser Gly Cys Ile Gly Gly Glu Ala Phe Thr Cys Asp
450                 455                 460

Glu Gln Gln Pro Trp Ser Ile Asn Asp Asp Leu Ala Tyr Gly Phe Ala

```
            465                 470                 475                 480
Ala Ala Ser Leu Ala Gly Gly Ser Glu Asp Ser Ser Cys Cys Thr Cys
                485                 490                 495
Met Lys Leu Thr Phe Thr Ser Ser Ile Ala Gly Lys Thr Met Ile
                500                 505                 510
Val Gln Leu Thr Asn Thr Gly Ala Asp Leu Gly Ser Asn His Phe Asp
                515                 520                 525
Ile Ala Leu Pro Gly Gly Leu Gly Ile Phe Thr Glu Gly Cys Ser
            530                 535                 540
Ser Gln Phe Gly Ser Gly Tyr Gln Trp Gly Asn Gln Tyr Gly Ile
545                 550                 555                 560
Ser Ser Leu Ala Glu Cys Asp Gly Leu Pro Ser Glu Leu Gln Pro Gly
                565                 570                 575
Cys Gln Phe Arg Phe Gly Trp Phe Glu Asn Ala Asp Asn Pro Ser Val
                580                 585                 590
Glu Phe Glu Gln Val Ser Cys Pro Pro Glu Ile Thr Ser Ile Thr Gly
                595                 600                 605
Cys Ala Arg Thr Asp Glu
            610

<210> SEQ ID NO 58
<211> LENGTH: 410
<212> TYPE: PRT
<213> ORGANISM: Piromyces equi

<400> SEQUENCE: 58

Met Arg Leu Ala Leu Thr Ser Cys Ile Ala Leu Ala Ala Ser Ile Ala
1               5                   10                  15
Lys Val Ser Ala Ala Cys Trp Ala Gln Ser Gln Gly Tyr Asn Cys Cys
                20                  25                  30
Asn Asn Pro Ser Ser Thr Lys Val Glu Tyr Thr Asp Ala Ser Gly Gln
            35                  40                  45
Trp Gly Val Gln Asn Gly Gln Trp Cys Gly Ile Asp Tyr Ser Tyr Gly
50                  55                  60
Gln Asn Gln Gly Asn Glu Ser Cys Thr Gly Asn Gly Tyr Pro Cys
65                  70                  75                  80
Cys Asn Thr Cys Gln Ala Thr Tyr Thr Asp Gly Asp Gly Asp Trp Ala
                85                  90                  95
Phe Glu Asn Gly Asn Trp Cys Gly Ile Lys Asn Ser Cys Lys Gln Gln
                100                 105                 110
Pro Gln Asn Asn Gln Cys Thr Gly Asn Gly Ala Tyr Arg Cys Cys
            115                 120                 125
Asn Thr Cys Gln Ala Thr Tyr Thr Asp Asn Glu Gly Lys Trp Ala Phe
130                 135                 140
Glu Asn Gly Asp Trp Cys Gly Ile Lys Tyr Ser Cys Pro Ser Gln Gln
145                 150                 155                 160
Val Thr Thr Thr Thr Thr Arg Arg Thr Thr Thr Thr Gln Gln Gln
                165                 170                 175
Gln Pro Thr Gly Ser Gly Gly Asn Ser Asn Val Pro Leu Asn Pro Pro
            180                 185                 190
Asp Phe Ser Gly Gln Thr Gly Lys Thr Thr Arg Tyr Trp Asp Cys Cys
            195                 200                 205
Leu Ala Ser Cys Ser Trp Gln Glu Asn Cys Lys Asn Asp Gly Ala Gln
        210                 215                 220
```

```
Gly Val Val Arg Ser Cys Asn Val Asp Gly Ile Thr Pro Phe Thr Asp
225                 230                 235                 240

Leu Ser Asn Leu Trp Arg Val Lys Ser Gly Cys Asn Gly Gly Ser Val
            245                 250                 255

Tyr Met Cys Asn Asp Gln Gln Pro Trp Ala Ile Asn Asp Asn Val Ala
        260                 265                 270

Tyr Gly Phe Val Ala Ser His Glu Lys Cys Cys Thr Cys Gln Arg Leu
    275                 280                 285

Lys Phe Thr Ser Gly Pro Ile Ala Gly Lys Gln Met Ile Val Gln Thr
290                 295                 300

Thr Asn Thr Gly Gly Asp Leu Ser Ser Asn His Phe Asp Ile Gln Met
305                 310                 315                 320

Pro Gly Gly Gly Phe Gly Ile Phe Asp Gly Cys Thr Ser Gln Phe Gly
            325                 330                 335

Gly Ser Tyr Gln Trp Gly Glu Arg Tyr Gly Gly Ile Ser Ser Ala Ser
        340                 345                 350

Gln Cys Ala Asn Leu Pro Pro Gln Leu Lys Ala Gly Cys Glu Trp Arg
    355                 360                 365

Phe Asn Trp Phe Lys Asn Ala Asp Asn Pro Ala Val Val Phe Glu Arg
370                 375                 380

Val Gln Cys Pro Lys Glu Leu Thr Glu Ile Thr Gly Cys Val Pro Gly
385                 390                 395                 400

Asp Asp Ala Ser Ala Lys Lys Leu Pro Trp
            405                 410

<210> SEQ ID NO 59
<211> LENGTH: 237
<212> TYPE: PRT
<213> ORGANISM: Apriona germari

<400> SEQUENCE: 59

Met Lys Val Phe Val Ala Ile Leu Ala Val Phe Cys Thr Phe Glu Val
1               5                   10                  15

Ser Leu Ser Lys Val Tyr Asn Leu Asn Lys Val Pro Tyr Gly Ile Ser
            20                  25                  30

Gly Ser Gly Thr Thr Thr Arg Tyr Trp Asp Cys Cys Lys Pro Ser Cys
        35                  40                  45

Gly Trp Val Glu Asn Leu Ala Lys Glu Gly Thr Pro Val Ala Thr Cys
    50                  55                  60

Ser Ala Asp Gly Ser Thr Thr Val Ala Ala Ser Val Lys Ser Ser Cys
65                  70                  75                  80

Val Gly Gly Thr Ser Tyr Met Cys Ser Asn Gln Gln Pro Lys Ser Val
                85                  90                  95

Asn Ser Thr Phe Ala Leu Gly Phe Val Ala Ala Ser Phe Thr Gly Gly
            100                 105                 110

Ala Asp Thr Asn Tyr Cys Cys Ala Cys Ile Lys Leu Thr Phe Gln Asp
        115                 120                 125

Ala Leu Gln Gly Lys Thr Met Val Gln Val Thr Asn Thr Gly Gly
    130                 135                 140

Asp Leu Gly Ser Asn Gln Phe Asp Ile Ala Ile Pro Gly Gly Gly Val
145                 150                 155                 160

Gly Ile Phe Thr Asp Gly Cys Ser Ser Gln Trp Gly Thr Pro Ser Asn
                165                 170                 175

Gly Trp Gly Asp Gln Tyr Trp Val Trp Gly Ser Glu Ala Asp Cys
            180                 185                 190
```

```
Ala Gln Leu Pro Ser Asp Leu Gln Glu Gly Cys Lys Phe Arg Phe Glu
        195                 200                 205

Phe Met Glu Gly Ala Ser Asn Pro Gly Val Thr Phe Glu Gln Val Asp
    210                 215                 220

Cys Pro Ser Glu Leu Val Ser Ile Thr Gly Cys Asn Tyr
225                 230                 235
```

<210> SEQ ID NO 60
<211> LENGTH: 239
<212> TYPE: PRT
<213> ORGANISM: Apriona germari

<400> SEQUENCE: 60

```
Met Lys Val Leu Leu Ala Val Val Ala Val Leu Cys Thr Phe Glu Ala
1               5                   10                  15

Ser Leu Ser Gln Asp Tyr His Val Thr Pro Leu Val Gly Gly Val Ser
            20                  25                  30

Gly Thr Gly Lys Thr Thr Arg Tyr Trp Asp Cys Cys Lys Pro Ser Cys
        35                  40                  45

Ser Trp Lys Ala Asn Leu Lys Ser Lys Ser Gly Lys Pro Val Glu Ala
    50                  55                  60

Cys Ala Ala Asp Gly Lys Thr Val Val Lys Glu Ser Thr Lys Ser Ala
65                  70                  75                  80

Cys Glu Glu Gly Ala Gly Ala Tyr Met Cys Ser Asp Gln Gln Pro Lys
                85                  90                  95

Val Val Asn Ser Thr Phe Ala Leu Gly Tyr Val Ala Ala Ser Phe Thr
            100                 105                 110

Gly Gly Ile Asp Val Asn Met Cys Cys Ala Cys Leu Arg Leu Lys Phe
        115                 120                 125

Gln Gly Asp Leu Ser Gly Lys Gln Met Ile Val Gln Val Thr Asn Thr
    130                 135                 140

Gly Ser Asp Leu Gly Ser Asn Gln Phe Asp Ile Ala Ile Pro Gly Gly
145                 150                 155                 160

Gly Val Gly Ile Phe Thr Lys Gly Cys Ser Ser Gln Trp Gly Thr Pro
                165                 170                 175

Ser Asn Gly Trp Gly Asp Gln Tyr Gly Gly Val Ser Ser Glu Ser Gln
            180                 185                 190

Cys Ser Gln Leu Pro Ser Ser Leu Arg Glu Gly Cys Lys Phe Arg Phe
        195                 200                 205

Thr Phe Met Lys Ser Val Ser Asn Pro Ala Val Thr Phe Glu Gln Val
    210                 215                 220

Ser Cys Pro Ser Glu Ile Val Ser Ala Ser Gly Cys Asn Tyr Ser
225                 230                 235
```

<210> SEQ ID NO 61
<211> LENGTH: 271
<212> TYPE: PRT
<213> ORGANISM: Alternaria alternata

<400> SEQUENCE: 61

```
Met Pro Gln His Leu Arg Asn Ile Ala Leu Thr Ile Glu Phe Phe Ala
1               5                   10                  15

Val Leu Ala Arg Cys Ala His Leu Asn Tyr Thr Gly Glu Ala Val Thr
            20                  25                  30

Thr Arg Phe Trp Asp Cys Cys Lys Pro Ser Cys Gly Trp Asn Gly Lys
        35                  40                  45
```

```
Ala Gln Phe Ser Arg Pro Val Glu Ser Cys Thr Ala Asp Asp Lys Pro
 50                  55                  60

Thr Asp Ile Ala Ala Gly Thr Gly Cys Asn Ser Gly Ser Ala Phe Gln
 65                  70                  75                  80

Cys Ser Asn Gln Gln Pro Trp Ala Ile Asn Asp Thr Leu Ser Tyr Gly
                 85                  90                  95

Tyr Ala Gly Val Tyr Ile Thr Pro Asp Leu Thr His Gly Gly Ile Glu
                100                 105                 110

Asp Ala Trp Cys Cys Ala Cys Tyr Gln Leu Asn Phe Thr Ser Glu Pro
            115                 120                 125

Leu Ile Gly Lys Ser Met Ile Val Gln Ala Ser Asn Thr Ala Tyr Asp
130                 135                 140

Val Thr Asn Ala Asn Arg Phe Ser Leu Ala Val Pro Gly Gly Asn Thr
145                 150                 155                 160

Thr Ser Thr Asn Ala Cys Ala Gln Gln Tyr Gly Val Ser Gln Ser Val
                165                 170                 175

Phe Gly Glu Asn Met Ala Gly Val Lys Ser Ile Asp Asp Cys Gln Asn
                180                 185                 190

Leu Pro Glu Asn Leu Arg Ala Gly Cys Glu Trp Arg Phe Asp Trp Phe
            195                 200                 205

Lys Asn Ala Ser Phe Pro Ser Ala Asn Phe Lys Arg Val Val Cys Pro
210                 215                 220

Ser Glu Ile Thr Ala Lys Thr Asn Cys Ile Arg Asn Asp Asp Lys Val
225                 230                 235                 240

Leu Ala Gly Glu Ala Ser Ser Ala Gln Ser Leu Thr Pro Ser Ser Ser
                245                 250                 255

Thr Met Ala Phe Phe Ala Val Ile Ile Leu Gly Leu Ile Ser Ile
                260                 265                 270

<210> SEQ ID NO 62
<211> LENGTH: 242
<212> TYPE: PRT
<213> ORGANISM: Phaedon cochleariae

<400> SEQUENCE: 62

Met Gln Val Ile Val Leu Pro Leu Val Phe Leu Ala Thr Phe Ala Thr
 1                   5                  10                  15

Ser Gly Ser Leu Ala Ala Pro Asp Ala Ser Pro Glu Ile Val Pro Val
                 20                  25                  30

Asp Gly Gly Leu Ser Gly Tyr Gly Thr Thr Arg Tyr Trp Asp Cys Cys
            35                  40                  45

Cys Lys Pro Ser Cys Ala Trp Lys Glu Asn Ile Asn Thr Pro Thr Met
 50                  55                  60

Thr Pro Val Gln Thr Cys Ala Ile Asp Gly Asn Thr Val Val Asn Ala
 65                  70                  75                  80

Ser Val Gln Ser Gly Cys Ile Gly Gly Ser Ser Tyr Met Cys Ser Asn
                 85                  90                  95

Gln Gln Ala Phe Val Val Asn Ser Thr Leu Ala Phe Gly Phe Ala Ala
                100                 105                 110

Gly Ser Phe Thr Gly Gly Val Asp Asn Asn Leu Cys Cys Ser Cys Met
            115                 120                 125

Leu Leu Thr Phe Gln Gly Gln Leu Ala Gly Lys Gln Phe Leu Val Gln
130                 135                 140

Ile Thr Asn Thr Gly Gly Asp Leu Gly Ser Thr Ser Ser Ile Trp Pro
```

```
                145                 150                 155                 160
Phe Pro Gly Gly Gly Val Gly Ile Phe Thr Gln Gly Cys His Asp Gln
                    165                 170                 175

Trp Thr Pro Arg Gly Ala Ala Gly Gly Asp Gln Tyr Gly Gly Val Tyr
            180                 185                 190

Ser Val Glu Gln Cys Ser Asp Leu Pro Glu Val Leu Gln Pro Gly Cys
                195                 200                 205

Arg Phe Arg Phe Glu Phe Leu Glu Asn Val Ser Asn Pro Gln Val Ser
    210                 215                 220

Phe Gln Gln Val Gln Cys Pro Ala Glu Ile Val Ala Ile Ser Asn Cys
225                 230                 235                 240

Ala Leu

<210> SEQ ID NO 63
<211> LENGTH: 222
<212> TYPE: PRT
<213> ORGANISM: Talaromyces emersonii

<400> SEQUENCE: 63

Met Asn Val Arg Ala Val Val Ser Val Ser Ala Phe Leu Leu Thr Pro
1               5                   10                  15

Leu Ala Ser Ala Leu Thr Gly Thr Thr Thr Thr Trp Asp Cys Cys
            20                  25                  30

Lys Pro Ala Cys Ser Trp Thr Gln Asn Ala Gln Ala Gly Gly Ala Ser
        35                  40                  45

Gly Thr Val Ala Thr Cys Asn Ile Asn Asn Gln Val Leu Ser Asn Gly
    50                  55                  60

Ala Ser Ala Pro Ser Ala Cys Gln Gly Gly Asp Ala Tyr Ser Cys Ser
65                  70                  75                  80

Asp Phe Gln Pro Ile Ile Ile Ser Asp Thr Leu Ser Tyr Gly Phe Ala
                85                  90                  95

Gly Asn Trp Glu Thr Ser Asn Cys Cys Lys Cys Phe Gln Phe Thr Trp
            100                 105                 110

Thr Ser Gly Ala Gly Ala Gly Lys Ser Met Ile Val Gln Val Val Asn
        115                 120                 125

Ser Gly Gly Val Ser Thr Gly Asp Phe Asp Ile Tyr Thr Pro Gly Gly
    130                 135                 140

Gly Val Gly Asp Tyr Asn Ala Cys Thr Ser Gln Tyr Gly Ala Pro Pro
145                 150                 155                 160

Gln Gly Trp Gly Ala Gln Tyr Gly Gly Val Ser Ser Asp Ala Glu Cys
                165                 170                 175

Asp Gln Leu Pro Ser Ile Leu Gln Pro Gly Cys His Trp Arg Phe Glu
            180                 185                 190

Trp Ala Gly Gly Gly Ile Asn Gly Trp Thr Thr Glu Tyr Glu Glu Val
        195                 200                 205

Asp Cys Pro Ser Gln Leu Thr Ser Ile Ser Gly Cys Tyr Pro
    210                 215                 220

<210> SEQ ID NO 64
<211> LENGTH: 393
<212> TYPE: PRT
<213> ORGANISM: Ustilago maydis

<400> SEQUENCE: 64

Met Ala Phe Lys Leu Asn Ile Gly Leu Leu Ala Leu Ser Leu Ser Leu
1               5                   10                  15
```

Ser Leu Val His Leu Asp Gly Val Arg Ala Gly Met Ala Thr Arg Tyr
            20                  25                  30

Trp Asp Cys Cys Leu Ala Ser Ala Ser Trp Glu Gly Lys Ala Pro Val
            35                  40                  45

Tyr Ala Pro Val Asp Ala Cys Lys Ala Asp Gly Val Thr Leu Ile Asp
 50                  55                  60

Ser Lys Lys Asp Pro Ser Gly Gln Ser Gly Cys Asn Gly Gly Asn Lys
 65                  70                  75                  80

Phe Met Cys Ser Cys Met Gln Pro Phe Asp Asp Glu Thr Asp Pro Thr
                 85                  90                  95

Leu Ala Phe Gly Phe Gly Ala Phe Thr Thr Gly Gln Glu Ser Asp Thr
             100                 105                 110

Asp Cys Ala Cys Phe Tyr Ala Glu Phe Glu His Asp Ala Gln Gly Lys
             115                 120                 125

Ala Met Lys Arg Asn Lys Leu Ile Phe Gln Val Thr Asn Val Gly Gly
 130                 135                 140

Asp Val Gln Ser Gln Asn Phe Asp Phe Gln Ile Pro Gly Gly Gly Leu
145                 150                 155                 160

Gly Ala Phe Pro Lys Gly Cys Pro Ala Gln Trp Gly Val Glu Ala Ser
                 165                 170                 175

Leu Trp Gly Asp Gln Tyr Gly Gly Val Lys Ser Ala Thr Glu Cys Ser
             180                 185                 190

Lys Leu Pro Lys Pro Leu Gln Glu Gly Cys Lys Trp Arg Phe Ser Glu
             195                 200                 205

Trp Gly Asp Asn Pro Val Leu Lys Gly Ser Pro Lys Arg Val Lys Cys
 210                 215                 220

Pro Lys Ser Leu Ile Asp Arg Ser Gly Cys Gln Arg Lys Asp Asn
225                 230                 235                 240

Thr Ile Ser Pro Tyr Ser Gly Lys Val Asp Ser Ala Asn Thr Ala Ala
                 245                 250                 255

Pro Ala Gln Tyr Lys Arg Asp Arg Ser Val Cys Leu Ala Gly Gly Lys
             260                 265                 270

Lys Gly Lys Ser Ala Ala Gly Gly Val Asp Gly Ser Gly Asp Ala Ser
             275                 280                 285

Gly Gly Ala Asp Ala Ser Gly Ala Gly Ala Ala Glu Gly Ser Gln
 290                 295                 300

Gly Gln Pro Glu Gly Tyr Gly Gln Pro Ser Gly Gly Asn Asp Gln Gly
305                 310                 315                 320

Ser Ser Asn Gly Asp Ala Thr Thr Gly Ala Gly Ser Gly Ser Gly Ser
                 325                 330                 335

Asp Ser Gly Ser Thr Ala Asn Gly Ser Gly Ser Gly Ala Pro Thr Ser
             340                 345                 350

Gly Ser Asp Gly Ser Ala Val Ala Pro Pro Ser Gly Gly Ser Asn Pro
             355                 360                 365

Gly Ala Ala Gln Gly Gly Gln Gly Gly Ala Gln Pro Gly Pro Ser Gly
 370                 375                 380

Gly His Lys Lys Cys His Lys Lys His
385                 390

<210> SEQ ID NO 65
<211> LENGTH: 410
<212> TYPE: PRT
<213> ORGANISM: Penicillium janthinellum

<400> SEQUENCE: 65

```
Met Met Ala Gln Asp Lys Arg Thr Leu Leu Ala Leu Leu Ala Leu Gly
1               5                   10                  15

Gly Ser Ala Leu Gly Gln Gln Thr Ala Trp Gly Gln Cys Gly Gly Gln
            20                  25                  30

Gly Trp Thr Gly Ala Thr Thr Cys Val Ser Gly Tyr Tyr Cys Ser Phe
                35                  40                  45

Gln Asn Asn Trp Tyr Ser Gln Cys Leu Pro Gly Ala Ala Ser Thr Thr
        50                  55                  60

Ser Thr Ser Thr Thr Thr Thr Thr Val Tyr Ser Thr Thr Leu Lys Thr
65                  70                  75                  80

Thr Thr Thr Ser Ser Thr Ser Ser Ala Pro Thr Gly Lys Val Arg Phe
                85                  90                  95

Ala Gly Val Asn Ile Ala Gly Phe Asp Phe Gly Val Val Thr Ser Gly
            100                 105                 110

Thr Gln Asp Leu Ser Gln Val Val Asp Glu Ser Val Asp Gly Val Asn
        115                 120                 125

Gln Met Ser His Phe Val Asn Ala Asp Thr Phe Asn Ile Phe Arg Leu
130                 135                 140

Pro Thr Gly Trp Gln Phe Ile Val Asn Asn Asn Leu Gly Gly Ser Leu
145                 150                 155                 160

Asp Ser Asn Asn Phe Gly Lys Tyr Glu Gln Val Gly Ser Gly Leu Ser
                165                 170                 175

Leu Ser Gly Ala Tyr Cys Ile Val Asp Ile His Asn Tyr Ala Arg Trp
            180                 185                 190

Asn Gly Gly Val Ile Gly Gln Gly Gly Pro Thr Asp Asp Gln Phe Ile
        195                 200                 205

Ser Leu Trp Thr Gln Leu Ala Thr His Tyr Lys Ser Asn Ser Arg Val
210                 215                 220

Ile Phe Gly Ile Met Asn Glu Pro His Asp Leu Asn Ile Ala Thr Trp
225                 230                 235                 240

Ala Ala Thr Val Gln Lys Thr Val Thr Ala Ile Arg Asn Thr Gly Ala
                245                 250                 255

Thr Ser Gln Met Ile Leu Leu Pro Gly Thr Asp Tyr Thr Ser Ala Ala
            260                 265                 270

Asn Phe Ile Glu Asn Gly Ser Gly Ala Ala Leu Leu Pro Val Thr Asn
        275                 280                 285

Pro Asp Gly Ser Thr Thr Asn Leu Ile Phe Asp Val His Lys Tyr Leu
290                 295                 300

Asp Ser Asp Asn Ser Gly Thr His Ala Glu Cys Val Thr Asn Asn Ala
305                 310                 315                 320

Asp Ala Phe Asn Asn Leu Ala Thr Trp Leu Arg Ser Asn Lys Arg Gln
                325                 330                 335

Ala Leu Leu Ser Glu Thr Gly Gly Gly Asn Val Gln Ser Cys Ala Thr
            340                 345                 350

Tyr Met Cys Gln Gln Leu Asp Ile Leu Asn Ala Asn Ser Asp Val Tyr
        355                 360                 365

Leu Gly Trp Thr Ser Trp Ser Ala Gly Gly Phe Gln Ala Ser Trp Asn
370                 375                 380

Tyr Val Leu Thr Glu Val Pro Val Asn Gly Val Asp Gln Tyr Leu Val
385                 390                 395                 400

Gln Gln Cys Phe Val Pro Lys Trp Lys Asn
                405                 410
```

<210> SEQ ID NO 66
<211> LENGTH: 368
<212> TYPE: PRT
<213> ORGANISM: Macrophomina phaseolina

<400> SEQUENCE: 66

```
Met Lys Thr Ala Thr Leu Ala Ala Ala Ser Leu Phe Thr Ser Ala
1               5                   10                  15

Ala Leu Ala Ala Pro Thr Ser Thr Leu Lys Ala Ala Ala Ser Lys
                20                  25                  30

Val Lys Phe Ala Gly Val Asn Ile Ala Gly Phe Asp Phe Gly Cys Gly
            35                  40                  45

Thr Asp Gly Thr Cys Thr Gln Thr Ala Ser Thr Ala Thr Asp Pro Leu
        50                  55                  60

Thr Asp Ser Asp Gly Gln Gly Gln Met Asp His Phe Val Lys Asp Asp
65                  70                  75                  80

Lys Leu Asn Ala Phe Arg Leu Pro Val Gly Trp Gln Tyr Leu Val Ala
                85                  90                  95

Asn Lys Leu Gly Gly Asp Leu Asp Ser Ala Asn Ala Gly Lys Tyr Asp
                100                 105                 110

Asn Leu Val Gln Gly Cys Leu Lys Ser Gly Ala Glu Leu Cys Ile Ile
            115                 120                 125

Asp Ile His Asn Tyr Ala Leu Leu Glu Arg Pro Asp His Arg Gln Gly
        130                 135                 140

Gly Pro Thr Asn Asp Gln Phe Val Ser Leu Trp Lys Gln Leu Ala Thr
145                 150                 155                 160

Lys Tyr Lys Asp Asn Thr Lys Val Ala Phe Gly Val Met Asn Glu Pro
                165                 170                 175

His Asp Val Pro Asp Ile Asn Lys Trp Ala Asp Thr Val Gln Gln Val
            180                 185                 190

Val Thr Ala Ile Arg Asn Arg Gly Ala Thr Thr Gln Tyr Val Leu Leu
        195                 200                 205

Pro Gly Asn Asp Trp Thr Ser Ala Ala Ala Phe Ile Asp Asn Gly Ser
210                 215                 220

Ala Ala Ala Leu Lys Lys Val Thr Asn Pro Asp Gly Ser Thr Asp Asn
225                 230                 235                 240

Leu Ile Phe Asp Val His Lys Tyr Leu Asp Ser Asp Asn Ser Gly Thr
                245                 250                 255

His Thr Glu Cys Val Thr Asn Asn Ile Asp Asp Ala Phe Lys Pro Leu
            260                 265                 270

Ala Asp Trp Leu Arg Gln Asn Lys Arg Met Ala Ile Asn Thr Glu Ser
        275                 280                 285

Gly Gly Gly Asn Thr Asp Ser Cys Glu Lys Tyr Phe Cys Glu Gln Ile
290                 295                 300

Gln Tyr Leu Asn Gln Asn Ala Asp Val Phe Leu Gly Tyr Thr Ala Trp
305                 310                 315                 320

Ser Ala Gly Gly Phe Asp Gln Thr Tyr Glu Leu Val Gln Thr Pro Ile
                325                 330                 335

Ser Ser Pro Met Ala Arg Thr Lys Ile Leu His Ser Arg Ser Ala
            340                 345                 350

Leu Leu Val Leu Gly Arg Met Leu Glu Gly Arg His Glu Phe Met Tyr
        355                 360                 365
```

<210> SEQ ID NO 67
<211> LENGTH: 341
<212> TYPE: PRT
<213> ORGANISM: Cryptococcus flavus

<400> SEQUENCE: 67

Met Lys Thr Ala Thr Leu Leu Ala Ala Leu Ser Val Leu Ala Gly Ala
1               5                   10                  15

Leu Ala Ala Pro Leu Ala Gly Asp Ser Ala Leu His Arg Arg Ser Leu
            20                  25                  30

Pro Arg Leu Gly Gly Val Asn Leu Ala Gly Cys Asp Phe Gly Ile Asp
        35                  40                  45

Ile Tyr Gly Asn Ser Gly Thr Pro Ala Cys Pro Gly Thr Glu Gln Val
    50                  55                  60

Gly His Phe Ile Ala Asp Gly Ala Asn Leu Phe Arg Leu Pro Ala Gly
65                  70                  75                  80

Trp Gln Tyr Leu Val Gly Asn Asn Gln Ala Ser Thr Ser Leu Ala Pro
                85                  90                  95

Asp Phe Phe Ala Gln Tyr Asp Ala Leu Val Gln Ala Val Ile Ser Lys
            100                 105                 110

Gly Ala Tyr Ala Ile Ile Asp Val His Asn Tyr Ala Arg Trp Asn Gly
        115                 120                 125

Ala Ile Ile Gly Gln Gly Gly Pro Ser Asn Gln Asp Phe Ala Asn Leu
    130                 135                 140

Trp Thr Leu Leu Ala Thr Lys Val Thr Ser Asn Asp Pro Asn Val Ile
145                 150                 155                 160

Phe Gly Leu Met Asn Glu Pro His Asp Leu Asp Val Ser Thr Trp Ala
                165                 170                 175

Gly Ser Val Gln Ala Ala Val Asn Ala Ile Arg Ala Ala Gly Ala Thr
            180                 185                 190

Ser Gln Tyr Ile Leu Ile Pro Gly Thr Gly Phe Thr Asn Ala Asn Ala
        195                 200                 205

Trp Phe Gln Gly Gln Asp Asn Ala Leu Leu Gly Val Thr Asp Pro Val
    210                 215                 220

Gly Gly Thr Asp Lys Leu Leu Leu Asp Val His Arg Tyr Asn Asp Val
225                 230                 235                 240

Asp Phe Ser Gly Thr His Ala Glu Cys Thr Thr Asn Ser Leu Asp Val
                245                 250                 255

Leu Ser Ser Leu Asp Ser Trp Leu Lys Gly Asn Gly Arg Lys Ala Ile
            260                 265                 270

Val Ser Glu Thr Gly Gly Gly His Thr Thr Ser Cys Glu Thr Asp Leu
        275                 280                 285

Gly Glu Phe Leu Asn Gly Ile Lys Glu Asp Tyr Pro Ser Val Leu Gly
    290                 295                 300

Phe Ala Val Trp Ala Ala Gly Ser Phe Asp Pro Ser Tyr Val Leu Ser
305                 310                 315                 320

Ile Thr Pro Thr Asn Gly Val Asp Asn Gln Leu Phe Asp Ile Ala Val
                325                 330                 335

Lys Pro Asn Leu Pro
            340

<210> SEQ ID NO 68
<211> LENGTH: 326
<212> TYPE: PRT
<213> ORGANISM: Aspergillus nidulans

<400> SEQUENCE: 68

```
Met Arg Ser Leu Val Leu Leu Ser Ser Val Leu Ala Leu Val Ala Pro
1               5                   10                  15
Ser Lys Gly Ala Phe Thr Trp Leu Gly Thr Asn Glu Ala Gly Ala Glu
                20                  25                  30
Phe Gly Glu Gly Ser Tyr Pro Gly Glu Leu Gly Thr Glu Tyr Ile Trp
            35                  40                  45
Pro Asp Leu Gly Thr Ile Gly Thr Leu Arg Asn Glu Gly Met Asn Ile
        50                  55                  60
Phe Arg Val Ala Phe Ser Met Glu Arg Leu Val Pro Asp Ser Leu Ala
65                  70                  75                  80
Gly Pro Val Ala Asp Glu Tyr Phe Gln Asp Leu Val Glu Thr Val Asn
                85                  90                  95
Gly Ile Thr Ala Leu Gly Ala Tyr Ala Val Leu Asp Pro His Asn Tyr
            100                 105                 110
Gly Arg Tyr Tyr Gly Asn Ile Ile Thr Ser Thr Asp Asp Phe Ala Ala
        115                 120                 125
Phe Trp Thr Ile Leu Ala Thr Glu Phe Ala Ser Asn Glu Leu Val Ile
130                 135                 140
Phe Asp Thr Asn Asn Glu Tyr His Thr Met Asp Gln Ser Leu Val Leu
145                 150                 155                 160
Asn Leu Asn Gln Ala Ala Ile Asp Ala Ile Arg Ala Ser Gly Ala Thr
                165                 170                 175
Ser Gln Tyr Ile Phe Ala Glu Gly Asn Ser Trp Thr Gly Ala Trp Thr
            180                 185                 190
Trp Val Asp Val Asn Asp Asn Met Lys Ala Leu Thr Asp Pro Gln Asp
        195                 200                 205
Lys Leu Ile Tyr Glu Met His Gln Tyr Leu Asp Ser Asp Gly Ser Gly
        210                 215                 220
Thr Asn Thr Ala Cys Val Ser Ser Thr Ile Gly Ser Glu Arg Val Thr
225                 230                 235                 240
Ala Ala Thr Asn Trp Leu Arg Glu Asn Gly Lys Leu Gly Val Leu Gly
                245                 250                 255
Glu Phe Ala Gly Ala Asn Asn Gln Val Cys Lys Asp Ala Val Ala Asp
            260                 265                 270
Leu Leu Glu Tyr Leu Glu Glu Asn Ser Asp Val Trp Leu Gly Ala Leu
        275                 280                 285
Trp Trp Ala Ala Gly Pro Trp Trp Gly Asp Tyr Met Phe Asn Met Glu
        290                 295                 300
Pro Thr Ser Gly Ile Ala Tyr Gln Glu Tyr Ser Glu Ile Leu Gln Pro
305                 310                 315                 320
Tyr Phe Val Gly Ser Gln
                325
```

<210> SEQ ID NO 69
<211> LENGTH: 521
<212> TYPE: PRT
<213> ORGANISM: Aspergillus kawachii

<400> SEQUENCE: 69

```
Met Arg Ile Ser Asn Leu Ile Val Ala Ala Ser Ala Ala Thr Met Val
1               5                   10                  15
Ser Ala Leu Pro Ser Arg Gln Met Lys Lys Arg Asp Ser Gly Phe Lys
                20                  25                  30
```

-continued

```
Trp Val Gly Thr Ser Glu Ser Gly Ala Glu Phe Gly Ser Ala Leu Pro
         35                  40                  45

Gly Thr Leu Gly Thr Asp Tyr Thr Trp Pro Glu Thr Ser Lys Ile Gln
 50                  55                  60

Val Leu Arg Asn Lys Gly Met Asn Ile Phe Arg Ile Pro Phe Leu Met
 65                  70                  75                  80

Glu Arg Leu Thr Pro Asp Gly Leu Thr Gly Ser Phe Ala Ser Thr Tyr
                 85                  90                  95

Leu Ser Asp Leu Lys Ser Thr Val Glu Phe Val Thr Asn Ser Gly Ala
                100                 105                 110

Tyr Ala Val Leu Asp Pro His Asn Tyr Gly Arg Phe Asp Gly Ser Ile
            115                 120                 125

Ile Glu Ser Thr Ser Asp Phe Lys Thr Trp Trp Lys Asn Val Ala Thr
        130                 135                 140

Glu Phe Ala Asp Asn Asp Lys Val Ile Phe Asp Thr Asn Asn Glu Tyr
145                 150                 155                 160

His Asp Met Glu Gln Ser Leu Val Leu Asn Leu Asn Gln Ala Ala Ile
                165                 170                 175

Asn Gly Ile Arg Ala Ala Gly Ala Thr Thr Gln Tyr Ile Phe Val Glu
            180                 185                 190

Gly Asn Ala Tyr Thr Gly Ala Trp Asp Trp Thr Thr Tyr Asn Asp Asp
        195                 200                 205

Leu Ser Gly Leu Thr Asp Ser Glu Asp Lys Ile Ile Tyr Glu Met His
    210                 215                 220

Gln Tyr Leu Asp Ser Asp Ser Ser Gly Thr Ser Glu Thr Cys Val Ser
225                 230                 235                 240

Ser Thr Ile Gly Lys Glu Arg Ile Glu Lys Ala Thr Glu Trp Leu Lys
                245                 250                 255

Thr Asn Asn Lys Gln Gly Ile Ile Gly Glu Phe Ala Gly Gly Val Asn
            260                 265                 270

Ser Val Cys Glu Glu Ala Val Glu Gly Met Leu Ala Tyr Met Ser Glu
        275                 280                 285

Asn Ser Asp Val Trp Val Gly Ala Ser Trp Trp Ser Ala Gly Pro Trp
    290                 295                 300

Trp Gly Thr Tyr Met Tyr Ser Leu Glu Pro Thr Asp Gly Thr Ala Tyr
305                 310                 315                 320

Ser Thr Tyr Leu Pro Ile Leu Glu Lys Tyr Phe Pro Ser Gly Asp Ala
                325                 330                 335

Ser Ser Ser Ser Ser Ala Ser Ala Ser Val Ala Ala Thr Ser Ala
            340                 345                 350

Val Ser Thr Thr Thr Thr Ala Ala Phe Glu Gln Thr Thr Pro Ala
    355                 360                 365

Thr Gln Val Glu Ile Ala Ser Ser Ser Ser Ser Ser Ala Val Ala
370                 375                 380

Ala Ser Gln Thr Thr Leu Ser Lys Val Lys Ser Lys Ser Lys Ser Pro
385                 390                 395                 400

Cys Lys Leu Ser Ser Ala Thr Ser Ser Ala Val Ser Ser Ala Ala Ala
                405                 410                 415

Val Thr Thr Pro Ala Val Ala Ala Thr Thr Pro Ala Ala Pro Thr
            420                 425                 430

Ser Ser Ser Val Ala Phe Ala Thr Thr Ser Val Tyr Val Pro Thr Thr
            435                 440                 445

Thr Ala Ala Ala Pro Ser Gln Val Ser Ser Ser Ala Ala Ala Ser Ser
```

Ser Gly Val Val Gly Val Ser Asp Pro Gln Gly Pro Ser Ala Thr Asn
465                 470                 475                 480

Ser Ala Gly Glu Val Asn Gln Tyr Tyr Gln Cys Gly Gly Ile Asn Trp
            485                 490                 495

Thr Gly Pro Thr Val Cys Ala Ser Pro Tyr Thr Cys Lys Val Gln Asn
        500                 505                 510

Asp Tyr Tyr Tyr Gln Cys Val Ala Glu
        515                 520

<210> SEQ ID NO 70
<211> LENGTH: 333
<212> TYPE: PRT
<213> ORGANISM: Macrophomina phaseolina

<400> SEQUENCE: 70

Met Arg Leu Ser Thr Leu Leu Ile Ala Gly Ser Ala Ser Leu Ala Leu
1               5                   10                  15

Ala Ala Pro Val Gln Lys Glu Glu Lys Arg Ala Ser Asn Phe Gln Phe
            20                  25                  30

Phe Gly Val Asn Glu Ser Gly Pro Glu Phe Gly Glu Thr Lys Leu Pro
        35                  40                  45

Gly Thr Lys Asn Thr Asp Tyr Val Trp Pro Thr Leu Ser Thr Ile Asp
50                  55                  60

Thr Phe Val Gly Lys Gly Met Asn Thr Phe Arg Val Asn Ile Leu Met
65                  70                  75                  80

Glu Arg Leu Thr His Asn Ser Leu Thr Ala Ser Leu Asp Ser Gln Tyr
                85                  90                  95

Leu Ala Asp Leu Lys Thr Thr Val Asn Tyr Ile Thr Gly Lys Gly Ala
            100                 105                 110

Tyr Ala Met Ile Val Pro His Asn Tyr Gly Arg Phe Asn Ser Gln Ile
        115                 120                 125

Ile Thr Asp Thr Ala Gly Phe Lys Thr Trp Trp Thr Asn Val Ala Lys
130                 135                 140

Glu Phe Ala Gly Asn Ser Lys Val Ile Phe Asp Ile Asn Asn Glu Phe
145                 150                 155                 160

His Asp Met Asp Gln Thr Leu Val Val Asn Leu Asn Gln Ala Gly Ile
                165                 170                 175

Asp Gly Ile Arg Ala Ala Gly Ala Thr Ser Gln Tyr Ile Thr Ala Glu
            180                 185                 190

Gly Asn Ser Trp Thr Gly Ala Trp Thr Trp Thr Thr Ser Glu Asn Gly
        195                 200                 205

Lys Thr Met Ala Ala Leu Lys Asp Pro Gln Asn Lys Leu Ile Tyr Gln
210                 215                 220

Met His Gln Tyr Leu Asp Ser Asp Gly Ser Gly Thr Asn Glu Ala Cys
225                 230                 235                 240

Val Ser Ser Thr Ile Gly Lys Glu Arg Ile Thr Ala Ala Thr Lys Trp
                245                 250                 255

Leu Lys Asp Asn Gly Lys Lys Gly Leu Ile Gly Glu Phe Ala Gly Gly
            260                 265                 270

Asn Asn Ser Gln Cys Lys Thr Ala Val Glu Gly Met Leu Thr Tyr Met
        275                 280                 285

Gln Glu Asn Lys Asp Val Trp Thr Gly Ala Leu Trp Trp Ala Ala Gly
290                 295                 300

```
Pro Trp Trp Ala Ser Tyr Met Phe Ser Met Glu Pro Lys Thr Gly Thr
305                 310                 315                 320

Ala Tyr Thr Ala Tyr Leu Asp Leu Ile Ser Lys Phe Lys
                325                 330
```

<210> SEQ ID NO 71
<211> LENGTH: 389
<212> TYPE: PRT
<213> ORGANISM: Volvariella volvacea

<400> SEQUENCE: 71

```
Met Arg Ser Leu Leu Ser Ser Val Ala Ser Leu Ala Val Leu Phe Ala
1               5                   10                  15

Val Ala Lys Pro Ala Leu Ala Ala Val Pro Val Trp Gly Gln Cys Gly
                20                  25                  30

Gly Asn Gly Trp Ser Gly Glu Thr Thr Cys Ala Ser Gly Ser Thr Cys
            35                  40                  45

Val Val Val Asn Glu Trp Tyr His Gln Cys Gln Pro Gly Ala Gly Pro
50                  55                  60

Thr Thr Thr Ser Ser Ala Pro Asn Pro Thr Ser Ser Gly Cys Pro Asn
65                  70                  75                  80

Ala Thr Lys Phe Arg Phe Phe Gly Val Asn Gln Ala Gly Ala Glu Phe
                85                  90                  95

Gly Glu Asn Val Ile Pro Gly Leu Gly Thr His Tyr Thr Trp Pro
                100                 105                 110

Ser Pro Ser Ser Ile Asp Tyr Phe Val Asn Gln Gly Phe Asn Thr Phe
            115                 120                 125

Arg Val Ala Phe Lys Ile Glu Arg Leu Ser Pro Pro Gly Thr Gly Leu
130                 135                 140

Thr Gly Pro Phe Asp Gln Ala Tyr Leu Asn Gly Leu Lys Thr Ile Val
145                 150                 155                 160

Asn Tyr Ile Thr Gly Lys Asn Ala Tyr Ala Val Leu Asp Pro His Asn
                165                 170                 175

Tyr Met Arg Tyr Asn Gly Asn Val Ile Thr Ser Thr Ser Asn Phe Gln
            180                 185                 190

Thr Trp Trp Asn Lys Leu Ala Thr Glu Phe Arg Ser Asn Thr Arg Val
195                 200                 205

Ile Phe Asp Val Met Asn Glu Pro Tyr Gln Ile Asp Ala Ser Val Val
210                 215                 220

Phe Asn Leu Asn Gln Ala Ala Ile Asn Gly Ile Arg Ala Ser Gly Ala
225                 230                 235                 240

Thr Ser Gln Leu Ile Leu Val Glu Gly Thr Ala Trp Thr Gly Ala Trp
                245                 250                 255

Ser Trp Glu Ser Ser Gly Asn Gly Ala Val Phe Gly Ala Ile Arg Asp
            260                 265                 270

Pro Asn Asn Asn Thr Ala Ile Glu Met His Gln Tyr Leu Asp Ser Asp
275                 280                 285

Ser Ser Gly Thr Ser Ala Thr Cys Val Ser Ser Thr Val Gly Val Glu
            290                 295                 300

Arg Leu Arg Val Ala Thr Asp Trp Leu Arg Arg Asn Asn Leu Lys Gly
305                 310                 315                 320

Phe Leu Gly Glu Met Gly Ala Gly Ser Asn Asp Val Cys Ile Ala Ala
                325                 330                 335

Val Lys Gly Ala Leu Cys Ala Met Gln Gln Ser Gly Val Trp Ile Gly
                340                 345                 350
```

```
Tyr Leu Trp Trp Ala Ala Gly Pro Trp Trp Gly Thr Tyr Phe Gln Ser
        355                 360                 365

Ile Glu Pro Pro Asn Gly Ala Ser Ile Ala Arg Ile Leu Pro Glu Ala
370                 375                 380

Leu Lys Pro Phe Val
385

<210> SEQ ID NO 72
<211> LENGTH: 335
<212> TYPE: PRT
<213> ORGANISM: Thermoascus aurantiacus

<400> SEQUENCE: 72

Met Lys Leu Gly Ser Leu Val Leu Ala Leu Ser Ala Ala Arg Leu Thr
1               5                   10                  15

Leu Ser Ala Pro Leu Ala Asp Arg Lys Gln Glu Thr Lys Arg Ala Lys
            20                  25                  30

Val Phe Gln Trp Phe Gly Ser Asn Glu Ser Gly Ala Glu Phe Gly Ser
        35                  40                  45

Gln Asn Leu Pro Gly Val Glu Gly Lys Asp Tyr Ile Trp Pro Asp Pro
    50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
            100                 105                 110

Gln Lys Gly Ala Tyr Ala Val Val Asp Pro His Asn Tyr Gly Arg Tyr
        115                 120                 125

Tyr Asn Ser Ile Ile Ser Ser Pro Ser Asp Phe Gln Thr Phe Trp Lys
    130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
            180                 185                 190

Ile Phe Val Glu Gly Asn Ser Trp Thr Gly Ala Trp Thr Trp Thr Asn
        195                 200                 205

Val Asn Asp Asn Met Lys Ser Leu Thr Asp Pro Ser Asp Lys Ile Ile
    210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
            260                 265                 270

Gly Gly Ala Asn Asp Val Cys Glu Thr Ala Ile Thr Gly Met Leu Asp
        275                 280                 285

Tyr Met Ala Gln Asn Thr Asp Val Trp Thr Gly Ala Ile Trp Trp Ala
    290                 295                 300

Ala Gly Pro Trp Trp Gly Asp Tyr Ile Phe Ser Met Glu Pro Asp Asn
305                 310                 315                 320

Gly Ile Ala Tyr Gln Gln Ile Leu Pro Ile Leu Thr Pro Tyr Leu
```

<210> SEQ ID NO 73
<211> LENGTH: 332
<212> TYPE: PRT
<213> ORGANISM: Aspergillus aculeatus

<400> SEQUENCE: 73

Met Lys Leu Leu Asn Leu Leu Val Ala Ala Ala Gly Ser Ala
1               5                   10                  15

Val Ala Ala Pro Thr His Glu His Thr Lys Arg Ala Ser Val Phe Glu
            20                  25                  30

Trp Ile Gly Ser Asn Glu Ser Asp Ala Glu Phe Gly Thr Ala Ile Pro
        35                  40                  45

Gly Thr Trp Gly Ile Asp Tyr Ile Phe Pro Asp Thr Ser Ala Ile Ala
    50                  55                  60

Thr Leu Val Ser Lys Gly Met Asn Ile Phe Arg Val Gln Phe Met Met
65                  70                  75                  80

Glu Arg Leu Val Pro Asn Ser Met Thr Gly Ser Tyr Asp Asp Ala Tyr
                85                  90                  95

Leu Asn Asn Leu Thr Thr Val Val Asn Ala Ile Ala Ala Ala Gly Val
            100                 105                 110

His Ala Ile Val Asp Pro His Asn Tyr Gly Arg Tyr Asn Asn Glu Ile
        115                 120                 125

Ile Ser Ser Thr Ala Asp Phe Gln Thr Phe Trp Gln Asn Leu Ala Gly
    130                 135                 140

Gln Phe Lys Asp Asn Asp Leu Val Ile Phe Asp Thr Asn Asn Glu Tyr
145                 150                 155                 160

Asn Thr Met Asp Gln Thr Leu Val Leu Asp Leu Asn Gln Ala Ala Ile
                165                 170                 175

Asp Gly Ile Arg Ala Ala Gly Ala Thr Ser Gln Tyr Ile Phe Ala Glu
            180                 185                 190

Gly Asn Ser Trp Ser Gly Ala Trp Thr Trp Ala Asp Ile Asn Asp Asn
        195                 200                 205

Met Lys Ala Leu Thr Asp Pro Gln Asp Lys Leu Val Tyr Glu Met His
    210                 215                 220

Gln Tyr Leu Asp Ser Asp Gly Ser Gly Thr Ser Gly Val Cys Val Ser
225                 230                 235                 240

Glu Thr Ile Gly Ala Glu Arg Leu Gln Ala Ala Thr Gln Trp Leu Lys
                245                 250                 255

Asp Asn Gly Lys Val Asp Ile Leu Gly Glu Tyr Ala Gly Gly Ala Asn
            260                 265                 270

Asp Val Cys Arg Thr Ala Ile Ala Gly Met Leu Glu Tyr Met Ala Asn
        275                 280                 285

Asn Thr Asp Val Trp Lys Gly Ala Val Trp Trp Thr Ala Gly Pro Trp
    290                 295                 300

Trp Ala Asp Tyr Met Phe Ser Met Glu Pro Ser Gly Pro Ala Tyr
305                 310                 315                 320

Ser Gly Met Leu Asp Val Leu Glu Pro Tyr Leu Gly
                325                 330

<210> SEQ ID NO 74
<211> LENGTH: 388
<212> TYPE: PRT
<213> ORGANISM: Humicola insolens

<400> SEQUENCE: 74

```
Met Lys His Ser Val Leu Ala Gly Leu Phe Ala Thr Gly Ala Leu Ala
1               5                   10                  15

Gln Gly Gly Ala Trp Gln Gln Cys Gly Gly Val Gly Phe Ser Gly Ser
            20                  25                  30

Thr Ser Cys Val Ser Gly Tyr Thr Cys Val Tyr Leu Asn Asp Trp Tyr
        35                  40                  45

Ser Gln Cys Gln Pro Gln Pro Thr Thr Leu Arg Thr Thr Thr Thr Pro
    50                  55                  60

Gly Ala Thr Ser Thr Arg Ser Ala Pro Ala Ala Thr Ser Thr Thr Thr
65                  70                  75                  80

Pro Ala Lys Gly Lys Phe Lys Trp Phe Gly Ile Asn Gln Ser Cys Ala
                85                  90                  95

Glu Phe Gly Lys Gly Glu Tyr Pro Gly Leu Trp Gly Lys His Phe Thr
            100                 105                 110

Phe Pro Ser Thr Ser Ser Ile Gln Thr His Ile Asn Asp Gly Phe Asn
        115                 120                 125

Met Phe Arg Val Ala Phe Ser Met Glu Arg Leu Ala Pro Asn Gln Leu
130                 135                 140

Asn Ala Ala Phe Asp Ala Asn Tyr Leu Arg Asn Leu Thr Glu Thr Val
145                 150                 155                 160

Asn Phe Ile Thr Gly Lys Gly Lys Tyr Ala Met Leu Asp Pro His Asn
                165                 170                 175

Phe Gly Arg Tyr Tyr Glu Arg Ile Ile Thr Asp Lys Ala Ala Phe Ala
            180                 185                 190

Ser Phe Phe Thr Lys Leu Ala Thr His Phe Ala Ser Asn Pro Leu Val
        195                 200                 205

Val Phe Asp Thr Asn Asn Glu Tyr His Asp Met Asp Gln Gln Leu Val
210                 215                 220

Phe Asp Leu Asn Gln Ala Ala Ile Asp Ala Ile Arg Ala Ala Gly Ala
225                 230                 235                 240

Thr Ser Gln Tyr Ile Met Val Glu Gly Asn Ser Trp Thr Gly Ala Trp
                245                 250                 255

Thr Trp Asn Val Thr Asn Asn Leu Ala Ala Leu Arg Asp Pro Glu
            260                 265                 270

Asn Lys Leu Val Tyr Gln Met His Gln Tyr Leu Asp Ser Asp Gly Ser
        275                 280                 285

Gly Thr Ser Thr Ala Cys Val Ser Thr Gln Val Gly Leu Gln Arg Val
290                 295                 300

Ile Gly Ala Thr Asn Trp Leu Arg Gln Asn Gly Lys Val Gly Leu Leu
305                 310                 315                 320

Gly Glu Phe Ala Gly Gly Ala Asn Ser Val Cys Gln Gln Ala Ile Glu
                325                 330                 335

Gly Met Leu Thr His Leu Gln Glu Asn Ser Asp Val Trp Thr Gly Ala
            340                 345                 350

Leu Trp Trp Ala Gly Gly Pro Trp Trp Gly Asp Tyr Ile Tyr Ser Phe
        355                 360                 365

Glu Pro Pro Ser Gly Ile Gly Tyr Thr Tyr Tyr Asn Ser Leu Leu Lys
        370                 375                 380

Lys Tyr Val Pro
385
```

<210> SEQ ID NO 75

```
<211> LENGTH: 477
<212> TYPE: PRT
<213> ORGANISM: Orpinomyces joyonii

<400> SEQUENCE: 75
```

| | | | | | | | | | | | | | | |
|---|---|---|---|---|---|---|---|---|---|---|---|---|---|---|
Met | Lys | Phe | Phe | Lys | Asn | Thr | Leu | Ala | Leu | Leu | Thr | Pro | Val | Ile | Ala
1 | | | | 5 | | | | | 10 | | | | | 15 |

Gly Ser Asn Ala Met Arg Asn Ile Pro Ser Lys Asp Leu Val Lys Glu
　　　　　　20　　　　　　　　　　25　　　　　　　　　　30

Leu Asn Ile Gly Trp Asn Leu Gly Asn Ala Leu Asp Ala His Cys Leu
　　　　35　　　　　　　　　　40　　　　　　　　　　45

Asp Lys Leu Asp Tyr Asn Lys Asp Gln Leu Ala Ser Glu Thr Cys Trp
50　　　　　　　　　　55　　　　　　　　　　60

Ala Asn Pro Lys Ala Thr Pro Gly Leu Phe Ser Ala Leu Lys Asn Gln
65　　　　　　　　　　70　　　　　　　　75　　　　　　　　　　80

Gly Phe Asn Val Phe Arg Ile Pro Thr Thr Trp Thr Gly His Phe Gly
　　　　　　　　　　85　　　　　　　　　　90　　　　　　　　95

Asn Gly Pro Asp Tyr Lys Ile Ser Asp Val Trp Met Arg Arg Val His
　　　　　　100　　　　　　　　　　105　　　　　　　　　110

Glu Val Val Asp Tyr Ala Leu Asn Thr Gly Ser Tyr Val Ile Leu Asn
　　　115　　　　　　　　　　120　　　　　　　　　125

Ile His His Glu Asn Trp Asn Tyr Ala Phe Ser Asn Asn Leu Gln Lys
130　　　　　　　　　　135　　　　　　　　　140

Ala Lys Pro Ile Leu Ala Ile Trp Lys Gln Ile Ala Ala Glu Phe
145　　　　　　　　150　　　　　　　　　155　　　　　　　　160

Ala Asn Tyr Asp Glu His Leu Ile Phe Glu Gly Met Asn Glu Pro Arg
　　　　　　　　165　　　　　　　　　　170　　　　　　　　　175

Lys Val Asp His Pro Asn Glu Trp Asn Gly Gly Asp Gln Lys Gly Trp
　　　　　　180　　　　　　　　　185　　　　　　　　　190

Asp Phe Val Asn Glu Met Asn Ala Val Phe Leu Gln Thr Val Arg Ala
　　　195　　　　　　　　　　200　　　　　　　　　205

Ser Gly Gly Asn Asn Ala Ile Arg His Leu Met Ile Pro Thr Tyr Ala
　　　210　　　　　　　　　　215　　　　　　　　　220

Ala Cys Val Asn Asn Gly Ala Leu Glu Ser Tyr Phe Lys Lys Ser Pro
225　　　　　　　　　　230　　　　　　　　　235　　　　　　　　　240

Thr Asn Asp Asn Lys Val Ile Ala Ser Val His Ser Tyr Val Pro Tyr
　　　　　　　　245　　　　　　　　　　250　　　　　　　　　255

Asn Phe Ala Leu Asn Thr Gly Ala Gly Ala Glu Lys Thr Phe Gly Ser
　　　　　　　　260　　　　　　　　　265　　　　　　　　　270

Thr Ser Asp Ile Glu Trp Ala Met Asn Asn Ile Lys Arg Phe Leu Val
　　　　　275　　　　　　　　　　280　　　　　　　　　285

Asp Arg Asn Ile Pro Val Ile Ile Gly Glu Phe Gly Ala Met Asn Arg
　　　290　　　　　　　　　　295　　　　　　　　　300

Asp Asn Glu Ser Glu Arg Ala Arg Trp Ala Glu Tyr Tyr Ile Lys Ser
305　　　　　　　　　　310　　　　　　　　　　315　　　　　　　　　320

Ala Thr Ala Met Gly Val Pro Cys Val Leu Trp Asp Asn Gly Tyr Thr
　　　　　　　　　325　　　　　　　　　　330　　　　　　　　　335

Gln Gly Thr Gly Glu Leu Phe Gly Val Ile Asp Arg Asn Phe Tyr Arg
　　　　　　　340　　　　　　　　　　345　　　　　　　　　350

Ile Ile Phe Gln Gln Phe Ile Asn Gly Leu Met Lys Gly Leu Gly Gly
　　　　　　355　　　　　　　　　　360　　　　　　　　　365

Lys Lys Thr Val Ala Pro Ala Pro Thr Thr Ile Thr Thr Thr Thr Thr
　　　370　　　　　　　　　375　　　　　　　　　380

Thr Val Lys Val Gln Pro Thr Asn Asn Asn Glu Cys Phe Ser Thr Arg

```
                385                 390                 395                 400
Leu Gly Tyr Asn Cys Cys Asn Gly Cys Asp Val Phe Tyr Thr Asp Asn
                    405                 410                 415
Asp Gly Lys Trp Gly Val Glu Asn Gly Asn Trp Cys Gly Ile Lys Ser
                420                 425                 430
Ser Cys Asp Asn Asn Gln Arg Tyr Cys Trp Ser Glu Arg Leu Gly Tyr
                435                 440                 445
Pro Cys Cys Gln Tyr Thr Thr Asn Val Glu Tyr Thr Asp Asn Asp Gly
            450                 455                 460
Arg Trp Gly Val Glu Asn Gly Asn Trp Cys Gly Ile Tyr
465                 470                 475

<210> SEQ ID NO 76
<211> LENGTH: 562
<212> TYPE: PRT
<213> ORGANISM: Acidothermus cellulolyticus

<400> SEQUENCE: 76

Met Pro Arg Ala Leu Arg Arg Val Pro Gly Ser Arg Val Met Leu Arg
1               5                   10                  15
Val Gly Val Val Ala Val Leu Ala Leu Val Ala Ala Leu Ala Asn
                20                  25                  30
Leu Ala Val Pro Arg Pro Ala Arg Ala Ala Gly Gly Gly Tyr Trp His
                35                  40                  45
Thr Ser Gly Arg Glu Ile Leu Asp Ala Asn Asn Val Pro Val Arg Ile
            50                  55                  60
Ala Gly Ile Asn Trp Phe Gly Phe Glu Thr Cys Asn Tyr Val Val His
65                  70                  75                  80
Gly Leu Trp Ser Arg Asp Tyr Arg Ser Met Leu Asp Gln Ile Lys Ser
                85                  90                  95
Leu Gly Tyr Asn Thr Ile Arg Leu Pro Tyr Ser Asp Ile Leu Lys
                100                 105                 110
Pro Gly Thr Met Pro Asn Ser Ile Asn Phe Tyr Gln Met Asn Gln Asp
                115                 120                 125
Leu Gln Gly Leu Thr Ser Leu Gln Val Met Asp Lys Ile Val Ala Tyr
            130                 135                 140
Ala Gly Gln Ile Gly Leu Arg Ile Ile Leu Asp Arg His Arg Pro Asp
145                 150                 155                 160
Cys Ser Gly Gln Ser Ala Leu Trp Tyr Thr Ser Ser Val Ser Glu Ala
                165                 170                 175
Thr Trp Ile Ser Asp Leu Gln Ala Leu Ala Gln Arg Tyr Lys Gly Asn
                180                 185                 190
Pro Thr Val Val Gly Phe Asp Leu His Asn Glu Pro His Asp Pro Ala
            195                 200                 205
Cys Trp Gly Cys Gly Asp Pro Ser Ile Asp Trp Arg Leu Ala Ala Glu
210                 215                 220
Arg Ala Gly Asn Ala Val Leu Ser Val Asn Pro Asn Leu Leu Ile Phe
225                 230                 235                 240
Val Glu Gly Val Gln Ser Tyr Asn Gly Asp Ser Tyr Trp Trp Gly Gly
                245                 250                 255
Asn Leu Gln Gly Ala Gly Gln Tyr Pro Val Val Leu Asn Val Pro Asn
                260                 265                 270
Arg Leu Val Tyr Ser Ala His Asp Tyr Ala Thr Ser Val Tyr Pro Gln
            275                 280                 285
```

```
Thr Trp Phe Ser Asp Pro Thr Phe Pro Asn Asn Met Pro Gly Ile Trp
    290                 295                 300

Asn Lys Asn Trp Gly Tyr Leu Phe Asn Gln Asn Ile Ala Pro Val Trp
305                 310                 315                 320

Leu Gly Glu Phe Gly Thr Thr Leu Gln Ser Thr Thr Asp Gln Thr Trp
                325                 330                 335

Leu Lys Thr Leu Val Gln Tyr Leu Arg Pro Thr Ala Gln Tyr Gly Ala
                340                 345                 350

Asp Ser Phe Gln Trp Thr Phe Trp Ser Trp Asn Pro Asp Ser Gly Asp
                355                 360                 365

Thr Gly Gly Ile Leu Lys Asp Asp Trp Gln Thr Val Asp Thr Val Lys
    370                 375                 380

Asp Gly Tyr Leu Ala Pro Ile Lys Ser Ser Ile Phe Asp Pro Val Gly
385                 390                 395                 400

Ala Ser Ala Ser Pro Ser Ser Gln Pro Ser Pro Ser Val Ser Pro Ser
                405                 410                 415

Pro Ser Pro Ser Pro Ser Ala Ser Arg Thr Pro Thr Pro Thr Pro Thr
                420                 425                 430

Pro Thr Ala Ser Pro Thr Pro Thr Leu Thr Pro Thr Ala Thr Pro Thr
                435                 440                 445

Pro Thr Ala Ser Pro Thr Pro Ser Pro Thr Ala Ala Ser Gly Ala Arg
    450                 455                 460

Cys Thr Ala Ser Tyr Gln Val Asn Ser Asp Trp Gly Asn Gly Phe Thr
465                 470                 475                 480

Val Thr Val Ala Val Thr Asn Ser Gly Ser Val Ala Thr Lys Thr Trp
                485                 490                 495

Thr Val Ser Trp Thr Phe Gly Gly Asn Gln Thr Ile Thr Asn Ser Trp
                500                 505                 510

Asn Ala Ala Val Thr Gln Asn Gly Gln Ser Val Thr Ala Arg Asn Met
                515                 520                 525

Ser Tyr Asn Asn Val Ile Gln Pro Gly Gln Asn Thr Thr Phe Gly Phe
    530                 535                 540

Gln Ala Ser Tyr Thr Gly Ser Asn Ala Ala Pro Thr Val Ala Cys Ala
545                 550                 555                 560

Ala Ser

<210> SEQ ID NO 77
<211> LENGTH: 499
<212> TYPE: PRT
<213> ORGANISM: Bacillus subtilis

<400> SEQUENCE: 77

Met Lys Arg Ser Ile Ser Ile Phe Ile Thr Cys Leu Leu Ile Thr Leu
1               5                   10                  15

Leu Thr Met Gly Gly Met Ile Ala Ser Pro Ala Ser Ala Ala Gly Thr
                20                  25                  30

Lys Thr Pro Val Ala Lys Asn Gly Gln Leu Ser Ile Lys Gly Thr Gln
                35                  40                  45

Leu Val Asn Arg Asp Gly Lys Ala Val Gln Leu Lys Gly Ile Ser Ser
    50                  55                  60

His Gly Leu Gln Trp Tyr Gly Glu Phe Val Asn Lys Asp Ser Leu Lys
65                  70                  75                  80

Trp Leu Arg Asp Asp Trp Gly Ile Thr Val Phe Arg Ala Ala Met Tyr
                85                  90                  95
```

```
Thr Ala Asp Gly Gly Tyr Ile Asp Asn Pro Ser Val Lys Asn Lys Val
            100                 105                 110

Lys Glu Ala Val Glu Ala Lys Glu Leu Gly Ile Tyr Val Ile Ile
        115                 120                 125

Asp Trp His Ile Leu Asn Asp Gly Asn Pro Asn Gln Asn Lys Glu Lys
    130                 135                 140

Ala Lys Glu Phe Phe Lys Glu Met Ser Ser Leu Tyr Gly Asn Thr Pro
145                 150                 155                 160

Asn Val Ile Tyr Glu Ile Ala Asn Glu Pro Asn Gly Asp Val Asn Trp
                165                 170                 175

Lys Arg Asp Ile Lys Pro Tyr Ala Glu Glu Val Ile Ser Val Ile Arg
            180                 185                 190

Lys Asn Asp Pro Asp Asn Ile Ile Val Gly Thr Gly Thr Trp Ser
        195                 200                 205

Gln Asp Val Asn Asp Ala Ala Asp Gln Leu Lys Asp Ala Asn Val
    210                 215                 220

Met Tyr Ala Leu His Phe Tyr Ala Gly Thr His Gly Gln Phe Leu Arg
225                 230                 235                 240

Asp Lys Ala Asn Tyr Ala Leu Ser Lys Gly Ala Pro Val Phe Val Thr
                245                 250                 255

Glu Trp Gly Thr Ser Asp Ala Ser Gly Asn Gly Val Phe Leu Asp
            260                 265                 270

Gln Ser Arg Glu Trp Leu Asn Tyr Leu Asp Ser Lys Thr Ile Ser Trp
        275                 280                 285

Val Asn Trp Asn Leu Ser Asp Lys Gln Glu Ser Ser Ala Leu Lys
    290                 295                 300

Pro Gly Ala Ser Lys Thr Gly Gly Trp Arg Leu Ser Asp Leu Ser Ala
305                 310                 315                 320

Ser Gly Thr Phe Val Arg Glu Asn Ile Leu Gly Thr Lys Asp Ser Thr
                325                 330                 335

Lys Asp Ile Pro Glu Thr Pro Ala Lys Asp Lys Pro Thr Gln Glu Asn
            340                 345                 350

Gly Ile Ser Val Gln Tyr Arg Ala Gly Asp Gly Ser Met Asn Ser Asn
        355                 360                 365

Gln Ile Arg Pro Gln Leu Gln Ile Lys Asn Asn Gly Asn Thr Thr Val
    370                 375                 380

Asp Leu Lys Asp Val Thr Ala Arg Tyr Trp Tyr Asn Ala Lys Asn Lys
385                 390                 395                 400

Gly Gln Asn Val Asp Cys Asp Tyr Ala Gln Leu Gly Cys Gly Asn Met
                405                 410                 415

Thr His Lys Phe Val Thr Leu His Lys Pro Lys Gln Gly Ala Asp Thr
            420                 425                 430

Tyr Leu Glu Leu Gly Phe Lys Asn Gly Thr Leu Ala Pro Gly Ala Ser
        435                 440                 445

Thr Gly Asn Ile Gln Leu Arg Leu His Asn Asp Asp Trp Ser Asn Tyr
    450                 455                 460

Ala Gln Ser Gly Asp Tyr Ser Phe Phe Lys Ser Asn Thr Phe Lys Thr
465                 470                 475                 480

Thr Lys Lys Ile Thr Leu Tyr Asp Gln Gly Lys Leu Ile Trp Gly Thr
                485                 490                 495

Glu Pro Asn

<210> SEQ ID NO 78
```

```
<211> LENGTH: 409
<212> TYPE: PRT
<213> ORGANISM: Bacillus cellulosilyticus

<400> SEQUENCE: 78

Met Lys Lys Ile Thr Thr Ile Phe Val Val Leu Leu Met Thr Leu Ala
1               5                   10                  15

Leu Phe Ile Ile Gly Asn Thr Thr Ala Ala Asp Asp Tyr Ser Val Val
            20                  25                  30

Glu Glu His Gly Gln Leu Ser Ile Ser Asn Gly Glu Leu Val Asn Asp
        35                  40                  45

Arg Gly Glu Pro Val Gln Leu Lys Gly Met Ser Ser His Gly Leu Gln
    50                  55                  60

Trp Tyr Gly Gln Phe Val Asn Tyr Glu Ser Met Lys Trp Leu Arg Asp
65                  70                  75                  80

Asp Trp Gly Ile Thr Val Phe Arg Ala Ala Met Tyr Thr Ser Ser Gly
                85                  90                  95

Gly Tyr Ile Glu Asp Pro Ser Val Lys Glu Lys Val Lys Glu Ala Val
            100                 105                 110

Glu Ala Ala Ile Asp Leu Gly Ile Tyr Val Ile Ile Asp Trp His Ile
        115                 120                 125

Leu Ser Asp Asn Asp Pro Asn Ile Tyr Lys Glu Glu Ala Lys Asp Phe
    130                 135                 140

Phe Asp Glu Met Ser Glu Leu Tyr Gly Asp Tyr Pro Asn Val Ile Tyr
145                 150                 155                 160

Glu Ile Ala Asn Glu Pro Asn Gly Ser Asp Val Thr Trp Asp Asn Gln
                165                 170                 175

Ile Lys Pro Tyr Ala Glu Glu Val Ile Pro Val Ile Arg Asn Asn Asp
            180                 185                 190

Pro Asn Asn Ile Ile Ile Val Gly Thr Gly Thr Trp Ser Gln Asp Val
        195                 200                 205

His His Ala Ala Asp Asn Gln Leu Thr Asp Pro Asn Val Met Tyr Ala
    210                 215                 220

Phe His Phe Tyr Ala Gly Thr His Gly Gln Asn Leu Arg Asp Gln Val
225                 230                 235                 240

Asp Tyr Ala Leu Asp Gln Gly Ala Ala Ile Phe Val Ser Glu Trp Gly
                245                 250                 255

Thr Ser Glu Ala Thr Gly Asp Gly Gly Val Phe Leu Asp Glu Ala Gln
            260                 265                 270

Val Trp Ile Asp Phe Met Asp Glu Arg Asn Leu Ser Trp Ala Asn Trp
        275                 280                 285

Ser Leu Thr His Lys Asp Glu Ser Ser Ala Ala Leu Met Pro Gly Ala
    290                 295                 300

Ser Pro Thr Gly Gly Trp Thr Glu Ala Glu Leu Ser Pro Ser Gly Thr
305                 310                 315                 320

Phe Val Arg Glu Lys Ile Arg Glu Ser Ala Thr Thr Pro Pro Ser Asp
                325                 330                 335

Pro Thr Pro Pro Ser Asp Pro Asp Pro Gly Glu Pro Glu Pro Asp Pro
            340                 345                 350

Gly Glu Pro Asp Pro Thr Pro Pro Ser Asp Pro Gly Asp Tyr Pro Ala
        355                 360                 365

Trp Asp Pro Asn Thr Ile Tyr Thr Asp Glu Ile Val Tyr His Asn Gly
    370                 375                 380

Gln Leu Trp Gln Ala Lys Trp Trp Thr Gln Asn Gln Glu Pro Gly Asp
```

```
385                 390                 395                 400
Pro Tyr Gly Pro Trp Glu Pro Leu Asn
                405

<210> SEQ ID NO 79
<211> LENGTH: 471
<212> TYPE: PRT
<213> ORGANISM: Hypocrea koningii

<400> SEQUENCE: 79

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Gly
            85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
            165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
            245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
            325                 330                 335

Ser Pro Pro Ser Tyr Thr Gln Gly Asn Ala Val Tyr Asn Glu Lys Leu
            340                 345                 350
```

```
Tyr Ile His Ala Ile Gly Arg Leu Ala Asn His Gly Trp Ser Asn
            355                 360                 365

Ala Phe Phe Ile Thr Asp Gln Gly Arg Ser Gly Lys Gln Pro Thr Gly
370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
435                 440                 445

Pro Gln Ala Gly Ala Trp Phe Gln Ala Tyr Phe Val Gln Leu Leu Thr
450                 455                 460

Asn Ala Asn Pro Ser Phe Leu
465                 470

<210> SEQ ID NO 80
<211> LENGTH: 471
<212> TYPE: PRT
<213> ORGANISM: Trichoderma viride

<400> SEQUENCE: 80

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255
```

```
Pro Lys Cys Ala Asn Ala Pro Ser Ala Tyr Leu Glu Cys Ile Asn Tyr
            260                 265                 270

Ala Val Thr Gln Leu Asn Leu Pro Asn Val Ala Met Tyr Leu Asp Ala
            275                 280                 285

Gly His Ala Gly Trp Leu Gly Trp Pro Ala Asn Gln Asp Pro Ala Ala
            290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
            355                 360                 365

Ala Phe Phe Ile Thr Asp Gln Gly Arg Ser Gly Lys Gln Pro Thr Gly
            370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
            435                 440                 445

Pro Gln Ala Gly Ala Trp Phe Gln Ala Tyr Phe Val Gln Leu Leu Thr
            450                 455                 460

Asn Ala Asn Pro Ser Phe Leu
465                 470

<210> SEQ ID NO 81
<211> LENGTH: 470
<212> TYPE: PRT
<213> ORGANISM: Hypocrea koningii

<400> SEQUENCE: 81

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Ala Trp Gly
            20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
            50                  55                  60

Ala Ala Ser Ser Ser Ser Thr Arg Ala Ser Ser Thr Thr Ala Arg
65                  70                  75              80

Ala Ser Ser Thr Thr Ser Arg Ser Ser Ala Thr Pro Pro Pro Gly Ser
                85                  90                  95

Ser Thr Thr Arg Val Pro Pro Val Gly Ser Gly Thr Ala Thr Tyr Ser
            100                 105                 110

Gly Asn Pro Phe Val Gly Val Thr Pro Trp Ala Asn Ala Tyr Tyr Ala
            115                 120                 125

Ser Glu Val Ser Ser Leu Ala Ile Pro Ser Leu Thr Gly Ala Met Ala
            130                 135                 140

Thr Ala Ala Ala Ala Val Ala Lys Val Pro Ser Phe Met Trp Leu Asp
```

```
            145                 150                 155                 160

Thr Phe Asp Lys Thr Pro Leu Met Glu Gln Thr Leu Ala Asp Ile Arg
                    165                 170                 175

Thr Ala Asn Lys Asn Gly Gly Asn Tyr Ala Gly Gln Phe Val Val Tyr
                    180                 185                 190

Asp Leu Pro Asp Arg Asp Cys Ala Ala Leu Ala Ser Asn Gly Glu Tyr
                    195                 200                 205

Ser Ile Ala Asp Gly Gly Val Asp Lys Tyr Lys Asn Tyr Ile Asp Thr
    210                 215                 220

Ile Arg Gln Ile Val Glu Tyr Ser Asp Ile Arg Thr Leu Leu Val
    225                 230                 235                 240

Ile Glu Pro Asp Ser Leu Ala Asn Leu Val Thr Asn Leu Gly Thr Pro
                    245                 250                 255

Lys Cys Ala Asn Ala Gln Ser Ala Tyr Leu Glu Cys Ile Asn Tyr Ala
                    260                 265                 270

Val Thr Gln Leu Asn Leu Pro Asn Val Ala Met Tyr Leu Asp Ala Gly
                    275                 280                 285

His Ala Gly Trp Leu Gly Trp Pro Ala Asn Gln Asp Pro Ala Ala Gln
                    290                 295                 300

Leu Phe Ala Asn Val Tyr Lys Asn Ala Ser Ser Pro Arg Ala Leu Arg
    305                 310                 315                 320

Gly Leu Ala Thr Asn Val Ala Asn Tyr Asn Gly Trp Asn Ile Thr Ser
                    325                 330                 335

Pro Pro Ser Tyr Thr Gln Gly Asn Ala Val Tyr Asn Glu Gln Leu Tyr
                    340                 345                 350

Ile His Ala Ile Gly Pro Leu Leu Ala Asn His Gly Trp Ser Asn Ala
                    355                 360                 365

Phe Phe Ile Thr Asp Gln Gly Arg Ser Gly Lys Gln Pro Thr Gly Gln
                    370                 375                 380

Gln Gln Trp Gly Asp Trp Cys Asn Val Ile Gly Thr Gly Phe Gly Ile
    385                 390                 395                 400

Arg Pro Ser Ala Asn Thr Gly Asp Ser Leu Leu Asp Ser Phe Val Trp
                    405                 410                 415

Ile Lys Pro Gly Gly Glu Cys Asp Gly Thr Ser Asp Ser Ser Ala Pro
                    420                 425                 430

Arg Phe Asp Ser His Cys Ala Leu Pro Asp Ala Leu Gln Pro Ala Pro
                    435                 440                 445

Gln Ala Gly Ala Trp Phe Gln Ala Tyr Phe Val Gln Leu Leu Thr Asn
    450                 455                 460

Ala Asn Pro Ser Phe Leu
    465                 470

<210> SEQ ID NO 82
<211> LENGTH: 470
<212> TYPE: PRT
<213> ORGANISM: Hypocrea koningii

<400> SEQUENCE: 82

Met Ile Val Gly Ile Leu Thr Thr Leu Ala Thr Leu Ala Thr Leu Ala
    1               5                   10                  15

Ala Ser Val Pro Leu Glu Glu Arg Gln Ala Cys Ser Ser Val Trp Gly
                    20                  25                  30

Gln Cys Gly Gly Gln Asn Trp Ser Gly Pro Thr Cys Cys Ala Ser Gly
                    35                  40                  45
```

-continued

```
Ser Thr Cys Val Tyr Ser Asn Asp Tyr Tyr Ser Gln Cys Leu Pro Gly
 50                  55                  60

Ala Ala Ser Ser Ser Ser Thr Arg Ala Ser Ser Thr Thr Ala Arg
 65                  70                  75                  80

Ala Ser Ser Thr Thr Ser Arg Ser Ser Ala Thr Pro Pro Gly Ser
                 85                  90                  95

Ser Thr Thr Arg Val Pro Pro Val Gly Ser Gly Thr Ala Thr Tyr Ser
                100                 105                 110

Gly Asn Pro Phe Val Gly Val Thr Pro Trp Ala Asn Ala Tyr Tyr Ala
            115                 120                 125

Ser Glu Val Ser Ser Leu Ala Ile Pro Ser Leu Thr Gly Ala Met Ala
130                 135                 140

Thr Ala Ala Ala Val Ala Lys Val Pro Ser Ser Met Trp Leu Asp
145                 150                 155                 160

Thr Phe Asp Lys Thr Pro Leu Met Glu Gln Thr Leu Ala Asp Ile Arg
                165                 170                 175

Thr Ala Asn Lys Asn Gly Gly Asn Tyr Ala Gly Gln Phe Val Val Tyr
                180                 185                 190

Asp Leu Pro Asp Arg Asp Cys Ala Ala Leu Ala Ser Asn Gly Glu Tyr
            195                 200                 205

Ser Ile Ala Asp Gly Gly Val Asp Lys Tyr Lys Asn Tyr Ile Asp Thr
210                 215                 220

Ile Arg Gln Ile Val Val Glu Tyr Ser Asp Ile Arg Thr Leu Leu Val
225                 230                 235                 240

Ile Glu Pro Asp Ser Leu Ala Asn Leu Val Thr Asn Leu Gly Thr Pro
                245                 250                 255

Lys Cys Ala Asn Ala Gln Ser Ala Tyr Leu Glu Cys Ile Asn Tyr Ala
                260                 265                 270

Val Thr Gln Leu Asn Leu Pro Asn Val Ala Met Tyr Leu Asp Ala Gly
            275                 280                 285

His Ala Gly Trp Leu Gly Trp Pro Ala Asn Gln Asp Pro Ala Ala Gln
290                 295                 300

Leu Phe Ala Asn Val Tyr Lys Asn Ala Ser Ser Pro Arg Ala Leu Arg
305                 310                 315                 320

Gly Leu Ala Thr Asn Val Ala Asn Tyr Asn Gly Trp Asn Ile Thr Ser
                325                 330                 335

Pro Pro Ser Tyr Thr Gln Gly Asn Ala Val Tyr Asn Glu Gln Leu Tyr
                340                 345                 350

Ile His Ala Ile Gly Pro Leu Leu Ala Asn His Gly Trp Ser Asn Ala
            355                 360                 365

Phe Phe Ile Thr Asp Gln Gly Arg Ser Gly Lys Gln Pro Thr Gly Gln
370                 375                 380

Gln Gln Trp Gly Asp Trp Cys Asn Val Ile Gly Thr Gly Phe Gly Ile
385                 390                 395                 400

Arg Pro Ser Ala Asn Thr Gly Asp Ser Leu Leu Asp Ser Phe Val Trp
                405                 410                 415

Ile Lys Pro Gly Gly Glu Cys Asp Gly Thr Ser Asp Ser Ser Ala Pro
                420                 425                 430

Arg Phe Asp Ser His Cys Ala Leu Pro Asp Ala Leu Gln Pro Ala Pro
            435                 440                 445

Gln Ala Gly Ala Trp Phe Gln Ala Tyr Phe Val Gln Leu Leu Thr Asn
450                 455                 460

Ala Asn Pro Ser Phe Leu
```

<210> SEQ ID NO 83
<211> LENGTH: 470
<212> TYPE: PRT
<213> ORGANISM: Trichoderma parceramosum

<400> SEQUENCE: 83

```
Met Ile Val Gly Ile Leu Thr Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ala Gly
        35                  40                  45

Ser Thr Cys Val Tyr Ser Asn Asp Tyr Tyr Ser Gln Cys Pro Pro Gly
    50                  55                  60

Ala Ala Ser Ser Ser Ser Thr Arg Ala Ser Ser Thr Thr Asn Arg
65                  70                  75                  80

Val Ser Ser Thr Thr Ser Thr Ser Ser Ala Thr Pro Pro Gly Ser
                85                  90                  95

Thr Thr Thr Arg Val Pro Pro Val Gly Ser Gly Thr Ala Thr Tyr Ser
                100                 105                 110

Gly Asn Pro Phe Val Gly Val Thr Pro Trp Ala Asn Ala Tyr Tyr Ala
            115                 120                 125

Ser Glu Val Ser Ser Leu Ala Ile Pro Ser Leu Thr Gly Ala Met Ala
        130                 135                 140

Thr Ala Ala Ala Val Ala Lys Val Pro Ser Phe Met Trp Leu Asp
145                 150                 155                 160

Thr Leu Asp Lys Thr Pro Leu Met Glu Gln Thr Leu Ala Asp Ile Arg
                165                 170                 175

Thr Ala Asn Lys Asn Gly Gly Asn Tyr Ala Gly Gln Phe Val Val Tyr
            180                 185                 190

Asp Leu Pro Asp Arg Asp Cys Ala Ala Leu Ala Ser Asn Gly Glu Tyr
        195                 200                 205

Ser Ile Ala Asp Gly Gly Val Ala Lys Tyr Lys Asn Tyr Ile Asp Thr
    210                 215                 220

Ile Arg Gln Ile Val Val Glu Tyr Ser Asp Ile Arg Thr Ile Leu Val
225                 230                 235                 240

Ile Glu Pro Asp Ser Leu Ala Asn Leu Val Thr Asn Leu Gly Thr Pro
                245                 250                 255

Lys Cys Ala Asn Ala Gln Ser Ala Tyr Leu Glu Cys Ile Asn Tyr Ala
            260                 265                 270

Ile Thr Gln Leu Asn Leu Pro Asn Ile Ala Met Tyr Leu Asp Ala Gly
        275                 280                 285

His Ala Gly Trp Leu Gly Trp Pro Ala Asn Gln Asp Pro Ala Ala Gln
    290                 295                 300

Leu Phe Ala Asn Val Tyr Lys Asn Ala Ser Ser Pro Ser Ala Leu Arg
305                 310                 315                 320

Gly Leu Ala Thr Asn Val Ala Asn Tyr Asn Gly Trp Asn Ile Thr Ser
                325                 330                 335

Pro Pro Ser Tyr Thr Gln Gly Asn Ala Val Tyr Asn Glu Lys Leu Tyr
            340                 345                 350

Ile His Ala Ile Gly Pro Leu Leu Ala Asn His Gly Trp Ser Asn Ala
        355                 360                 365
```

```
Phe Phe Ile Thr Asp Gln Gly Arg Ser Gly Lys Gln Pro Thr Gly Gln
    370                 375                 380

Gln Gln Trp Gly Asp Trp Cys Asn Val Ile Gly Thr Gly Phe Gly Ile
385                 390                 395                 400

Arg Pro Ser Ser Asn Thr Gly Asp Ser Leu Leu Asp Ser Phe Val Trp
                405                 410                 415

Val Lys Pro Gly Gly Glu Cys Asp Gly Thr Ser Asp Ser Ser Ala Pro
                420                 425                 430

Arg Phe Asp Ser His Cys Ala Leu Pro Asp Ala Leu Gln Pro Ala Pro
                435                 440                 445

Gln Ala Gly Ala Trp Phe Gln Ala Tyr Phe Val Gln Leu Leu Thr Asn
450                 455                 460

Ala Asn Pro Ser Phe Leu
465                 470

<210> SEQ ID NO 84
<211> LENGTH: 455
<212> TYPE: PRT
<213> ORGANISM: Aspergillus nidulans

<400> SEQUENCE: 84

Met His Tyr Ser Ala Ser Gly Leu Ala Leu Ala Phe Leu Leu Pro Ala
1               5                   10                  15

Ile Gln Ala Gln Gln Thr Leu Tyr Gly Gln Cys Gly Gly Ser Gly Trp
                20                  25                  30

Thr Gly Ala Thr Ser Cys Val Ala Gly Ala Ala Cys Ser Thr Leu Asn
            35                  40                  45

Gln Trp Tyr Ala Gln Cys Leu Pro Ala Ala Thr Thr Thr Ser Thr Thr
    50                  55                  60

Leu Thr Thr Thr Thr Ser Ser Val Thr Thr Thr Ser Asn Pro Gly Ser
65                  70                  75                  80

Thr Thr Thr Thr Ser Ser Val Thr Val Thr Ala Thr Ala Ser Gly Asn
                85                  90                  95

Pro Phe Ser Gly Tyr Gln Leu Tyr Val Asn Pro Tyr Tyr Ser Ser Glu
                100                 105                 110

Val Gln Ser Ile Ala Ile Pro Ser Leu Thr Gly Thr Leu Ser Ser Leu
            115                 120                 125

Ala Pro Ala Ala Thr Ala Ala Lys Val Pro Ser Phe Val Trp Leu
    130                 135                 140

Asp Val Ala Ala Lys Val Pro Thr Met Ala Thr Tyr Leu Ala Asp Ile
145                 150                 155                 160

Arg Ser Gln Asn Ala Ala Gly Ala Asn Pro Pro Ile Ala Gly Gln Phe
                165                 170                 175

Val Val Tyr Asp Leu Pro Asp Arg Asp Cys Ala Ala Leu Ala Ser Asn
                180                 185                 190

Gly Glu Phe Ala Ile Ser Asp Gly Gly Val Gln His Tyr Lys Asp Tyr
            195                 200                 205

Ile Asp Ser Ile Arg Glu Ile Leu Val Glu Tyr Ser Asp Val His Val
    210                 215                 220

Ile Leu Val Ile Glu Pro Asp Ser Leu Ala Asn Leu Val Thr Asn Leu
225                 230                 235                 240

Asn Val Ala Lys Cys Ala Asn Ala Gln Ser Ala Tyr Leu Glu Cys Thr
                245                 250                 255

Asn Tyr Ala Val Thr Gln Leu Asn Leu Pro Asn Val Ala Met Tyr Leu
                260                 265                 270
```

```
Asp Ala Gly His Ala Gly Trp Leu Gly Trp Pro Ala Asn Leu Gln Pro
            275                 280                 285

Ala Ala Asn Leu Tyr Ala Gly Val Tyr Ser Asp Ala Gly Ser Pro Ala
        290                 295                 300

Ala Leu Arg Gly Leu Ala Thr Asn Val Ala Asn Tyr Asn Ala Trp Ala
305                 310                 315                 320

Ile Asp Thr Cys Pro Ser Tyr Thr Gln Gly Asn Ser Val Cys Asp Glu
            325                 330                 335

Lys Asp Tyr Ile Asn Ala Leu Ala Pro Leu Leu Arg Ala Gln Gly Phe
            340                 345                 350

Asp Ala His Phe Ile Thr Asp Thr Gly Arg Asn Gly Lys Gln Pro Thr
            355                 360                 365

Gly Gln Gln Ala Trp Gly Asp Trp Cys Asn Val Ile Gly Thr Gly Phe
        370                 375                 380

Gly Ala Arg Pro Ser Thr Asn Thr Gly Asp Ser Leu Leu Asp Ala Phe
385                 390                 395                 400

Val Trp Val Lys Pro Gly Gly Glu Ser Asp Gly Thr Ser Asp Thr Ser
            405                 410                 415

Ala Ala Arg Tyr Asp Ala His Cys Gly Tyr Ser Asp Ala Leu Gln Pro
            420                 425                 430

Ala Pro Glu Ala Gly Thr Trp Phe Gln Ala Tyr Phe Val Gln Leu Leu
            435                 440                 445

Gln Asn Ala Asn Pro Ser Phe
            450                 455

<210> SEQ ID NO 85
<211> LENGTH: 459
<212> TYPE: PRT
<213> ORGANISM: Aspergillus niger

<400> SEQUENCE: 85

Met His Tyr Pro Leu Ser Leu Ala Leu Ala Phe Leu Pro Phe Gly Ile
1               5                   10                  15

Gln Ala Gln Gln Thr Leu Trp Gly Gln Cys Gly Gly Gln Gly Tyr Ser
            20                  25                  30

Gly Ala Thr Ser Cys Val Ala Gly Ala Thr Cys Ala Thr Val Asn Glu
        35                  40                  45

Tyr Tyr Ala Gln Cys Thr Pro Ala Ala Gly Thr Ser Ser Ala Thr Thr
    50                  55                  60

Leu Lys Thr Thr Thr Ser Ser Thr Thr Ala Ala Val Thr Thr Thr Thr
65                  70                  75                  80

Thr Thr Gln Ser Pro Thr Gly Ser Ala Ser Pro Thr Thr Thr Ala Ser
                85                  90                  95

Ala Ser Gly Asn Pro Phe Ser Gly Tyr Gln Leu Tyr Val Asn Pro Tyr
            100                 105                 110

Tyr Ser Ser Glu Val Ala Ser Leu Ala Ile Pro Ser Leu Thr Gly Ser
        115                 120                 125

Leu Ser Ser Leu Gln Ala Ala Thr Ala Ala Lys Val Pro Ser
130                 135                 140

Phe Val Trp Leu Asp Thr Ala Ala Lys Val Pro Thr Met Gly Asp Tyr
145                 150                 155                 160

Leu Ala Asp Ile Gln Ser Gln Asn Ala Ala Gly Ala Asn Pro Pro Ile
            165                 170                 175

Ala Gly Gln Phe Val Val Tyr Asp Leu Pro Asp Arg Asp Cys Ala Ala
```

```
                180                 185                 190
Leu Ala Ser Asn Gly Glu Tyr Ser Ile Ala Asp Asn Gly Val Glu His
            195                 200                 205

Tyr Lys Ser Tyr Ile Asp Ser Ile Arg Glu Ile Leu Val Gln Tyr Ser
        210                 215                 220

Asp Val His Thr Leu Leu Val Ile Glu Pro Asp Ser Leu Ala Asn Leu
225                 230                 235                 240

Val Thr Asn Leu Asn Val Ala Lys Cys Ala Asn Ala Glu Ser Ala Tyr
                245                 250                 255

Leu Glu Cys Thr Asn Tyr Ala Leu Thr Gln Leu Asn Leu Pro Asn Val
            260                 265                 270

Ala Met Tyr Leu Asp Ala Gly His Ala Gly Trp Leu Gly Trp Pro Ala
        275                 280                 285

Asn Gln Gln Pro Ala Ala Asp Leu Phe Ala Ser Val Tyr Lys Asn Ala
                290                 295                 300

Ser Ser Pro Ala Ala Val Arg Gly Leu Ala Thr Asn Val Ala Asn Tyr
305                 310                 315                 320

Asn Ala Trp Thr Ile Ser Ser Cys Pro Ser Tyr Thr Gln Gly Asn Ser
                325                 330                 335

Val Cys Asp Glu Gln Gln Tyr Ile Asn Ala Ile Ala Pro Leu Leu Gln
            340                 345                 350

Ala Gln Gly Phe Asp Ala His Phe Ile Val Asp Thr Gly Arg Asn Gly
        355                 360                 365

Lys Gln Pro Thr Gly Gln Gln Ala Trp Gly Asp Trp Cys Asn Val Ile
        370                 375                 380

Asn Thr Gly Phe Gly Glu Arg Pro Thr Thr Asp Thr Gly Asp Ala Leu
385                 390                 395                 400

Val Asp Ala Phe Val Trp Val Lys Pro Gly Gly Glu Ser Asp Gly Thr
                405                 410                 415

Ser Asp Ser Ser Ala Thr Arg Tyr Asp Ala His Cys Gly Tyr Ser Asp
            420                 425                 430

Ala Leu Gln Pro Ala Pro Glu Ala Gly Thr Trp Phe Gln Ala Tyr Phe
        435                 440                 445

Val Gln Leu Leu Thr Asn Ala Asn Pro Ala Phe
        450                 455

<210> SEQ ID NO 86
<211> LENGTH: 494
<212> TYPE: PRT
<213> ORGANISM: Aspergillus oryzae

<400> SEQUENCE: 86

Met Ala Thr Arg Pro Val Glu Pro Ser Thr Phe Asn Cys Met Ile Ser
1               5                   10                  15

Cys Arg Asn Tyr Ser Ala Ser Trp His His Leu Thr Asp Ser Ser Phe
            20                  25                  30

Gln Leu His Thr Gln Val Thr Asp Arg Val Cys Leu Asn Ile Cys Ile
        35                  40                  45

Ser Asp Gly Asp Gln Gln Ser Leu Lys Pro Val Thr Val Pro Ser
    50                  55                  60

Pro Glu Phe Gly Thr Pro Thr His His Leu Gln Ser Ser Val Asn Ser
65                  70                  75                  80

Lys Leu Ser Tyr Leu Phe Ile Met His Thr Leu Asn Met Gln Ala Leu
                85                  90                  95
```

Val Ala Leu Ser Pro Leu Leu Phe Ser Ala Ala Thr Ala Leu Pro Gln
                100                 105                 110

Ala Ser Val Thr Pro Ser Pro Ser Ser Val Pro Ala Ser Ser Gly
            115                 120                 125

Pro Ala Pro Thr Ala Thr Ala Gly Gly Asn Pro Phe Glu Gly Tyr Asp
        130                 135                 140

Leu Tyr Val Asn Pro Tyr Tyr Lys Ser Glu Val Glu Ser Leu Ala Ile
145                 150                 155                 160

Pro Ser Met Thr Gly Ser Leu Ala Glu Lys Ala Ser Ala Ala Ala Asn
                165                 170                 175

Val Pro Ser Phe His Trp Leu Asp Thr Thr Asp Lys Val Pro Gln Met
            180                 185                 190

Gly Glu Phe Leu Glu Asp Ile Lys Thr Lys Asn Ala Ala Gly Ala Asn
        195                 200                 205

Pro Pro Thr Ala Gly Ile Phe Val Tyr Asp Leu Pro Asp Arg Asp
210                 215                 220

Cys Ala Ala Leu Ala Ser Asn Gly Glu Phe Leu Ile Ser Asp Gly Gly
225                 230                 235                 240

Val Glu Lys Tyr Lys Ala Tyr Ile Asp Ser Ile Arg Glu Gln Val Glu
                245                 250                 255

Lys Tyr Ser Asp Thr Gln Ile Ile Leu Val Ile Glu Pro Asp Ser Leu
            260                 265                 270

Ala Asn Leu Val Thr Asn Leu Asn Val Gln Lys Cys Ala Asn Ala Gln
        275                 280                 285

Asp Ala Tyr Leu Glu Cys Thr Asn Tyr Ala Leu Thr Gln Leu Asn Leu
    290                 295                 300

Pro Asn Val Ala Met Tyr Leu Asp Ala Gly His Ala Gly Trp Leu Gly
305                 310                 315                 320

Trp Pro Ala Asn Ile Gly Pro Ala Ala Glu Leu Tyr Ala Ser Val Tyr
                325                 330                 335

Lys Asn Ala Ser Ser Pro Ala Ala Val Arg Gly Leu Ala Thr Asn Val
            340                 345                 350

Ala Asn Tyr Asn Ala Phe Ser Ile Asp Ser Cys Pro Ser Tyr Thr Gln
        355                 360                 365

Gly Ser Thr Val Cys Asp Glu Lys Thr Tyr Ile Asn Asn Phe Ala Pro
    370                 375                 380

Gln Leu Lys Ser Ala Gly Phe Asp Ala His Phe Ile Val Asp Thr Gly
385                 390                 395                 400

Arg Asn Gly Asn Gln Pro Thr Gly Gln Ser Gln Trp Gly Asp Trp Cys
                405                 410                 415

Asn Val Lys Asn Thr Gly Phe Gly Val Arg Pro Thr Thr Asp Thr Gly
            420                 425                 430

Asp Glu Leu Val Asp Ala Phe Val Trp Val Lys Pro Gly Gly Glu Ser
        435                 440                 445

Asp Gly Thr Ser Asp Thr Ser Ala Glu Arg Tyr Asp Ala His Cys Gly
    450                 455                 460

Tyr Ala Asp Ala Leu Thr Pro Ala Pro Glu Ala Gly Thr Trp Phe Gln
465                 470                 475                 480

Ala Tyr Phe Glu Gln Leu Val Glu Asn Ala Asn Pro Ser Leu
                485                 490

<210> SEQ ID NO 87
<211> LENGTH: 400
<212> TYPE: PRT

<213> ORGANISM: Aspergillus niger

<400> SEQUENCE: 87

```
Met Arg Ala Ile Trp Pro Leu Val Ser Leu Phe Ser Ala Val Lys Ala
1               5                   10                  15

Leu Pro Ala Ala Ser Ala Thr Ala Ser Ala Ser Val Ala Ala Ser Ser
            20                  25                  30

Ser Pro Ala Pro Thr Ala Ser Ala Thr Gly Asn Pro Phe Glu Gly Tyr
        35                  40                  45

Gln Leu Tyr Ala Asn Pro Tyr Tyr Lys Ser Gln Val Glu Ser Ser Ala
    50                  55                  60

Ile Pro Ser Leu Ser Ala Ser Ser Leu Val Ala Gln Ala Ser Ala Ala
65                  70                  75                  80

Ala Asp Val Pro Ser Phe Tyr Trp Leu Asp Thr Ala Asp Lys Val Pro
                85                  90                  95

Thr Met Gly Glu Tyr Leu Glu Asp Ile Gln Thr Gln Asn Ala Ala Gly
            100                 105                 110

Ala Ser Pro Pro Ile Ala Gly Ile Phe Val Val Tyr Asp Leu Pro Asp
        115                 120                 125

Arg Asp Cys Ser Ala Leu Ala Ser Asn Gly Glu Tyr Ser Ile Ser Asp
130                 135                 140

Gly Gly Val Glu Lys Tyr Lys Ala Tyr Ile Asp Ser Ile Arg Glu Gln
145                 150                 155                 160

Val Glu Thr Tyr Ser Asp Val Gln Thr Ile Leu Ile Glu Pro Asp
                165                 170                 175

Ser Leu Ala Asn Leu Val Thr Asn Leu Asp Val Ala Lys Cys Ala Asn
            180                 185                 190

Ala Glu Ser Ala Tyr Leu Glu Cys Thr Asn Tyr Ala Leu Glu Gln Leu
        195                 200                 205

Asn Leu Pro Asn Val Ala Met Tyr Leu Asp Ala Gly His Ala Gly Trp
    210                 215                 220

Leu Gly Trp Pro Ala Asn Ile Gly Pro Ala Ala Gln Leu Tyr Ala Ser
225                 230                 235                 240

Val Tyr Lys Asn Ala Ser Ser Pro Ala Ala Val Arg Gly Leu Ala Thr
                245                 250                 255

Asn Val Ala Asn Phe Asn Ala Trp Ser Ile Asp Ser Cys Pro Ser Tyr
            260                 265                 270

Thr Ser Gly Asn Asp Val Cys Asp Glu Lys Ser Tyr Ile Asn Ala Ile
        275                 280                 285

Ala Pro Glu Leu Ser Ser Ala Gly Phe Asp Ala His Phe Ile Thr Asp
    290                 295                 300

Thr Gly Arg Asn Gly Lys Gln Pro Thr Gly Gln Ser Ala Trp Gly Asp
305                 310                 315                 320

Trp Cys Asn Val Lys Asp Thr Gly Phe Gly Ala Gln Pro Thr Thr Asp
                325                 330                 335

Thr Gly Asp Glu Leu Ala Asp Ala Phe Val Trp Val Lys Pro Gly Gly
            340                 345                 350

Glu Ser Asp Gly Thr Ser Asp Thr Ser Ser Ser Arg Tyr Asp Ala His
        355                 360                 365

Cys Gly Tyr Ser Asp Ala Leu Gln Pro Ala Pro Glu Ala Gly Thr Trp
    370                 375                 380

Phe Gln Ala Tyr Phe Glu Gln Leu Leu Thr Asn Ala Asn Pro Ser Leu
385                 390                 395                 400
```

<210> SEQ ID NO 88
<211> LENGTH: 457
<212> TYPE: PRT
<213> ORGANISM: Acremonium cellulolyticus

<400> SEQUENCE: 88

```
Met Leu Arg Tyr Leu Ser Ile Val Ala Ala Thr Ala Ile Leu Thr Gly
1               5                   10                  15

Val Glu Ala Gln Gln Ser Val Trp Gly Gln Cys Gly Gly Gln Gly Trp
            20                  25                  30

Ser Gly Ala Thr Ser Cys Ala Ala Gly Ser Thr Cys Ser Thr Leu Asn
        35                  40                  45

Pro Tyr Tyr Ala Gln Cys Ile Pro Gly Thr Ala Thr Ser Thr Thr Leu
    50                  55                  60

Val Lys Thr Thr Ser Ser Thr Ser Val Gly Thr Thr Ser Pro Pro Thr
65                  70                  75                  80

Thr Thr Thr Thr Lys Ala Ser Thr Thr Ala Thr Thr Ala Ala Ala
                85                  90                  95

Ser Gly Asn Pro Phe Ser Gly Tyr Gln Leu Tyr Ala Asn Pro Tyr Tyr
            100                 105                 110

Ser Ser Glu Val His Thr Leu Ala Ile Pro Ser Leu Thr Gly Ser Leu
        115                 120                 125

Ala Ala Ala Ala Thr Lys Ala Ala Glu Ile Pro Ser Phe Val Trp Leu
    130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Pro Ile Ala Gly Ile Phe
                165                 170                 175

Val Val Tyr Asp Leu Pro Asp Arg Asp Cys Ala Ala Ala Ser Asn
            180                 185                 190

Gly Glu Tyr Thr Val Ala Asn Asn Gly Val Ala Asn Tyr Lys Ala Tyr
        195                 200                 205

Ile Asp Ser Ile Val Ala Gln Leu Lys Ala Tyr Pro Asp Val His Thr
    210                 215                 220

Ile Leu Ile Ile Glu Pro Asp Ser Leu Ala Asn Met Val Thr Asn Leu
225                 230                 235                 240

Ser Thr Ala Lys Cys Ala Glu Ala Gln Ser Ala Tyr Tyr Glu Cys Val
                245                 250                 255

Asn Tyr Ala Leu Ile Asn Leu Asn Leu Ala Asn Val Ala Met Tyr Ile
            260                 265                 270

Asp Ala Gly His Ala Gly Trp Leu Gly Trp Ser Ala Asn Leu Ser Pro
        275                 280                 285

Ala Ala Gln Leu Phe Ala Thr Val Tyr Lys Asn Ala Ser Ala Pro Ala
    290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
            340                 345                 350

Pro Asn Ala His Phe Ile Met Asp Thr Ser Arg Asn Gly Val Gln Pro
        355                 360                 365

Thr Lys Gln Gln Ala Trp Gly Asp Trp Cys Asn Val Ile Gly Thr Gly
    370                 375                 380
```

Phe Gly Val Gln Pro Thr Thr Asn Thr Gly Asp Pro Leu Glu Asp Ala
385                 390                 395                 400

Phe Val Trp Val Lys Pro Gly Gly Glu Ser Asp Gly Thr Ser Asn Ser
            405                 410                 415

Ser Ala Thr Arg Tyr Asp Phe His Cys Gly Tyr Ser Asp Ala Leu Gln
        420                 425                 430

Pro Ala Pro Glu Ala Gly Thr Trp Phe Gln Ala Tyr Phe Val Gln Leu
    435                 440                 445

Leu Thr Asn Ala Asn Pro Ala Leu Val
    450                 455

<210> SEQ ID NO 89
<211> LENGTH: 459
<212> TYPE: PRT
<213> ORGANISM: Talaromyces emersonii

<400> SEQUENCE: 89

Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
            20                  25                  30

Thr Gly Ala Thr Ser Cys Ala Ala Gly Ala Thr Cys Ser Thr Ile Asn
        35                  40                  45

Pro Tyr Tyr Ala Gln Cys Val Pro Ala Thr Ala Thr Pro Thr Thr Leu
    50                  55                  60

Thr Thr Thr Thr Lys Pro Thr Ser Thr Gly Ala Ala Pro Thr Thr
65                  70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
    130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Val Ile Glu Pro Asp Ser Leu Ala Asn Val
225                 230                 235                 240

Val Thr Asn Leu Asn Val Pro Lys Cys Ala Asn Ala Gln Asp Ala Tyr
                245                 250                 255

Leu Glu Cys Ile Asn Tyr Ala Ile Thr Gln Leu Asp Leu Pro Asn Val
            260                 265                 270

Ala Met Tyr Leu Asp Ala Gly His Ala Gly Trp Leu Gly Trp Gln Ala
        275                 280                 285

Asn Leu Ala Pro Ala Ala Gln Leu Phe Ala Ser Val Tyr Lys Asn Ala

```
            290                 295                 300
Ser Ser Pro Ala Ser Val Arg Gly Leu Ala Thr Asn Val Ala Asn Tyr
305                 310                 315                 320

Asn Ala Trp Ser Ile Ser Arg Cys Pro Ser Tyr Thr Gln Gly Asp Ala
                325                 330                 335

Asn Cys Asp Glu Glu Asp Tyr Val Asn Ala Leu Gly Pro Leu Phe Gln
            340                 345                 350

Glu Gln Gly Phe Pro Ala Tyr Phe Ile Ile Asp Thr Ser Arg Asn Gly
        355                 360                 365

Val Arg Pro Thr Lys Gln Ser Gln Trp Gly Asp Trp Cys Asn Val Ile
    370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
        435                 440                 445

Glu Gln Leu Leu Thr Asn Ala Asn Pro Leu Phe
    450                 455

<210> SEQ ID NO 90
<211> LENGTH: 457
<212> TYPE: PRT
<213> ORGANISM: Gibberella zeae

<400> SEQUENCE: 90

Met Thr Ala Tyr Lys Leu Phe Leu Ala Ala Ala Phe Ala Thr Ala
1               5                   10                  15

Leu Ala Ala Pro Val Glu Glu Arg Gln Ser Cys Ser Asn Gly Val Trp
                20                  25                  30

Ser Gln Cys Gly Gly Gln Asn Trp Ser Gly Thr Pro Cys Cys Thr Ser
            35                  40                  45

Gly Asn Lys Cys Val Lys Val Asn Asp Phe Tyr Ser Gln Cys Gln Pro
        50                  55                  60

Gly Ser Ala Asp Pro Ser Pro Thr Ser Thr Ile Val Ser Ala Thr Thr
65                  70                  75                  80

Thr Lys Ala Thr Thr Thr Gly Ser Gly Gly Ser Val Thr Ser Pro Pro
                85                  90                  95

Pro Val Ala Thr Asn Asn Pro Phe Ser Gly Val Asp Leu Trp Ala Asn
            100                 105                 110

Asn Tyr Tyr Arg Ser Glu Val Ser Thr Leu Ala Ile Pro Lys Leu Ser
        115                 120                 125

Gly Ala Met Ala Thr Ala Ala Lys Val Ala Asp Val Pro Ser Phe
    130                 135                 140

Gln Trp Met Asp Thr Tyr Asp His Ile Ser Phe Met Glu Asp Ser Leu
145                 150                 155                 160

Ala Asp Ile Arg Lys Ala Asn Lys Ala Gly Gly Asn Tyr Ala Gly Gln
                165                 170                 175

Phe Val Val Tyr Asp Leu Pro Asp Arg Asp Cys Ala Ala Ala Ser
            180                 185                 190

Asn Gly Glu Tyr Ser Leu Asp Lys Asp Gly Lys Asn Lys Tyr Lys Ala
        195                 200                 205
```

```
Tyr Ile Ala Asp Gln Gly Ile Leu Gln Asp Tyr Ser Asp Thr Arg Ile
    210                 215                 220

Ile Leu Val Ile Glu Pro Asp Ser Leu Ala Asn Met Val Thr Asn Met
225                 230                 235                 240

Asn Val Pro Lys Cys Ala Asn Ala Ala Ser Ala Tyr Lys Glu Leu Thr
                245                 250                 255

Ile His Ala Leu Lys Glu Leu Asn Leu Pro Asn Val Ser Met Tyr Ile
            260                 265                 270

Asp Ala Gly His Gly Gly Trp Leu Gly Trp Pro Ala Asn Leu Pro Pro
        275                 280                 285

Ala Ala Gln Leu Tyr Gly Gln Leu Tyr Lys Asp Ala Gly Lys Pro Ser
    290                 295                 300

Arg Leu Arg Gly Leu Val Thr Asn Val Ser Asn Tyr Asn Ala Trp Lys
305                 310                 315                 320

Leu Ser Ser Lys Pro Asp Tyr Thr Glu Ser Asn Pro Asn Tyr Asp Glu
                325                 330                 335

Gln Lys Tyr Ile His Ala Leu Ser Pro Leu Leu Glu Gln Glu Gly Trp
            340                 345                 350

Pro Gly Ala Lys Phe Ile Val Asp Gln Gly Arg Ser Gly Lys Gln Pro
        355                 360                 365

Thr Gly Gln Lys Ala Trp Gly Asp Trp Cys Asn Ala Pro Gly Thr Gly
    370                 375                 380

Phe Gly Leu Arg Pro Ser Ala Asn Thr Gly Asp Ala Leu Val Asp Ala
385                 390                 395                 400

Phe Val Trp Val Lys Pro Gly Gly Glu Ser Asp Gly Thr Ser Asp Thr
                405                 410                 415

Ser Ala Ala Arg Tyr Asp Tyr His Cys Gly Ile Asp Gly Ala Val Lys
            420                 425                 430

Pro Ala Pro Glu Ala Gly Thr Trp Phe Gln Ala Tyr Phe Glu Gln Leu
        435                 440                 445

Leu Lys Asn Ala Asn Pro Ser Phe Leu
    450                 455

<210> SEQ ID NO 91
<211> LENGTH: 462
<212> TYPE: PRT
<213> ORGANISM: Fusarium oxysporum

<400> SEQUENCE: 91

Met Ala Tyr Lys Leu Ile Leu Ala Ala Phe Ala Ala Thr Ala Leu Ala
1               5                   10                  15

Ala Pro Val Glu Glu Arg Gln Ser Cys Ser Asn Gly Val Trp Ala Gln
            20                  25                  30

Cys Gly Gly Gln Asn Trp Ser Gly Thr Pro Cys Cys Thr Ser Gly Asn
        35                  40                  45

Lys Cys Val Lys Leu Asn Asp Phe Tyr Ser Gln Cys Gln Pro Gly Ser
    50                  55                  60

Ala Glu Pro Ser Ser Thr Ala Ala Gly Pro Ser Ser Thr Thr Ala Thr
65                  70                  75                  80

Lys Thr Thr Ala Thr Gly Gly Ser Ser Thr Thr Ala Gly Gly Ser Val
                85                  90                  95

Thr Ser Ala Pro Pro Ala Ala Ser Asp Asn Pro Tyr Ala Gly Val Asp
            100                 105                 110

Leu Trp Ala Asn Asn Tyr Tyr Arg Ser Glu Val Met Asn Leu Ala Val
        115                 120                 125
```

Pro Lys Leu Ser Gly Ala Lys Ala Thr Ala Ala Ala Lys Val Ala Asp
        130                 135                 140

Val Pro Ser Phe Gln Trp Met Asp Thr Tyr Asp His Ile Ser Leu Met
145                 150                 155                 160

Glu Asp Thr Leu Ala Asp Ile Arg Lys Ala Asn Lys Ala Gly Gly Lys
                165                 170                 175

Tyr Ala Gly Gln Phe Val Val Tyr Asp Leu Pro Asn Arg Asp Cys Ala
            180                 185                 190

Ala Ala Ala Ser Asn Gly Glu Tyr Ser Leu Asp Lys Asp Gly Ala Asn
        195                 200                 205

Lys Tyr Lys Ala Tyr Ile Ala Lys Ile Lys Gly Ile Leu Gln Asn Tyr
    210                 215                 220

Ser Asp Thr Lys Val Ile Leu Val Ile Glu Pro Asp Ser Leu Ala Asn
225                 230                 235                 240

Leu Val Thr Asn Leu Asn Val Asp Lys Cys Ala Lys Ala Glu Ser Ala
                245                 250                 255

Tyr Lys Glu Leu Thr Val Tyr Ala Ile Lys Glu Leu Asn Leu Pro Asn
            260                 265                 270

Val Ser Met Tyr Leu Asp Ala Gly His Gly Gly Trp Leu Gly Trp Pro
        275                 280                 285

Ala Asn Ile Gly Pro Ala Ala Lys Leu Tyr Ala Gln Ile Tyr Lys Asp
    290                 295                 300

Ala Gly Lys Pro Ser Arg Val Arg Gly Leu Val Thr Asn Val Ser Asn
305                 310                 315                 320

Tyr Asn Gly Trp Lys Leu Ser Thr Lys Pro Asp Tyr Thr Glu Ser Asn
                325                 330                 335

Pro Asn Tyr Asp Glu Gln Arg Tyr Ile Asn Ala Phe Ala Pro Leu Leu
            340                 345                 350

Ala Gln Glu Gly Trp Ser Asn Val Lys Phe Ile Val Asp Gln Gly Arg
        355                 360                 365

Ser Gly Lys Gln Pro Thr Gly Gln Lys Ala Gln Gly Asp Trp Cys Asn
    370                 375                 380

Ala Lys Gly Thr Gly Phe Gly Leu Arg Pro Ser Thr Asn Thr Gly Asp
385                 390                 395                 400

Ala Leu Ala Asp Ala Phe Val Trp Val Lys Pro Gly Gly Glu Ser Asp
                405                 410                 415

Gly Thr Ser Asp Thr Ser Ala Ala Arg Tyr Asp Tyr His Cys Gly Leu
            420                 425                 430

Asp Asp Ala Leu Lys Pro Ala Pro Glu Ala Gly Thr Trp Phe Gln Ala
        435                 440                 445

Tyr Phe Glu Gln Leu Leu Asp Asn Ala Asn Pro Ser Phe Leu
    450                 455                 460

<210> SEQ ID NO 92
<211> LENGTH: 484
<212> TYPE: PRT
<213> ORGANISM: Neurospora crassa

<400> SEQUENCE: 92

Met Ala Ala Lys Lys Leu Leu Leu Ala Ala Ala Leu Thr Ala Ser Ala
1               5                   10                  15

Leu Ala Ala Pro Val Leu Glu Asp Arg Gln Asn Cys Gly Ser Ala Trp
            20                  25                  30

Ser Gln Cys Gly Gly Ile Gly Trp Ser Gly Ala Thr Cys Cys Ser Ser

```
              35                  40                  45
Gly Asn Ser Cys Val Glu Ile Asn Ser Tyr Tyr Ser Gln Cys Leu Pro
 50                  55                  60

Gly Ala Gln Val Thr Thr Thr Ala Gly Ala Ser Ser Thr Ser Pro Thr
 65                  70                  75                  80

Ser Thr Ser Lys Val Ser Ser Thr Thr Ser Lys Val Thr Ser Ser Ser
                 85                  90                  95

Ala Ala Gln Pro Ile Thr Thr Thr Thr Ala Pro Ser Val Pro Thr Thr
                100                 105                 110

Thr Ile Ala Gly Gly Ala Ser Ser Thr Ala Ser Phe Thr Gly Asn Pro
                115                 120                 125

Phe Leu Gly Val Gln Gly Trp Ala Asn Ser Tyr Tyr Ser Ser Glu Ile
                130                 135                 140

Tyr Asn His Ala Ile Pro Ser Met Thr Gly Ser Leu Ala Ala Gln Ala
145                 150                 155                 160

Ser Ala Val Ala Lys Val Pro Thr Phe Gln Trp Leu Asp Arg Asn Val
                165                 170                 175

Thr Val Asp Thr Leu Met Lys Ser Thr Leu Glu Glu Ile Arg Ala Ala
                180                 185                 190

Asn Lys Ala Gly Ala Asn Pro Pro Tyr Ala Ala His Phe Val Val Tyr
                195                 200                 205

Asp Leu Pro Asp Arg Asp Cys Ala Ala Ala Ser Asn Gly Glu Phe
210                 215                 220

Ser Ile Ala Asn Gly Gly Val Ala Asn Tyr Lys Thr Tyr Ile Asn Ala
225                 230                 235                 240

Ile Arg Lys Leu Leu Ile Glu Tyr Ser Asp Ile Arg Thr Ile Leu Val
                245                 250                 255

Ile Glu Pro Asp Ser Leu Ala Asn Leu Val Thr Asn Thr Asn Val Ala
                260                 265                 270

Lys Cys Ala Asn Ala Ala Ser Ala Tyr Arg Glu Cys Thr Asn Tyr Ala
                275                 280                 285

Ile Thr Gln Leu Asp Leu Pro His Val Ala Gln Tyr Leu Asp Ala Gly
                290                 295                 300

His Gly Gly Trp Leu Gly Trp Pro Ala Asn Ile Gln Pro Ala Ala Thr
305                 310                 315                 320

Leu Phe Ala Asp Ile Tyr Lys Ala Ala Gly Lys Pro Lys Ser Val Arg
                325                 330                 335

Gly Leu Val Thr Asn Val Ser Asn Tyr Asn Gly Trp Ser Leu Ser Ser
                340                 345                 350

Ala Pro Ser Tyr Thr Thr Pro Asn Pro Asn Tyr Asp Glu Lys Lys Tyr
                355                 360                 365

Ile Glu Ala Phe Ser Pro Leu Leu Asn Ala Ala Gly Phe Pro Ala Gln
                370                 375                 380

Phe Ile Val Asp Thr Gly Arg Ser Gly Lys Gln Pro Thr Gly Gln Ile
385                 390                 395                 400

Glu Gln Gly Asp Trp Cys Asn Ala Ile Gly Thr Gly Phe Gly Val Arg
                405                 410                 415

Pro Thr Thr Asn Thr Gly Ser Ser Leu Ala Asp Ala Phe Val Trp Val
                420                 425                 430

Lys Pro Gly Gly Glu Ser Asp Gly Thr Ser Thr Ser Ala Thr Arg
                435                 440                 445

Tyr Asp Tyr His Cys Gly Leu Ser Asp Ala Leu Lys Pro Ala Pro Glu
                450                 455                 460
```

```
Ala Gly Gln Trp Phe Gln Ala Tyr Phe Glu Gln Leu Leu Lys Asn Ala
465                 470                 475                 480

Asn Pro Ala Phe
```

<210> SEQ ID NO 93
<211> LENGTH: 435
<212> TYPE: PRT
<213> ORGANISM: Aspergillus nidulans

<400> SEQUENCE: 93

```
Met Gln Ile Glu Phe Tyr Gln Gly Arg Arg His Cys Ser Ala Trp
1               5                   10                  15

Ala Phe Leu Asp Arg Phe Gly Ile Gly Val Pro Gly Arg Asp Ser Ile
                20                  25                  30

Leu Ser Ile Ser Met Arg Ala Leu Ala Thr Met Leu Thr Leu Gly Ala
            35                  40                  45

Val Ser Val Asn Ala Leu Pro Gln Ala Thr Ser Thr Pro Ala Gly Thr
50                  55                  60

Pro Ser Ser Ser Gly Ile Pro Val Gln Ala Thr Gly Asn Pro Phe Glu
65                  70                  75                  80

Gly Tyr Gln Leu Tyr Ala Asn Pro Tyr Tyr Ser Ser Glu Val Met Thr
                85                  90                  95

Leu Ala Val Pro Ser Met Thr Gly Ser Leu Ala Glu Gln Ala Thr His
            100                 105                 110

Ala Ala Glu Ile Pro Ser Phe His Trp Leu Asp Thr Thr Ala Lys Val
        115                 120                 125

Pro Thr Met Gly Glu Tyr Leu Ala Asp Ile Lys Glu Gln Asn Asp Ala
130                 135                 140

Gly Ala Asn Pro Pro Ile Ala Gly Ile Phe Val Val Tyr Asn Leu Pro
145                 150                 155                 160

Asp Arg Asp Cys Ala Ala Leu Ala Ser Asn Gly Glu Leu Ser Ile Ala
                165                 170                 175

Asp Gly Gly Val Glu Lys Tyr Lys Glu Tyr Ile Asp Ala Ile Arg Ala
            180                 185                 190

His Ala Val Glu Tyr Ser Asp Thr Asn Ile Ile Leu Ile Ile Glu Pro
        195                 200                 205

Asp Ser Leu Ala Asn Leu Val Thr Asn Leu Asn Val Glu Lys Cys Ala
210                 215                 220

Asn Ala Gln Asp Ala Tyr Leu Glu Cys Thr Asn Tyr Ala Ile Thr Gln
225                 230                 235                 240

Leu Asp Leu Pro Asn Val Ser Met Tyr Leu Asp Ala Gly His Ala Gly
                245                 250                 255

Trp Leu Gly Trp Pro Ala Asn Ile Gly Pro Ala Ala Gln Leu Phe Ala
            260                 265                 270

Gly Val Tyr Gln Asp Ala Gly Ala Pro Ala Ala Leu Arg Gly Leu Ala
        275                 280                 285

Thr Asn Val Ala Asn Tyr Asn Ala Phe Ser Ile Asp Thr Cys Pro Ser
290                 295                 300

Tyr Thr Ser Gln Asn Ala Val Cys Asp Glu Lys Gly Tyr Ile Asn Ser
305                 310                 315                 320

Phe Ala Pro Glu Leu Ser Ala Ala Gly Trp Asp Ala His Phe Ile Val
                325                 330                 335

Asp Thr Gly Arg Asn Gly Lys Gln Pro Thr Gly Gln Ile Glu Trp Gly
            340                 345                 350
```

```
Asp Trp Cys Asn Val Lys Gly Thr Gly Phe Gly Val Arg Pro Thr Thr
        355                 360                 365

Asp Thr Gly Asp Glu Leu Val Asp Ala Phe Val Trp Val Lys Pro Gly
        370                 375                 380

Gly Glu Ser Asp Gly Thr Ser Asp Gln Ser Ala Glu Arg Tyr Asp Ala
385                 390                 395                 400

His Cys Gly Ala Ala Ala Leu Gln Pro Ala Pro Glu Ala Gly Thr
                405                 410                 415

Trp Phe Gln Ala Tyr Phe Glu Gln Leu Val Ala Asn Ala Asn Pro Pro
                420                 425                 430

Leu Ser Ser
        435

<210> SEQ ID NO 94
<211> LENGTH: 407
<212> TYPE: PRT
<213> ORGANISM: Aspergillus tubingensis
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid

<400> SEQUENCE: 94

Met Asn Met His Ser Ile Asn Met Arg Ala Ile Trp Pro Leu Val Ser
1               5                   10                  15

Leu Phe Ser Ala Val Lys Ala Leu Pro Ala Ala Ser Ala Thr Ala Ser
                20                  25                  30

Ala Ser Val Ala Ala Ser Ser Pro Ala Pro Thr Ala Ser Ala Thr
                35                  40                  45

Gly Asn Pro Phe Glu Gly Tyr Gln Leu Tyr Val Asn Pro Tyr Tyr Lys
50                  55                  60

Ser Gln Val Glu Ser Ser Ala Ile Pro Ser Leu Ser Ala Ser Ser Leu
65                  70                  75                  80

Val Ala Gln Ala Ser Ala Ala Asp Val Pro Ser Phe Tyr Trp Leu
                85                  90                  95

Asp Thr Ala Asp Lys Val Pro Thr Met Gly Glu Tyr Leu Asp Asp Ile
                100                 105                 110

Gln Thr Gln Asn Ala Ala Gly Ala Asn Pro Pro Ile Ala Gly Ile Phe
                115                 120                 125

Val Val Tyr Asp Leu Pro Asp Arg Asp Cys Ala Ala Leu Ala Ser Asn
                130                 135                 140

Gly Glu Tyr Ala Ile Ser Asp Gly Gly Val Glu Lys Tyr Lys Ala Tyr
145                 150                 155                 160

Ile Asp Ser Ile Arg Glu Gln Val Glu Thr Tyr Ser Asp Val Gln Thr
                165                 170                 175

Ile Leu Ile Ile Glu Pro Asp Ser Leu Ala Asn Leu Val Thr Asn Leu
                180                 185                 190

Asp Val Ala Lys Cys Ala Asn Ala Gln Ser Ala Tyr Leu Glu Cys Thr
                195                 200                 205

Asn Tyr Ala Leu Glu Gln Leu Asn Leu Pro Asn Val Ala Met Tyr Leu
```

```
            210                 215                 220
Asp Ala Gly His Ala Gly Trp Leu Gly Trp Pro Ala Asn Ile Gly Pro
225                 230                 235                 240

Ala Ala Glu Leu Tyr Ala Ser Val Tyr Lys Asn Ala Ser Ser Pro Ala
            245                 250                 255

Ala Val Arg Gly Leu Ala Thr Asx Val Ala Asn Phe Asn Ala Trp Ser
        260                 265                 270

Ile Asp Thr Cys Pro Ser Tyr Thr Ser Gly Asn Asp Val Cys Asp Glu
            275                 280                 285

Lys Ser Tyr Ile Asn Ala Phe Ala Pro Glu Leu Ser Xaa Ala Gly Phe
        290                 295                 300

Asp Ala His Phe Ile Thr Asp Thr Gly Arg Asn Gly Lys Gln Pro Thr
305                 310                 315                 320

Gly Gln Ser Ala Trp Gly Asp Trp Gly Asn Val Lys Asp Thr Gly Phe
            325                 330                 335

Gly Ala Xaa Pro Thr Thr Asp Thr Gly Asn Glu Leu Ala Asp Ala Phe
        340                 345                 350

Val Trp Xaa Asn Pro Gly Gly Lys Ser Asp Gly Thr Ser Asp Thr Ser
        355                 360                 365

Ser Ser Arg Tyr Asp Ala His Cys Gly Tyr Ser Asp Ala Leu Gln Pro
        370                 375                 380

Ala Pro Glu Ala Gly Thr Trp Phe Gln Ala Tyr Phe Glu Gln Leu Leu
385                 390                 395                 400

Thr Asn Ala Asn Pro Ser Leu
                405

<210> SEQ ID NO 95
<211> LENGTH: 487
<212> TYPE: PRT
<213> ORGANISM: Magnaporthe grisea

<400> SEQUENCE: 95

Met Ala Ser Lys Leu Phe Leu Ala Ala Leu Leu Gln Gly Ala Leu
1               5                   10                  15

Ser Ser Pro Leu Ala Val Glu Glu Arg Gln Ala Cys Ala Ala Gln Trp
            20                  25                  30

Gly Gln Cys Gly Gly Gln Asp Tyr Thr Gly Pro Thr Cys Cys Gln Ser
        35                  40                  45

Gly Ser Thr Cys Val Val Ser Asn Gln Trp Tyr Ser Gln Cys Leu Pro
    50                  55                  60

Gly Ser Ser Asn Pro Thr Thr Thr Ser Arg Thr Ser Thr Ser Ser Ser
65                  70                  75                  80

Ser Ser Thr Ser Arg Thr Ser Ser Thr Ser Arg Pro Pro Ser Ser
            85                  90                  95

Val Pro Thr Thr Pro Thr Ser Val Pro Pro Thr Ile Thr Thr Thr Pro
            100                 105                 110

Thr Thr Thr Pro Thr Gly Gly Ser Gly Pro Gly Thr Thr Ala Ser Phe
        115                 120                 125

Thr Gly Asn Pro Phe Ala Gly Val Asn Leu Phe Pro Asn Lys Phe Tyr
    130                 135                 140

Ser Ser Glu Val His Thr Leu Ala Ile Pro Ser Leu Thr Gly Ser Leu
145                 150                 155                 160

Val Ala Lys Ala Ser Ala Val Ala Gln Val Pro Ser Phe Gln Trp Leu
            165                 170                 175
```

```
Asp Ile Ala Ala Lys Val Glu Thr Leu Met Pro Gly Ala Leu Ala Asp
            180                 185                 190

Val Arg Ala Ala Asn Ala Ala Gly Gly Asn Tyr Ala Ala Gln Leu Val
        195                 200                 205

Val Tyr Asp Leu Pro Asp Arg Asp Cys Ala Ala Ala Ser Asn Gly
    210                 215                 220

Glu Phe Ser Ile Ala Asp Gly Val Val Lys Tyr Lys Ala Tyr Ile
225             230                 235                 240

Asp Ala Ile Arg Lys Gln Leu Leu Ala Tyr Ser Asp Val Arg Thr Ile
            245                 250                 255

Leu Val Ile Glu Pro Asp Ser Leu Ala Asn Met Val Thr Asn Met Gly
        260                 265                 270

Val Pro Lys Cys Ala Gly Ala Lys Asp Ala Tyr Leu Glu Cys Thr Ile
    275                 280                 285

Tyr Ala Val Lys Gln Leu Asn Leu Pro His Val Ala Met Tyr Leu Asp
    290                 295                 300

Gly Gly His Ala Gly Trp Leu Gly Trp Pro Ala Asn Leu Gln Pro Ala
305             310                 315                 320

Ala Asp Leu Phe Gly Lys Leu Tyr Ala Asp Ala Gly Lys Pro Ser Gln
            325                 330                 335

Leu Arg Gly Met Ala Thr Asn Val Ala Asn Tyr Asn Ala Trp Asp Leu
        340                 345                 350

Thr Thr Ala Pro Ser Tyr Thr Thr Pro Asn Pro Asn Phe Asp Glu Lys
    355                 360                 365

Lys Tyr Ile Ser Ala Phe Ala Pro Leu Leu Ala Ala Lys Gly Trp Ser
    370                 375                 380

Ala His Phe Ile Ile Asp Gln Gly Arg Ser Gly Lys Gln Pro Thr Gly
385             390                 395                 400

Gln Lys Glu Trp Gly His Trp Cys Asn Gln Gln Gly Val Gly Phe Gly
            405                 410                 415

Arg Arg Pro Ser Ala Asn Thr Gly Ser Glu Leu Ala Asp Ala Phe Val
        420                 425                 430

Trp Ile Lys Pro Gly Gly Glu Cys Asp Gly Val Ser Asp Pro Thr Ala
    435                 440                 445

Pro Arg Phe Asp His Phe Cys Gly Thr Asp Tyr Gly Ala Met Ser Asp
    450                 455                 460

Ala Pro Gln Ala Gly Gln Trp Phe Gln Lys Tyr Phe Glu Met Leu Leu
465             470                 475                 480

Thr Asn Ala Asn Pro Pro Leu
            485

<210> SEQ ID NO 96
<211> LENGTH: 477
<212> TYPE: PRT
<213> ORGANISM: Chaetomium thermophilum

<400> SEQUENCE: 96

Met Ala Lys Gln Leu Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
            20                  25                  30

Gln Cys Gly Gly Ile Asn Tyr Asn Gly Pro Thr Cys Cys Gln Ser Gly
        35                  40                  45

Ser Val Cys Thr Tyr Leu Asn Asp Trp Tyr Ser Gln Cys Ile Pro Gly
    50                  55                  60
```

```
Gln Ala Gln Pro Gly Thr Thr Ser Thr Thr Ala Arg Thr Thr Ser Thr
 65                  70                  75                  80
Ser Thr Thr Ser Thr Ser Ser Val Arg Pro Thr Thr Ser Asn Thr Pro
                 85                  90                  95
Val Thr Thr Ala Pro Pro Thr Thr Thr Ile Pro Gly Gly Ala Ser Ser
            100                 105                 110
Thr Ala Ser Tyr Asn Gly Asn Pro Phe Ser Gly Val Gln Leu Trp Ala
            115                 120                 125
Asn Thr Tyr Tyr Ser Ser Glu Val His Thr Leu Ala Ile Pro Ser Leu
            130                 135                 140
Ser Pro Glu Leu Ala Ala Lys Ala Ala Lys Val Ala Glu Val Pro Ser
145                 150                 155                 160
Phe Gln Trp Leu Asp Arg Asn Val Thr Val Asp Thr Leu Phe Ser Gly
                165                 170                 175
Thr Leu Ala Glu Ile Arg Ala Ala Asn Gln Arg Gly Ala Asn Pro Pro
            180                 185                 190
Tyr Ala Gly Ile Phe Val Val Tyr Asp Leu Pro Asp Arg Asp Cys Ala
            195                 200                 205
Ala Ala Ala Ser Asn Gly Glu Trp Ser Ile Ala Asn Asn Gly Ala Asn
210                 215                 220
Asn Tyr Lys Arg Tyr Ile Asp Arg Ile Arg Glu Leu Leu Ile Gln Tyr
225                 230                 235                 240
Ser Asp Ile Arg Thr Ile Leu Val Ile Glu Pro Asp Ser Leu Ala Asn
                245                 250                 255
Met Val Thr Asn Met Asn Val Gln Lys Cys Ser Asn Ala Ala Ser Thr
            260                 265                 270
Tyr Lys Glu Leu Thr Val Tyr Ala Leu Lys Gln Leu Asn Leu Pro His
            275                 280                 285
Val Ala Met Tyr Met Asp Ala Gly His Ala Gly Trp Leu Gly Trp Pro
290                 295                 300
Ala Asn Ile Gln Pro Ala Ala Glu Leu Phe Ala Gln Ile Tyr Arg Asp
305                 310                 315                 320
Ala Gly Arg Pro Ala Ala Val Arg Gly Leu Ala Thr Asn Val Ala Asn
                325                 330                 335
Tyr Asn Ala Trp Ser Ile Ala Ser Pro Pro Ser Tyr Thr Ser Pro Asn
            340                 345                 350
Pro Asn Tyr Asp Glu Lys His Tyr Ile Glu Ala Phe Ala Pro Leu Leu
            355                 360                 365
Arg Asn Gln Gly Phe Asp Ala Lys Phe Ile Val Asp Thr Gly Arg Asn
            370                 375                 380
Gly Lys Gln Pro Thr Gly Gln Leu Glu Trp Gly His Trp Cys Asn Val
385                 390                 395                 400
Lys Gly Thr Gly Phe Gly Val Arg Pro Thr Ala Asn Thr Gly His Glu
                405                 410                 415
Leu Val Asp Ala Phe Val Trp Val Lys Pro Gly Gly Glu Ser Asp Gly
            420                 425                 430
Thr Ser Ala Asp Thr Ser Ala Ala Arg Tyr Asp Tyr His Cys Gly Leu
            435                 440                 445
Ser Asp Ala Leu Thr Pro Ala Pro Glu Ala Gly Gln Trp Phe Gln Ala
            450                 455                 460
Tyr Phe Glu Gln Leu Leu Ile Asn Ala Asn Pro Pro Leu
465                 470                 475
```

<210> SEQ ID NO 97
<211> LENGTH: 476
<212> TYPE: PRT
<213> ORGANISM: Chaetomium thermophilum

<400> SEQUENCE: 97

| Met | Ala | Lys | Gln | Leu | Leu | Thr | Ala | Ala | Leu | Ala | Ala | Ile | Ser | Leu |
|---|---|---|---|---|---|---|---|---|---|---|---|---|---|---|
| 1 | | | | 5 | | | | | 10 | | | | | 15 |

Ala Ala Pro Leu Leu Glu Glu Arg Gln Ser Cys Ser Ser Val Trp Gly
              20                  25                  30

Gln Cys Gly Gly Ile Asn Tyr Asn Gly Pro Thr Cys Cys Gln Ser Gly
              35                  40                  45

Ser Val Cys Ala Tyr Leu Asn Asp Trp Tyr Ser Gln Cys Ile Pro Gly
    50                  55                  60

Gln Ala Gln Pro Gly Thr Thr Ser Thr Thr Ala Arg Thr Thr Ser Thr
65                  70                  75                  80

Ser Thr Thr Ser Thr Ser Ser Val Arg Pro Thr Thr Ser Asn Thr Pro
                85                  90                  95

Val Thr Thr Ala Pro Pro Thr Thr Thr Ile Pro Gly Gly Ala Ser Ser
              100                 105                 110

Thr Ala Ser Tyr Asn Gly Asn Pro Phe Ser Gly Val Gln Leu Trp Ala
              115                 120                 125

Asn Thr Tyr Tyr Ser Ser Glu Val His Thr Leu Ala Ile Pro Ser Leu
    130                 135                 140

Ser Pro Glu Leu Ala Ala Lys Ala Ala Lys Val Ala Glu Val Pro Ser
145                 150                 155                 160

Phe Gln Trp Leu Asp Arg Asn Val Thr Val Asp Thr Leu Phe Ser Gly
                165                 170                 175

Thr Leu Ala Glu Ile Arg Ala Ala Asn Gln Arg Gly Ala Asn Pro Pro
              180                 185                 190

Tyr Ala Gly Ile Phe Val Val Tyr Asp Leu Pro Asp Arg Asp Cys Ala
              195                 200                 205

Ala Ala Ala Ser Asn Gly Glu Trp Ser Ile Ala Asn Asn Gly Ala Asn
    210                 215                 220

Asn Leu Gln Arg Tyr Ile Asp Arg Ile Arg Glu Leu Leu Ile Gln Tyr
225                 230                 235                 240

Ser Asp Ile Arg Thr Ile Leu Val Ile Glu Pro Asp Ser Leu Ala Asn
                245                 250                 255

Met Val Thr Asn Met Asn Val Gln Lys Cys Ser Asn Ala Ala Ser Thr
              260                 265                 270

Tyr Lys Glu Leu Thr Val Tyr Ala Leu Lys Gln Leu Asn Leu Pro His
    275                 280                 285

Val Ala Met Tyr Met Asp Ala Gly His Ala Gly Trp Leu Gly Trp Pro
290                 295                 300

Ala Asn Ile Gln Pro Ala Ala Glu Leu Phe Ala Gln Ile Tyr Arg Asp
305                 310                 315                 320

Ala Gly Arg Pro Ala Ala Val Arg Gly Leu Ala Thr Asn Val Ala Asn
                325                 330                 335

Tyr Asn Ala Trp Ser Ile Ala Ser Pro Pro Ser Tyr Thr Ser Pro Asn
              340                 345                 350

Pro Asn Tyr Asp Glu Lys His Tyr Ile Glu Ala Phe Ala Pro Leu Leu
    355                 360                 365

Arg Asn Gln Gly Phe Asp Ala Lys Phe Ile Val Asp Thr Gly Arg Asn
370                 375                 380

```
Gly Lys Gln Pro Thr Gly Gln Leu Glu Trp Gly His Trp Cys Asn Val
385                 390                 395                 400

Lys Gly Thr Gly Phe Gly Val Arg Pro Thr Ala Asn Thr Gly His Glu
            405                 410                 415

Leu Val Asp Ala Phe Val Trp Val Lys Pro Gly Gly Glu Ser Asp Gly
        420                 425                 430

Thr Ser Asp Thr Ser Ala Ala Arg Tyr Asp Tyr His Cys Gly Leu Ser
        435                 440                 445

Asp Ala Leu Thr Pro Ala Pro Glu Ala Gly Gln Trp Phe Gln Ala Tyr
        450                 455                 460

Phe Glu Gln Leu Leu Ile Asn Ala Asn Pro Pro Phe
465                 470                 475
```

<210> SEQ ID NO 98
<211> LENGTH: 458
<212> TYPE: PRT
<213> ORGANISM: Stilbella annulata

<400> SEQUENCE: 98

```
Met Ala Gly Arg Phe Phe Leu Ser Ala Ala Phe Leu Ala Ser Ala Ala
1               5                   10                  15

Leu Ala Val Pro Leu Glu Glu Arg Gln Asn Cys Ser Pro Gln Trp Ala
            20                  25                  30

Gln Cys Gly Gly Asn Gly Trp Ser Gly Pro Thr Cys Cys Ala Ser Gly
        35                  40                  45

Ser Asn Cys Gln Val Thr Asn Glu Trp Tyr Ser Gln Cys Val Pro Gly
    50                  55                  60

Ala Ala Pro Pro Pro Pro Val Thr Thr Thr Arg Ser Thr Thr Thr
65                  70                  75                  80

Pro Pro Thr Thr Thr Arg Thr Thr Ala Asp Ala Pro Pro Pro Thr
                85                  90                  95

Gly Gly Ala Thr Tyr Thr Gly Asn Pro Phe Leu Gly Val Asn Gln Trp
            100                 105                 110

Ala Asn Asn Phe Tyr Arg Ser Glu Ile Met Asn Ile Ala Val Pro Ser
        115                 120                 125

Leu Ser Gly Ala Met Ala Thr Ala Ala Lys Val Ala Asp Val Pro
130                 135                 140

Thr Phe Gln Trp Ile Asp Lys Met Asp Lys Leu Pro Leu Ile Asp Glu
145                 150                 155                 160

Ala Leu Ala Asp Val Arg Ala Ala Asn Ala Arg Gly Gly Asn Tyr Ala
            165                 170                 175

Ser Ile Leu Val Val Tyr Asn Leu Pro Asp Arg Asp Cys Ala Ala Ala
        180                 185                 190

Ala Ser Asn Gly Glu Phe Ala Ile Ala Asp Gly Gly Val Ala Lys Tyr
    195                 200                 205

Lys Asn Tyr Ile Asp Glu Ile Arg Lys Leu Val Ile Lys Tyr Asn Asp
210                 215                 220

Leu Arg Ile Ile Leu Val Ile Glu Pro Asp Ser Leu Ala Asn Met Val
225                 230                 235                 240

Thr Asn Met Asn Val Ala Lys Cys Gln Asn Ala Ala Ser Ala Tyr Arg
            245                 250                 255

Glu Cys Thr Asn Tyr Ala Leu Thr Asn Leu Asp Leu Pro Asn Val Ala
        260                 265                 270

Gln Tyr Met Asp Ala Gly His Ala Gly Trp Leu Gly Trp Pro Ala Asn
```

```
            275                 280                 285
Ile Thr Pro Ala Ala Gln Leu Phe Ala Glu Val Tyr Lys Gln Ala Gly
    290                 295                 300

Ser Pro Lys Ser Val Arg Gly Leu Ala Ile Asn Val Ser Asn Tyr Asn
305                 310                 315                 320

Ala Trp Ser Val Ser Pro Pro Tyr Thr Ser Pro Asn Pro Asn
                    325                 330                 335

Tyr Asp Glu Arg His Phe Val Glu Ala Phe Ala Pro Leu Leu Arg Gln
                340                 345                 350

Asn Gly Trp Asp Ala Lys Phe Ile Val Asp Gln Gly Arg Ser Gly Arg
            355                 360                 365

Gln Pro Thr Gly Gln Gln Glu Trp Gly His Trp Cys Asn Ala Ile Gly
        370                 375                 380

Thr Gly Phe Gly Gln Arg Pro Thr Ser Asn Thr Gly His Ala Asp Val
385                 390                 395                 400

Asp Ala Phe Val Trp Ile Lys Pro Gly Gly Glu Cys Asp Gly Thr Ser
                    405                 410                 415

Asp Thr Ser Ala Ala Arg Tyr Asp His Phe Cys Gly Asn Pro Asp Ala
                420                 425                 430

Leu Lys Pro Ala Pro Glu Ala Gly Glu Trp Phe Gln Ala Tyr Phe Glu
            435                 440                 445

Gln Leu Leu Arg Asn Ala Asn Pro Ala Phe
450                 455

<210> SEQ ID NO 99
<211> LENGTH: 476
<212> TYPE: PRT
<213> ORGANISM: Humicola insolens

<400> SEQUENCE: 99

Met Ala Lys Phe Phe Leu Thr Ala Ala Phe Ala Ala Ala Ala Leu Ala
1               5                   10                  15

Ala Pro Val Val Glu Glu Arg Gln Asn Cys Ala Pro Thr Trp Gly Gln
                20                  25                  30

Cys Gly Gly Ile Gly Phe Asn Gly Pro Thr Cys Cys Gln Ser Gly Ser
            35                  40                  45

Thr Cys Val Lys Gln Asn Asp Trp Tyr Ser Gln Cys Leu Pro Gly Ser
    50                  55                  60

Gln Val Thr Thr Thr Ser Thr Thr Ser Thr Ser Ser Ser Ser Thr Thr
65                  70                  75                  80

Ser Arg Ala Thr Ser Thr Thr Arg Thr Gly Gly Val Thr Ser Ile Thr
                85                  90                  95

Thr Ala Pro Thr Arg Thr Val Thr Ile Pro Gly Gly Ala Thr Thr Thr
            100                 105                 110

Ala Ser Tyr Asn Gly Asn Pro Phe Glu Gly Val Gln Leu Trp Ala Asn
        115                 120                 125

Asn Tyr Tyr Arg Ser Glu Val His Thr Leu Ala Ile Pro Gln Ile Thr
    130                 135                 140

Asp Pro Ala Leu Arg Ala Ala Ser Ala Val Ala Glu Val Pro Ser
145                 150                 155                 160

Phe Gln Trp Leu Asp Arg Asn Val Thr Val Asp Thr Leu Leu Val Glu
                165                 170                 175

Thr Leu Ser Glu Ile Arg Ala Ala Asn Gln Ala Gly Ala Asn Pro Pro
            180                 185                 190
```

```
Tyr Ala Ala Gln Ile Val Val Tyr Asp Leu Pro Asp Arg Asp Cys Ala
            195                 200                 205

Ala Ala Ala Ser Asn Gly Glu Trp Ala Ile Ala Asn Asn Gly Ala Asn
210                 215                 220

Asn Tyr Lys Gly Tyr Ile Asn Arg Ile Arg Glu Ile Leu Ile Ser Phe
225                 230                 235                 240

Ser Asp Val Arg Thr Ile Leu Val Ile Glu Pro Asp Ser Leu Ala Asn
            245                 250                 255

Met Val Thr Asn Met Asn Val Ala Lys Cys Ser Gly Ala Ala Ser Thr
            260                 265                 270

Tyr Arg Glu Leu Thr Ile Tyr Ala Leu Lys Gln Leu Asp Leu Pro His
            275                 280                 285

Val Ala Met Tyr Met Asp Ala Gly His Ala Gly Trp Leu Gly Trp Pro
            290                 295                 300

Ala Asn Ile Gln Pro Ala Ala Glu Leu Phe Ala Lys Ile Tyr Glu Asp
305                 310                 315                 320

Ala Gly Lys Pro Arg Ala Val Arg Gly Leu Ala Thr Asn Val Ala Asn
            325                 330                 335

Tyr Asn Ala Trp Ser Ile Ser Ser Pro Pro Tyr Thr Ser Pro Asn
            340                 345                 350

Pro Asn Tyr Asp Glu Lys His Tyr Ile Glu Ala Phe Arg Pro Leu Leu
            355                 360                 365

Glu Ala Arg Gly Phe Pro Ala Gln Phe Ile Val Asp Gln Gly Arg Ser
            370                 375                 380

Gly Lys Gln Pro Thr Gly Gln Lys Glu Trp Gly His Trp Cys Asn Ala
385                 390                 395                 400

Ile Gly Thr Gly Phe Gly Met Arg Pro Thr Ala Asn Thr Gly His Gln
            405                 410                 415

Tyr Val Asp Ala Phe Val Trp Val Lys Pro Gly Gly Glu Cys Asp Gly
            420                 425                 430

Thr Ser Asp Thr Thr Ala Ala Arg Tyr Asp Tyr His Cys Gly Leu Glu
            435                 440                 445

Asp Ala Leu Lys Pro Ala Pro Glu Ala Gly Gln Trp Phe Gln Ala Tyr
450                 455                 460

Phe Glu Gln Leu Leu Arg Asn Ala Asn Pro Pro Phe
465                 470                 475

<210> SEQ ID NO 100
<211> LENGTH: 360
<212> TYPE: PRT
<213> ORGANISM: Humicola insolens

<400> SEQUENCE: 100

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
    50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95
```

```
Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
            115                 120                 125

Thr Ile Leu Val Ile Glu Pro Asp Ser Leu Ala Asn Met Val Thr Asn
        130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
        195                 200                 205

Arg Ala Val Arg Gly Leu Ala Thr Asn Val Ala Asn Tyr Asn Ala Trp
210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Gln Phe Ile Val Asp Gln Gly Arg Ser Gly Lys Gln Pro
            260                 265                 270

Thr Gly Gln Lys Glu Trp Gly His Trp Cys Asn Ala Ile Gly Thr Gly
        275                 280                 285

Phe Gly Met Arg Pro Thr Ala Asn Thr Gly His Gln Tyr Val Asp Ala
            290                 295                 300

Phe Val Trp Val Lys Pro Gly Gly Glu Cys Asp Gly Thr Ser Asp Thr
305                 310                 315                 320

Thr Ala Ala Arg Tyr Asp Tyr His Cys Gly Leu Glu Asp Ala Leu Lys
                325                 330                 335

Pro Ala Pro Glu Ala Gly Gln Trp Phe Asn Glu Tyr Phe Ile Gln Leu
            340                 345                 350

Leu Arg Asn Ala Asn Pro Pro Phe
            355                 360

<210> SEQ ID NO 101
<211> LENGTH: 389
<212> TYPE: PRT
<213> ORGANISM: Cochliobolus heterostrophus

<400> SEQUENCE: 101

Met Leu Ser Asn Val Phe Leu Thr Ala Ala Leu Ala Ala Gly Leu Ala
1               5                   10                  15

Gln Ala Leu Pro Gln Ala Thr Pro Thr Pro Thr Ala Ala Pro Ser Gly
            20                  25                  30

Asn Pro Phe Ala Gly Lys Asn Pro Tyr Ala Asn Pro Tyr Tyr Ser Ser
        35                  40                  45

Glu Val His Thr Leu Ala Met Pro Ser Leu Pro Ala Ser Leu Lys Pro
    50                  55                  60

Ala Ala Thr Ala Val Ala Lys Val Gly Ser Phe Val Trp Met Asp Thr
65                  70                  75                  80

Met Ala Lys Val Pro Leu Met Asp Thr Tyr Leu Ala Asp Ile Lys Ala
                85                  90                  95

Lys Asn Ala Ala Gly Ala Asn Leu Met Gly Thr Phe Val Val Tyr Asp
```

Leu Pro Asp Arg Asp Cys Ala Ala Leu Ala Ser Asn Gly Glu Leu Lys
            115                 120                 125

Ile Asp Glu Gly Gly Val Glu Lys Tyr Lys Thr Gln Tyr Ile Asp Lys
130                 135                 140

Ile Ala Ala Ile Ile Lys Lys Tyr Pro Asp Val Lys Ile Asn Leu Ala
145                 150                 155                 160

Ile Glu Pro Asp Ser Leu Ala Asn Met Val Thr Asn Met Gly Val Gln
                165                 170                 175

Lys Cys Ser Arg Ala Ala Pro Tyr Tyr Lys Glu Leu Thr Ala Tyr Ala
            180                 185                 190

Leu Lys Thr Leu Asn Phe Asn Asn Val Asp Met Tyr Met Asp Gly Gly
        195                 200                 205

His Ala Gly Trp Leu Gly Trp Asp Ala Asn Ile Gly Pro Thr Ala Lys
    210                 215                 220

Leu Phe Ala Glu Val Tyr Lys Ala Ala Gly Ser Pro Arg Gly Val Arg
225                 230                 235                 240

Gly Ile Val Thr Asn Val Ser Asn Tyr Asn Ala Leu Arg Val Ser Ser
                245                 250                 255

Cys Pro Ser Ile Thr Gln Gly Asn Lys Asn Cys Asp Glu Glu Arg Tyr
            260                 265                 270

Ile Asn Ala Leu Ala Pro Leu Leu Lys Asn Glu Gly Phe Pro Ala His
        275                 280                 285

Phe Ile Val Asp Gln Gly Arg Ser Gly Lys Val Pro Thr Asn Gln Gln
    290                 295                 300

Glu Trp Gly Asp Trp Cys Asn Val Ser Gly Ala Gly Phe Gly Thr Arg
305                 310                 315                 320

Pro Thr Thr Asn Thr Gly Asn Ala Leu Ile Asp Ala Ile Val Trp Val
                325                 330                 335

Lys Pro Gly Gly Glu Ser Asp Gly Thr Ser Asp Thr Ser Ala Ala Arg
            340                 345                 350

Tyr Asp Ala His Cys Gly Arg Asn Ser Ala Phe Lys Pro Ala Pro Glu
        355                 360                 365

Ala Gly Thr Trp Phe Gln Ala Tyr Phe Glu Met Leu Leu Lys Asn Ala
    370                 375                 380

Asn Pro Ala Leu Ala
385

<210> SEQ ID NO 102
<211> LENGTH: 438
<212> TYPE: PRT
<213> ORGANISM: Agaricus bisporus

<400> SEQUENCE: 102

Met Phe Lys Phe Ala Ala Leu Leu Ala Leu Ala Ser Leu Val Pro Gly
1               5                   10                  15

Phe Val Gln Ala Gln Ser Pro Val Trp Gly Gln Cys Gly Gly Asn Gly
            20                  25                  30

Trp Thr Gly Pro Thr Thr Cys Ala Ser Gly Ser Thr Cys Val Lys Gln
        35                  40                  45

Asn Asp Phe Tyr Ser Gln Cys Leu Pro Asn Asn Gln Ala Pro Pro Ser
    50                  55                  60

Thr Thr Thr Gln Pro Gly Thr Pro Pro Ala Thr Thr Ser Gly
65                  70                  75                  80

Gly Thr Gly Pro Thr Ser Gly Ala Gly Asn Pro Tyr Thr Gly Lys Thr
                85                  90                  95

Val Trp Leu Ser Pro Phe Tyr Ala Asp Glu Val Ala Gln Ala Ala Ala
            100                 105                 110

Asp Ile Ser Asn Pro Ser Leu Ala Thr Lys Ala Ala Ser Val Ala Lys
        115                 120                 125

Ile Pro Thr Phe Val Trp Phe Asp Thr Val Ala Lys Val Pro Asp Leu
    130                 135                 140

Gly Gly Tyr Leu Ala Asp Ala Arg Ser Lys Asn Gln Leu Val Gln Ile
145                 150                 155                 160

Val Val Tyr Asp Leu Pro Asp Arg Asp Cys Ala Ala Leu Ala Ser Asn
                165                 170                 175

Gly Glu Phe Ser Leu Ala Asn Asp Gly Leu Asn Lys Tyr Lys Asn Tyr
            180                 185                 190

Val Asp Gln Ile Ala Ala Gln Ile Lys Gln Phe Pro Asp Val Ser Val
        195                 200                 205

Val Ala Val Ile Glu Pro Asp Ser Leu Ala Asn Leu Val Thr Asn Leu
    210                 215                 220

Asn Val Gln Lys Cys Ala Asn Ala Gln Ser Ala Tyr Lys Glu Gly Val
225                 230                 235                 240

Ile Tyr Ala Val Gln Lys Leu Asn Ala Val Gly Val Thr Met Tyr Ile
                245                 250                 255

Asp Ala Gly His Ala Gly Trp Leu Gly Trp Pro Ala Asn Leu Ser Pro
            260                 265                 270

Ala Ala Gln Leu Phe Ala Gln Ile Tyr Arg Asp Ala Gly Ser Pro Arg
        275                 280                 285

Asn Leu Arg Gly Ile Ala Thr Asn Val Ala Asn Phe Asn Ala Leu Arg
    290                 295                 300

Ala Ser Ser Pro Asp Pro Ile Thr Gln Gly Asn Ser Asn Tyr Asp Glu
305                 310                 315                 320

Ile His Tyr Ile Glu Ala Leu Ala Pro Met Leu Ser Asn Ala Gly Phe
                325                 330                 335

Pro Ala His Phe Ile Val Asp Gln Gly Arg Ser Gly Val Gln Asn Ile
            340                 345                 350

Arg Asp Gln Trp Gly Asp Trp Cys Asn Val Lys Gly Ala Gly Phe Gly
        355                 360                 365

Gln Arg Pro Thr Thr Asn Thr Gly Ser Ser Leu Ile Asp Ala Ile Val
    370                 375                 380

Trp Val Lys Pro Gly Gly Glu Cys Asp Gly Thr Ser Asp Asn Ser Ser
385                 390                 395                 400

Pro Arg Phe Asp Ser His Cys Ser Leu Ser Asp Ala His Gln Pro Ala
                405                 410                 415

Pro Glu Ala Gly Thr Trp Phe Gln Ala Tyr Phe Glu Thr Leu Val Ala
            420                 425                 430

Asn Ala Asn Pro Ala Leu
            435

<210> SEQ ID NO 103
<211> LENGTH: 454
<212> TYPE: PRT
<213> ORGANISM: Polyporus arcularius

<400> SEQUENCE: 103

Met Ser Lys Phe Ala Ser Leu Leu Ala Leu Leu Ala Ile Val Pro Ser
1               5                   10                  15

```
Leu Ala Tyr Ala Gln Ala Pro Val Tyr Gly Gln Cys Gly Gly Ile Gly
            20                  25                  30

Trp Ser Gly Ala Thr Thr Cys Val Ser Gly Ser Val Cys Thr Lys Gln
            35                  40                  45

Asn Asp Tyr Tyr Ser Gln Cys Leu Pro Gly Ala Ala Ser Ser Ala Pro
 50                  55                  60

Thr Ser Pro Pro Thr Thr Ser Ala Pro Ser Ser Thr Pro Val Ser Thr
 65                  70                  75                  80

Pro Pro Thr Gly Thr Thr Gly Gly Ser Ala Pro Ser Ser Thr Pro
                85                  90                  95

Ala Ala Gly Asn Pro Phe Val Gly Val Thr Pro Phe Leu Ser Pro Tyr
            100                 105                 110

Tyr Ala Ala Glu Val Ala Ala Ala Asp Ala Ile Thr Asp Ser Thr
            115                 120                 125

Leu Lys Ala Lys Ala Ala Ser Val Ala Lys Ile Pro Thr Phe Thr Trp
            130                 135                 140

Leu Asp Ser Val Ala Lys Val Pro Asp Leu Gly Thr Tyr Leu Ala Asp
145                 150                 155                 160

Ala Ser Ala Leu Gln Lys Ser Ser Gly Gln Pro Gln Val Val Gln Ile
            165                 170                 175

Val Val Tyr Asp Leu Pro Asp Arg Asp Cys Ala Ala Lys Ala Ser Asn
            180                 185                 190

Gly Glu Phe Ser Ile Ala Asp Gly Gly Gln Ala Lys Tyr Tyr Asp Tyr
            195                 200                 205

Ile Asp Gln Ile Val Ala Gln Ile Lys Lys Phe Pro Asp Val Arg Val
210                 215                 220

Ile Ala Val Ile Glu Pro Asp Ser Leu Ala Asn Leu Val Thr Asn Leu
225                 230                 235                 240

Asn Val Gln Lys Cys Ala Asn Ala Gln Thr Thr Tyr Lys Ala Cys Val
            245                 250                 255

Thr Tyr Ala Leu Asn Gln Leu Ala Ser Val Gly Val Tyr Gln Tyr Met
            260                 265                 270

Asp Ala Gly His Ala Gly Trp Leu Gly Trp Pro Ala Asn Ile Gln Pro
            275                 280                 285

Ala Ala Gln Leu Phe Ala Asp Met Phe Lys Ser Ala Asn Ser Ser Lys
            290                 295                 300

Phe Val Arg Gly Leu Ala Thr Asn Val Ala Asn Tyr Asn Ala Leu Ser
305                 310                 315                 320

Ala Ala Ser Pro Asp Pro Ile Thr Gln Gly Asp Pro Asn Tyr Asp Glu
            325                 330                 335

Leu His Tyr Ile Asn Ala Leu Gly Pro Met Leu Ala Gln Gln Gly Phe
            340                 345                 350

Pro Ala Gln Phe Val Val Asp Gln Gly Arg Ser Gly Gln Gln Asn Leu
            355                 360                 365

Arg Gln Gln Trp Gly Asp Trp Cys Asn Ile Lys Gly Ala Gly Phe Gly
            370                 375                 380

Thr Arg Pro Thr Thr Asn Thr Gly Ser Ser Leu Ile Asp Ala Ile Val
385                 390                 395                 400

Trp Val Lys Pro Gly Gly Glu Ser Asp Gly Thr Ser Asn Ser Ser Ser
            405                 410                 415

Pro Arg Phe Asp Ser Thr Cys Ser Leu Ser Asp Ala Thr Gln Pro Ala
            420                 425                 430
```

```
Pro Glu Ala Gly Thr Trp Phe Gln Thr Tyr Phe Glu Thr Leu Val Ser
            435                 440                 445

Lys Ala Asn Pro Pro Leu
    450

<210> SEQ ID NO 104
<211> LENGTH: 444
<212> TYPE: PRT
<213> ORGANISM: Lentinula edodes Stamets

<400> SEQUENCE: 104

Met Lys Ile Thr Ser Thr Gly Leu Leu Ala Leu Ser Ser Leu Leu Pro
1               5                   10                  15

Phe Ala Leu Gly Gln Ser Gln Leu Tyr Gly Gln Cys Gly Gly Ile Gly
                20                  25                  30

Trp Ser Gly Ala Thr Thr Cys Val Ser Gly Ala Thr Cys Thr Val Val
            35                  40                  45

Asn Ala Tyr Tyr Ser Gln Cys Leu Pro Gly Ser Ala Ser Ala Pro Pro
50                  55                  60

Thr Ser Thr Ser Ser Ile Gly Thr Gly Thr Thr Thr Ser Ser Ala Pro
65                  70                  75                  80

Gly Ser Thr Gly Thr Thr Pro Ala Ala Gly Asn Pro Phe Thr Gly
                85                  90                  95

Tyr Glu Ile Tyr Leu Ser Pro Tyr Tyr Ala Asn Glu Ile Ala Ala Ala
                100                 105                 110

Val Thr Gln Ile Ser Asp Pro Thr Thr Ala Ala Ala Ala Lys Val
                115                 120                 125

Ala Asn Ile Pro Thr Phe Ile Trp Leu Asp Gln Val Ala Lys Val Pro
130                 135                 140

Asp Leu Gly Thr Tyr Leu Ala Asp Ala Ser Ala Lys Gln Lys Ser Glu
145                 150                 155                 160

Gly Lys Asn Tyr Leu Val Gln Ile Val Val Tyr Asp Leu Pro Asp Arg
                165                 170                 175

Asp Cys Ala Ala Leu Ala Ser Asn Gly Glu Phe Thr Ile Ala Asp Asn
                180                 185                 190

Gly Glu Ala Asn Tyr His Asp Tyr Ile Asp Gln Ile Val Ala Gln Ile
                195                 200                 205

Lys Gln Tyr Pro Asp Val His Val Val Ala Val Ile Glu Pro Asp Ser
210                 215                 220

Leu Ala Asn Leu Val Thr Asn Leu Ser Val Ala Lys Cys Ala Asn Ala
225                 230                 235                 240

Gln Thr Thr Tyr Leu Glu Cys Val Thr Tyr Ala Met Gln Gln Leu Ser
                245                 250                 255

Ala Val Gly Val Thr Met Tyr Leu Asp Ala Gly His Ala Gly Trp Leu
                260                 265                 270

Gly Trp Pro Ala Asn Leu Ser Pro Ala Ala Gln Leu Phe Thr Ser Leu
                275                 280                 285

Tyr Ser Asn Ala Gly Ser Pro Ser Gly Val Arg Gly Leu Ala Thr Asn
290                 295                 300

Val Ala Asn Tyr Asn Ala Leu Val Ala Thr Thr Pro Asp Pro Ile Thr
305                 310                 315                 320

Gln Gly Asp Pro Asn Tyr Asp Glu Met Leu Tyr Ile Glu Ala Leu Ala
                325                 330                 335

Pro Leu Leu Gly Ser Phe Pro Ala His Phe Ile Val Asp Gln Gly Arg
                340                 345                 350
```

Ser Gly Val Gln Asp Ile Arg Gln Gln Trp Gly Asp Trp Cys Asn Val
        355                 360                 365

Leu Gly Ala Gly Phe Gly Thr Gln Pro Thr Thr Asn Thr Gly Ser Ser
    370                 375                 380

Leu Ile Asp Ser Ile Val Trp Val Lys Pro Gly Gly Glu Cys Asp Gly
385                 390                 395                 400

Thr Ser Asn Thr Ser Ser Pro Arg Tyr Asp Ala His Cys Gly Leu Pro
                405                 410                 415

Asp Ala Thr Pro Asn Ala Pro Glu Ala Gly Thr Trp Phe Gln Ala Tyr
            420                 425                 430

Phe Glu Thr Leu Val Glu Lys Ala Asn Pro Pro Leu
            435                 440

<210> SEQ ID NO 105
<211> LENGTH: 443
<212> TYPE: PRT
<213> ORGANISM: Lentinula edodes

<400> SEQUENCE: 105

Met Lys Ile Thr Ser Thr Gly Leu Leu Ala Leu Ser Ser Leu Leu Pro
1               5                   10                  15

Phe Ala Leu Gly Gln Ser Gln Leu Tyr Ala Gln Cys Gly Gly Ile Gly
            20                  25                  30

Trp Ser Gly Ala Thr Thr Cys Val Ser Gly Ala Thr Cys Thr Val Val
        35                  40                  45

Asn Ala Tyr Tyr Ser Gln Cys Leu Pro Gly Ser Ala Ser Ala Pro Pro
    50                  55                  60

Thr Ser Thr Ser Ser Ile Gly Thr Gly Thr Thr Thr Ser Ser Ala Pro
65                  70                  75                  80

Gly Ser Thr Gly Thr Thr Thr Pro Ala Ala Gly Asn Pro Phe Thr Glu
                85                  90                  95

Gln Ile Tyr Leu Ser Pro Tyr Tyr Ala Asn Glu Ile Ala Ala Ala Val
            100                 105                 110

Thr Gln Ile Ser Asp Pro Thr Thr Ala Ala Ala Ala Lys Val Ala
            115                 120                 125

Asn Ile Pro Thr Phe Ile Trp Leu Asp Gln Val Ala Lys Val Pro Asp
    130                 135                 140

Leu Gly Thr Tyr Leu Ala Asp Ala Ser Ala Lys Gln Lys Ser Glu Gly
145                 150                 155                 160

Lys Asn Tyr Leu Val Gln Ile Val Val Tyr Asp Leu Pro Asp Arg Asp
                165                 170                 175

Cys Ala Ala Leu Ala Ser Asn Gly Glu Phe Thr Ile Ala Asp Asn Gly
            180                 185                 190

Glu Ala Asn Tyr His Asp Tyr Ile Asp Gln Ile Val Ala Gln Ile Lys
        195                 200                 205

Gln Tyr Pro Asp Val His Val Ala Val Ile Glu Pro Asp Ser Leu
    210                 215                 220

Ala Asn Leu Val Thr Asn Leu Ser Val Ala Lys Cys Ala Asn Ala Gln
225                 230                 235                 240

Thr Thr Tyr Leu Glu Cys Val Thr Tyr Ala Met Gln Gln Leu Ser Ala
                245                 250                 255

Val Gly Val Thr Met Tyr Leu Asp Ala Gly His Ala Gly Trp Leu Gly
            260                 265                 270

Trp Pro Ala Asn Leu Ser Pro Ala Ala Gln Leu Phe Thr Ser Leu Tyr

-continued

```
                275                 280                 285
Ser Asn Ala Gly Ser Pro Ser Gly Val Arg Gly Leu Ala Thr Asn Val
290                 295                 300

Ala Asn Tyr Asn Ala Leu Val Ala Thr Thr Pro Asp Pro Ile Thr Gln
305                 310                 315                 320

Gly Asp Pro Asn Tyr Asp Glu Met Leu Tyr Ile Glu Ala Leu Ala Pro
                325                 330                 335

Leu Leu Gly Ser Phe Pro Ala His Phe Ile Val Asp Gln Gly Arg Ser
                340                 345                 350

Gly Val Gln Asp Ile Arg Gln Gln Trp Gly Asp Trp Cys Asn Val Leu
                355                 360                 365

Gly Ala Gly Phe Gly Thr Gln Pro Thr Thr Asn Thr Gly Ser Ser Leu
370                 375                 380

Ile Asp Ser Ile Val Trp Val Lys Pro Gly Gly Glu Cys Asp Gly Thr
385                 390                 395                 400

Ser Asn Thr Ser Ser Pro Arg Tyr Asp Ala His Cys Gly Leu Pro Asp
                405                 410                 415

Ala Thr Pro Asn Ala Pro Glu Ala Gly Thr Trp Phe Gln Ala Tyr Phe
                420                 425                 430

Glu Thr Leu Val Glu Lys Ala Asn Pro Pro Leu
435                 440

<210> SEQ ID NO 106
<211> LENGTH: 390
<212> TYPE: PRT
<213> ORGANISM: Malbranchea cinnamomea

<400> SEQUENCE: 106

Met Arg Asp Ser Leu Phe Thr Leu Leu Ser Leu Ala Leu Gly Ser Ala
1               5                   10                  15

Ser Ala Ser Pro Phe Leu Leu Pro Arg Gln Ala Asn Ser Ser Asn Pro
                20                  25                  30

Phe Ala Gly His Thr Ile Tyr Pro Asn Pro Tyr Tyr Ser Asn Glu Ile
                35                  40                  45

Asp Glu Phe Ala Ile Pro Ala Leu Gln Glu Thr Asp Pro Ala Leu Val
        50                  55                  60

Glu Lys Ala Ala Leu Val Lys Glu Val Gly Thr Phe Phe Trp Ile Asp
65                  70                  75                  80

Val Val Ala Lys Val Pro Asp Ile Gly Pro Tyr Leu Gln Gly Ile Gln
                85                  90                  95

Glu Ala Asn Ala Ala Gly Gln Asn Pro Pro Tyr Ile Gly Ala Ile Val
                100                 105                 110

Val Tyr Asp Leu Pro Asn Arg Asp Cys Ala Ala Ala Ser Asn Gly
                115                 120                 125

Glu Phe Ser Leu Glu Asp Gly Gly Glu Glu Lys Tyr Arg Gly Tyr Ile
130                 135                 140

Asp Gly Ile Arg Glu Gln Ile Glu Lys Tyr Pro Asp Val Arg Val Ala
145                 150                 155                 160

Leu Val Ile Glu Pro Asp Ser Leu Ala Asn Met Val Thr Asn Leu Asn
                165                 170                 175

Val Pro Lys Cys Ala Glu Ser Glu Gln Ala Tyr Arg Asp Gly Val Ala
                180                 185                 190

Tyr Ala Leu Lys Gln Leu Asp Leu Pro Asn Val Trp Thr Tyr Ile Asp
                195                 200                 205
```

Ala Gly His Ser Gly Trp Leu Gly Trp Pro Ala Asn Ile Glu Pro Ala
        210                 215                 220

Ala Glu Ile Phe Val Glu Val Trp Asn Ala Ala Gly Arg Pro Lys Ser
225                 230                 235                 240

Thr Arg Gly Phe Ala Thr Asn Val Ser Asn Tyr Asn Gly Tyr Ser Leu
                245                 250                 255

Ser Thr Ala Pro Pro Tyr Thr Glu Pro Asn Pro Asn Phe Asp Glu Val
                260                 265                 270

Arg Tyr Ile Asn Ala Phe Arg Pro Leu Leu Glu Ala Arg Gly Phe Pro
                275                 280                 285

Ala Tyr Phe Ile Val Asp Gln Gly Arg Ser Gly Val Gln Pro Thr Ala
        290                 295                 300

Gln Ile Glu Gln Gly His Trp Cys Asn Val Ile Asp Thr Gly Phe Gly
305                 310                 315                 320

Thr Arg Pro Thr Thr Asp Thr Gly Asn Glu Tyr Val Asp Ser Ile Val
                325                 330                 335

Trp Val Lys Pro Gly Gly Glu Ser Asp Gly Thr Ser Thr Ser Ala
                340                 345                 350

Glu Arg Tyr Asp Tyr His Cys Gly Leu Glu Asp Ala Leu Lys Pro Ala
                355                 360                 365

Pro Glu Ala Gly Gln Trp Phe Gln Ala Tyr Phe Glu Gln Leu Leu Arg
370                 375                 380

Asn Ala Asn Pro Pro Phe
385                 390

<210> SEQ ID NO 107
<211> LENGTH: 460
<212> TYPE: PRT
<213> ORGANISM: Phanerochaete chrysosporium

<400> SEQUENCE: 107

Met Lys Ser Thr Ala Phe Phe Ala Ala Leu Val Thr Leu Leu Pro Ala
1               5                   10                  15

Tyr Val Ala Gly Gln Ala Ser Glu Trp Gly Gln Cys Gly Gly Ile Gly
                20                  25                  30

Trp Thr Gly Pro Thr Thr Cys Val Ser Gly Thr Thr Cys Thr Val Leu
        35                  40                  45

Asn Pro Tyr Tyr Ser Gln Cys Leu Pro Gly Ser Ala Val Thr Thr Thr
    50                  55                  60

Ser Val Ile Thr Ser His Ser Ser Val Ser Ser Val Ser Ser His
65                  70                  75                  80

Ser Gly Ser Ser Thr Ser Thr Ser Ser Pro Thr Gly Pro Thr Gly Thr
                85                  90                  95

Asn Pro Pro Pro Pro Ser Ala Asn Asn Pro Trp Thr Gly Phe Gln
                100                 105                 110

Ile Phe Leu Ser Pro Tyr Ala Asn Glu Val Ala Ala Ala Lys
    115                 120                 125

Gln Ile Thr Asp Pro Thr Leu Ser Ser Lys Ala Ala Ser Val Ala Asn
130                 135                 140

Ile Pro Thr Phe Thr Trp Leu Asp Ser Val Ala Lys Ile Pro Asp Leu
145                 150                 155                 160

Gly Thr Tyr Leu Ala Ser Ala Ser Ala Leu Gly Lys Ser Thr Gly Thr
                165                 170                 175

Lys Gln Leu Val Gln Ile Val Ile Tyr Asp Leu Pro Asp Arg Asp Cys
                180                 185                 190

Ala Ala Lys Ala Ser Asn Gly Glu Phe Ser Ile Ala Asn Asn Gly Gln
            195                 200                 205

Ala Asn Tyr Glu Asn Tyr Ile Asp Gln Ile Val Ala Gln Ile Gln Gln
        210                 215                 220

Phe Pro Asp Val Arg Val Val Ala Val Ile Glu Pro Asp Ser Leu Ala
225                 230                 235                 240

Asn Leu Val Thr Asn Leu Asn Val Gln Lys Cys Ala Asn Ala Lys Thr
                245                 250                 255

Thr Tyr Leu Ala Cys Val Asn Tyr Ala Leu Thr Asn Leu Ala Lys Val
            260                 265                 270

Gly Val Tyr Met Tyr Met Asp Ala Gly His Ala Gly Trp Leu Gly Trp
        275                 280                 285

Pro Ala Asn Leu Ser Pro Ala Ala Gln Leu Phe Thr Gln Val Trp Gln
290                 295                 300

Asn Ala Gly Lys Ser Pro Phe Ile Lys Gly Leu Ala Thr Asn Val Ala
305                 310                 315                 320

Asn Tyr Asn Ala Leu Gln Ala Ser Pro Asp Pro Ile Thr Gln Gly
                325                 330                 335

Asn Pro Asn Tyr Asp Glu Ile His Tyr Ile Asn Ala Leu Ala Pro Leu
            340                 345                 350

Leu Gln Gln Ala Gly Trp Asp Ala Thr Phe Ile Val Asp Gln Gly Arg
        355                 360                 365

Ser Gly Val Gln Asn Ile Arg Gln Gln Trp Gly Asp Trp Cys Asn Ile
370                 375                 380

Lys Gly Ala Gly Phe Gly Thr Arg Pro Thr Thr Asn Thr Gly Ser Gln
385                 390                 395                 400

Phe Ile Asp Ser Ile Val Trp Val Lys Pro Gly Gly Glu Cys Asp Gly
                405                 410                 415

Thr Ser Asn Ser Ser Pro Arg Tyr Asp Ser Thr Cys Ser Leu Pro
            420                 425                 430

Asp Ala Ala Gln Pro Ala Pro Glu Ala Gly Thr Trp Phe Gln Ala Tyr
        435                 440                 445

Phe Gln Thr Leu Val Ser Ala Ala Asn Pro Pro Leu
450                 455                 460

<210> SEQ ID NO 108
<211> LENGTH: 442
<212> TYPE: PRT
<213> ORGANISM: Volvariella volvacea

<400> SEQUENCE: 108

Met Ser Arg Phe Ser Ala Leu Thr Ala Leu Leu Leu Ser Leu Pro Leu
1               5                   10                  15

Leu Ala Ile Ala Gln Ser Pro Leu Tyr Gly Gln Cys Gly Gly Asn Gly
            20                  25                  30

Trp Thr Gly Pro Lys Thr Cys Val Ser Gly Ala Thr Cys Thr Val Ile
        35                  40                  45

Asn Asp Trp Tyr Trp Gln Cys Leu Pro Gly Asn Gly Pro Thr Ser Ser
    50                  55                  60

Ser Pro Thr Ser Thr Pro Thr Thr Thr Thr Thr Gly Gly Pro Gln
65                  70                  75                  80

Pro Thr Val Pro Ala Ala Gly Asn Pro Tyr Thr Gly Tyr Glu Ile Tyr
                85                  90                  95

Leu Ser Pro Tyr Tyr Ala Ala Glu Ala Gln Ala Ala Ala Ala Gln Ile

```
            100                 105                 110
Ser Asp Ala Thr Gln Lys Ala Lys Ala Leu Lys Val Ala Gln Ile Pro
            115                 120                 125

Thr Phe Thr Trp Phe Asp Val Ile Ala Lys Thr Ser Thr Leu Gly Asp
            130                 135                 140

Tyr Leu Ala Glu Ala Ser Ala Leu Gly Lys Ser Ser Gly Lys Lys Tyr
145                 150                 155                 160

Leu Val Gln Ile Val Tyr Asp Leu Pro Asp Arg Asp Cys Ala Ala
                165                 170                 175

Leu Ala Ser Asn Gly Glu Phe Ser Ile Ala Asn Asn Gly Leu Asn Asn
                180                 185                 190

Tyr Lys Gly Tyr Ile Asp Gln Leu Val Ala Gln Ile Lys Lys Tyr Pro
            195                 200                 205

Asp Val Arg Val Val Ala Val Ile Glu Pro Asp Ser Leu Ala Asn Leu
            210                 215                 220

Val Thr Asn Leu Asn Val Ser Lys Cys Ala Asn Ala Gln Thr Ala Tyr
225                 230                 235                 240

Lys Ala Gly Val Thr Tyr Ala Leu Gln Gln Leu Asn Ser Val Gly Val
                245                 250                 255

Tyr Met Tyr Leu Asp Ala Gly His Ala Gly Trp Leu Gly Trp Pro Ala
            260                 265                 270

Asn Leu Asn Pro Ala Ala Gln Leu Phe Ser Gln Leu Tyr Arg Asp Ala
            275                 280                 285

Gly Ser Pro Gln Tyr Val Arg Gly Leu Ala Thr Asn Val Ala Asn Tyr
            290                 295                 300

Asn Ala Leu Ser Ala Ser Ser Pro Asp Pro Val Thr Gln Gly Asn Pro
305                 310                 315                 320

Asn Tyr Asp Glu Leu His Tyr Ile Asn Ala Leu Ala Pro Ala Leu Gln
                325                 330                 335

Ser Gly Gly Phe Pro Ala His Phe Ile Val Asp Gln Gly Arg Ser Gly
            340                 345                 350

Val Gln Asn Ile Arg Gln Gln Trp Gly Asp Trp Cys Asn Val Lys Gly
            355                 360                 365

Ala Gly Phe Gly Gln Arg Pro Thr Leu Ser Thr Gly Ser Ser Leu Ile
            370                 375                 380

Asp Ala Ile Val Trp Ile Lys Pro Gly Gly Glu Cys Asp Gly Thr Thr
385                 390                 395                 400

Asn Thr Ser Ser Pro Arg Tyr Asp Ser His Cys Gly Leu Ser Asp Ala
                405                 410                 415

Thr Pro Asn Ala Pro Glu Ala Gly Gln Trp Phe Gln Ala Tyr Phe Glu
            420                 425                 430

Thr Leu Val Arg Asn Ala Ser Pro Pro Leu
            435                 440

<210> SEQ ID NO 109
<211> LENGTH: 395
<212> TYPE: PRT
<213> ORGANISM: Chrysosporium lucknowense

<400> SEQUENCE: 109

Met Lys Phe Val Gln Ser Ala Thr Leu Ala Phe Ala Ala Thr Ala Leu
1               5                   10                  15

Ala Ala Pro Ser Arg Thr Thr Pro Gln Lys Pro Arg Gln Ala Ser Ala

-continued

```
Gly Cys Ala Ser Ala Val Thr Leu Asp Ala Ser Thr Asn Val Phe Gln
             35                  40                  45

Gln Tyr Thr Leu His Pro Asn Asn Phe Tyr Arg Ala Glu Val Glu Ala
 50                  55                  60

Ala Ala Glu Ala Ile Ser Asp Ser Ala Leu Ala Glu Lys Ala Arg Lys
 65                  70                  75                  80

Val Ala Asp Val Gly Thr Phe Leu Trp Leu Asp Thr Ile Glu Asn Ile
                 85                  90                  95

Gly Arg Leu Glu Pro Ala Leu Glu Asp Val Pro Cys Glu Asn Ile Val
                100                 105                 110

Gly Leu Val Ile Tyr Asp Leu Pro Gly Arg Asp Cys Ala Ala Lys Ala
            115                 120                 125

Ser Asn Gly Glu Leu Lys Val Gly Glu Leu Asp Arg Tyr Lys Thr Glu
130                 135                 140

Tyr Ile Asp Lys Ile Ala Glu Ile Leu Lys Ala His Ser Asn Thr Ala
145                 150                 155                 160

Phe Ala Leu Val Ile Glu Pro Asp Ser Leu Pro Asn Leu Val Thr Asn
                165                 170                 175

Ser Asp Leu Gln Thr Cys Gln Gln Ser Ala Ser Gly Tyr Arg Glu Gly
            180                 185                 190

Val Ala Tyr Ala Leu Lys Gln Leu Asn Leu Pro Asn Val Val Met Tyr
        195                 200                 205

Ile Asp Ala Gly His Gly Gly Trp Leu Gly Trp Asp Ala Asn Leu Lys
210                 215                 220

Pro Gly Ala Gln Glu Leu Ala Ser Val Tyr Lys Ser Ala Gly Ser Pro
225                 230                 235                 240

Ser Gln Val Arg Gly Ile Ser Thr Asn Val Ala Gly Trp Asn Ala Trp
                245                 250                 255

Asp Gln Glu Pro Gly Glu Phe Ser Asp Ala Ser Asp Ala Gln Tyr Asn
            260                 265                 270

Lys Cys Gln Asn Glu Lys Ile Tyr Ile Asn Thr Phe Gly Ala Glu Leu
        275                 280                 285

Lys Ser Ala Gly Met Pro Asn His Ala Ile Ile Asp Thr Gly Arg Asn
290                 295                 300

Gly Val Thr Gly Leu Arg Asp Glu Trp Gly Asp Trp Cys Asn Val Asn
305                 310                 315                 320

Gly Ala Gly Phe Gly Val Arg Pro Thr Ala Asn Thr Gly Asp Glu Leu
                325                 330                 335

Ala Asp Ala Phe Val Trp Val Lys Pro Gly Gly Glu Ser Asp Gly Thr
            340                 345                 350

Ser Asp Ser Ser Ala Ala Arg Tyr Asp Ser Phe Cys Gly Lys Pro Asp
        355                 360                 365

Ala Phe Lys Pro Ser Pro Glu Ala Gly Thr Trp Asn Gln Ala Tyr Phe
370                 375                 380

Glu Met Leu Leu Lys Asn Ala Asn Pro Ser Phe
385                 390                 395

<210> SEQ ID NO 110
<211> LENGTH: 465
<212> TYPE: PRT
<213> ORGANISM: Pleurotus sajor-caju

<400> SEQUENCE: 110

Met Phe Lys Phe Ser Thr Leu Leu Gly Leu Val Ala Leu Val Pro Ala
 1               5                  10                  15
```

-continued

Phe Thr Leu Ala Val Gly Glu Trp Gly Gln Cys Gly Ile Asn Tyr
         20              25              30

Thr Gly Ser Thr Thr Cys Asp Ala Gly Leu Val Cys Asn Val Ile Asn
     35              40              45

Asp Tyr Tyr His Gln Cys Leu Pro Thr Pro Ala Gly Asn Pro Tyr
 50              55              60

Ile Gly Tyr Asp Val Ser His Val Leu Trp Cys Gln Ile Tyr Leu Ser
 65              70              75              80

Pro Tyr Tyr Ala Asp Glu Val Ala Ala Val Ser Ala Ile Ser Asn
             85              90              95

Pro Ala Leu Ala Ala Lys Ala Ala Ser Val Ala Asn Ile Pro Thr Phe
             100             105             110

Ile Trp Phe Asp Val Val Ala Lys Val Pro Thr Leu Gly Thr Tyr Leu
         115             120             125

Ala Asp Ala Leu Ser Ile Gln Gln Ser Thr Gly Arg Asn Gln Leu Val
 130             135             140

Gln Ile Val Val Tyr Asp Leu Pro Asp Arg Asp Cys Ala Ala Leu Ala
145             150             155             160

Ser Asn Gly Glu Phe Ser Ile Ala Asn Asn Gly Leu Ala Asn Tyr Lys
             165             170             175

Asn Tyr Val Asp Gln Ile Val Ala Gln Ile Ala Arg Thr Cys Cys Pro
             180             185             190

Leu Val Thr Ser Ala Ile Thr Asp Leu Ala Cys Leu Ser Glu Tyr Pro
         195             200             205

Gln Ile Arg Val Val Ala Val Val Glu Pro Asp Ser Leu Ala Asn Met
     210             215             220

Val Thr Asn Leu Asn Val Pro Lys Cys Ala Gly Ala Gln Ala Ala Tyr
225             230             235             240

Thr Glu Gly Val Thr Tyr Ala Leu Gln Lys Leu Asn Thr Val Gly Val
             245             250             255

Tyr Ser Tyr Val Asp Ala Gly His Ala Gly Trp Leu Gly Trp Pro Ala
             260             265             270

Asn Leu Gly Pro Ala Ala Gln Leu Phe Ala Asn Leu Tyr Thr Asn Ala
         275             280             285

Gly Ser Pro Ser Phe Phe Arg Gly Leu Ala Thr Asn Val Ala Asn Tyr
 290             295             300

Asn Leu Leu Asn Ala Pro Ser Pro Asp Pro Val Thr Ser Pro Asn Ala
305             310             315             320

Asn Tyr Asp Glu Ile His Tyr Ile Asn Val Ser Asp Cys Phe Val Leu
             325             330             335

Ile Trp Thr Ser Leu Thr Ile Cys Ile Ile Ala Leu Ala Pro Glu Leu
         340             345             350

Ser Ser Arg Gly Phe Pro Ala His Phe Ile Val Asp Gln Gly Arg Ser
         355             360             365

Ala Val Gln Gly Ile Arg Gly Ala Trp Gly Asp Trp Cys Asn Val Asp
         370             375             380

Asn Ala Gly Phe Gly Thr Arg Pro Thr Thr Ser Thr Gly Ser Ser Leu
385             390             395             400

Ile Asp Ala Ile Val Trp Val Lys Pro Gly Gly Glu Ser Asp Gly Thr
             405             410             415

Ser Asp Thr Ser Ala Val Arg Tyr Asp Gly His Cys Gly Leu Ala Ser
         420             425             430

-continued

Ala Lys Lys Pro Ala Pro Glu Ala Met Ala Ser Val Tyr Ser His Ser
            435                 440                 445

Ser Phe Gln Ala Tyr Phe Glu Met Leu Val Ala Asn Ala Val Pro Ala
    450                 455                 460

Leu
465

<210> SEQ ID NO 111
<211> LENGTH: 436
<212> TYPE: PRT
<213> ORGANISM: Trametes versicolor

<400> SEQUENCE: 111

Met Phe Lys Phe Ala Ala Ala Gly Gln Cys Gly Gly Val Gly Trp Thr
1               5                   10                  15

Gly Arg Thr Thr Cys Val Ser Gly Ser Val Cys Ser Lys Gln Asn Asp
            20                  25                  30

Tyr Tyr Ser Gln Cys Ile Ser Gly Ala Gly Ala Pro Gly Thr Thr Val
        35                  40                  45

Ala Pro Thr Thr Ala Pro Thr Ala Pro Ala Thr Ser Ala Pro Gly Gly
    50                  55                  60

Ser Pro Thr Thr Val Ser Ala Pro Ser Thr Pro Ser Ser Thr Pro Ala
65                  70                  75                  80

Ala Gly Asn Pro Phe Thr Gly Phe Gln Val Tyr Leu Ser Pro Tyr Tyr
                85                  90                  95

Ser Ala Glu Ile Ala Ser Ala Ala Ala Val Thr Asp Ser Ser Leu
            100                 105                 110

Lys Ala Lys Ala Ala Ser Val Ala Asn Ile Pro Thr Phe Thr Trp Leu
        115                 120                 125

Asp Ser Val Ala Lys Val Pro Asp Leu Gly Thr Tyr Leu Ala Asp Ala
    130                 135                 140

Ser Ser Ile Gln Thr Lys Thr Gly Gln Lys Gln Leu Val Pro Ile Val
145                 150                 155                 160

Val Tyr Glu Leu Pro Asp Arg Asp Cys Ala Ala Lys Ala Ser Asn Gly
                165                 170                 175

Glu Phe Ser Ile Ala Asp Ala Gly Ala Glu Asn Tyr Lys Asp Tyr Ile
            180                 185                 190

Asp Gln Ile Val Pro Gln Ile Lys Gln Phe Pro Asp Val Arg Val Val
        195                 200                 205

Ala Val Ile Glu Pro Asp Ser Leu Ala Asn Leu Val Thr Asn Leu Asn
    210                 215                 220

Val Gln Lys Cys Ala Asn Gly Gly Thr Tyr Lys Ala Ser Val Thr Tyr
225                 230                 235                 240

Ala Leu Gln Gln Leu Ser Ser Val Gly Val Thr Met Tyr Met Asp Ala
                245                 250                 255

Gly His Ala Gly Trp Leu Gly Trp Pro Ala Asn Ile Gln Pro Gly Ser
            260                 265                 270

Glu Val Phe Ala Glu Met Phe Lys Ser Ala Asp Phe Val Ala Phe Val
        275                 280                 285

Arg Ala Phe Ala Thr Asn Val Arg Glu Tyr Asn Ala Leu Thr Ala Ala
    290                 295                 300

Phe Pro Arg Pro Ile Thr Gln Gly Asn Pro Asn Tyr Asp Glu Phe Pro
305                 310                 315                 320

Tyr Ile Gln Arg Val Arg Pro Met Leu Lys Ser Pro Gly Phe Pro Ala
                325                 330                 335

```
Gln Phe Val Val Asp Gln Gly Arg Ala Gly Gln Gln Asn Phe Arg Gln
                340                 345                 350

Gln Trp Gly Asp Trp Cys Asn Ile Lys Gly Ala Gly Phe Gly Thr Arg
                355                 360                 365

Pro Thr Thr Ser Thr Gly Asn Pro Leu Ile Asp Ala Ile Ile Trp Val
            370                 375                 380

Lys Pro Gly Gly Glu Ser Asp Gly Thr Ser Asn Ser Ser Ser Pro Arg
385                 390                 395                 400

Tyr Asp Ser Thr Leu Leu Ser Val Arg Arg Asp Pro Ala Pro Glu
                405                 410                 415

Ala Gly Thr Trp Phe Gln Ala Tyr Phe Glu Thr Leu Val Ser Lys Pro
                420                 425                 430

Thr Arg Pro Leu
            435

<210> SEQ ID NO 112
<211> LENGTH: 396
<212> TYPE: PRT
<213> ORGANISM: Neurospora crassa

<400> SEQUENCE: 112

Met Lys Phe Ser Asn Ser Ala Ala Leu Ala Phe Ala Ala Thr Ala Ile
1               5                   10                  15

Ala Ala Pro Ser Thr Pro Thr Leu Gln Glu Lys Pro Arg Glu Val Gln
                20                  25                  30

Ala Gly Cys Ala Ser Ala Val Thr Leu Asp Ala Ser Thr Asn Val Trp
            35                  40                  45

Lys Lys Tyr Thr Leu His Ala Asn Lys Phe Tyr Arg Thr Glu Val Glu
    50                  55                  60

Ala Ala Val Ala Ala Ile Ser Asp Ser Ser Leu Ala Ala Lys Ala Ala
65                  70                  75                  80

Lys Val Ala Asn Val Gly Ser Phe Leu Trp Leu Asp Ser Ile Glu Asn
                85                  90                  95

Ile Gly Lys Leu Glu Pro Ala Leu Glu Asp Val Pro Cys Asp His Ile
            100                 105                 110

Leu Gly Leu Val Ile Tyr Asp Leu Pro Gly Arg Asp Cys Ala Ala Lys
        115                 120                 125

Ala Ser Asn Gly Glu Leu Ala Val Gly Glu Leu Ser Arg Tyr Lys Thr
    130                 135                 140

Glu Tyr Ile Asp Ala Ile Val Lys Ile Leu Lys Ala His Pro Lys Thr
145                 150                 155                 160

Ala Phe Ala Leu Val Ile Glu Pro Asp Ser Leu Pro Asn Leu Val Thr
                165                 170                 175

Asn Ser Asp Leu Gln Thr Cys Lys Asp Ser Ala Ser Gly Tyr Arg Asp
            180                 185                 190

Gly Val Ala Tyr Ala Leu Arg Asn Leu Asn Leu Pro Asn Val Val Met
        195                 200                 205

Tyr Ile Asp Ala Gly His Gly Gly Trp Leu Gly Trp Asp Ala Asn Leu
    210                 215                 220

Lys Pro Gly Ala Gln Glu Leu Ala Lys Ala Tyr Lys Ala Ala Gly Ser
225                 230                 235                 240

Pro Lys Gln Val Arg Gly Ile Ala Thr Asn Val Ala Gly Trp Asn Gln
                245                 250                 255

Trp Asp Leu Thr Pro Gly Glu Phe Ser Lys Ala Ser Asp Ala Lys Tyr
```

```
                        260                 265                 270
Asn Lys Cys Gln Asn Glu Lys Leu Tyr Leu Asp Asn Phe Gly Pro Ala
            275                 280                 285

Leu Lys Ser Ala Gly Met Pro Asn His Ala Ile Val Asp Thr Gly Arg
            290                 295                 300

Asn Gly Val Ser Gly Leu Arg Gln Glu Trp Gly Asn Trp Cys Asn Val
305                 310                 315                 320

Asn Gly Ala Gly Phe Gly Val Arg Pro Thr Ser Ser Thr Gly His Asp
            325                 330                 335

Leu Ala Asp Ala Phe Val Trp Val Lys Pro Gly Gly Glu Ser Asp Gly
            340                 345                 350

Thr Ser Asp Ser Ser Ala Thr Arg Tyr Asp Ser Phe Cys Gly Lys Ser
            355                 360                 365

Asp Ala Tyr Gln Pro Ser Pro Glu Ala Gly Ser Trp Asn Gln Asp Tyr
            370                 375                 380

Phe Glu Met Leu Val Lys Asn Ala Lys Pro Ser Phe
385                 390                 395

<210> SEQ ID NO 113
<211> LENGTH: 395
<212> TYPE: PRT
<213> ORGANISM: Magnaporthe grisea

<400> SEQUENCE: 113

Met Lys Phe Cys His Ser Ala Leu Leu Ala Leu Val Gly Thr Ala Leu
1               5                   10                  15

Ala Ser Pro Ser Arg Thr Val Lys Ser Gln Pro Gly Gln Ala Ala Ala
            20                  25                  30

Gly Cys Ser Ser Ala Val Thr Leu Asp Ala Ser Thr Asn Val Phe Ser
        35                  40                  45

Lys Tyr Thr Leu His Pro Asn Ser Phe Tyr Arg Ala Glu Val Glu Ala
50                  55                  60

Ala Ala Glu Ala Ile Ser Asp Ser Thr Leu Lys Ala Gln Ala Leu Lys
65                  70                  75                  80

Val Ala Asp Val Gly Ser Phe Leu Trp Ile Asp Thr Ile Ser Ala Ile
                85                  90                  95

Ser Arg Ile Glu Pro Gly Val Ser Asp Gln Pro Cys Asp His Ile Leu
            100                 105                 110

Gly Leu Val Ile Tyr Asp Leu Pro Gly Arg Asp Cys Ala Ala Lys Ala
        115                 120                 125

Ser Asn Gly Glu Leu Lys Val Gly Glu Leu Ala Lys Tyr Lys Ser Gln
    130                 135                 140

Tyr Ile Asp Pro Ile Ala Ala Leu Leu Lys Tyr Asn Asn His Ala
145                 150                 155                 160

Phe Ala Leu Leu Ile Glu Pro Asp Ser Leu Pro Asn Leu Val Thr Asn
                165                 170                 175

Ser Asp Leu Ser Ala Cys Gln Gln Ser Ala Ala Gly Tyr Arg Asp Gly
            180                 185                 190

Val Ala Tyr Ala Leu Lys Thr Leu Asn Leu Pro Asn Val Val Met Tyr
        195                 200                 205

Ile Asp Ala Gly His Gly Gly Trp Leu Gly Trp Asn Asp Asn Leu Lys
    210                 215                 220

Pro Gly Ala Glu Glu Leu Ala Lys Ala Tyr Lys Ala Ala Gly Ser Pro
225                 230                 235                 240
```

```
Lys Gln Phe Arg Gly Phe Ala Thr Asn Val Ala Gly Trp Asn Ala Trp
                245                 250                 255
Asp Leu Thr Pro Gly Glu Phe Ser Ala Ser Asp Ala Gln Trp Asn
        260                 265                 270
Lys Cys Gln Asn Glu Lys Ile Tyr Val Glu Thr Phe Gly Pro Leu Leu
            275                 280                 285
Lys Asn Ala Gly Met Pro Asn His Ala Ile Val Asp Val Gly Arg Asn
        290                 295                 300
Ala Val Gln Gly Leu Arg Glu Glu Trp Gly His Trp Cys Asn Val Asn
305                 310                 315                 320
Gly Ala Gly Phe Gly Val Arg Pro Thr Thr Ser Thr Gly Ser Ser Leu
                325                 330                 335
Thr Asp Ala Leu Leu Trp Val Lys Pro Gly Gly Glu Ser Asp Gly Thr
            340                 345                 350
Ser Asp Thr Ser Ala Thr Arg Tyr Asp Ser Phe Cys Gly Met Ser Asp
        355                 360                 365
Ala Tyr Lys Pro Ser Pro Glu Ala Gly Gln Trp Asn Gln Asp Tyr Phe
        370                 375                 380
Glu Met Leu Leu Arg Asn Ala Lys Pro Gln Phe
385                 390                 395

<210> SEQ ID NO 114
<211> LENGTH: 1116
<212> TYPE: DNA
<213> ORGANISM: Artificial
<220> FEATURE:
<223> OTHER INFORMATION: DNA coding sequemce

<400> SEQUENCE: 114
cagggcggtg catggcagca gtgtggtggc gttggcttct cgggctctac gtcctgtgtg      60
tccggttaca cgtgcgtgta cttgaacgac tggtacagcc aatgccagcc gcagccgacg     120
acgttacgga caacaacaac gccaggggca acatcgacaa caaggtcagc cccggctgcc     180
acttcaacca ctccggccaa gggcaagttc aagtggtttg gcatcaacca gtcctgcgct     240
gagttcggca agggagagta tcccgggcta tggggcaagc actttacctt ccctcgacg      300
tcgtcgattc agacgcacat caatgacggc ttcaacatgt tccgcgtggc cttctcaatg     360
gagcggctgg cacccaacca gctgaacgcc gcgttcgatg ccaactacct ccgaaacctg     420
actgagaccg tcaatttcat cacgggcaag ggaaagtatg cgatgcttga cccccacaac     480
ttcggccgct attatgagag aatcatcacg gacaaggccg ccttcgccag cttcttcacc     540
aagctggcca cgcacttcgc gtcgaaccct cttgtcgtct ttgacaccaa caacgagtac     600
cacgacatgg accagcagct cgtcttcgat ctcaaccagg ctgccatcga cgccatccgc     660
gccgcgggtg ctacgtcgca gtacatcatg gtcgagggca actcgtggac cggggcgtgg     720
acgtggaacg tgaccaacaa caacttggcg gcgctacgcg acccggagaa caagctggtg     780
taccagatgc atcagtacct cgactcggac gggtccggca cgagcacggc ctgcgtcagc     840
acccaggtcg gccttcagcg cgtcattggc gcgaccaact ggctcaggca aaacggcaag     900
gttggactgc tcggcgagtt cgccggcggc gccaactcgg tttgccagca ggccattgag     960
ggcatgctca cccacctcca ggagaatagc gatgtctgga caggtgcgct ctggtgggcg    1020
ggaggcccgt ggtggggtga ctatatctac tcgtttgaac ctccttcggg tattggctac    1080
acctactaca attcccttct caagaaatac gtgcca                              1116
```

```
<210> SEQ ID NO 115
<211> LENGTH: 852
<212> TYPE: DNA
<213> ORGANISM: Artificial
<220> FEATURE:
<223> OTHER INFORMATION: DNA coding sequemce

<400> SEQUENCE: 115
gccgacggtc gcagtacccg ctactgggac tgctgcaagc ccagttgcgg ttgggccaag      60
aaggcccccg tcaaccagcc cgtcttcagt tgcaacgcca acttccagcg catcaccgac     120
ttcgacgcca agagtggttg cgagcccggt ggtgtcgcct acagttgcgc cgaccagacc     180
ccctgggccg tcaacgacga cttcgccctc ggtttcgccg ccaccagtat cgccggtagt     240
aacgaggccg gttggtgctg cgcctgctac gagctgacct tcaccagtgg tcccgtcgcc     300
ggtaagaaga tggtcgtcca gagtaccagt acgggtggtg acctcggtag taaccacttc     360
gacctcaaca tccccggtgg tggtgtcggt atcttcgacg gttgcacccc ccagttcggt     420
ggtctccccg tcagcgata cggtggtatc agtagtcgca acgagtgcga ccgcttcccc     480
gacgccctca agcccggttg ctactggcgc ttcgactggt tcaagaacgc cgacaacccc     540
agtttcagtt tccgccaggt ccagtgcccc gccgagctgg tcgcccgcac gggttgccgc     600
cgcaacgacg acggtaactt ccccgccgtc cagatcccca gtagtagtac cagtagtccc     660
gtcaaccagc ccaccagtac cagtaccacc agtaccagta ccaccagtag tcccccccgtc     720 cagcccacca cccccagtgg ttgcaccgcc gagcggtggg ctcagtgcgg tggtaacggt     780
tggagtggtt gcaccacctg cgtcgccggt agtacctgca ccaagatcaa cgactggtat     840
caccagtgcc tc                                                         852
```

CELLULASE ENZYME MIXTURES FOR DEPILLING AND USES THEREOF

CROSS-REFERENCE TO RELATED APPLICATIONS

This application is a 35 U.S.C. 371 national application of PCT/CA2012/050074/filed Feb. 9, 2012, which claims priority or the benefit under 35 U.S.C. 119 of U.S. provisional application No. 61/440,985 filed Feb. 9, 2011, the contents of which are fully incorporated herein by reference.

FIELD OF THE INVENTION

The present invention relates to a cellulase enzyme mixture and uses thereof, in particular to a cellulase enzyme mixture for use in treating cellulose-containing goods.

BACKGROUND OF THE INVENTION

Cellulase enzymes are widely used to improve the appearance and softness of cellulose-containing fabrics. A widespread application of cellulase enzymes is to remove cotton fuzz and loose surface fibers in or on the fabric. This process is referred to as "depilling", "biopolishing" and "biofinishing" and smoothes the surface of the fabric, which in turn improves its softness and appearance. Cellulase treatment also aids in the prevention of subsequent formation of fiber pills that make the garments appear worn. During depilling it is desirable to minimize strength loss of the fabric due to the hydrolytic action of the cellulases.

Another industrial application of cellulase enzymes is for treating denim fabrics so as to impart to them a "stonewashed" appearance. Such a process is known in the industry as "bio-stoning". The term bio-stoning was adopted as pumice stones were traditionally used to treat the fabric. However, cellulases have largely replaced pumice stones in recent years. Bio-stoning is quite different from depilling: biostoning aims to remove colour from denim and control its redeposition on the fabric while depilling aims to solely improve softness and appearance as in depilling.

Cellulase enzymes are a group of glycoside hydrolase enzymes that catalyze the hydrolysis of beta-1,4-glycosidic linkages in the cellulose polymer and often comprise a cellulose binding domain (CBD) and a catalytic domain. A region between these two domains known as a "linker" or "linker peptide" serves as a flexible spacer between the CBD and the catalytic domain. The catalytic domains of individual cellulase components are classified by both the Enzyme Commission (EC) and the Glycoside Hydrolase (GH) family systems. The Enzyme Commission distinguishes two classes of cellulases based on their preference for cleavage of internal beta-1, 4 linkages (endoglucanase or "EG", EC 3.2.1.4) or the release of cellobiose from the reducing or non-reducing end of the cellulose polymer (cellobiohydrolases or "CBH", EC 3.2.1. 91, sometimes also referred to as exoglucanases). In contrast, the GH family system distinguishes the catalytic domains of cellulase components based on the conservation of primary and secondary structure, as well as the stereochemistry of the catalytic reaction. The GH family designations for all known cellulase catalytic and binding domains is provided and continually updated through the Carbohydrate-Active EnZymes (CAZy) database (Cantarel et al., 2009, Nucleic Acids Res 37:D233-238) available at the URL: cazy.org. Cellulase enzymes may be found in a number of GH Families including, but not limited to, Families 5, 6, 7, 8, 9, 10, 12, 16, 18, 19, 26, 44, 45, 48, 51, 61 and 74. Further, cellulase in some of the larger GH Families may be grouped into subfamilies.

Under the GH system, all cellulase catalytic domains, whether CBH or EG enzymes, are designated by "Cel" followed by the GH Family number. For example, cellulase comprising catalytic domains belonging to GH Families, 5, 6 and 7 may be referred to as Cel5, Cel6 and Cel7 cellulases, cellobiohydrolases or endoglucanases or as Family 5, Family 6, and Family 7 cellulases, cellobiohydrolases or endoglucanases. Designations such as Cel5, Cel6 and Cel7 may be followed by the capital letters A, B, C and so forth, which indicate the order in which the enzymes of the same family were identified from the source organisms. Further, the Cel designations may be preceded by a genus, species identifier such as "Tr" for Trichoderma reesei.

Fungi such as Trichoderma secrete a number of different cellulase enzymes (also referred to herein as an "enzyme mixture", "cellulase mixture" or "cellulase enzyme mixture") that are individually known as components. The more prevalent of these enzyme components include cellobiohydrolase (CBH), also called exo-1,4-beta-D-glucanases, endoglucanase (EG), or endo-1,4-beta-D-glucanases, and beta-glucosidase enzymes. This classification is based on the enzymes' substrate specificities, i.e. affinity towards the chain ends (exo), the interior of the glucose chain (endo), or glycosidic bonds of soluble cellooligosaccharides and cellobiose (betaglucosidase).

Trichoderma reesei is a widely studied and industrially important fungus for the production of cellulases. It produces at least six genetically different cellulases: two cellobiohydrolases, referred to as Cel6A (SEQ ID NO:3) and Cel7A (SEQ ID NO:5), also known as CBHII and CBHI, and at least four endoglucanases Cel5A (SEQ ID NO:2), Cel7B (SEQ ID NO:6), Cel12A and Cel45A (SEQ ID NO:4), also known as EGII, EGI, EGIII and EGV, respectively. Some of these cellulase components have been identified as contributing to improvements in depilling, while others are seen as detrimental as they can cause fabric strength loss, as discussed below.

Efforts have been made to improve the properties of cellulase mixtures for textile depilling by increasing the proportion of endoglucanase components in the secreted enzyme mixture relative to the natural mixture. For instance, WO 92/17574 discloses an approach that involves adjusting the amounts of EG type components relative to CBH I type components (Cel7A) so that the protein weight ratio of the EG to CBH I type components is greater than 5:1. Cotton-containing fabrics treated with such compositions exhibited decreased strength loss during depilling treatment compared to fabrics containing greater amounts of CBH I type (Cel7A) components. In addition, EP 866 165 discloses enzyme compositions enriched in EG II (Cel5A), which exhibit improvements in depilling efficiency and reduced strength loss. In embodiments, the enzyme compositions contain a cellulase protein content of at least 95% EG II.

U.S. Pat. No. 6,162,782 discloses that reduced strength loss of cotton fabrics can be achieved with cellulase detergent compositions that contain one or more endoglucanase components and reduced levels (less than 5 wt %) of CBH I (Cel7A). In these studies, it was found that CBH I, and to a certain extent CBH II, played a role in strength loss. The EG-enriched detergent compositions were reportedto impart improvements in softening, washing and color restoration. Similarly, Miettinen-Oinonen et al. (Applied and Environmental Microbiology, 2002, 68(8):3956-3964) reported improvements in visual appearance and reductions in pilling tendency with EG II-enriched cellulase preparations devoid of CBH I and CBH II. Miettinen-Oinonen et al. (VTT Publications 550, 2004, *Trichoderma reesei* strains for production of cellulases for the textile industry) also report good depilling results with EG II-enriched cellulase preparations. The use of endoglucanases in textile applications is also discussed in WO 2004/053039, EP 495 258 and U.S. Pat. Nos. 6,001, 639, 5,958,082 and 5,948,672.

Moreover, a number of groups have contemplated the use of Cel45 cellulases in depilling. WO 97/14804 discloses a neutral Cel45A cellulase (20 K cellulase) from *Melanocarpus* origin for use in the textile and detergent industry .... WO2010/076388 discloses the production and use of *Geomyces* or *Fusarium* Cel45 endoglucanases in denim washing and depilling. U.S. Publication No. 2007/0111278 discloses the use of STCE1. a Cel45 endoglucanase, derived from *Staphylotrichum*, in washing or depilling of cellulose-containing fabrics. U.S. Pat. No. 7,741,093 discloses fusion of the *Melanocarpus* Cel45 endoglucanase to a linker peptide of *Trichoderma reesei* CBH I and a cellulose binding domain for bio-stoning and biofinishing. The purpose of constructing such fusion proteins was to increase the size of the *Melanocarpus* Cel45A enzyme, thereby decreasing the ability of the enzyme to penetrate the fabric, which in turn reduces strength loss. Similar approaches with Cel45 endoglucansaes and other cellulase enzymes are disclosed in WO 2007/118935 and U.S. Pat. No. 7,256,032.

Other groups have focused on elucidating whether or not cellulase enzyme components synergize with one another. The identification of synergistic combinations of enzyme components that provide for enhanced depilling could be a step forward with respect to improving process economics. Such improvements may be achieved since less enzyme protein, which is costly, would be necessary to impart the desired depilling effect.

Heikinheimo and Buchert (Textile Research Journal, 2001, 71(8):672-677) investigated the depilling properties of *Trichoderma reesei* EG I and II and CBH I and II cellulase components alone and in combination. Treatment of cotton interlock fabric with EG II-based combinations with CBH I or CBH II resulted in favourable depilling properties. However, the investigators also reported decreased depilling activity for combinations of the two endoglucanases, EG I and EG II. That is, no endo-endo synergy between the cellulase components was observed.

Cavaco-Paulo and Almeida (Textile Chemist and Colorist, 1996, 28(6):28-32) observed a high activity of EGI and II-deleted *Trichoderma reesei* cellulase mixtures on cotton cellulose. The authors state therein that the effect may possibly be due to synergy between the two CBH components or the CBH components and residual EG III or EG V. In Cavaco-Paulo, Carbohydrate Polymers, 1998, 37:273-277, it was stated that minor EG components seem to cooperate with the CBHs, in a synergistic fashion, to fully hydrolyse cotton. However, no testing was carried out to examine which particular components exhibited synergism with one another.

U.S. Pat. No. 5,958,083 discloses binary cellulase enzyme mixtures for use in bio-stoning. The first component is a Family 5 endoglucanase derived from *Bacillus* or *Clostridium*, or Family 7 endoglucanase derived from *Humicolainsolens*. The second component is a mechanical abrading agent, and/or an abrading cellulase (to form localized variation in color density), which may be a Family 12 or a Family 45 cellulase with a cellulose binding domain. Although improved bio-stoning with low backstaining was obtained, the properties of these compositions in depilling assays were not investigated.

Miettinen-Oinonen et al. (Enzyme and Microbial Technology, 2004, 34:332-341) examined the effect of Family 45 enzymes in biostoning, alone or in combination with other cellulase components, including endoglucanases. However, the depilling properties of these enzyme compositions were not tested in these studies.

Synergy between cellulase components has been reported in the literature in the hydrolysis of cellulosic substrates, or complete degradation and conversion of cellulose into ultimately glucose (Gusakov et al., Biotechnology and Bioengineering, 2007, 97(5):1028-1038; Andersen et al, Enzyme and Microbial Technology, 2008, 42(4):362-370; Boisset al., Biotechnology and Bioengineering, 2001, 72(3):339-345; Igarashi et al., Applied and Environmental Microbiology, 2008, 74:5628-5634; and Zhang et al., Biotechnology and Bioengineering, 2004, 7(88):797-824). However, extended hydrolysis is generally not a desired effect in depilling, as it may result in destruction of the fabric or severe strength loss. Furthermore, as reported by Ramos et al. (Biocatalysis and Biotransformation, 2007, 25(1):35-42) hydrolysis may not correlate with biopolishing effects.

Despite these efforts, there is still a need for improved combinations of cellulase enzymes and compositions thereof that are more effective in depilling of cellulose-containing goods. In particular, there is a continuous need for more efficient cellulase enzyme mixtures to improve the process economics. The present invention aims to meet these needs.

SUMMARY OF THE INVENTION

It is an object of the present invention to provide an improved cellulase enzyme mixture for use in treating cellulose-containing goods.

According to a second aspect of the invention, there is provided a depilling composition comprising an enzyme mixture, which enzyme mixture comprises a Family 45 cellulase enzyme component and one or more additional cellulase enzyme components selected from a Family 5 cellulase, a Family 6 cellulase or a combination thereof. The enzyme mixture is secreted by a genetically modified microbe overexpressing (i) a Family 45 cellulase gene encoding said Family 45 cellulase enzyme; and (ii) a gene or genes encoding the one or more additional cellulase enzyme component selected from a Family 5 cellulase, a Family 6 cellulase or a combination thereof, wherein the Family 45 cellulase has at least 75% sequence identity to amino acids 1-213 of SEQ ID NO:7 (HiCel45) or at least 20% sequence identity to amino acids 1-166 of SEQ ID NO:4 (TrCel45).

According to one embodiment of the invention, the depilling composition comprises both the Family 45 cellulase and the Family 5 cellulase. In a further embodiment of the invention, the depilling composition further comprises the Family 6 cellulase. In yet another embodiment of the invention, the depilling composition further comprises a Family 7 cellulase. Alternatively, the depilling composition lacks a Family 7 cellulase.

The Family 5 cellulase may comprise a substitution of an amino acid at position 363 with a non-native alanine, serine or threonine, which position is determined from alignment of the modified Family 5 cellulase with a wild-type *Trichoderma reesei* Cel5A amino acid sequence as set forth in SEQ ID NO:2.

The present invention also provides a process for depilling that comprises a step of contacting cellulose-containing goods with the depilling composition set forth above.

According to a further aspect of the invention, there is provided a genetically modified microbe overexpressing (i) a Family 45 cellulase gene encoding said Family 45 cellulase enzyme; and (ii) a gene or genes encoding the one or more additional cellulase enzyme component selected from a Family 5 cellulase, a Family 6 cellulase or a combination thereof, wherein the Family 45 cellulase has at least 75% sequence identity to amino acids 1-213 of SEQ ID NO:7 (HiCel45) or at least 20% sequence identity to amino acids 1-166 of SEQ ID NO:4 (TrCel45).

According to one embodiment of the invention, the genetically modified microbe overexpresses at least the Family 45 cellulase and the Family 5 cellulase. Alternatively, the genetically modified microbe overexpresses the Family 6 cellulase.

According to a further embodiment of the invention, the genetically modified microbe expresses a Family 7 cellulase. Alternatively, the genetically modified microbe does not express a Family 7 cellulase.

The genetically modified microbe may express a Family 5 cellulase that comprises a substitution of an amino acid at position 363 with a non-native alanine, serine or threonine, which position is determined from alignment of the modified Family 5 cellulase with a wild-type *Trichoderma reesei* Cel5A amino acid sequence as set forth in SEQ ID NO:2.

The Family 45 cellulase and the one or more additional cellulase enzyme component selected from a Family 5 cellulase, a Family 6 cellulase or a combination thereof, may be expressed from coding sequences in said genetically modified microbe that are endogenous or heterologous to the microbe.

According to another aspect of the invention, there is provided a depilling composition comprising an enzyme mixture, which enzyme mixture comprises (i) a Family 45 cellulase enzyme component; and (ii) at least one or more additional cellulase enzyme components that are selected from the group consisting of a Family 5 cellulase, a Family 6 cellulase, and a combination thereof, wherein said enzyme mixture is characterized by having a weight ratio of the Family 45 and the Family 5 cellulase enzyme components or the Family 45 and the Family 6 cellulase enzyme components that exhibits synergy in an assay that measures specific depilling activity.

Disclosed herein are combinations of cellulase enzymes that are particularly effective in the depilling of cotton-containing goods. The Applicants have identified combinations of cellulase enzyme components that provide for enhanced depilling of cotton-containing goods relative to the combined depilling effect of the individual enzyme components. The utilization of such enzyme combinations could be a step forward with respect to improving process economics. Such improvements may be achieved since less enzyme protein, which is costly, would be necessary to impart a desired depilling effect.

BRIEF DESCRIPTION OF THE DRAWINGS

FIG. 1 shows an amino acid sequence alignment of eight selected Glycoside hydrolase (GH) Family 45 cellulases to amino acids 1-166 of a wild-type *Trichoderma reesei* Family 45 cellulase abbreviated TrCel45A (SEQ ID NO:4). Conserved amino acid motifs characteristic of Family 45 cellulases are underlined.

FIGS. 2A, 2B, 2C, 2D, 2E, 2F, and 2G show an amino acid sequence alignment of 49 selected Glycoside hydrolase (GH) Family 45 cellulases to amino acids 1-213 a *Humicolainsolens* Family 45 cellulase abbreviated HiCel45A (SEQ ID NO:7). Conserved amino acid motifs characteristic of Family 45 cellulases are underlined.

FIGS. 3A, 3B, 3C, 3D, 3E, 3F, and 3G show an amino acid sequence alignment among 14 selected Glycoside hydrolase (GH) Family 5 cellulases to amino acids 71-397 of a *Trichoderma reesei* Family 5 cellulase abbreviated TrCel5A (SEQ ID NO:2). The catalytic amino acids at the equivalent position 218 and 329 in TrCel5A are indicated with an arrow. The conserved amino acids at the equivalent position 130, 174, 217, 288, and 290 in TrCel5A are indicated with an asterisk. For cellulases with a cellulose-binding domain, only the catalytic core sequences are presented.

FIGS. 9A, 9B, 9C, 9D, 9E, 9F, 9G, 9H, 9I, 9J, and 9K show an amino acid sequence alignment of 35 selected Glycoside hydrolase (GH) Family 6 cellulases to amino acids 83-477 of a *Trichoderma reesei* Family 6 cellulase abbreviated TrCel6A (SEQ ID NO:3). The Family 6 cellulases correspond to those provided in Table 4 and appear in the order presented in the table.

FIG. 10 is a map of the *Trichoderma reesei* transformation vector pChHiCel5A-pyr4-TV.

FIG. 11 is a map of the *Trichoderma reesei* transformation vector Pc/x-TrHiCel45a-ble-TV.

FIG. 12 is a Western blot of culture filtrates of *Trichoderma reesei* transformants of parental strain P579A expressing HiCel45A (P1622A and P1622F).

FIG. 13 shows the relative depilling activity of cellulase enzyme mixtures produced by *Trichoderma reesei* transformants overexpressing HiCMC3 (strain P579A) or overexpressing both HiCMC3 and HiCel45A (strain P1622A), relative to that produced by parental strains BTR213. The strain names are indicated under each bar and the relative depilling activity is indicated on the corresponding bar.

FIG. 14 shows the depilling activity (in terms of the percentage of fines released from a fabric sample) by increasing dosages of purified TrCel45A, purified TrCel5A-G363A, or a blend of TrCel45A+TrCel5A-G363A.

FIG. 15 shows the depilling activity (in terms of the percentage of fines released from a fabric sample) by increasing dosages of purified TrCel45A, a blend of TrCel6A+TrCel5A-G363A+TrCel5A or a blend of TrCel45A+TrCel6A+TrCel5A-G363A+TrCel5A.

DETAILED DESCRIPTION OF THE INVENTION

Figure 4:
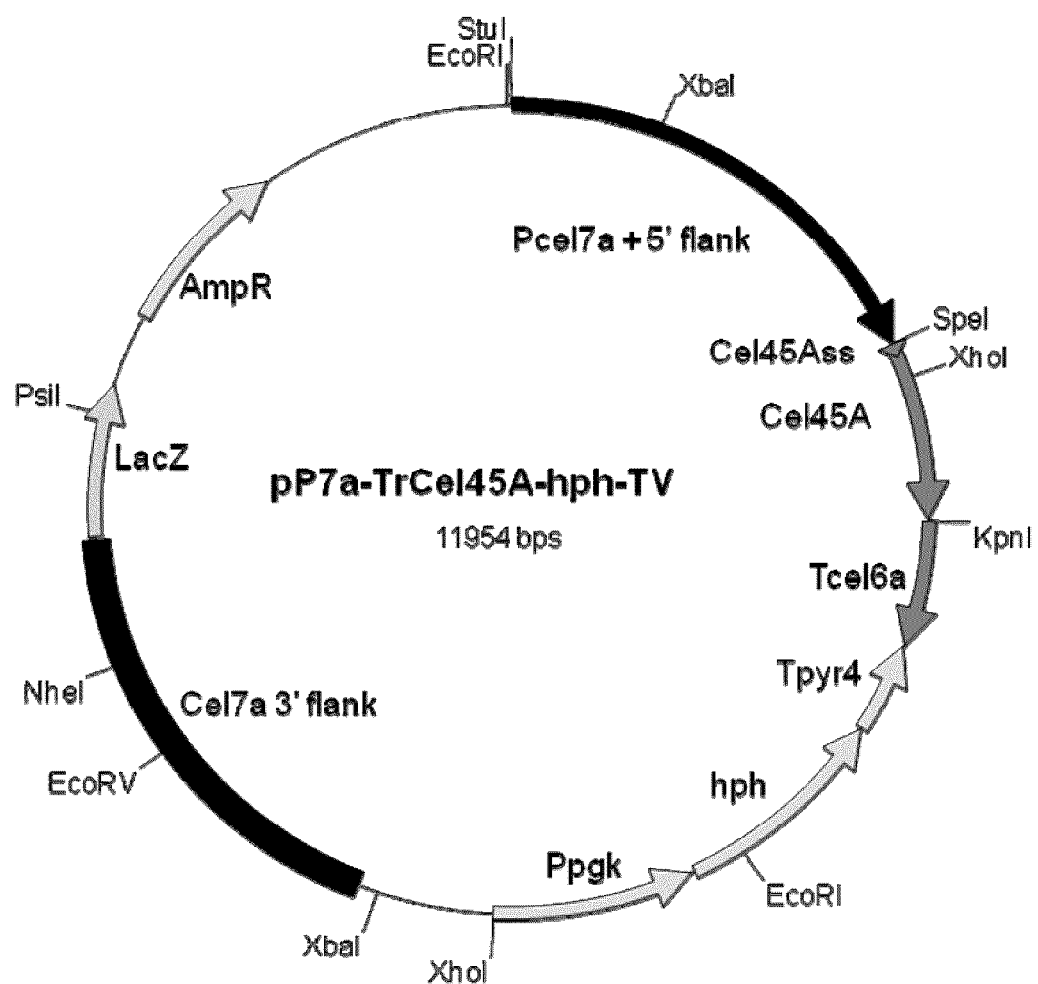
FIG. 4 is a map of the *Trichodermareesei* transformation vector pP7a-TrCel45A-hph-TV.

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Family 45 Cellulases

Glycoside hydrolases (GHs) are a large group of enzymes that cleave glycosidic bonds between individual carbohydrate monomers in large polysaccharide molecules. Cellulases cleave the beta 1-4 bond between glucose monomers in the cellulose polymer. GH enzymes all share one of two common mechanisms, called inverting and retaining, for introducing a water molecule at a glycosidic bond thus cleaving the polysaccharide.

The GH Family 45 cellulase enzymes (formerly Family K) act with inversion of anomeric configuration to generate the α-D anomer of the oligosaccharide as a product. It has been elucidated that, in the active site, one aspartic acid amino acid acts as a general acid and another as a general base.

The three dimensional structure of Family 45 enzymes has been elucidated (see, for example, the structure of *Humicolainsolens* in Davies et al., 1996, ActaCrystallographica Section D-Biological Crystallography 52:7-17 Part 1). The enzymes contain a six-stranded beta-barrel to which a seventh strand is appended. The structure contains both parallel and anti-parallel beta-strands. The active center is located in an open substrate-binding groove.

As used herein, the term "Family 45 cellulase" or "Cel45" means a carbohydrate active cellulase enzyme that contains a glycoside hydrolase Family 45 catalytic domain that is classified under EC 3.2.1.4. The term encompasses a carbohydrate active enzyme that hydrolyzes cellulose and cello-oligosaccharides using an inverting mechanism, and has either of the following two signature sequences in the vicinity of the catalytic aspartic acid amino acids: (i) both a first conserved signature sequence of A/S/T-T-R/N/T-Y/F/T-X-D-X-X-X-X-X-C/A-A/G/S-W/C and a second conserved signature sequence of H/Q/D/N-F/L-D-I/L/F; or (ii) has the second conserved signature sequence of H/Q/D/N-F/L-D-I/L/F but lacks said first conserved sequence. In one embodiment, the second conserved signature sequence is H—F-D-I. Such conserved signature sequences may be found, for example, at amino acids 6-19 and 115-118 of SEQ ID NO:

Family 45 cellulase enzymes have been divided into at least two subfamilies referred to as "A" and "B" (Igarashi et al., Applied and Environmental Microbiology, 2008, 74(18): 5628-5634). According to one embodiment of the invention, the Family 45 cellulase enzyme is a subfamily A member. According to another embodiment of the invention, the Family 45 cellulase enzyme is a subfamily B member. This includes, but is not limited to, those subfamily A and subfamily B enzymes listed in the tables below. It should be understood that amino acid numbering of the Cel45A sequences disclosed herein are based on the sequences of the mature, secreted protein—i.e., the protein without a secretion signal peptide and/or leader peptide Table 1 and Table 2 below provide a representative list of family members from subfamilies "B" and "A", respectively. Sequence identity for each amino acid sequence with a reference subfamily A or B family member is also provided in each table. For the subfamily B sequences in Table 1, sequence identity was determined by alignment with amino acids 1-166 of *Trichoderma reesei* Cel45A (TrCel45A; SEQ ID NO:4) and for the subfamily A sequences in Table 2, sequence identity was determined by alignment with amino acids 1-213 of *Humicolainsolens* Cel45A (HiCel45A; SEQ ID NO:7). FIGS. 1 and 2 show amino acid sequence alignments of the Family 45 cellulases provided in Tables 1 and 2, respectively, below. It should be noted that the letter appearing after the abbreviated name does not denote inclusion of the Family 45 in any particular subfamily. For instance, the *T. reesei* Family 45 cellulase belongs to subfamily B but is abbreviated TrCel45A because it is the first Family 45 cellulase isolated from *T. reesei*.

TABLE 1

Family 45 cellulase subfamily B members and sequence identity with amino acids 1-166 of TrCel45A (%).

| Organism | Abreviated Name | GenBank Accession Number | SEQ ID NO: | Percent identity with TrCel45A amino acids 1-166 of SEQ ID NO: 4 |
|---|---|---|---|---|
| *Trichoderma reesei* | TrCel45A | CAA83846.1 | 4 | 100.0 |
| *Trichoderma viride* | TvEGV | AAQ21385.1 | 8 | 100.0 |
| *Penicillium decumbens* | PdCel45A | ACF33814.1 | 9 | 84.0 |
| *Aspergillus nidulans* | AnAN6786.2 | EAA58604.1 | 10 | 49.4 |
| *Haliotis discus discus* | HddEG1 | ABO26608.1 | 11 | 36.1 |
| *Ampullaria crossean* | AcEG27I | ABR92637.1 | 12 | 34.6 |
| *Ampullaria crossean* | AcEG27II | ABR92638.1 | 13 | 33.5 |
| *Mytilus edulis* | MeEg | CAC59695.1 | 14 | 30.3 |
| *Phanerochaete chrysosporium** | PcCel45A | BAG68300.1 | 15 | 26.2 |

*For the purpose of this specification, PcCel45A is categorized as a subfamily B member. Igarashi et al. (supra) define a subfamily "C" Family 45 cellulase and indicate that PcCel45A would be a member of this family, although they report that the enzyme exhibits some similarity to that of subfamily B.

TABLE 2

Family 45 cellulase subfamily A members and sequence identity with HiCel45A (%).

| Organism | Abreviated Name | GenBank Accession Number | SEQ ID NO: | Percent identity with HiCel45A amino acids 1-213 of SEQ ID NO: 7 |
|---|---|---|---|---|
| *Humicola insolens* | HiCel45A | AAE16508.1 | 7 | 100.0 |
| *Humicola grisea* var. thermoidea | HgEgl3 | BAA74956.1 | 16 | 98.5 |
| *Humicola nigrescens* | HnCel45A | CAB42308.1 | 17 | 85.4 |

TABLE 2-continued

Family 45 cellulase subfamily A members and sequence identity with HiCel45A (%).

| Organism | Abreviated Name | GenBank Accession Number | SEQ ID NO: | Percent identity with HiCel45A amino acids 1-213 of SEQ ID NO: 7 |
|---|---|---|---|---|
| Staphylo trichumcoccos porum | ScSTCE1 | BAG69187.1 | 18 | 80.7 |
| Melanocarpus albomyces | MaCel45A | CAD56665.1 | 19 | 77.9 |
| Podospora anserina | PaCel45A | CAP61565.1 | 20 | 74.1 |
| Acremonium thermophilum | AtSEQ6 | ACE10216.1 | 21 | 73.7 |
| Thielavia terrestris | TtCel45A | CAH03187.1 | 22 | 73.7 |
| Trichothecium roseum | TroCel45A | CAB42312.1 | 23 | 73.3 |
| Acremonium thermophilum | AtSEQ2 | ABW41463.1 | 24 | 73.2 |
| Fusarium anguioides | FaCel45A | CAB42310.1 | 25 | 72.8 |
| Clonostachys rosea f. catenulata | CrCel45A | CAB42311.1 | 26 | 72.3 |
| Neurospora crassa | NcCel45A | CAD70529.1 | 27 | 69.4 |
| Volutella colletotrichoides | VcSEQ22 | AAY00854.1 | 28 | 64.4 |
| Gibberella zeae | GzCel45A | AAR02399.1 | 29 | 62.6 |
| Fusarium oxysporum | FoCel45A | AAA65589.1 | 30 | 62.1 |
| Acremonium sp. | AsSEQ10 | AAY00848.1 | 31 | 60.8 |
| Acremonium sp. | AsSEQ8 | AAY00847.1 | 32 | 59.3 |
| Chrysosporium lucknowense | ClCel45A | AAQ38150.1 | 33 | 57.3 |
| Thielavia heterothallica | ThSEQ2 | AAY00844.1 | 34 | 57.3 |
| Mucor circinelloides | McMce1 | BAD95808.1 | 35 | 56.8 |
| Reticulitermes speratus hindgut protist | RshpCel45A | BAA98037.1 | 36 | 56.8 |
| Bursaphelenchus xylophilus | BxEng1 | BAD34546.1 | 37 | 55.9 |
| Botryotinia fuckeliana | BfCel45A | XP_001547700.1 | 38 | 55.8 |
| Acremonium thermophilum | AtSEQ4 | ABW41464.1 | 39 | 55.3 |
| Scopulariopsis brevicaulis | SbEgI | Q7M4T4* | 40 | 55.0 |
| Syncephalas trumracemosum | SrCBHI | ABU49185.2 | 41 | 55.0 |
| Rhizopus oryzae | RoRce1 | BAC53956.1 | 42 | 54.7 |
| Crinipelliss cabella | CsSEQ16 | AAY00851.1 | 43 | 53.9 |
| Macrophomina phaseolina | MpSEQ14 | AAY00850.1 | 44 | 53.9 |
| Podospora anserina | PaCel45B | CAP69443.1 | 45 | 53.9 |
| Rhizopus oryzae | RoRce3 | BAC53988.1 | 46 | 53.8 |
| Bursaphelenchus xylophilus | BxEng2 | BAD34544.1 | 47 | 53.6 |
| Bursaphelenchus xylophilus | BxEng3 | BAD34548.1 | 48 | 53.6 |
| Humicola grisea var. thermoidea | HgEgl4 | BAA74957.1 | 49 | 53.4 |
| Phycomyces nitens | PnPce1 | BAD77808.1 | 50 | 53.2 |
| Rhizopus oryzae | RoRce2 | BAC53987.1 | 51 | 52.9 |
| Mastotermes darwiniensis hindgut symbiont sp. | MdhsFm4 | CAD39200.1 | 52 | 52.7 |
| Magnaporthe grisea | MgCel45A | XP_363402.1 | 53 | 51.8 |
| Mastotermes darwiniensis hindgut symbiont sp. | MdhsFm3 | CAD39199.1 | 54 | 51.8 |
| Mastotermes darwiniensis hindgut symbiont sp. | MdhsFm1 | CAD39197.1 | 55 | 51.3 |
| Mastotermes darwiniensis hindgut symbiont sp. | MdhsFm2 | CAD39198.1 | 56 | 51.3 |
| Pichia pastoris GS115 | PpCel45A | CAY71902.1 | 57 | 51.3 |
| Piromyces equi | PeCel45A | CAB92325.1 | 58 | 48.2 |
| Apriona germari | AgCelI | AAN78326.1 | 59 | 43.8 |
| Apriona germari | AgCelII | AAR22385.1 | 60 | 43.6 |
| Alternaria alternata | AaK1 | AAF05700.1 | 61 | 41.4 |
| Phaedon cochleariae | PcEg | CAA76931.1 | 62 | 40.4 |
| Talaromyces emersonii | TeCel45A | CAJ75963.1 | 63 | 37.6 |
| Ustilago maydis | UmEgl1 | AAB36147.1 | 64 | 33.6 |

*Uniprot entry

The sequence identities of the Family 45 cellulases reported in Tables 1 and 2 above are determined as follows. The full sequence of each enzyme (including CBM and signal peptide if present) is aligned with either amino acids 1 to 213 of the reference sequence HiCel45A (SEQ ID NO:7) or amino acids 1 to 166 of the reference sequence TrCel45A (SEQ ID NO:4) using ClustalW Multiple Alignment tool (Thompson et al., Nucleic Acids Research, 1994, 22(22): 4673-4680), with default settings, found in the BioEdit software version 7.0.9.0 (Jun. 27, 2007). All amino acids that are found before or after the reference enzyme's first or last amino acids are cropped from the alignment. The alignment is performed a second time using the cropped sequences and again, all amino acids that are found before or after the reference enzyme's first or last amino acid are cropped from the alignment. Percent identity with the reference sequence's selected amino acids is then calculated.

Other sequence alignment algorithms are known to those of skill in the art, including the BLAST algorithm (BLAST and BLAST 2.0; Altschul et al., Nuc. Acids Res., 1997, 25:3389-3402; and Altschul et al., J. Mol. Biol., 1990, 215: 403-410; the algorithm disclosed by Smith and Waterman, Adv. Appl. Math., 1981, 2:482-489, by the homology alignment algorithm of Needleman and Wunsch, J. Mol. Biol., 1970, 48:443-453, by the search for similarity method of Pearson and Lipman, J. Proc Natl Acad Sci., 1988, 85(8): 2444-8, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology, John Wiley & Sons, Ausubel et al., eds. 1995 supplement). When conducting BLAST alignments and sequence identity determinations for cellulase enzymes, the amino acid sequences comprising the catalytic domains and CBDs may be considered separately or as one contiguous sequence.

According to one embodiment, the Family 45 cellulase is a sub-family B cellulase and has 20% to 100% amino acid sequence identity to amino acids 1-166 of SEQ ID NO:4 (TrCel45A), or more preferably 30% to 100% amino acid sequence identity to amino acids 1-166 of SEQ ID NO:4. For example, the Family 45 cellulase may comprise an amino acid sequence that is 20, 30, 40, 50, 60, 65, 70, 75, 80, 85, 90, 95 or 100% identical to amino acids 1-166 of SEQ ID NO:4.

According to a further embodiment, the Family 45 cellulase is a sub-family A cellulase and has 30% to 100% amino acid sequence identity to amino acids 1-213 of SEQ ID NO:7 (HiCel45A), or more preferably 40% to 100% amino acid sequence identity to amino acids 1-213 of SEQ ID NO:7. For example, the Family 45 cellulase may comprise an amino acid sequence that is 30, 40, 50, 60, 65, 70, 75, 80, 85, 90, 95 or 100% identical to amino acids 1-213 of SEQ ID NO:7.

The Family 45 cellulase may be a naturally-occurring or wild-type Family 45 cellulase or a modified Family 45 cellulase. By "modified Family 45 cellulase", it is meant a Family 45 cellulase that contains one or more genetic alteration, introduced by genetic engineering techniques, which do not significantly compromise the structure and function of the enzyme. Such techniques include, but are not limited to, site-directed mutagenesis, cassette mutagenesis, random mutagenesis, including that conducted on isolated DNA or by exposing a microorganism to a mutagen, such as UV light, synthetic oligonucleotide construction, cloning, sub-cloning, amplification by PCR, in vitro synthesis and other genetic engineering techniques. As would be appreciated by those of ordinary skill in the art, but without being limiting in any manner, mutations introduced in regions of low sequence conservation among Family 45 cellulases are expected to have a lower probability of reducing or altering the catalytic activity of the enzyme.

It will be understood that the modified Family 45 cellulase may be derived from any suitable Family 45 cellulase. That is, it may be derived from a naturally-occurring or "wild-type" Family 45 cellulase or from a Family 45 cellulase that already contains other amino acid substitutions, deletions or insertions. By the term "wild-type Family 45 cellulase" it is meant a Family 45 cellulase that does not contain any genetic alteration(s) introduced by molecular biology techniques.

Family 5 Cellulases

The amino acid sequences for over 3,000 naturally occurring Family 5 cellulases of fungal and bacterial origin have been elucidated. Regions of Family 5 cellulases are well conserved in most Family 5 cellulase enzymes and this has allowed the alignment of parts of the catalytic domains of family members.

Table 3 below includes a representative list of 14 known Family 5 cellulases and FIG. 3 shows an amino acid sequence alignment among the cellulases provided in the table. The percent sequence identities of the Family 5 cellulases of Table 3 are determined using the procedure described previously for the Family 45 cellulases.

TABLE 3

Family 5 cellulase family members and sequence identity with TrCel5A catalytic domain (%).

| Organism | Abbreviated Name | GenBank Accession Number | SEQ ID NO: | Percent identity with TrCel5A amino acids 71-397 of SEQ ID NO: 2 |
|---|---|---|---|---|
| Trichoderma reesei | TrCel5A | AAA34213.1 | 2 | 100.0 |
| Penicillium janthinellum | PjEgl2 | CAA61740.1 | 65 | 62.0 |
| Macrophomina phaseolina | MpEgl2 | AAB03889.1 | 66 | 58.1 |
| Cryptococcus flavus | CfEgl1 | AAC60541.1 | 67 | 43.2 |
| Aspergillus nidulans | AnEglA | EAA65878.1 | 68 | 28.8 |
| Aspergillus kawachii | AkCel5A | BAB62317.1 | 69 | 27.1 |
| Macrophomina phaseolina | MpEgl1 | AAB51451.1 | 70 | 27.8 |
| Volvariella volvacea | VvEG1 | AAG59832.1 | 71 | 27.6 |
| Thermoascus aurantiacus | TaEg1 | AAL88714.2 | 72 | 27.5 |
| Aspergillus aculeatus | AaCel1 | AAC08587.1 | 73 | 26.3 |
| Humicola insolens | HiCMC3 | CAA53631.1 | 74 | 26.6 |
| Orpinomyces joyonii | OjCelB29 | AAB69347.1 | 75 | 14.4 |
| Acidothermus cellulolyticus | AcCel5A | AAA75477.1 | 76 | 16.0 |
| Bacillus subtilis | BsCel5A | ACI15227.1 | 77 | 14.6 |
| Bacillus cellulosilyticus | BcNK1 | AAA22299.1 | 78 | 14.5 |

As used herein, the term "Family 5 cellulase" or "Cel5A" encompasses a carbohydrate active cellulase enzyme that contains aglycohydrolase (GH) Family 5 catalytic domain that is classified under EC 3.2.1.4. The term encompasses any carbohydrate active enzyme that exhibits at least hydrolysis of (1→4)-beta-D-glucosidic linkages using a retaining mechanism, including enzymes with conserved R130, H174, E217, E218, H288, Y290 and E329 amino acids (determined by alignment with a Trichoderma reesei Family 5 cellulase, SEQ ID NO:2).

Enzymes of Family 5 share a common (beta/alpha)$_8$-barrel fold and a catalytic mechanism resulting in a net retention of the anomeric sugar conformation. Glycoside hydrolase catalysis is driven by two carboxylic acids found on the side chain of aspartic acid and/or glutamic acid. These two amino acids are highly conserved among family members.

The Family 5 cellulase of the invention may be a modified Family 5 cellulase comprising at least a mutation at position 363 to an alanine, serine or threonine, for example, Cel5A-G363A (SEQ ID NO:1). Generally, the amino acid introduced at position 363 is "non-native", meaning that that it does not naturally occur at the corresponding position in the wild-type Family 5 cellulase sequence from which it is derived.

By "modified Family 5 cellulase", it is meant a Family 5 cellulase that contains one or more genetic alteration introduced by genetic engineering techniques that do not significantly compromise the structure and function of the enzyme. Such techniques include, but are not limited to, site-directed mutagenesis, cassette mutagenesis, random mutagenesis, including that conducted on isolated DNA or by exposing a microorganism to a mutagen, such as UV light, synthetic oligonucleotide construction, cloning, sub-cloning, amplification by PCR, in vitro synthesis and other genetic engineering techniques. It will be understood that the modified Family 5 cellulase may be derived from any suitable Family 5 cellulase. That is, it may be derived from a naturally-occurring or "wild-type" Family 5 cellulase or from a Family 5 cellulase that already contains other amino acid substitutions, deletions or insertions.

By the term "wild-type Family 5 cellulase" it is meant a Family 5 cellulase as found in nature that does not contain any genetic alteration(s) introduced by molecular biology techniques.

The position of the 363 mutation is determined by alignment with a wild-type *Trichoderma reesei* Family 5 enzyme, also referred to herein as "TrCel5A", the amino acid sequence of which is provided in SEQ ID NO:2. By aligning the amino acids to optimize the sequence similarity between the Family 5 catalytic domains of cellulase enzymes, and by using the amino acid numbering of TrCel5A as the basis for numbering (also referred to herein as "TrCel5A numbering"), the positions of amino acids within other Family 5 cellulases can be determined relative to TrCel5A. The amino acid numbering is based on the sequence of the mature, secreted protein, i.e., the protein sequence after removal of the secretion signal peptide or leader peptide.

Additional mutations may be introduced into the modified Family 5 cellulase, provided that such mutations do not significantly compromise the structure and function of the enzyme. As would be appreciated by those of ordinary skill in the art, but without being limiting in any manner, additional mutations may be introduced in regions of low sequence conservation among Family 5 cellulases.

The modified Family 5 cellulase of the invention may contain amino acid modifications "consisting essentially of the amino acid substitution at position 363". By this it is meant that the modified Family 5 cellulase contains no more than 20 other amino acid modifications in its sequence relative to a corresponding wild-type Family 5 cellulase. In another example of the invention, the modified Family 5 cellulase contains no more than 15 other amino acid modifications, no more than 10 other amino acid modifications or no more than 5 other amino acid modifications in its sequence. As mentioned previously, such additional amino acid modifications may be introduced at non-conserved positions in the amino acid sequence. Without being limiting in any manner, such modifications are typically amino acid substitutions.

The additional amino acid modification(s), including, but not limited to amino acid substitutions, may be introduced by standard molecular biology techniques such as random mutagenesis, site-directed mutagenesis or directed evolution.

Representative examples of Family 5 cellulases that do not contain an alanine at position 363 of the wild-type sequence (TrCel5A numbering) and that can be modified in accordance with the invention include enzyme species from the genera of *Trichoderma, Hypocrea, Penicillium, Botryotinia, Macrophomina, Aspergillus, Orpinomyces, Acidothermus, Pestalotiopsis* and *Xylella*. In one example of the invention, the modified Family 5 cellulase is derived from species selected from the group consisting of *Trichoderma reesei* (SEQ ID NO:2), *Trichoderma viride, Hypocreajecorina, Penicilliumdecumbens, Penicilliumjanthinellum, Botryotiniafuckeliana, Xylellafastidiosa, Macrophominaphaseolina, Aspergilluskawachii, Aspergillusaculeatus, Orpinomycesjoyonii* and *Acidothermuscellulolyticus*. Table 3 provides the SEQ ID NO: and database accession number for the amino acid sequences of wild-type, nativeFamily 5 cellulases from these organisms.

Modified Family 5 cellulases of the invention may have conserved R130, H174, E217, E218, H288, Y290 and E329 amino acids and exhibit greater than about 20% or greater than about 30% sequence identity with the TrCel5A catalytic domain (amino acids 71-397 of SEQ ID NO:2).

In another embodiment of the invention, the modified Family 5 cellulase has greater than about 30% sequence identity, greater than about 40% sequence identity, greater than about 50% sequence identity or greater than about 60% sequence identity with the TrCel5A catalytic domain (amino acids 71-397 of SEQ ID NO:2).

Family 6 Cellulase

Family 6 cellulases comprise two aspartic acid (D) amino acids which may serve as catalytic amino acids. These aspartic acid amino acids are found at positions 175 and 221, as determined by alignment with a wild-type *Trichoderma reesei* enzyme. Most of the Family 6 cellulases identified thus far are mesophilic; however, this family also includes thermostable cellulases from *Thermobifidafusca* (TfCel6A and TfCel6B) and the alkalophilic cellulases from *Humicolainsolens* (HiCel6A and HiCel6B). Family 6 cellulases also share a similar three dimensional structure: an alpha/beta-barrel with a central beta-barrel containing seven parallel beta-strands connected by five alpha-helices. The three dimensional structures of several Family 6 cellulases are known, such as TrCel6A, *Thermobifidafusca* endo-beta-1,4-glucanase Cel6A, *Humicolainsolens* cellobiohydrolase Cel6A, *Humicolainsolens* endo-beta-1,4-glucanase Cel6B and *Mycobacterium tuberculosis* H37Rv Cel6A.

As used herein, the term "Family 6 cellulase" or "Cel6" encompasses a carbohydrate active cellulase enzyme that contains aglycohydrolase (GH) Family 6 catalytic domain that is classified under EC 3.2.1.91 or EC 3.2.1.4. The term encompasses any carbohydrate active enzyme that exhibits at least hydrolysis of (1-4)-beta-D-glucosidic linkages in cellulose linkages using an inverting mechanism, including enzymes with conserved aspartic acid amino acids found at positions 175 and 221 (based on alignment with *Trichoderma reesei* Cel6A amino acid numbering; SEQ ID NO:3).

According to one embodiment, the Family 6 cellulase has 60% to 100% amino acid sequence identity to amino acids 83-447 of SEQ ID NO:3 (*Trichoderma reesei* Family 6 cellulase), or, in a further embodiment, 65% to 100% amino acid sequence identity to amino acids 83-447 of SEQ ID NO:3. For example, the Family 6 cellulase may comprise an amino acid sequence that is 60, 65, 70, 75, 80, 85, 90, 95 or 100% identical to amino acids 83-447 of SEQ ID NO:3.

Table 4 below provides a representative list of known Family 6 cellulases and FIG. 9 shows an amino acid sequence alignment among the cellulases provided in the table. The percent sequence identities of the Family 6 cellulases of Table 4 are determined using the procedure described previously for the Family 45 cellulases.

TABLE 4

Family 6 cellulase family members and sequence identity with the TrCel6A catalytic domain (%).

| Organism | GenBank Accession Number | SEQ ID NO: | Percent identity with amino acids 83-447 of TrCel6A ((SEQ ID NO: 3)) |
|---|---|---|---|
| Trichoderma reesei | AAA34210.1 | 3 | 100.0 |
| Hypocrea koningii | AAK01367.1 | 79 | 98.9 |
| Trichoderma viride CICC 13038 | AAQ76094.1 | 80 | 98.9 |
| Hypocrea koningii 3.2774 | ABF56208.1 | 81 | 98.1 |
| Hypocrea koningii AS3.2774 | ABG48766.1 | 82 | 97.8 |
| Trichoderma parceramosum | AAU05379.2 | 83 | 97.8 |
| Aspergillus nidulans FGSC A4 | ABF50873.1 | 84 | 72.4 |
| Aspergillus niger CBS 513.88 | CAK41068.1 | 85 | 72.4 |
| Aspergillus oryzae RIB 40 | BAE64227.1 | 86 | 67.8 |
| Aspergillus niger CBS 513.88 | CAK39856.1 | 87 | 67.7 |
| Acremonium cellulolyticus Y-94 | AAE50824.1 | 88 | 67.3 |
| Talaromyces emersonii | AAL78165.2 | 89 | 66.8 |
| Gibberella zeae K59 | AAQ72468.1 | 90 | 66.1 |
| Fusarium oxysporum | AAA65585.1 | 91 | 66.1 |
| Neurospora crassa OR74A | CAD70733.1 | 92 | 65.9 |
| Aspergillus nidulans FGSC A4 | EAA65866.1 | 93 | 65.5 |
| Aspergillus tubingensis | CAH05675.1 | 94 | 65.5 |
| Magnaporthe grisea 70-15 | XP_360146.1 | 95 | 65.4 |
| Chaetomium thermophilum | CAH05669.1 | 96 | 65.1 |
| Chaetomium thermophilum CT2 | AAW64927.1 | 97 | 65.0 |
| Stilbella annulata | CAH05678.1 | 98 | 64.9 |
| Humicola insolens | BAB39154.1 | 99 | 63.7 |
| Humicola insolens | 1BVW* | 100 | 63.1 |
| Cochliobolus heterostrophus C4 | AAM76664.1 | 101 | 59.6 |
| Agaricus bisporus D649 | AAA50607.1 | 102 | 57.7 |
| Polyporus arcularius 69B-8 | BAF80327.1 | 103 | 57.1 |
| Lentinula edodes Stamets CS-2 | AAK95564.1 | 104 | 56.3 |
| Lentinula edodes L54 | AAK28357.1 | 105 | 56.0 |
| Malbranchea cinnamomea | CAH05679.1 | 106 | 54.9 |
| Phanerochaete chrysosporium | AAB32942.1 | 107 | 54.9 |
| Volvariella volvacea | AAT64008.1 | 108 | 53.8 |
| Chrysosporium lucknowense | AAQ38151.1 | 109 | 49.5 |
| Pleurotus sajor-caju | AAL15037.1 | 110 | 47.2 |
| Trametes versicolor | AAF35251.1 | 111 | 47.0 |
| Neurospora crassa OR74A | XP_323315.1 | 112 | 46.8 |
| Magnaporthe grisea 70-15 | XP_362054.1 | 113 | 45.1 |

*Protein databank entry

The Family 6 cellulase may be a naturally-occurring or wild-type Family 6 cellulase or a modified Family 6 cellulase. By "modified Family 6 cellulase", it is meant a Family 6 cellulase that contains one or more genetic alteration, introduced by molecular biology techniques, which do not significantly compromise the structure and function of the enzyme. Such techniques include, but are not limited to, site-directed mutagenesis, cassette mutagenesis, random mutagenesis, including that conducted on isolated DNA or by exposing a microorganism to a mutagen, such as UV light, synthetic oligonucleotide construction, cloning, sub-cloning, amplification by PCR, in vitro synthesis and other genetic engineering techniques. As would be appreciated by those of ordinary skill in the art, but without being limiting in any manner, mutations introduced in regions of low sequence conservation among Family 6 cellulases are expected to have a lower probability of reducing or altering the catalytic activity of the enzyme.

It will be understood that a modified Family 6 cellulase may be derived from any suitable Family 6 cellulase. That is, it may be derived from a naturally-occurring or "wild-type" Family 6 cellulase or from a Family 6 cellulase that already contains other amino acid substitutions, deletions or insertions. By the term "wild-type Family 46 cellulase" it is meant a Family 6 cellulase that does not contain any genetic alteration(s) introduced by molecular biology techniques.

Measurement of the Specific Depilling Activity of the Enzyme Mixture

The depilling composition of the present invention comprises an enzyme mixture, which enzyme mixture comprises (i) a Family 45 cellulase enzyme component; and (ii) at least one or more additional cellulase enzyme components that are selected from the group consisting of a Family 5 cellulase, a Family 6 cellulase, and a combination thereof, wherein said enzyme mixture is enriched in the Family 45 cellulase and the Family 5 and/or Family 6 cellulase components relative to a reference enzyme mixture.

By "enriched" it is meant that the amount of the of the Family 45 and Family 5 and/or Family 6 cellulases, is increased relative to all of the other cellulase components present in the enzyme mixture relative to those present in a reference or parental enzyme mixture. This may be achieved by increasing the amounts of the Family 45 and Family 5 and/or Family 6 cellulases present in the enzyme mixture and/or decreasing the amounts of one or more other cellulase components present in the reference enzyme mixture.

By "reference enzyme mixture" it is meant an enzyme mixture comprising the same Family 45 cellulase component and the same Family 5 and/or Family 6 cellulase component(s) as the enzyme mixture in the depilling composition but at naturally-occurring amounts. By "naturally occurring amounts" it is meant the amount of the Family 45 and Family 5 and/or Family 6 cellulase components produced by a parental microbe under essentially the same culturing conditions those used to produce the enzyme mixture of the depilling composition from a genetically modified microbe.

For example, such enzyme mixtures enriched in the Family 45 cellulase and the Family 5 or Family 6 cellulase components exhibit a specific depilling activity that is greater than that exhibited by the corresponding reference enzyme mixture.

In order to determine the specific depilling activity of the cellulase components in isolation and in combination, they are typically purified using known techniques. Examples of purification techniques that can be utilized include affinity based purification technologies. Such technologies are well known in the art and include any suitable method to selectively bind a component of a biological mixture to a solid support based on a highly specific biological interaction such as that between antigen and antibody or enzyme and substrate. Moreover, the purification can comprise fractionation methods including selective precipitation such as ammonium sulfate precipitation, isoelectric precipitation, selective thermal denaturation or any other suitable method that selectively precipitates the cellulase components. In another example, the purification methodology can comprise chromatographic methods including gel filtration, size exclusion, anion exchange, cation exchange, gel electrophoresis, or other chromatic separation methods known in the art for physically separating proteins.

The "specific depilling activity" as used herein, is determined as set forth in Example 1.6. The effectiveness of the Family 45 cellulase in combination with the Family 5 cellulase or the Family 6 cellulase and the respective individual cellulase components in removing small balls of fuzz, referred to as pills, from fabric is measured by directly weighing released insoluble cellulose. The depilling is expressed as the depilling activity per unit of protein (i.e., specific depilling activity).

According to one embodiment of the invention, (i) the Family 45 cellulase enzyme component and the Family 5 cellulase; or (ii) the Family 45 cellulase and the Family 6 cellulase enzyme component are present in the enzyme mixture at a weight ratio that exhibits synergy in an assay that measures specific depilling activity.

By "weight ratio that exhibits synergy", it is meant that the cellulase enzyme components are present in a weight ratio that results in a specific depilling activity that is greater than the sum of the specific depilling activity of each of said cellulase enzyme components assayed in isolation. The weight ratio is measured relative to the two cellulase enzyme components in the enzyme mix.

For example, in those embodiments in which the Family 45 and Family 5 cellulase components are included in the enzyme mixture at a weight ratio that differs from that present in an enzyme mixture secreted by the parental strain, the enzyme mixture will be characterized in that the Family 45 and Family 5 cellulase components, in combination, exhibit a specific depilling activity that is greater than the sum of the Family 45 and Family 5 cellulase components assayed individually in isolation.

In some embodiments, the weight ratio of the Family 45 cellulase component to the Family 5 cellulase enzyme component is between 0.20:1 and 9:1 (wt:wt) or any value therebetween. For example, the weight ratio of the Family 45 cellulase component to the Family 5 cellulase enzyme component may be between 0.20:1 and 5:1 or between 0.25:1 and 4:1 or between 0.25:1 and 3:1 or between 0.25 and 2:1 or between 0.25:1 and 1.5:1 or between 0.25 and 1.25:1 or between 0.25 and 1.0:1 (wt:wt), or any value therebetween. In some embodiments, the weight ratio of the Family 45 cellulase component to the Family 6 cellulase component is between 5:1 and 1:1 (wt:wt) or any value therebetween. For example, the weight ratio of the Family 45 cellulase component to the Family 6 cellulase component may be between 4:1 and 1:1 or between 3:1 and 1:1 or between 2.7:1 and 1:1 or between 2.7:1 and 1.25:1 (wt:wt) or any value therebetween.

Expression of the Cellulase Mixture in a Host Microbe

The present invention provides a genetically modified microbe expressing a Family 45 cellulase and one or more additional cellulase enzyme component selected from a Family 5 cellulase, a Family 6 cellulase or a combination thereof.

The host microbe may be any suitable yeast or a filamentous fungus, such as those microbes that are members of the phylum Ascomycota. Genera of yeasts useful as host microbes for the expression of the enzyme mixture of the present invention include *Saccharomyces* spp, *Pichia* spp, *Hansenula* spp, *Kluyveromyces* spp, *Yarrowia* spp, and *Arxula* spp. Genera of fungi useful as microbes for the expression of cellulases of the present invention include *Trichoderma* spp, *Hypocrea* spp, *Aspergillus* spp, *Fusarium* spp, *Humicola* spp, *Neurospora* spp, *Myceliopthora* sp., *Chrysosporium* spp, and *Penicillium* spp. In a most preferred embodiment, the host microbe is an industrial strain of *Trichoderma reesei*.

A parental host microbe is a microbe that is capable of the production and secretion of cellulase enzymes, but which exhibits wild-type or native copy number or expression of the identified genes that are increased in copy number or expression in the genetically modified microbe. In the case of the expression of a heterologous cellulase, the parental host microbe is a strain that is capable of the production and secretion of cellulase enzymes, but which does not express, or contain a copy of the gene encoding, the heterologous cellulase.

Overexpression

Overexpression of a cellulase enzyme refers to any state in which that cellulase enzyme is caused to be expressed at an elevated rate or level as compared to either (a) the endogenous expression rate or level of that same cellulase enzyme by the host microbe or (b) the expression rate or level of one or more other enzymes produced and secreted by the host microbe. As such, overexpression of a cellulase enzyme may result from overexpression of a gene encoding the cellulase enzyme of interest as well as a decrease in expression of one or more genes encoding one or more other enzymes produced and secreted by the host microbe.

Overexpression of a gene encoding a Family 45, Family 5 or Family 6 cellulase enzyme refers to any state in which such gene is caused to be expressed at an elevated rate or level in the host microbe as compared to the endogenous expression rate or level for that gene in the parental host microbe. In some examples, overexpression refers to an elevated transcription rate or level of an endogenous gene compared to the endogenous translation rate or level for that gene. In other examples, overexpression refers to transcription of a gene encoding a heterologous cellulase from another organism, which gene is introduced into a host cell.

Overexpression of a gene encoding a Family 45, Family 5 or Family 6 cellulase enzyme may also refer to any state in which the rate or level of gene(s) encoding one or more other (cellulase) enzymes produced and secreted by the host microbe is reduced relative to the rate or level of the same gene(s) in the parental host microbe.

A Family 45, Family 5 or Family 6 cellulase will be considered as being overexpressed by a modified microbe if the Family 45, Family 5 or Family 6 cellulase is produced at higher levels by the modified microbe than by a parental host microbe at essentially the same fermentation conditions. For example, the Family 45, Family 5 or Family 6 cellulase may be produced at an amount that is greater than about 1.1-fold to about 50-fold, or any amount therebetween, than is produced by the parental host at essentially the same fermentation conditions. For example, the Family 45 cellulase may be produced at an amount that is greater than 1.1-, 1.5-, 2-, 5-, 10-, 20-, 30-, 40- or 50-fold higher, or an amount therebetween, than the amount produced by the parental host microbe at essentially the same fermentation conditions. Preferably, the Family 45 cellulase is produced at an amount that is at least 1.1-fold more than the parental host at the same fermentation conditions.

In at least some embodiments of the present invention, the increase or decrease in copy number or expression of a gene can be produced by any of various genetic engineering techniques. As used herein, the term genetic engineering technique refers to any of several well-known techniques for the direct manipulation of an organism's genes. For example, gene knockout (insertion of an inoperative DNA sequence, often replacing the endogenous operative sequence, into an organism's chromosome), gene knock-in (insertion of a protein-coding DNA sequence into an organism's chromosome), and gene knockdown (insertion of DNA sequences that encode antisense RNA or small interfering RNA, i.e., RNA interference (RNAi)) techniques are well known in the art. Methods for decreasing the expression of a gene also include partial or complete deletion of the gene, and disruption or replacement of the promoter of the gene such that transcription of the gene is greatly reduced or even inhibited. For example, the promoter of the gene can be replaced with a weak promoter, as exemplified by U.S. Pat. No. 6,933,133, which is incorporated by reference herein in its entirety. As used herein, a gene deletion or deletion mutation is a mutation in which part of a sequence of the polynucleotide sequence making up the gene is missing. Thus, a deletion is a loss or replacement of genetic material resulting in a complete or partial disruption of the sequence of the DNA making up the gene.

According to one embodiment of the invention, overexpression of a gene encoding the Family 45, Family 5 and/or Family 6 cellulase enzyme is achieved by introducing into a host microbe one or more genetic construct(s) comprising a polynucleotide sequence(s) encoding the cellulase enzyme(s) that is to be overexpressed. The polynucleotide sequence(s) encoding the cellulase enzyme(s) may be operably linked to regulatory sequences that direct the expression and secretion of the cellulase enzyme(s), including: (i) a polynucleotide sequence encoding a secretion signal peptide from a secreted protein that may be endogenous or heterologous to the host cell; and (ii) a constitutive or regulated promoter derived from a gene that is highly expressed in the host microbe under industrial fermentation conditions. In addition, a translational enhancer may be added to increase protein translation. These regulatory sequences may be derived from one or more genes, including, but not limited to, the gene encoding the cellulase enzyme to be expressed (provided that these regulatory sequences are functional in the host cell). Moreover, multiple copies of the genetic construct(s) comprising a polynucleotide sequence(s) encoding the cellulase enzyme(s) may be introduced into the microbe, thereby increasing expression levels. Changes in expression can also be achieved by mutagenesis and selection of strains with desired expression levels.

The genetic construct may comprise other polynucleotide sequences that allow it to recombine with sequences in the genome of the host microbe so that it integrates into the host genome. Alternatively, the genetic construct may not contain any polynucleotide sequences that direct sequence-specific recombination into the host genome. In such cases, the construct may integrate by random insertion through non-homologous end-joining and recombination. Alternatively, the construct may remain in the host in non-integrated from, in which case it replicates independently from the host microbe's genome.

The genetic construct(s) may further comprise a selectable marker gene to enable isolation of a genetically modified microbe transformed with the construct as is commonly known to those of skill in the art. The selectable marker gene may confer resistance to an antibiotic or the ability to grow on medium lacking a specific nutrient to the host organism that otherwise could not grow under these conditions. The present invention is not limited by the choice of selectable marker gene, and one of skill in the art may readily determine an appropriate gene. For example, the selectable marker gene may confer resistance to hygromycin, phleomycin, kanamycin, geneticin, or G418, or may complement a deficiency of the host microbe in one of the trp, arg, leu, pyr4, pyr, ura3, ura5, his, or ade genes or may confer the ability to grow on acetamide as a sole nitrogen source.

The genetic construct may further comprise other nucleic acid sequences as is commonly known to those of skill in the art, for example, transcriptional terminators, nucleic acid sequences encoding peptide tags, synthetic sequences to link the various other nucleic acid sequences together, origins of replication, and the like. The practice of the present invention is not limited by the presence of any one or more of these other nucleic acid sequences.

The genetic construct may be introduced into the host microbe by any number of methods known by one skilled in the art, including but not limited to, treatment of cells with CaCl2, electroporation, biolistic bombardment, PEG-mediated fusion of protoplasts (e.g. White et al., WO 2005/093072, which is incorporated herein by reference). After selecting the recombinant strains, such strains may be cultured in submerged liquid fermentations under conditions that enable the expression of the Family 45, Family 5 and/or Family 6 cellulase enzymes.

Depending on the host strain and the regulatory sequences present in the genetic construct, expression levels can be modulated by adjusting one or more parameters of the fermentation process used to produce the cellulase enzymes from the host microbe including, but not limited to, the carbon source, the temperature of the fermentation, or the pH of the fermentation. Yet another means for adjusting expression levels of cellulase involves the modification of cellulase secretion pathways or modification of cellulase transcriptional and/or translational regulation systems and/or post-translational protein maturation machinery (e.g. transcription factors, protein chaperones).

Homologous and Heterologous Expression

In some embodiments, the Family 45, Family 6 and/or Family 5 cellulase component(s) in the enzyme mixture is endogenous to the host cell. In other embodiments, the Family 45, Family 6 and/or Family 5 cellulase component is heterologous or exogenous to the host cell.

For purposes herein, a heterologous or exogenous cellulase enzyme refers to an enzyme that is encoded by a gene derived from a species that is distinct from the host microbe. An endogenous or homologous cellulase enzyme refers to an enzyme that is encoded by a gene derived from the same sequences as the host microbe. Thus, in some examples, a homologous or heterologous cellulase enzyme is encoded by a polynucleotide sequence that is derived from a species that is, respectively, the same as or different from the species of the host microbe expressing the cellulase enzyme, as well as recognized anamorphs, teleomorphs or taxanomic equivalents of the host microbe. As is appreciated by one of skill in the art, the amino acid sequence of a homologous or heterologous cellulase enzyme may be naturally-occurring (i.e., as it is found in nature when produced by the source organism) or may contain one or more amino acid insertions, deletions or substitutions relative to the naturally-occurring amino acid sequence as a result of genetic manipulation, adaptation or classical mutagenesis causing changes in the polynucleotide sequence encoding said heterologous cellulase enzyme.

Although expression from a single host microbe has been described, the Family 45, Family 6 and/or Family 5 cellulases may be expressed individually or in sub-groups from different strains of one or more host microbes. For example, it is contemplated that the Family 45, Family 6 and/or Family 5 cellulases may be expressed individually or in sub-groups from different strains of a single host microbe.

After selecting the recombinant host strains overexpressing the Family 45, Family 6 and/or Family 5 genes, they may be cultured in submerged liquid fermentations under conditions that induce the expression of the cellulases, as discussed below.

Production of the Cellulase Enzyme Mixture from the Host Microbe

Submerged liquid fermentations of microorganisms are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. A batch process for producing the enzyme mixture of the present invention may be carried out in a shake-flask or a bioreactor.

In a fed-batch process, the culture is fed continuously or sequentially with one or more media components without the removal of the culture fluid. In a continuous process, fresh medium is supplied and culture fluid is removed continuously at volumetrically equal rates to maintain the culture at a steady growth rate.

Fermentation medium typically comprises a carbon source, a nitrogen source and other nutrients, vitamins and minerals which can be added to the fermentation media to improve growth and enzyme production of the host cell. The various media components may be added prior to, simultaneously with or after inoculation of the culture with the host cell.

When producing the cellulase enzyme mixture of the present invention, the carbon source may comprise a carbohydrate that will induce the expression of the cellulase enzyme mixture from the genetically modified microbe. For example, the carbon source may comprise one or more of cellulose, cellobiose, sophorose, and related oligo- or polysaccharides known to induce expression of cellulases.

In the case of batch fermentation, the carbon source may be added to the fermentation medium prior to or simultaneously with inoculation. In the cases of fed-batch or continuous operations, the carbon source may be supplied continuously or intermittently during the fermentation process. For example, the carbon feed rate may be between 0.2 and 4.0 g carbon/L of culture/h, or any amount therebetween.

Following fermentation, the fermentation broth containing the cellulase enzyme mixture may be used directly, or the cellulase enzyme mixture may be separated from the host cells, for example by filtration or centrifugation. Low molecular solutes such as unconsumed components of the fermentation medium may be removed by ultra-filtration. The enzyme mixture may be concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase enzyme to prevent growth of microbial contamination.

Treatment of Cellulose-Containing Goods Using the Enzyme Mixture

The enzyme mixture of the present invention is used in the depilling of "cellulose-containing goods".

The term "cellulose-containing goods" refers to fabrics, either as piece goods or goods sewn into garments or yarn, comprising cotton or non-cotton containing fibers. The cellulose-containing goods may be treated with the enzyme mixture of the invention either before or after dyeing and with or without a resinous finish. The term encompasses natural cellulosics and manmade cellulosics. Manmade cellulose containing fabrics include regenerated fabrics, such as rayon, that are well known in the art. The term excludes fabrics that are not prone to pilling, such as denim fabrics.

As used herein, the term "depilling" refers to the use of the enzyme mixture of the present invention in a controlled hydrolysis of cellulosic fibres in order to modify the surface of the cotton goods in a manner that clears the surface structure by reducing fuzzing. Such treatment can prevent pilling, or improve fabric handle like softness and smoothness, which can result in clarification of colour and/or improve moisture adsorbability and dyeability.

Depilling treatment may be carried out during the manufacturing process or in subsequent laundering. In either case, treatment is typically carried out by adding cotton goods to a rotating horizontal or vertical drum jet dryer, washing machine, or other device that contains the fabric, water, buffer and cellulase enzyme, while providing agitation and shear to the fabric, including loose fibrils. Detergents and surfactants may also be added during the depilling treatment. After treatment, the fabric is removed from the machine and dried.

When depilling takes place in a typical manufacturing process, the treatment time may be between about 15 to about 120 minutes; treatment temperature may be about 35° C. to about 60° C.; the weight ratio of liquor to fabric may be between about 2.5:1 and about 10:1; and the pH may be about 4.0 to about 6.0. When depilling takes place in a typical laundering, the treatment time is about 10 to about 60 minutes, the treatment temperature is about 20° C. to about 70° C., the weight ratio of liquor to fabric is between about 2.5:1 and about 10:1, and the pH is about 4.0 to about 9.5 or about 4.0 to about 6.0.

The amount of cellulase mixture used to depill depends on the concentration of active protein in the cellulase mixture, the amount of cotton goods being treated, the desired degree of depilling, the desired time of treatment, and other parameters well-known to those of ordinary skill in the art. When used for depilling in a typical manufacturing process, an example of a dose of cellulase is between about 0.1 and about 7 g of enzyme protein per kilogram of fabric and more preferably between about 0.5 g and about 4 g of enzyme protein per kilogram of fabric. When used for depilling in a typical laundering, the preferred amount of cellulase is generally between about 0.01 g and about 3 g of enzyme protein per kilogram of fabric and more preferably between about 0.05 g and about 2.5 g of enzyme protein per kilogram of fabric.

One option for controlling the action of the enzyme is to destroy the enzyme after treatment by heating the solution, adding chemicals to destroy enzyme activity or by drying the cotton goods.

Detergent compositions of the present invention may be in any form known in the art. This includes as a liquid diluent, in granules, in emulsions, in gels, or in pastes. When a solid detergent composition is employed, the enzyme mixture is typically formulated as granules.

EXAMPLES

Example 1

Generation and Characterization of Cel45A Overexpressing Strains

Example 1.1

Host *Trichoderma reesei* Strains for the Overexpression of Cel45A Cellulase

The parental *Trichoderma reesei* strain used for the overexpression of TrCel45Acellulase is P998A (described in co-pending and co-owned U.S. patent application No. 61/312,864). The strain P998A was generated by the transformation of a BTR213 uridine auxotroph strain with a transformation vector (Pc/x-cel5A-G363A-pyr4-TV) designed to express high levels of Cel5A-G363A (SEQ ID NO:1) enzyme and restore prototrophic growth in the absence of uridine (see U.S. patent application No. 61/312,864, supra). The strain BTR213 is a derivative of strain RutC30 (ATCC #56765) that was isolated as a high cellulase producing derivative of the progenitor strain QM6A (Montencourt et al., Proc. $3^{rd}$ Annual Symp. On Fuels from Biomass, Golden Colorado, 1979, pp. 85-89). Further cellulase hyper-producing strains were generated from RutC30 by random mutation and/or selection. Strain M2C38(ATCC 74252) was isolated based on its ability to produce larger clearing zones than RutC30 on minimal media agar containing 1% acid swollen cellulose and 4 g L$^{-1}$ 2-deoxyglucose. Subsequently, M2C38 was subjected to further random mutagenesis and strain BTR213 was isolated by selection on lactose media containing 0.2 µg/mL carbendazim. A uridine auxotroph of BTR213, BTR213aux, was obtained through selection of mutants spontaneously resistant to 0.15% w/v 5-fluoroorotic-acid (FOA). The prototrophy was restored by transformation with a heterologous *Neurosporacrassa* gene pyr4 encoding orotidine-5'-monophosphate decarboxylase used as a selection marker to generate the strain P998A.

Example 1.2

*T. reesei* Transformation Vectors for Overexpression of TrCel45A

Figure 5:
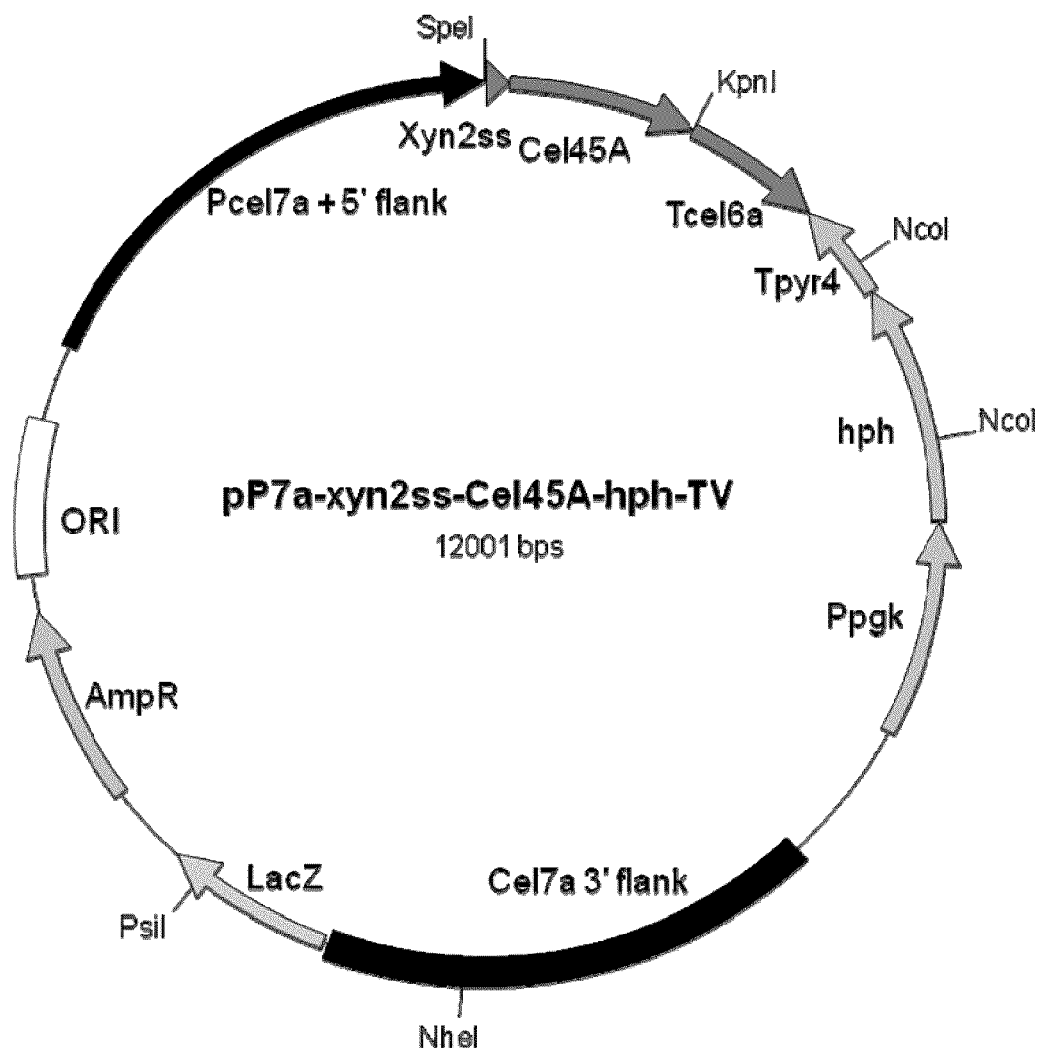
FIG. 5 is a map of the *Trichodermareesei* transformation vector pP7a-xyn2ss-Cel45A-hph-TV.
Figure 6:
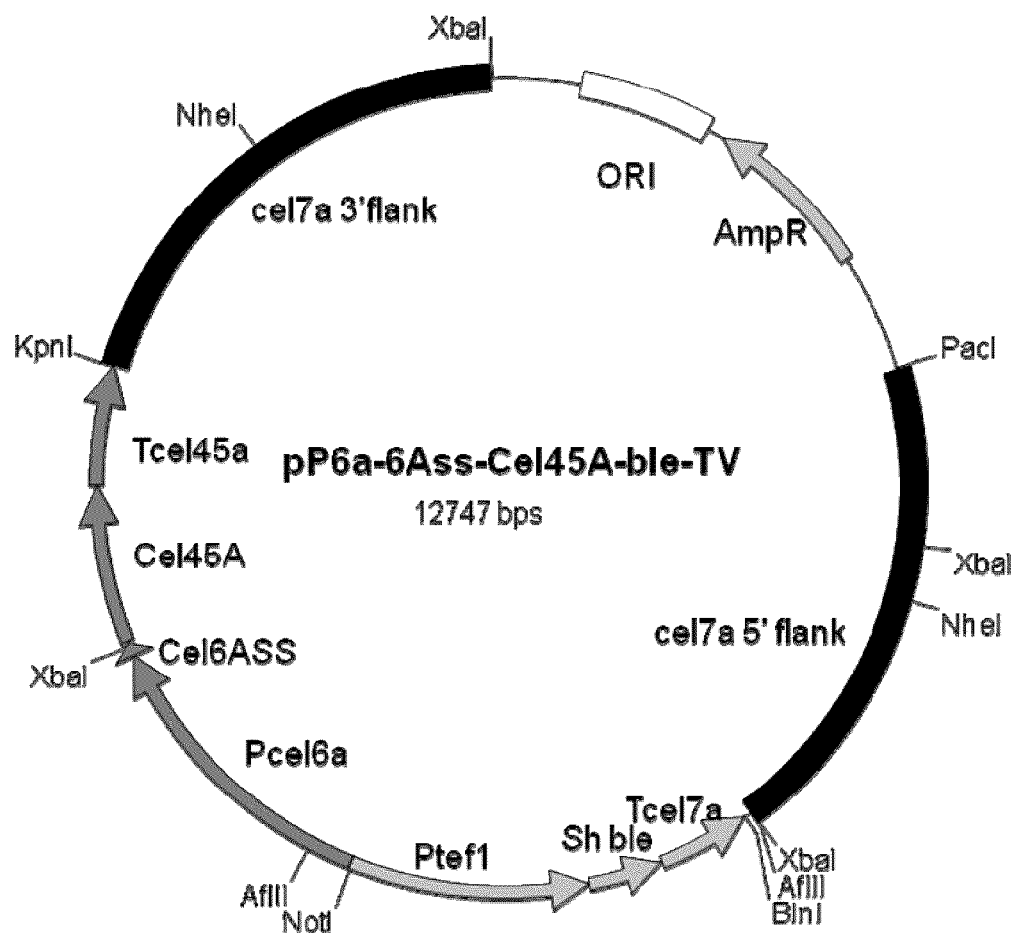
FIG. 6 is a map of the *Trichodermareesei* transformation vector pP6a-6Ass-Cel45A-ble-TV.

Three TrCel45A expression vectors were used for *T. reesei* transformations. All vectors were designed to target the native Trcel7a locus. To facilitate targeting, sequences adjacent to the 5' and 3' ends of the native Trcel7a gene amplified from BTR213 genomic DNA were inserted into the transformation vectors so as to flank the expression and selection cassettes (FIGS. 4-6).

The transformation vector, pP7a-TrCel45A-hph-TV (FIG. 4), contains the *E. coli* hygromycinphosphotransferase gene (hph) as a selectable marker. The transcription of the hph gene is driven by a *T. reesei* phophoglycerate kinase promoter (Ppgk) and terminated by the terminator sequence of an *N. crassa* orotidine-5'-monophosphate decarboxylase (pyr4) gene (Tpyr4). The expression cassette contains a *T. reesei* cel7a promoter (Pcel7a) as a part of the 5' flank of the Trcel7a targeting fragment, a *T. reesei* pre-mature Cel45A coding sequence (including the TrCel45A secretion signal) and a *T. reesei* cel6a terminator (TCel6a) as shown in FIG. 4. The vector pP7a-TrCel45A-hph-TV was linearized with PsiI before transformation.

The transformation vector, pP7a-xyn2ss-Cel45A-hph-TV (FIG. 5), also contains the *E. coli* hygromycinphosphotransferase gene (hph) as a selectable marker. The transcription of the hph gene is driven by the phophoglycerate kinase promoter and terminated by a pyr4(*N. crassa* orotidine-5'-monophosphate decarboxylase) terminator. The expression cassette contains a *T. reesei* cel7a promoter (Pcel7a) as a part of the 5' flank of the cel7a targeting fragment, a *T. reesei* xylanase 2 secretion signal coding sequence (Xyn2ss), a *T. reesei* mature Cel45A coding sequence and a *T. reesei* cel6a terminator (TCel6a) as shown in FIG. 5. The vector, pP7a-xyn2ss-Cel45A-hph-TV, was linearized with PsiI before transformation.

The transformation vector, pP6a-6Ass-Cel45A-ble-TV (FIG. 6), contains an Shble bleomycin resistance gene as a selectable marker. The Shble gene encodes the *Streptoallotei-chushindustanus* bleomycin resistance protein, ShBle, which confers resistance to bleomycin, zeocin and phloemycin. The transcription of the ShBle gene from the selection cassette is driven by a tef1 (translation elongation factor 1) promoter (Ptef1) and terminated by a cel7a terminator (Tcel7a). The expression cassette contains a *T. reesei* cel6a promoter (Pcel6a), a *T. reesei* Cel6A secretion signal coding sequence (Cel6ASS), a *T. reesei* mature Cel45A coding sequence and a *T. reesei* cel45a (Tcel45a) terminator as shown in FIG. 6. The vector, pP6a-6Ass-Cel45A-ble-TV, was linearized with PacI before transformation.

Example 1.3

Generation of TrCel45A Overexpressing *T. reesei* Strains

The strains overexpressing TrCel45A from a single integrated transgene copy were generated by transformation of the parental P998A strain with transformation vectors, pP7a-xyn2ss-Cel45A-hph-TV or pP7a-TrCel45A-hph-TV, designed to express high levels of native *T. reesei* Cel45A and target the native Trcel7a locus. The transformation vector was introduced by poly-ethylene glycol (PEG) mediated transformation. The P998A strain (5×10$^6$ spores) was plated onto sterile cellophane overlaid on Potato Dextrose agar (PDA) and the plates were incubated for 20 hours at 30° C. to facilitate spore germination and mycelial growth. Cellophane discs with mycelia were transferred to 10 mL of a protoplasting solution containing 7.5 g/LDriselase and 4 g/L beta-glucanase (InterSpex Products Inc., Cat. Nos. 0465-1 and 0439-2, respectively) in 50 mM potassium phosphate buffer, pH 6.5 containing 0.6 M ammonium sulfate (Buffer P). The mycelial mat was digested for 5 hours by gentle agitation at 60 rpm. Protoplasts were separated from the undigested mycelia by filtration through sterile No. 30 MIRACLOTH™ and collected into a sterile 50 mL round-bottom centrifuge tube and recovered by centrifugation at 1000-1500× g for 10 min at room temperature. Protoplasts were washed with 5 mL of Buffer P and centrifuged again at 1000-1500× g for 10 min at room temperature. Protoplasts were resuspended in 1 mL of STC buffer (1.2 M sorbitol, 10 mM CaCl$_2$, 10 mMTris-HCl, pH 7.5).

For transformation, 0.1 mL of resuspended protoplasts was combined with 0.01 mg of transformation vector linearized with PsiI restriction enzyme and 0.025 mL of PEG solution (25% PEG 3350, 50 mM CaCl$_2$, 10 mMTris-HCl, pH 7.5). After incubation in an ice water bath for 30 min, 1 mL of the PEG solution was added and the mixture incubated for 5 min at room temperature. The resultant transformation mix was diluted with 2 mL of STC buffer and the entire mix was added to 50 mL of molten MMSS agar media (Table 5 below) cooled to about 47° C. and poured into large plates. The plates were incubated at 30° C. overnight and an overlay of MMSS media supplemented with 60 U/mL of hygromycin was added for the selection of transformed cells. The plates were further incubated at 30° C. until colony growth was visible. Transformants were transferred to individual plates containing PDA agar supplemented with hygromycin and allowed to sporulate. Spores were collected and plated at high dilution on PDA-hygromycin media to isolate homokaryon transformants, which were then plated onto PDA to allow for growth and sufficient sporulation to inoculate the screening cultures described below. One transformant containing a single of the pP7a-xyn2ss-Cel45A-hph-TV vector integrated ectopically into the P998A genome was selected for further transformation.

The strains overexpressing TrCel45A from two integrated transgene copies were generated using P1498Se as a parental strain. This strain was transformed with the transformation vector, pP6a-6Ass-Cel45A-ble-TV, designed to express high levels of native *T. reesei* Cel45A and target the cel7a locus. This vector was also introduced by poly-ethylene glycol (PEG) mediated transformation as described above. The transformants were selected on PDA media containing 100 µg/mL of phleomycin.

TABLE 5

Minimal medium (MM) agar

| Component* | Amount per L |
|---|---|
| KH$_2$PO$_4$ | 10 g |
| (NH$_4$)$_2$SO$_4$ | 6 g |
| Na$_3$Citrate•2H$_2$O | 3 g |
| FeSO$_4$•7H$_2$O | 5 mg |
| MnSO$_4$•H$_2$O | 1.6 mg |
| ZnSO$_4$•7H$_2$O | 1.4 mg |
| CaCl$_2$•2H$_2$O | 2 mg |
| Agar | 20 g |
| 20% Glucose f.s. | 50 mL |
| 1M MgSO$_4$•7H$_2$O | 4 mL |
| | pH to 5.5 |

MMSS agar contains the same components as MM agar plus 1.2M sorbitol, 6.6 g/L YNB (Yeast Nitrogen Base without Amino Acids from DIFCO Cat. No. 291940) and 1.92 g/L amino acids (-Ura DO Supplement from Sigma Cat. No. Y1501-20G).

Example 1.4

Characterization of TrCel45A Overexpressing *T. reesei* Strains

To test the production of the TrCel45A, TrCel5A and TrCel7A proteins, spores of *Trichoderma* transformants and the parental strain grown on PDA plates were suspended in sterile water and about 10$^4$-10$^6$ spores per mL were used to inoculate each micro-culture in 24-deepwell plates. The components present in the micro-culture media are provided in Table 6.

TABLE 6

The composition of micro-culture media

| Component* | g/L |
|---|---|
| KH$_2$PO$_4$ | 8 |
| (NH$_4$)$_2$SO$_4$ | 12.7 |
| MgSO$_4$•7H$_2$O | 4 |
| CaCl$_2$•2H$_2$O | 1.02 |
| Corn steep liquor | 5 |
| CaCO$_3$ | 20 |
| Carbon source** | 35 |
| Trace elements* | 2 mL/L |

*Trace elements solution contains 5 g/L FeSO$_4$•7H$_2$O; 1.6 g/L MnSO$_4$•H$_2$O; and 1.4 g/L ZnSO$_4$•7H$_2$O.
**Glucose, Solkafloc, lactose, cellobiose, sophorose, corn syrup, or Avicel. The carbon source can be sterilized separately as an aqueous solution at pH 2 to 7 and added to the remaining media initially or through the course of the fermentation.

Cultures were grown for 6 days at 30° C. with shaking at 250 rpm. The biomass was separated from the growth media containing the secreted protein by centrifugation at 12,000 rpm. The protein concentration was determined using the Bio-Rad Protein Assay (Cat. No. 500-0001). The relative abundance (in weight % of total secreted protein) of TrCel45A, TrCel5A and TrCel7A was determined by ELISA. For ELISA measurements the enzymes were first desalted using Biospin columns (Biorad) following manufacturer instructions and total protein concentration was determined using a BCA kit (Sigma) with a bovine serum albumin (Sigma) control. The same assay was used to determine the concentration of purified protein standards. Culture supernatants and purified component standards were diluted to 0.01-10 µg/mL in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for 1 hour at room temperature. Blocked microtitre wells were washed with PBS/Tween. Rabbit polyclonal antisera specific for TrCel45A, TrCel5A or TrCel7A were diluted in PBS/BSA, added to separate microtitre plates and incubated for 2 hours at room temperature. Plates were washed and incubated with a goat anti-rabbit antibody coupled to horseradish peroxidase (Sigma #A6154), diluted 1/2000 in PBS/BSA, for 1 hour at room temperature. After washing, tetramethylbenzidine was added to each plate and incubated for 30 minutes at room temperature. The absorbance at 360 nm was measured in each well and converted into a protein concentration using standard curves for each component. The abundance of TrCel45A, TrCel5A and TrCel7A was expressed as the mass percent of each component as a fraction of total secreted protein (data not shown).

The strains P1467Ve, P1498Se, P1489Ct, P1489Et, P1554ABt, P1554Te and P1554Le were selected for further analysis in 14 L pilot fermentation as they produced higher levels of TrCel45A enzyme than the parental strains BTR213 and/or P998A and maintained high levels of TrCel5A-G363A enzyme. In addition to the increased expression of TrCel45A and TrCel5A-G363A, strains P1489Ct, P1489Et and P1554ABt also are deficient in the production of native TrCel7A cellulase. The modifications introduced into selected strains are shown in Table 7.

TABLE 7

Modifications introduced into selected Cel45A overexpressing strains.

| Strain | Parental strain | TrCel5A-G363A | TrCel7A | TrCel45A secretion signal 1st copy | TrCel45A secretion signal 2nd copy | Selection marker 1st copy | Selection marker 2nd copy |
|---|---|---|---|---|---|---|---|
| P1467Ve | P998A | OE | + | Cel45A | N/A | hph | N/A |
| P1498Se | P998A | OE | + | Xyn2 | N/A | hph | N/A |
| P1489Ct | P998A | OE | Δ | Xyn2 | N/A | hph | N/A |
| P1489Et | P998A | OE | Δ | Xyn2 | N/A | hph | N/A |
| P1554ABt | P1498Se | OE | Δ | Xyn2 | Cel6A | hph | Shble |
| P1554Te | P1498Se | OE | + | Xyn2 | Cel6A | hph | Shble |
| P1554Le | P1498Se | OE | + | Xyn2 | Cel6A | hph | Shble |

OE—overexpressed,
Δ - deletion,
N/A—not applicable

Example 1.5

Enzyme Production in 14 L Pilot Fermentation

*Trichoderma* spores of strains BTR213, P998A, P1467Ve, P1498Se, P1489Ct, P1489Et, P1554ABt, P1554Te and P1554Le grown on PDA media were suspended in sterile water and transferred to 2 L, baffled Erlenmeyer flasks containing 750 mL of liquid Berkley media (pH 5.5) supplemented with 5.1 g/L of corn steep liquor powder and 10 g/L glucose (Table 8). Flasks were incubated at 28° C. for 3 days using an orbital agitator (Model G-52 New Brunswick Scientific Co.) running at 100 rpm.

TABLE 8

Berkley Media for Flasks

| Component | g/L |
|---|---|
| $(NH_4)_2SO_4$ | 10.4 |
| $KH_2PO_4$ | 2.0 |
| $MgSO_4 \cdot 7H_2O$ | 0.31 |
| $CaCl_2 \cdot 2H_2O$ | 0.53 |
| Dry Corn Steep Liquor | 5.1 |
| Glucose | 10 |
| Trace elements* | 1 mL/L |

*Trace elements solution contains 5 g/L $FeSO_4 \cdot 7H_2O$, 1.6 g/L $MnSO_4 \cdot H_2O$ and 1.4 g/L $ZnSO_4 \cdot 7H_2O$.

The content of each inoculum flask was transferred to a 14 L pilot scale fermentation vessel (Model MF114 New Brunswick Scientific Co.) containing 10 L of Initial Pilot Media having a pH of 5.5 (Table 9). The vessel was run in batch mode until glucose in the media was depleted. At this point, the carbon source containing cellulase inducing carbohydrates was added on a continuous basis from a stock that was 35.5% w/v of solids dissolved in water. Peristaltic pumps were used to deliver the carbon source at a feed rate of 0.4 grams of carbon per liter culture per hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 4.0 during cellulase production using an automated controller connected to an online pH probe and a pump enabling the addition of a 10% ammonium hydroxide solution. Periodically, 100 mL samples of broth were drawn for biomass and protein analysis.

TABLE 9

Initial Media for Fed-Batch Fermentations

| Component | g/L |
|---|---|
| $(NH_4)_2SO_4$ | 2.20 |
| $KH_2PO_4$ | 1.39 |
| $MgSO_4 \cdot 7H_2O$ | 0.70 |
| $CaCl_2 \cdot 2H_2O$ | 0.185 |
| Dry Corn Steep Liquor | 6.00 |
| Glucose | 13.00 |
| Trace elements* | 0.38 mL/L |

*Trace elements solution contains 5 g/L $FeSO_4 \cdot 7H_2O$, 1.6 g/L $MnSO_4 \cdot H_2O$ and 1.4 g/L $ZnSO_4 \cdot 7H_2O$.

The biomass content of the culture broth was determined using aliquots of 5-10 mL of broth that had been weighed, vacuum filtered through glass microfiber filters, and oven dried at 100° C. for 4 to 24 hours. The concentration of biomass was determined according to the equation below.

$$\text{Biomass (g/L)} = \frac{\text{dry filter paper and cake (g)} - \text{filter mass (g)}}{\text{wet sample-mass (g)}} \times \text{broth density (g/mL)} \times 1000 \text{ mL/L}$$

The protein concentration of the culture filtrate was determined using the Bradford assay. Colour intensity changes in the Coomassie Brilliant Blue G-250 dye, that forms the basis of this assay, were quantified spectrophotometrically using absorbance measurements at 595 nm. The standard assay control used was a cellulase mixture of known composition and concentration. The final filtrates for enzyme analysis were collected after 162-170 hours.

Figure 7:
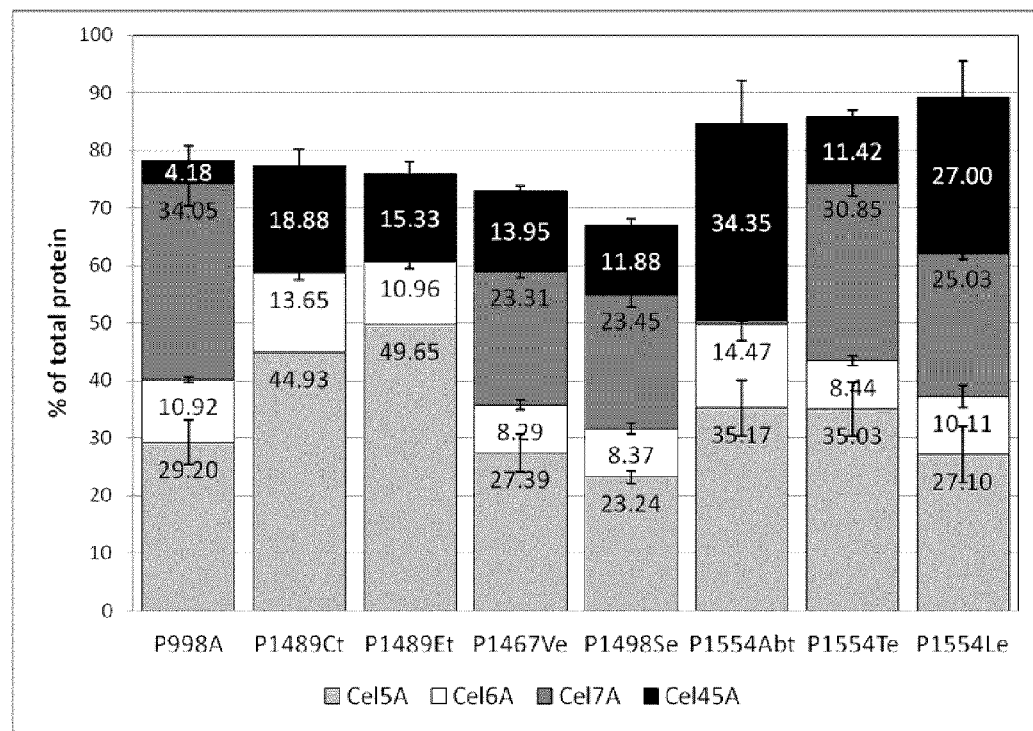
FIG. 7 depicts the relative abundance of TrCel7A, TrCel6A, TrCel45A and TrCel5A in cellulase mixtures produced by *Trichoderma reesei* transformants overexpressing TrCel45A and a modified TrCel5A, and by the parental strain P998A as assessed in a final fermentation sample by ELISA using component specific antibodies. The strain names are indicated under each bar and the relative abundance of each cellulase tested is indicated on the corresponding bars.

The relative concentrations (in weight percent of total secreted protein) of four cellulase components (TrCel7A, TrCel6A, TrCel45A, TrCel5A) were determined by ELISA using a component specific antibody as described above (Example 1.4). The abundance of TrCel6A cellulase is similar in all transformants and parental strains. The TrCel7A cellulase was not detected in transformants deleted in Trcel7a. Transformants with ectopically integrated Trcel45a genetic constructs have similar TrCel7A levels as their parental strains. The relative abundance of TrCel5A in Trcel7a deleted transformants increased compared to that of the parental strains or transformants that still produce the native TrCel7A enzyme. The abundance of TrCel45A increased in all transformants possessing either the single or double integrated Trcel45a transgene copy (FIG. 7).

Example 1.6

Depilling Activity of Enzyme Produced by *T. reesei* Transformants

For testing depilling activity, circles of 100% cotton flannelette fabric with an approximate 4.5" diameter and weighing ~1.0-2.0 g were cut. The initial weight of each piece of fabric was measured and recorded. Fabric circles were placed in the jars fuzzy side up and 90 g of steel ball bearings and 50 mM citrate buffer, pH 5.0 were added into each jar. The enzymes were diluted to obtain 1-10 mg of the total protein per jar. The diluted enzyme was added to the jars so that the total liquid in each jar equaled about 15 g. The jars were incubated at 50° C. for 2 hours with shaking at ~180 rpm. After incubation, 3 drops of 10 N NaOH were added to the jars to stop the depilling reaction. Subsequently, the contents of the jars were filtered and the fabric was returned to the jar. After addition of about 200 mL of deionized water, the jars were shaken vigorously for about 15 seconds to release the "fines" from the fabric and the fabric was discarded. The liquid was filtered, dried in a 100° C. oven for at least two hours and the total weight of filter paper and released fibers was recorded. The loss of fabric weight was calculated using equation below:

$$\% \text{ weight loss} = \frac{(\text{weight of the filter paper} + \text{collected fines}) - \text{weight of the filter paper}}{\text{initial weight of the fabric}} \times 100\%$$

The depilling activity was compared to that of an enzyme mixture produced from strain BTR213 and assayed at pH 5.0 (set to a depilling activity of 1.0).

Figure 8:
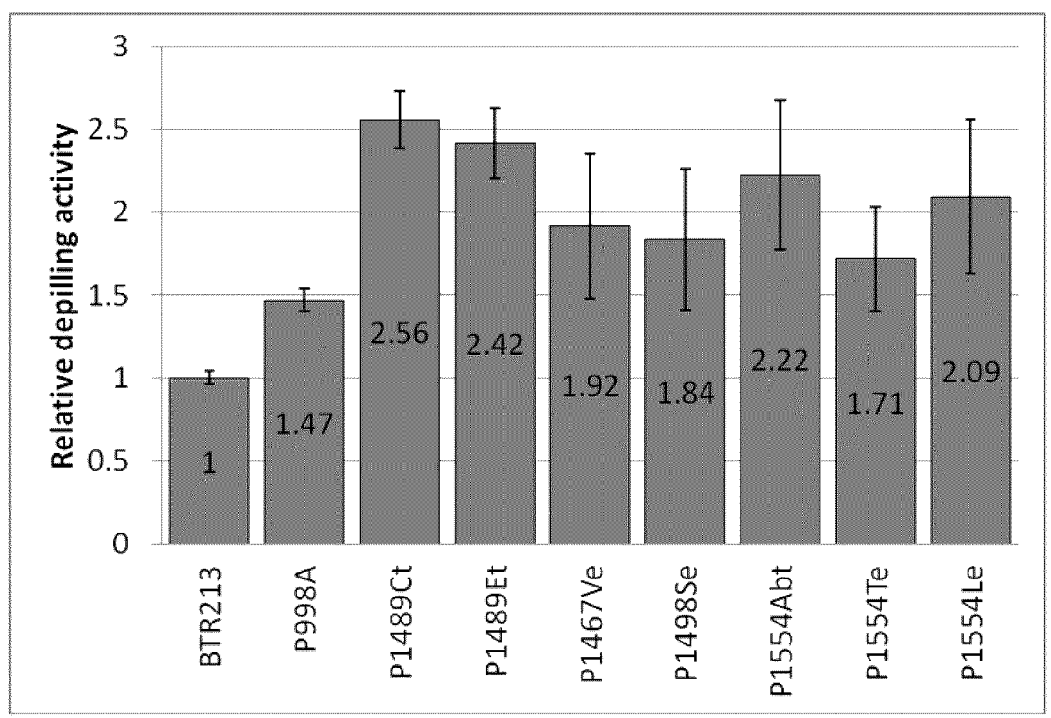
FIG. 8 shows the relative depilling activity of cellulase enzyme mixtures produced by *Trichoderma reesei* transformants overexpressing TrCel45A and a modified TrCel5A, and by parental strains BTR213 and P998A. The strain names are indicated under each bar and the relative depilling activity is indicated on the corresponding bar.

As shown in FIG. 8, enzyme mixtures produced by overexpression of TrCel45A and overexpression of the modified TrCel5A-G363A protein resulted in an increased depilling activity relative to the enzymes produced by the P998A parental strain.

Example 2

Generation and Characterization of HiCMC3 and HiCel45A Overexpressing Strains

Example 2.1

Expression of HiCel5A Cellulase in *T. reesei*

The HiCel5 overexpression strain P579A was generated by the transformation of a M2C38uridine auxotroph strain with the pChHiCel5A-pyr4-TV transformation vector (FIG. 9) designed to express the Hicel5a gene (SEQ ID NO:114), target the Trcel7a locus and restore prototrophic growth in the absence of uridine. The Hicel5a gene (SEQ ID NO:114) encodes a Family 5 cellulase having the amino acid sequence of SEQ ID NO: 74 (HiCMC3). A uridine auxotroph of M2C38, M2C38aux, was obtained through selection of mutants spontaneously resistant to 0.15% w/v 5-fluoroorotic-acid (FOA). The transcription of the *N. crassa* gene pyr4 from the selection cassette is driven by its native promoter (Ppyr4) and terminator (Tpyr4). The expression cassette contains a *T. reesei* cel7a promoter (Pcel7A) and secretion signal (as a part of the 5' flank of the cel7a targeting fragment), a *H. insolens* mature Cel5A coding sequence (Hicel5a; SEQ ID NO:114) and a *T. reesei* cel6a terminator. The vector, pChHICel5A-pyr4-TV, was linearized with EcoRI before transformation and was introduced by poly-ethylene glycol (PEG) mediated transformation as described in Example 1.3. Transformants containing at least one copy of integrated vector pChHiCel5A-pyr4-TV were identified by the amplification of a 1.7 kb product from genomic DNA using primers specific for the *T. reesei* cel7a promoter and the *T. reesei* cel6a terminator and subsequently confirmed by Southern blot analysis of genomic DNA using a probe specific for the Hicel5a coding region (data not shown). Integration of the vector into the Trcel7a locus was confirmed by Western blot analysis of filtrates from microcultures of transformants grown in cellulase-inducing medium (data not shown). Strain P579A was identified as having one copy of the pChHiCel5A-pyr4-TV integrated into the Trcel7a locus.

Example 2.2

*T. reesei* Transformation Vectors for Overexpression of HiCel45A

The transformation vector, Pc/x-TrHicel45a-ble-TV (FIG. 10) was used for the expression of the *H. insolens* Cel45A gene (Hicel45A; SEQ ID NO:115). It contains the Shble bleomycin resistance gene as a selectable marker. The Shble gene encodes the *Streptoalloteichushindustanus* bleomycin resistance protein, ShBle, which confers resistance to bleomycin, zeocin and phleomycin. The transcription of the *S. hindustanus* ShBle protein from the selection cassette is driven by a tef1 (translation elongation factor 1) promoter (Ptef1) and terminated by a cel7a terminator (Tcel7a). The expression cassette contains a hybrid *T. reesei* cel7a/xyn2 promoter (Pc/x; cel7a promoter 5448-6643 nucleotides and xyn2 promoter 664-6817 nucleotides), a xylanase 2 secretion signal (x2ss), a *T. reesei* sequence optimized *H. insolens* Cel45A coding sequence (Hicel45a; (SEQ ID NO:115) and a *T. reesei* cel7b terminator (Tcel7b) as shown in FIG. 10.

Example 2.3

Generation of *T. reesei* Strains Overexpressing HiCel45A and HiCel5A

The strains overexpressing HiCel45A from a single integrated transgene copy were generated by transformation of the HiCel45A overexpression strain P579A with the transformation vector, Pc/x-TrHicel45a-ble-TV. The transformation vector was introduced by poly-ethylene glycol (PEG) mediated transformation as described in Example 1.3.

Example 2.4

Characterization of HiCel45A+HiCel5A Overexpressing *T. reesei* Strains

To test the production of the HiCel45A, spores of *Trichoderma* transformants and the parental strain were grown in microcultures as described in Example 1.4. Cultures were grown for 6 days at 30° C. with shaking at 250 rpm. The biomass was separated from the growth media containing the secreted protein by centrifugation at 12,000 rpm. The protein concentration was determined using the Bio-Rad Protein Assay (Cat. No. 500-0001).

The presence of HiCel45A was determined by immunoblotting. Approximately 2 μg of total protein from microculture filtrates was fractionated on a 10% SDS-PAGE precast gel (BioRad) prior to Western hybridization with Cel45A antibody (data not shown). Samples were mixed with sample buffer for a final concentration of 2% w/v SDS, 10% v/v glycerol, 50 mMTris-HCl pH 6.8, 100 mM DTT, 0.05% bromophenol blue and 1.25% v/v β-mercaptoethanol. Samples comprised of 2 µg protein from microculturesbroth or 400 ng of PpHiCel45A purified from a 14 L fermentation of a *Pichia-pastoris* strain expressing HiCel45A. Samples were boiled for 5 min prior to be loaded on the 10% precast Tris-HCl gel (Biorad). Following electrophoresis at 100 V for 10 min and 1 hr at 120V, gels were transferred to a PVDF membrane for Western hybridization. Transfer was done at 100V for 1.5 hours at room temperature with an ice pack. The membrane was then rinsed at room temperature as follows: 5 min Milli-Q H$_2$O, 20 min TTBS. The membrane was then incubated overnight at 4° C. in 20 ml of a 1:5 000 dilution of a HiCel45A probing rabbit raised polyclonal antisera in HST solution. Following the overnight incubation with the primary antibody, the membrane was rinsed at room temperature as follows: 2×5 min in TTBS, 1×5 min in HST, 2×5 min in TTBS. The secondary antibody (Goat raised anti-Rabbit HRP conjugated) was diluted 1:2000 in HST. 20 ml of the diluted solution was added to the membrane and incubated for 1 hour at room temperature. Following the incubation with the secondary antibody, the membrane was rinsed at room temperature as follows: 3 times 5 min in TTBS, 10 min in HST, 3 times 5 min in TTBS, 5 min in TBS. The Western blot was developed using the SuperSignal West Dura extended duration substrate kit (Thermo Scientific) as per manufacturer's recommendation. The images were captured with an imager with no light, no filter for the chemiluminescence signal and white light, EtBr/UV filter for the molecular weight marker. A ~48 kDa band was detected in all transformants but not in the parent strain P579A. Two strains, P1622A and P1622F, were chosen for fermentations in 14 L vessels.

| Immunoblotting Solution | Component | g/L |
|---|---|---|
| TTBS (Tris buffered saline with Tween-20). pH7.5 | Tris-base | 2.42 |
| | NaCl | 29.22 |
| | Tween-20 | 1 ml |
| HST pH7.5 | Tris-base | 2.42 |
| | NaCl | 58.44 |
| | Tween-20 | 5 ml |
| TTBS (Tris buffered saline) pH7.5 | Tris-base | 2.42 |
| | NaCl | 29.22 |

TABLE 10

Modifications introduced into selected HiCel45A overexpressing strains.

| Strain | Parental strain | HiCel5A | TrCel7A | HiCel45A secretion signal | Selection marker |
|---|---|---|---|---|---|
| P1622A | P579A | OE | Δ | Xyn2 | ble |
| P1622F | P579A | OE | Δ | Xyn2 | ble |

OE—overexpressed,
Δ—deletion

Example 2.5

Production of Cellulase Mixtures Enriched in HiCel5A and HiCel45A+HiCel5A in 14 L Pilot Fermentation Cellulase mixtures were produced from strains P579A, P1622A and P1622F in 14 L fermentations as described in Example 1.5. The expression of HiCel45A was determined by immunoblotting using a Cel45A subfamily A specific antibody as described above (Example 2.4). A ~48 kDa band was detected in both transformants but is absent in the parent strain P579A. The abundance of HiCel45A is similar in both transformants (FIG. 11).

Example 2.6

Depilling Activity of Cellulase Mixtures Enriched in HiCel5A and HiCel45A+HiCel5A The depilling activity of enzyme mixtures produced in 14 L fermentation from strains BTR213 P579A and P1622A, was determined as in Example 1.6, except that the depilling reactions were carried out in 50 mM phosphate, 50 mM citrate buffer, pH 6.5 and the jars were shaken vertically for about 60 seconds at 750 rpm on a 2.54 cm span shaking table to release the "fines" from the fabric. The depilling activity was compared to that of an enzyme mixture produced from strain BTR213 and assayed at pH 5.0 (set to a depilling activity of 1.0).

As shown in FIG. 12, enzyme mixtures enriched in HiCel45A and HiCel5A (from strain P1622A) show increased depilling activity relative to an enzymes mixture enriched only in HiCel5A (the cellulase mixtures from parental strain P579A) or to an enzyme mixture that is not enriched in either component (i.e., the cellulase mixtures from strain BTR213).

Example 3

Purification of TrCel45A, TrCel5A-G363A. TrCel5A and TrCel6A

Example 3.1 Purification of *Trichoderma reesei* TrCel5A and TrCel6A

TrCel5A and TrCel6A were purified from a complete cellulase mixture produced by *T. reesei* strain BTR213 as described in U.S. Pat. No. 88,071,373.

Example 3.2 Purification of *Trichoderma reesei* Cel45A

A strain of *Trichoderma reesei* deleted in the genes encoding TrCel7A, TrCel6A and TrCel5A (strain P297J, described in WO2010/096931A1), was grown in submerged liquid fermentation under similar as those described in Example 1.5. The fungal cells were removed from the fermentation broth by filtration across a glass microfiber filter containing a Harborlite filter bed. TrCel45A was separated from other secreted proteins using anion exchange and size exclusion chromatography as described below.

A 60 mL column of DEAE-Sepharose was equilibrated in 10 mMTris/10 mMBis-Tris, pH 7.5 (Buffer 1). The cell-free fermentation broth, equivalent to about 260 mg of total protein, was adjusted to Buffer 1 conditions and applied to the column at 5 mL/min. The column was washed with 600 mL of Buffer 1, followed by 300 mL of 10 mMTris/10 mMBis-Tris, pH 6.5 (Buffer 2). These two steps elute a significant proportion of the non-TrCel45A protein from the column. A 900 mL linear gradient of 0-150 mMNaCl was applied to the column in a Buffer 2 background. Two major peaks elute during this gradient. Peak 2 contains TrCel45A and some other proteins. Fractions corresponding to Peak 2 were pooled and concentrated using a stirred ultrafiltration cell (Amicon) and a 10 kDa NMWL polyethersulfone membrane.

A concentrated preparation of Peak 2 was applied to a 170 mL column of Biogel P60 equilibrated in 50 mM sodium citrate, pH 5.0 (Buffer 3). The load was applied at 0.2 mL/min and 4 mL fractions were collected. The load was eluted with two bed volumes of Buffer 3 at 0.2 mL/min. Two major peaks were present and well separated in the elution profile as determined by absorbance at 280 nm. The second peak was TrCel45A as assessed by SDS-PAGE. The identity of this protein was confirmed by mass spectrometry. Fractions corresponding to the second peak from the Biogel P60 column were pooled and concentrated as described above. The purity of the TrCel45 in the concentrated fractions was confirmed by SDS-PAGE analysis.

Example 3.3

Purification of *Trichoderma reesei* TrCel5A-G363A

A strain of *Trichoderma reesei*, genetically altered such that it secretes the Cel5A (G363A) variant but not wild-type TrCel5A (strain P976M, as described in WO2011/109905A1), was grown in submerged liquid fermentation under conditions that induce cellulase production as known to those skilled in the art. The fungal cells were removed from the fermentation broth by filtration across a glass microfiber filter containing a Harborlite filter bed.

TrCel5A-G363A was then enriched in the cell-free fermentation broth by incubating the enzyme mixture under conditions that substantially precipitate other secreted *Trichoderma* proteins. The cell-free broth was adjusted to 50 mM sodium citrate, pH 3.5 and incubated at 55° C. for 17 h. At the end of this incubation, the enzyme mixture was centrifuged at 2000 rpm in a Sorvall Legend RT bench-top centrifuge for 5 min. The supernatant, containing TrCel5A-G363A was saved for further analysis and purification while the pellet, containing other *Trichoderma* proteins, was discarded.

The supernatant containing TrCel5A-G363A was then separated by anion exchange chromatography using the same procedure described above for TrCel45A. TrCel5A-G363A eluted with Buffer 1 in a substantially pure form as determined by SDS-PAGE. TrCel5A-G363A purified using this method was tested for activity on carboxymethyl cellulose using methods known to those skilled in the art and found to have similar activity (IU/mg protein) as wild-type TrCel5A.

Example 4

Depilling Activity of Cellulase Mixtures Enriched in Family 45 and Family 5 and/or Family 6 Cellulases A blend of the purified TrCel45A and TrCel5A-G363A cellulases was prepared with a weight ratio of TrCel45:TrCel5A of 20:80. The blend of components, as well as the individual purified components, was then assayed for depilling activity at dosages ranging from 1 to 6 mg total protein per g of fabric. The depilling activity measurements were performed as described in Example 1.6. As shown in FIG. 14, the 20:80 blend of TrCel45A and TrCel5A releases more fines from the fabric than either of the purified components in isolation.

A blend of purified TrCel45A, TrCel6A, wild-type TrCel5A and TrCel5A-G363A was prepared having a weight ratio of 20:80 TrCel45A:(TrCel6A+TrCel5A+TrCel5A-G363A in a ratio of 6:5:5). This blend, as well as the 6:5:5 TrCel6A:TrCel5A:TrCel5A-G363A blend and purified TrCel45A, was then assayed for depilling activity at dosages ranging from 0.7 to 7 mg total protein per g of fabric. The depilling activity measurements were performed as described in Example 1.6. As shown in FIG. 15, the blend containing all three types of cellulases consistently exhibited greater depilling activity (i.e., fines release) for all dosages than either the TrCel6A+TrCel5A+TrCel5A-G363 blend or the purified TrCel45A.

The invention claimed is:

1. A depilling composition comprising an enzyme mixture, which enzyme mixture comprises a Family 45 cellulase and one or more additional cellulases selected from a Family 5 cellulase, a Family 6 cellulase or a combination thereof, wherein the enzyme mixture is secreted by a genetically modified microbe overexpressing (a) a gene encoding the Family 45 cellulase; and (b) a gene or genes encoding the one or more additional cellulases, wherein the Family 45 cellulase has at least 90% sequence identity to the sequence of amino acids 1-213 of SEQ ID NO:7 (HiCel45) or to the sequence of amino acids 1-166 of SEQ ID NO:4 (TrCel45), wherein the enzyme mixture is characterized in that the Family 45 and the Family 5 cellulases or the Family 45 and the Family 6 cellulases are present at a weight ratio that exhibits synergy in an assay that measures specific depilling activity.

2. The depilling composition of claim 1, comprising the Family 45 cellulase and the Family 5 cellulase.

3. The depilling composition of claim 2, wherein the Family 45 cellulase comprises SEQ ID NO: 4 or SEQ ID NO: 7, and the Family 5 cellulase comprises SEQ ID NO: 2 or SEQ ID NO: 74.

4. The depilling composition of claim 1, wherein the Family 5 cellulase comprises a substitution of an amino acid at position 363 with a non-native alanine, serine or threonine, the position determined from alignment of the modified Family 5 cellulase with the amino acid sequence of SEQ ID NO:2.

5. The depilling composition of claim 4, wherein the Family 5 cellulase comprises SEQ ID NO: 1 (TrCel3A-G363A).

6. The depilling composition of claim 2, further comprising the Family 6 cellulase.

7. The depilling composition of claim 6, wherein the Family 6 cellulase comprises SEQ ID NO: 3.

8. The depilling composition of claim 2, wherein the Family 45 cellulase has at least 95% sequence identity to the sequence of amino acids 1-213 of SEQ ID NO:7 (HiCel45).

9. The depilling composition of claim 2, wherein the Family 45 cellulase has at least 95% sequence identity to the sequence of amino acids 1-166 of SEQ ID NO:4 (TrCel45).

10. The depilling composition of claim 1, wherein the enzyme mixture further comprises a Family 7 cellulase.

11. The depilling composition of claim 1, wherein the enzyme mixture lacks a Family 7 cellulase.

12. A process for depilling that comprises a step of contacting cellulose-containing goods with the depilling composition of claim 1.

13. A genetically modified microbe overexpressing (b) a gene encoding a Family 45 cellulase wherein the Family 45 cellulase has at least 90% sequence identity to the sequence of amino acids 1-213 of SEQ ID NO:7 (HiCel45) or to the sequence of amino acids 1-166 of SEQ ID NO:4 (TrCel45); and (ii) a gene or genes encoding one or more additional cellulases selected from a Family 5 cellulase, a Family 6 cellulase, or a combination thereof.

14. The genetically modified microbe of claim 13, wherein the genetically modified microbe overexpresses the Family 45 cellulase and the Family 5 cellulase.

15. The genetically modified microbe of claim 13, wherein the Family 45 cellulase comprises SEQ ID NO: 4 or SEQ ID NO: 7, and the Family 5 cellulase comprises SEQ ID NO: 2 or SEQ ID NO: 74.

16. The genetically modified microbe of claim 13, wherein the Family 5 cellulase comprises a substitution of an amino acid at position 363 with a non-native alanine, serine or threonine, the position determined from alignment of the modified Family 5 cellulase with the amino acid sequence of SEQ ID NO:2.

17. The genetically modified microbe of claim 16, wherein the Family 5 cellulase comprises SEQ ID NO:1 (TrCel5A-G363A).

18. The genetically modified microbe of claim 13, wherein the genetically modified microbe overexpresses the Family 6 cellulase.

19. The genetically modified microbe of claim 18, wherein the Family 6 cellulase comprises SEQ ID NO: 3.

* * * * *